(12) United States Patent
Saitoh et al.

(10) Patent No.: US 10,201,531 B2
(45) Date of Patent: Feb. 12, 2019

(54) INDAZOLYL-OXO-ISOTHIAZOLE COMPOUNDS

(71) Applicant: MOCHIDA PHARMACEUTICAL CO., LTD., Tokyo (JP)

(72) Inventors: Fumihiko Saitoh, Tokyo (JP); Tomoyuki Kamino, Tokyo (JP); Motoi Nakahara, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/751,273

(22) PCT Filed: Aug. 10, 2016

(86) PCT No.: PCT/JP2016/073604
§ 371 (c)(1),
(2) Date: Feb. 8, 2018

(87) PCT Pub. No.: WO2017/026516
PCT Pub. Date: Feb. 16, 2017

(65) Prior Publication Data
US 2018/0228776 A1 Aug. 16, 2018

(30) Foreign Application Priority Data

Aug. 12, 2015 (JP) .................. 2015-159295

(51) Int. Cl.
| | | |
|---|---|---|
| *A61K 31/427* | (2006.01) | |
| *A61K 31/4709* | (2006.01) | |
| *A61K 31/4545* | (2006.01) | |
| *A61K 31/496* | (2006.01) | |
| *A61K 31/444* | (2006.01) | |
| *A61K 31/4725* | (2006.01) | |
| *A61K 31/506* | (2006.01) | |
| *C07D 471/04* | (2006.01) | |
| *C07D 491/048* | (2006.01) | |
| *C07D 417/04* | (2006.01) | |
| *A61K 31/428* | (2006.01) | |
| *C07F 7/18* | (2006.01) | |
| *A61K 31/395* | (2006.01) | |
| *C07D 498/04* | (2006.01) | |

(Continued)

(52) U.S. Cl.
CPC .......... *A61K 31/427* (2013.01); *A61K 31/395* (2013.01); *A61K 31/4162* (2013.01); *A61K 31/428* (2013.01); *A61K 31/436* (2013.01); *A61K 31/437* (2013.01); *A61K 31/4355* (2013.01); *A61K 31/4375* (2013.01); *A61K 31/444* (2013.01); *A61K 31/4439* (2013.01); *A61K 31/454* (2013.01); *A61K 31/4545* (2013.01); *A61K 31/4709* (2013.01); *A61K 31/4725* (2013.01); *A61K 31/496* (2013.01); *A61K 31/497* (2013.01); *A61K 31/498* (2013.01); *A61K 31/4985* (2013.01); *A61K 31/501* (2013.01); *A61K 31/506* (2013.01); *A61K 31/519* (2013.01); *A61K 31/538* (2013.01); *A61K 31/5377* (2013.01); *A61K 31/5383* (2013.01); *A61K 31/55* (2013.01); *A61K 31/553* (2013.01); *A61K 31/695* (2013.01); *C07D 417/04* (2013.01); *C07D 417/14* (2013.01); *C07D 471/04* (2013.01); *C07D 487/04* (2013.01); *C07D 491/048* (2013.01); *C07D 491/056* (2013.01); *C07D 491/107* (2013.01); *C07D 498/04* (2013.01); *C07D 498/14* (2013.01); *C07D 519/00* (2013.01); *C07F 7/18* (2013.01)

(58) Field of Classification Search
CPC .. C07D 417/04; C07D 417/14; C07D 471/04; C07D 487/04; C07D 491/048; C07D 491/056; C07D 491/107; C07D 498/04; C07D 498/14; C07D 519/00
See application file for complete search history.

(56) References Cited

U.S. PATENT DOCUMENTS

2010/0197501 A1* 8/2010 Martelletti ............. A01N 43/78
504/266
2012/0277150 A1 11/2012 Ohkouchi

FOREIGN PATENT DOCUMENTS

| JP | 2009-126801 A | 6/2009 |
|---|---|---|
| JP | 2014-172893 A | 9/2014 |

(Continued)

OTHER PUBLICATIONS

Hybertson et al., "Role of the Nrf2 signaling system in health and disease", Clinical Genetics, 2014, vol. 86, pp. 447-452.

(Continued)

*Primary Examiner* — Valerie Rodriguez-Garcia
(74) *Attorney, Agent, or Firm* — Birch, Stewart, Kolasch & Birch, LLP

(57) ABSTRACT

The present invention provides a compound represented by Formula (I) or a pharmaceutically acceptable salt thereof or a solvate of these. A compound having Nrf2 activation ability is provided by the present invention.

18 Claims, No Drawings

(51) Int. Cl.
*A61K 31/4985* (2006.01)
*A61K 31/4439* (2006.01)
*C07D 498/14* (2006.01)
*C07D 487/04* (2006.01)
*A61K 31/538* (2006.01)
*A61K 31/436* (2006.01)
*A61K 31/4162* (2006.01)
*A61K 31/4355* (2006.01)
*A61K 31/437* (2006.01)
*A61K 31/4375* (2006.01)
*A61K 31/454* (2006.01)
*A61K 31/497* (2006.01)
*A61K 31/498* (2006.01)
*A61K 31/501* (2006.01)
*A61K 31/519* (2006.01)
*A61K 31/5377* (2006.01)
*A61K 31/5383* (2006.01)
*A61K 31/55* (2006.01)
*A61K 31/553* (2006.01)
*A61K 31/695* (2006.01)
*C07D 417/14* (2006.01)
*C07D 491/056* (2006.01)
*C07D 491/107* (2006.01)
*C07D 519/00* (2006.01)

(56) References Cited

FOREIGN PATENT DOCUMENTS

| | | |
|---|---|---|
| WO | WO 2011/156889 A1 | 12/2011 |
| WO | WO 2012/147518 A1 | 11/2012 |

OTHER PUBLICATIONS

International Search Report, issued in PCT/JP2016/073604, dated Nov. 8, 2016.
Magesh et al., "Small Molecule Modulators of Keap1-Nrf2-ARE Pathway as Potential Preventive and Therapeutic Agents", Medicinal Research Reviews, 2012, vol. 32, No. 4, pp. 687-726.
Suzuki et al., "Molecular basis of the Keap1-Nrf2 system", Elsevier, Free Radical Biology and Medicine, 2015, vol. 88, pp. 93-100.
Written Opinion of the International Searching Authority, issued in PCT/JP2016/073604, dated Nov. 8, 2016.

\* cited by examiner

INDAZOLYL-OXO-ISOTHIAZOLE COMPOUNDS

TECHNICAL FIELD

The present invention relates to a compound having Nrf2 activation ability, and particularly to a compound having an isothiazole structure represented by Formula (I) below or a pharmaceutically acceptable salt thereof or a solvate of these, and to a pharmacological composition having these as active ingredients. The present invention also relates to a preventative and/or treatment agent for diseases associated with Nrf2, such as multiple sclerosis, psoriasis and the like.

BACKGROUND ART

Nrf2 (nuclear factor erythroid 2-related factor 2) is a protein in the cap'n'collar transcription factor family that induces cytoprotective genes and plays an important role in protecting against oxidative stress. Under non-stress conditions, Nrf2 is negatively regulated by ubiquitination and proteasomal degradation triggered by Keap1 (Kelch-like ECH-associated protein 1). When Keap1 is exposed to oxidative stimulation and electrophilic stimulation, Nrf2 avoids proteasomal degradation. The Nrf2 then moves to the nucleus, where it forms heterodimers with small Maf proteins and binds to antioxidant response elements (AREs) in antioxidative genes and detoxification genes and induces expression of these genes. This stress response gene regulatory system is called the "Keap1-Nrf2 system".

In addition to its antioxidative function and detoxification function, the Keap1-Nrf2 system also appears to be involved in metabolic homeostasis, and compounds that activate this system have been considered as potential treatment agents for various diseases (NPL 1, NPL 2). Specific diseases associated with Nrf2 include autoimmune diseases (multiple sclerosis, psoriasis, rheumatoid arthritis, systemic lupus erythematosus, scleroderma, ulcerative colitis, etc.), central nervous system diseases (Friedreich ataxia, mitochondrial myopathy, amyotrophic lateral sclerosis, Parkinson's disease, Alzheimer's disease, Huntington's disease, etc.), malignant tumors (melanoma, lung cancer, medulloblastoma, neuroblastoma, etc.), respiratory diseases (chronic occlusive pulmonary disease, etc.), eye diseases (ocular inflammation, ocular pain, age-related macular degeneration, corneal endothelial disorder, etc.), skin diseases (dermatitis, radiation skin disorders, epidermolysis bullosa, etc.), kidney diseases (diabetic nephropathy, etc.), circulatory diseases (pulmonary arterial hypertension, etc.), liver diseases (hepatitis, liver cirrhosis, etc.), traumatic brain injury, aging, diabetes, obesity and the like.

Compounds having Nrf2 activation ability include sulforaphane, lithospermic acid B (LAB), oltipraz, bardoxolone methyl (CDDO-Me), curcumin and dimethyl fumarate (BG-12), and along with their Nrf2 activating effects, application of these to various diseases has been suggested (NPL 2 and NPL 3).

A compound having a purine ring and a tetrahydrothiophene structure is disclosed in WO 2011/156889 (PTL 1) as a compound having Nrf2 activation ability. However, its basic framework is different from that of a compound having an isothiazole ring structure, and the compound of the present invention is neither disclosed nor suggested.

In the field of drug development, strict criteria must be met not only in terms of the intended pharmacological activity, but also in the areas of absorption, distribution, metabolism, excretion and the like. For example, various tests are required for drug interactions, desensitization and resistance, gastrointestinal absorption upon oral administration, transfer rate into the small intestine, absorption rate and first pass effect, organ barriers, protein binding, induction and inhibition of drug metabolizing enzymes, excretory route and clearance, application methods (application site, methods, object) and the like, and it is rare that all of these criteria are satisfied. However, these problems are common to all medicines.

CITATION LIST

Patent Literature

[PTL 1] WO 2011/156889

Non Patent Literature

[NPL 1] Suzuki and Yamamoto, Molecular basis of the Keap1-Nrf2 system, Free Radic. Biol. Med., 2015, doi: 10.1016/j.freeradbiomed.2015.06.006

[NPL 2] Hybertson and Gao, Clinical Genetics, 86, 447-452, 2014

[NPL 3] Magesh et al., Med. Res. Rev., 32, 687-726, 2012

SUMMARY OF INVENTION

Technical Problem

There have been multiple reports of compounds having Nrf2 activation ability, but the general issues mentioned above with respect to drug development are always present. More particularly, there are problems of utility and safety, such as for example poor solubility, difficulty of systemic exposure through oral administration due to poor metabolic stability, poor pharmacokinetics such as absorbability and persistence, risk of arrhythmia due to inhibition of the hERG (human ether-a-go-go related gene) channel, induction or inhibition of drug metabolizing enzymes (such as cytochrome P450), and strong protein binding. Drugs need to be discovered that are highly effective while avoiding these problems as much as possible.

Solution to Problem

The inventors discovered as a result of exhaustive research aimed at finding a highly safe and/or highly effective Nrf2 activator that a compound having an isothiazole structure represented by Formula (I) or a pharmaceutically acceptable salt thereof or a solvate of these has Nrf2 activation ability. The compound of the present invention has Nrf2 activation ability, and preferably has an improving effect on diseases associated with Nrf2, especially multiple sclerosis, psoriasis and the like.

Advantageous Effects of Invention

[C1]

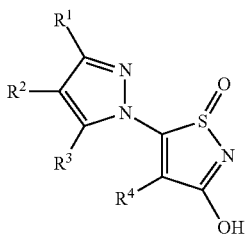

(I)

The present invention is a compound having an isothiazole structure represented by Formula (I), or a pharmaceutically acceptable salt thereof or a solvate of these, as well as a pharmacological composition containing these as an active ingredient.

The compound of the invention is a compound having Nrf2 activation ability, and preferably having an improving effect on diseases associated with Nrf2, especially multiple sclerosis, psoriasis and the like.

A pharmacological composition containing the compound of the present invention as an active ingredient is preferably one that can be orally administered, and holds promise as a preventative and/or treatment agent for diseases associated with Nrf2, such as multiple sclerosis and psoriasis.

Moreover, preferably the compounds of the present invention are highly useful because they have at least one feature such as good solubility, high metabolic stability, excellent oral absorbability, or a low inhibitory effect on the hERG channel.

DESCRIPTION OF EMBODIMENTS

The present invention is a compound having an isothiazole structure represented by Formula (I) below as shown in the following embodiments, or a pharmaceutically acceptable salt thereof or a solvate of these, as well as a pharmacological composition containing these as an active ingredient, a medicinal use of these, and an Nrf2 activator.

[Embodiments of the Invention]

The present invention comprises the following Embodiments [1] to [11].

[1] Embodiment 1 of the invention is a compound represented by Formula (I) below, or a pharmceutically acceptable salt thereof or a solvate of these:

[C2]

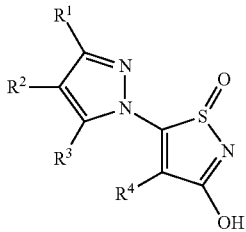

(I)

(in the formula, $R^1$ represents a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group and a $C_{6-14}$ arylcarbonyl group, $R^2$ represents a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group, a $C_{7-20}$ aralkyl group, a heteroaryl $C_{1-6}$ alkyl group, a $C_{6-14}$ aryloxy $C_{1-6}$ alkyl group and a heteroaryloxy $C_{1-6}$ alkyl group, $R^3$ represents a group arbitrarily selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{2-6}$ alkynyloxy group and a cyano group, $R^4$ represents a group arbitrarily selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{2-6}$ alkynyloxy group and a cyano group, each of $R^1$, $R^2$ and $R^3$ is optionally substituted with 1 to 5 of $R^5$, each $R^5$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{1-6}$ alkoxycarbonyl group, a $—NR^bR^c$ group (in which each of $R^b$ and $R^c$ independently represents a hydrogen atom, a $C_{1-6}$ alkyl group or a non-aromatic heterocyclic group), a mono/di-$C_{1-6}$ alkylamino $C_{1-6}$ alkyl group, a $C_{3-8}$ cycloalkyl group, a $C_{3-8}$ cycloalkenyl group, a $C_{6-14}$ aryl group, non-aromatic heterocyclic group, a heteroaryl group, a $C_{3-8}$ cycloalkyl $C_{1-6}$ alkyl group, a $C_{7-20}$ aralkyl group, non-aromatic heterocyclic $C_{1-6}$ alkyl group, a heteroaryl $C_{1-6}$ alkyl group, a $C_{6-14}$ aryloxy group, a heteroaryloxy group, a $C_{7-20}$ aralkyloxy group and a heteroaryl $C_{1-6}$ alkyloxy group, each of the $C_{3-8}$ cycloalkyl group, $C_{3-8}$ cycloalkenyl group, $C_{6-14}$ aryl group, non-aromatic heterocyclic group, heteroaryl group, $C_{3-8}$ cycloalkyl $C_{1-6}$ alkyl group, $C_{7-20}$ aralkyl group, non-aromatic heterocyclic $C_{1-6}$ alkyl group, heteroaryl $C_{1-6}$ alkyl group, $C_{6-14}$ aryloxy group, heteroaryloxy group, $C_{7-20}$ aralkyloxy group or heteroaryl $C_{1-6}$ alkyloxy group of each $R^5$ is optionally substituted with 1 to 5 of a group optionally selected from a halogen atom, $C_{1-6}$ alkyl group, a halogenated $C_{1-6}$ alkyl group, a $C_{1-6}$ alkoxy group, a cyano group, a $C_{1-6}$ alkoxycarbonyl group, a $C_{3-8}$ cycloalkyl group, a $C_{3-8}$ cycloalkenyl group, a $C_{6-14}$ aryl group (which is itself optionally substituted with 1 to 5 $C_{1-6}$ alkyl groups), a non-aromatic heterocyclic group and a heteroaryl group, $R^2$ may bind with $R^1$ or $R^3$ to form a fused ring group together with part of a pyrazole ring, and this fused ring group is a 5- to 10-member heterocyclic group or a $C_{6-10}$ aryl group optionally substituted with 1 to 5 of $R^6$, each $R^6$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{1-6}$ alkoxycarbonyl group, a $C_{3-8}$ cycloalkyl group, a $C_{3-8}$ cycloalkenyl group, a $C_{6-14}$ aryl group, a non-aromatic heterocyclic group, a heteroaryl group, a $C_{3-8}$ cycloalkyl $C_{1-6}$ alkyl group, a $C_{7-20}$ aralkyl group, a heteroaryl $C_{1-6}$ alkyl group, a $C_{6-14}$ aryloxy group, a heteroaryloxy group, a $C_{7-20}$ aralkyloxy group and a heteroaryl $C_{1-6}$ alkyloxy group, each $R_6$ is optionally substituted with 1 to 5 of $R^7$, each $R^7$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a $C_{1-6}$ alkoxy $C_{1-6}$ alkyl group, a cyano group, a $C_{1-6}$ alkoxycarbonyl group, a —$CONR^dR^e$ group (in which each of $R^d$ and $R^e$ independently represents a hydrogen atom, a $C_{1-6}$ alkyl group, $C_{3-8}$ cycloalkyl group or a $C_{6-14}$ aryl group), a mono/di-$C_{2-7}$ alkanoylamino group, an amino group, a mono/di-$C_{1-6}$ alkylamino group, a mono/di-$C_{1-6}$ alkylamino $C_{1-6}$ alkyl group, a $C_{3-8}$ cycloalkyl group, a $C_{3-8}$ cycloalkenyl group, a $C_{6-14}$ aryl group, a non-aromatic heterocyclic group, a heteroaryl group, a $C_{3-8}$ cycloalkyl $C_{1-6}$ alkyl group, a $C_{7-20}$ aralkyl group, a non-aromatic heterocyclic $C_{1-6}$ alkyl group, a heteroaryl $C_{1-6}$ alkyl group, a $C_{6-14}$ aryloxy group, a heteroaryloxy group, a $C_{3-8}$ cycloalkylcarbonyl group, a $C_{6-14}$ arylcarbonyl group and a non-aromatic heterocyclic carbonyl group, and each of the $C_{3-8}$ cycloalkyl group, $C_{3-8}$ cycloalkenyl group, $C_{6-14}$ aryl group, non-aromatic heterocyclic group, heteroaryl group, $C_{3-8}$ cycloalkyl $C_{1-6}$ alkyl group, $C_{7-20}$ aralkyl group, non-aromatic heterocyclic $C_{1-6}$ alkyl group, heteroaryl $C_{1-6}$ alkyl group, $C_{6-14}$ aryloxy group, heteroaryloxy group, $C_{3-8}$ cycloalkylcarbonyl group, $C_{6-14}$ arylcarbonyl group or non-aromatic heterocyclic carbonyl group of each $R_7$ is optionally substituted with 1 to 5 of a halogen atom, a $C_{1-6}$ alkyl group, a halogenated $C_{1-6}$ alkyl group, a $C_{1-6}$ alkoxy group or a $C_{1-6}$ alkoxy $C_{1-6}$ alkyl groups).

Each group in Formula (I) of Embodiment [1] above is explained in detail below.

In explanations of the compound of the invention, "$C_{1-6}$" for example indicates that the number of constituent carbon atoms is 1 to 6, and unless otherwise specified, this represents the total number of carbon atoms in a linear, branched or cyclic group. In a group containing a chain group and a cyclic group, it means the "total number of carbon atoms in the chain and the ring".

In this Description, unless otherwise specified, a "halogen atom" may be for example a fluorine atom, a chlorine atom, a bromine atom, an iodine atom or the like.

In this Description, unless otherwise specified, "halogenated" means having 1 to 5 of the aforementioned "halogen atom" as substituents.

In this Description, unless otherwise specified, examples of the "$C_{1-6}$ alkyl group" include methyl, ethyl, propyl, isopropyl, butyl, isobutyl, sec-butyl, tert-butyl, hexyl and the like. Examples of the "$C_{1-4}$ alkyl group" include methyl, ethyl, propyl, isopropyl, butyl, isobutyl, sec-butyl, tert-butyl and the like. Examples of the "$C_{1-2}$ alkyl group" include methyl and ethyl.

In this Description, unless otherwise specified, a "halogenated $C_{1-6}$ alkyl group" means a group comprising the "$C_{1-6}$ alkyl group" optionally substituted with 1 to 5 halogen atoms, and examples include difluoromethyl, trifluoromethyl, 2,2,2-trifluoroethyl, 1,1,2,2-tetrafluoroethyl, pentafluoroethyl and the like.

In this Description, unless otherwise specified, a "halogenated $C_{1-4}$ alkyl group" means a group comprising the "$C_{1-4}$ alkyl group" optionally substituted with 1 to 5 halogen atoms, and examples include difluoromethyl, trifluoromethyl, 2,2,2-trifluoroethyl, 1,1,2,2-tetrafluoroethyl, pentafluoroethyl and the like.

In this Description, unless otherwise specified, a "halogenated $C_{1-2}$ alkyl group" means a group comprising the "$C_{1-2}$ alkyl group" optionally substituted with 1 to 5 halogen atoms, and examples include difluoromethyl, trifluoromethyl, 2,2,2-trifluoroethyl, 1,1,2,2-tetrafluoroethyl, pentafluoroethyl and the like.

In this Description, unless otherwise specified, a "$C_{2-6}$ alkenyl group" may be a vinyl, allyl, isopropenyl, 1-propene-1-yl, butenyl, pentenyl, isopentenyl or hexenyl group or the like for example.

In this Description, unless otherwise specified, a "$C_{2-6}$ alkynyl group" may be an ethynyl, 1-propynyl (=1-propyn-1-yl), 2-propynyl (=2-propyn-1-yl), butynyl, pentynyl (=4-pentyn-1-yl), hexynyl (=5-hexyny-1-yl) group or the like for example.

In this Description, unless otherwise specified, a "$C_{3-8}$ cycloalkyl group" may be a cyclic alkyl group such as a cyclopropyl, cyclobutyl, cyclopentyl, cyclohexyl, cycloheptyl or cyclooctyl group or the like for example.

In this Description, unless otherwise specified, a "$C_{3-8}$ cycloalkenyl group" may be a cyclic alkenyl group such as a cyclopropenyl, cyclobutenyl, cyclopentenyl, cyclohexenyl, cycloheptenyl or cyclooctenyl group or the like for example.

In this Description, unless otherwise specified, a "$C_{3-6}$ cycloalkyl group" may be a cyclic alkyl group such as a cyclopropyl, cyclobutyl, cyclopentyl or cyclohexyl group or the like for example.

In this Description, unless otherwise specified, a "$C_{3-6}$ cycloalkenyl group" may be a cyclic alkenyl group such as a cyclopropenyl, cyclobutenyl, cyclopentenyl or cyclohexenyl group or the like for example.

In this Description, unless otherwise specified, an "aryl group" may be a "monocyclic aryl group", a "condensed cyclic aryl group (including bicyclic or tricyclic)" or a "partial hydrogenated condensed cyclic aryl group".

In this Description, unless otherwise specified, a "partially hydrogenated condensed cyclic aryl group" is a monovalent group obtained by removing any hydrogen atom from a partially hydrogenated fused ring in the aforementioned "condensed cyclic aryl group", and either a hydrogen atom of the aromatic ring portion of the fused ring or a hydrogen atom of the hydrogenated portion may be removed.

In this Description, unless otherwise specified, a "$C_{6-14}$ aryl group" may be a phenyl, 1-naphthyl, 2-naphthyl, phenanthryl, acenaphthyl, indanyl, indenyl, 1,2-dihydronaphthyl or 1,2,3,4-tetrahydronaphthyl group or the like for example.

In this Description, unless otherwise specified, a "$C_{6-10}$ aryl group" may be a phenyl, 1-naphthyl, 2-naphthyl, indanyl, indenyl, 1,2-dihydronaphthyl or 1,2,3,4-tetrahydronaphthyl group or the like for example.

In this Description, unless otherwise specified, a "heterocyclic group" is a monovalent group obtained by removing any hydrogen atom from a 3- to 14-member monocyclic or fused ring containing 1 to 5 hetero atoms selected from nitrogen, sulfur and oxygen atoms, and a carbonyl group may also be substituted for a carbon atom in a ring of this heterocyclic group.

In this Description, unless otherwise specified, examples of "heterocyclic groups" include a "heteroaryl group", a "non-aromatic heterocyclic group" and the like.

In this Description, unless otherwise specified, the aforementioned "heteroaryl group" is a 5- to 14-member heteroaryl group containing 1 to 5 hetero atoms selected from nitrogen, sulfur and oxygen atoms, and a carbonyl group may also be substituted for a carbon atom in a ring of this heteroaryl group.

In this Description, unless otherwise specified, examples of "heteroaryl groups" include a "monocyclic heteroaryl group", a "condensed cyclic heteroaryl group" and a "partially hydrogenated condensed cyclic heteroaryl group".

In this Description, unless otherwise specified, the aforementioned "monocyclic heteroaryl group" is preferably one having 5 to 7 ring members, and examples include pyrrolyl, furyl, thienyl, imidazolyl, pyrazolyl, oxazolyl, isoxazolyl, thiazolyl, isothiazolyl, thiadiazolyl, 1,2,3-triazolyl, 1,2,4-triazolyl, 1,2,3-oxadiazolyl, 1,2,4-oxadiazolyl, 1,3,4-oxadiazolyl, thiatriazolyl, oxatriazolyl, tetrazolyl, pyridyl, pyridazinyl, pyrimidinyl, pyrazinyl, triazyl, tetrazyl, 2-oxo-1H-pyridyl, 2,3'-bipyridinyl, 2,4'-bipyridinyl and the like.

In this Description, unless otherwise specified, the aforementioned "condensed cyclic heteroaryl group" is a monovalent group obtained by removing any arbitrary hydrogen atom from a fused ring formed by condensing a "heterocyclic group" with an "aryl group" or a "heterocyclic group" with a "heteroaryl group", and the arbitrary hydrogen atom may be removed from either condensed ring.

In this Description, unless otherwise specified, the aforementioned "condensed cyclic heteroaryl group" is preferably one having 8 to 14 ring members, and examples include indolyl, benzofuranyl, benzothienyl, benzooxazolyl, benzothiazolyl, 1H-benzimidazolyl, 1H-indazolyl, 2H-indazolyl, 1H-benzotriazolyl, quinolyl, isoquinolyl, quinoxalinyl, pyrido[2,3-b]pyrazinyl, pyrido[2,3-b][1,4]oxazinyl, furo[3,2-b]pyridyl, pyrrolo[3,2-b]pyridyl, pyrazolo[1,5-a]pyrimidinyl, pyrazolo[3,4-b]pyridyl, pyrazolo[3,4-c]pyridyl, pyrazolo[4,3-c]pyridyl, pyrazolo[4,3-b]pyridyl, pyrazolo[3,4-c]quinolyl, 1-oxo-2H-isoquinolyl, 2-oxobenzimidazolyl, 2-oxoindolyl, 2-oxo-1,3-benzooxazolyl and the like.

In this Description, unless otherwise specified, a "partially hydrogenated condensed cyclic heteroaryl group" is a monovalent group obtained by removing any arbitrary hydrogen atom from a partially hydrogenated condensed ring in a fused ring formed by condensing a "heterocyclic group" with an "aryl group" or a "heterocyclic group" with a "heteroaryl group". The arbitrary hydrogen atom may be removed either from any ring part (the "heterocyclic group", "aryl group" or "heteroaryl group") in the fused ring, or from a hydrogenated ring part, and for example in the case of tetrahydroquinolyl having partially hydrogenated quinoline, examples include 5,6,7,8-tetrahydroquinolyl or 1,2,3,4-tetrahydroquinolyl. Depending on the position from which the arbitrary hydrogen atom is removed, these groups may be substituted with -2-yl,-3-yl,-4-yl,-5-yl,-6-yl,-7-yl,-8-yl or the like in the case of 5,6,7,8-tetrahydroquinolyl, or with -1-yl,-2-yl,-3-yl,-4-yl,-5-yl,-6-yl,-7-yl,-8-yl or the like in the case of 1,2,3,4-tetrahydroquinolyl for example.

In this Description, unless otherwise specified, the "partially hydrogenated condensed cyclic heteroaryl group" is preferably one with 8 to 14 ring members, and examples include the following:
indolinyl,
2,3-dihydro-1H-pyrido [2,3-b] [1,4] oxazinyl,
2,3-dihydro-1H-pyrrolo [2,3-b] pyridyl,
3,4-dihydro-1H-1,8-naphthyridinyl,
2,3,4,5-tetrahydropyrido [3,2-b] [1,4] oxazepinyl,
6,7,8,9-tetrahydropyrido [3,2-b] [1,4] oxazocinyl,
7,8,9,10-tetrahydro-6H-pyrido [3,2-b] [1,4] oxazocinyl,
2,3-dihydropyrazino [2,3-b] [1,4] oxazinyl,
6a,7,8,9-tetrahydro-6H-pyrido [3,2-b] pyrrolo [1,2-d] [1,4] oxazinyl,
6,7-dihydro-5H-pyrimido [4,5-b] [1,4] oxazinyl,
3,4-dihydro-2H-pyrido [4,3-b] [1,4] oxazinyl,
3,4-dihydro-2H-pyrido [3,2-b] [1,4] oxazinyl,
3,4-dihydro-2H-pyrazino [2,3-b] [1,4] oxazinyl,
2,3-dihydro-[1, 4] dioxino [2,3-b] pyridyl,
2,3-dihydro-1,4-benzodioxinyl,
2,3-dihydrobenzo [b] [1,4] dioxinyl,
3,4-dihydro-2H-benzo [b] [1,4] oxazinyl,
2,3-dihydro-1H-benzo [d] imidazolyl,
2,3-dihydrobenzo [d] oxazolyl,
4,6-dihydropyrrolo [3,4-c] pyrazolyl,
6,7-dihydro-4H-pyrazolo [4,3-c] pyridyl,
4,6,7,8-tetrahydropyrazolo [4,3-c] azepinyl,
4,5,7,8-tetrahydropyrazolo [3,4-d] azepinyl,
2-oxo-1H-pyrido [2,3-b] [1,4] oxazinyl,
2-oxo-1H-3,4-dihydro-1,8-naphthyridinyl,
3-oxo-4H-pyrido [3,2-b] [1,4] oxazinyl,
3-oxo-4H-pyrazino [2,3-b] [1,4] oxazinyl, and
6-oxo-5H-pyrimido [4,5-b] [1,4] oxazinyl.

In this Description, unless otherwise specified, a "non-aromatic heterocyclic group" is a monovalent group obtained by removing any hydrogen atom from a saturated or unsaturated 3- to 14-member non-aromatic heterocyclic ring containing 1 to 5 hetero atoms selected from the oxygen, sulfur and nitrogen atoms, and a carbonyl group may also be substituted for a carbon atom in a ring of this non-aromatic heterocyclic group. In this Description, unless otherwise specified, rings comprising $C_{3-8}$ cycloalkyls or 3- to 8-member non-aromatic heterocyclic rings spiro bonded to "non-aromatic heterocyclic groups" are also considered "non-aromatic heterocyclic groups".

In this Description, unless otherwise specified, examples of "non-aromatic heterocyclic groups" include aziridinyl, azetidinyl, oxiranyl, thiiranyl, oxetanyl, thietanyl, pyrrolidinyl, tetrahydrofuryl, piperidinyl, 3,6-dihydro-2H-pyranyl, tetrahydropyranyl, tetrahydrothiopyranyl, 1,2,3,6-tetrahydropyridyl, piperazinyl, morpholinyl, thiomorpholinyl, 2-oxa-7-azaspiro[3.4]octanyl, 2-oxopyrrolidinyl and 2-oxopiperidinyl and the like.

In this Description, unless otherwise specified, a "cycloalkylalkyl group" is a group in which the aforementioned "cycloalkyl group" is substituted with the aforementioned "alkyl group", and examples of "$C_{3-8}$ cycloalkyl $C_{1-6}$ alkyl groups" include cyclopropylmethyl, cyclobutylmethyl, cyclopentylmethyl, cyclohexylmethyl, 1-cyclopropylethyl and 2-cyclopropylethyl and the like.

In this Description, unless otherwise specified, an "aralkyl group" is a group in which the aforementioned "aryl group" is substituted with the aforementioned "alkyl group", and examples of "$C_{7-20}$ aralkyl groups" include benzyl, phenethyl, diphenylmethyl, trityl, biphenylmethyl, naphthylmethyl, indanylmethyl and 1,2,3,4-tetrahydronaphthalene-1-ylmethyl and the like.

In this Description, unless otherwise specified, an "aralkyl group" is a group in which the "aryl group" is substituted with the "alkyl group", and examples of "$C_{7-14}$ aralkyl groups" include benzyl, phenethyl, diphenylmethyl, biphenylmethyl, naphthylmethyl, indanylmethyl and 1,2,3,4-tetrahydronaphthalene-1-ylmethyl and the like.

In this Description, unless otherwise specified, an "aralkyl group" is a group in which the "aryl group" is substituted with the "alkyl group", and examples of "$C_{7-8}$ aralkyl groups" include benzyl and phenethyl and the like.

In this Description, unless otherwise specified, a "non-aromatic heterocyclic alkyl group" is a group in which the aforementioned "non-aromatic heterocyclic group" is substituted with the aforementioned "alkyl group".

In this Description, unless otherwise specified, a "heteroarylalkyl group" is a group in which the aforementioned "heteroaryl group" is substituted with the aforementioned "alkyl group", such as morpholinemethyl for example.

In this Description, unless otherwise specified, a "$C_{1-6}$ alkoxy group" is a group in which the "$C_{1-6}$ alkyl group" is substituted with an oxygen atom.

In this Description, unless otherwise specified, examples of "$C_{1-6}$ alkoxy groups" include methoxy, ethoxy, propoxy, isopropoxy, butoxy, isobutoxy, sec-butoxy, tert-butoxy, pentyloxy and hexyloxy groups and the like. Examples of "$C_{1-4}$ alkoxy groups" include methoxy, ethoxy, propoxy, isopropoxy, butoxy, isobutoxy, sec-butoxy and tert-butoxy and the like, while examples of "$C_{1-2}$ alkoxy groups" include methoxy and ethoxy.

In this Description, unless otherwise specified, a "$C_{1-6}$ alkoxy $C_{1-6}$ alkyl group" is a group in which the aforementioned "$C_{1-6}$ alkoxy group" is substituted with the aforementioned "$C_{1-6}$ alkyl group", and examples of "$C_{1-6}$ alkoxy $C_{1-6}$ alkyl groups" include methoxymethyl, methoxyethyl, ethoxymethyl and ethoxyethyl and the like.

In this Description, unless otherwise specified, a "$C_{2-6}$ alkenyloxy group" is a group in which the "$C_{2-6}$ alkenyl group" is substituted with an oxygen atom, and examples include vinyloxy, allyloxy, isopropenyloxy, butenyloxy, pentenyloxy and hexenyloxy and the like.

In this Description, unless otherwise specified, a "$C_{2-6}$ alkynyloxy group" is a group in which the "$C_{2-6}$ alkynyl group" is substituted with an oxygen atom, and examples include ethynyloxy, 1-propynyloxy, 2-propynyloxy, butynyloxy, pentynyloxy and hexynyloxy and the like.

In this Description, unless otherwise specified, an "aryloxy group" is a group in which the "aryl group" is substituted with an oxygen atom, such as phenoxy for example.

In this Description, unless otherwise specified, a "heteroaryloxy group" is a group in which the "heteroaryl group" is substituted with an oxygen atom.

In this Description, unless otherwise specified, an "aralkyloxy group" is a group in which the "aralkyl group" is substituted with an oxygen atom.

In this Description, unless otherwise specified, a "heteroarylalkyloxy group" is a group in which the "heteroarylalkyl group" is substituted with an oxygen atom.

In this Description, unless otherwise specified, an "aryloxyalkyl group" is a group in which the "aryloxy group" is substituted with the "alkyl group".

In this Description, unless otherwise specified, a "heteroaryloxyalkyl group" is a group in which the "heteroaryloxy group" is substituted with the "alkyl group".

In this Description, unless otherwise specified, a "$C_{2-7}$ alkanoyl group" means a "$C_{1-6}$ alkylcarbonyl group" comprising a carbonyl group bound to the "$C_{1-6}$ alkyl group", and examples of "$C_{2-7}$ alkanoyl groups" include acetyl, propionyl, butyryl, isobutyryl, valeryl, isovaleryl, pivaloyl, hexanoyl and heptanoyl and the like.

In this Description, unless otherwise specified, a "cycloalkylcarbonyl group" is a group comprising a carbonyl group bound to the "cycloalkyl group", and examples of "$C_{3-8}$ cycloalkylcarbonyl groups" include cyclopropylcarbonyl, cyclobutylcarbonyl, cyclopentylcarbonyl and cyclohexylcarbonyl and the like.

In this Description, unless otherwise specified, an "arylcarbonyl group" is a group comprising a carbonyl group bound to the "aryl group", and examples of "$C_{6-14}$ arylcarbonyl groups" include benzoyl, 1-naphthoyl (1-naphthylcarbonyl), 2-naphthoyl (2-naphthylcarbonyl), indanylcarbonyl, indenylcarbonyl, 1,2,3,4-tetrahydronaphthylcarbonyl and the like.

In this Description, unless otherwise specified, an "arylcarbonyl group" is a group comprising a carbonyl group bound to the "aryl group", and examples of "$C_{6-10}$ arylcarbonyl groups" include benzoyl, 1-naphthoyl (1-naphthylcarbonyl), 2-naphthoyl (2-naphthylcarbonyl), indanylcarbonyl, indenylcarbonyl, 1,2,3,4-tetrahydronaphthylcarbonyl and the like.

In this Description, unless otherwise specified, a "non-aromatic heterocyclic carbonyl group" is a group comprising a carbonyl group bound to the "non-aromatic heterocyclic group", and examples of "non-aromatic heterocyclic carbonyl groups" include aziridinylcarbonyl, azetidinylcarbonyl, pyrrolidinylcarbonyl, tetrahydrofurylcarbonyl, piperidinylcarbonyl, tetrahydropyranylcarbonyl, piperazinylcarbonyl, morpholinylcarbonyl and the like.

In this Description, unless otherwise specified, each of $R^b$ and $R^c$ in a "—$NR^bR^c$ group" independently represents a hydrogen atom, "$C_{1-6}$ alkyl group" or "non-aromatic heterocyclic group", and a "—$NR^bR^c$ group" is a group in which the two hydrogen atoms on the nitrogen atom of an amino group are substituted with $R^b$ and $R^c$. Examples include dimethylamino, N,N-dimethyltetrahydro-2H-pyranyl-4-amino and the like.

In this Description, unless otherwise specified, a "mono/di-$C_{1-6}$ alkylamino group" is a group in which one or two hydrogen atoms of the amino group are substituted with the "$C_{1-6}$ alkyl group".

In this Description, unless otherwise specified, a "mono/di-$C_{2-7}$ alkanoylamino group" is a group in which one or two hydrogen atoms of the amino group are substituted with the "$C_{2-7}$ alkanoyl group".

In this Description, unless otherwise specified, a "mono/di-$C_{1-6}$ alkylamino $C_{1-6}$ alkyl group" is a group in which the "mono/di-$C_{1-6}$ alkylamino group" is substituted with the "$C_{1-6}$ alkyl group".

In this Description, unless otherwise specified, each of $R^d$ and $R^e$ in a "—$CONR^dR^e$ group" independently represents a hydrogen atom, "$C_{1-6}$ alkyl group", "$C_{3-8}$ cycloalkyl group" or "$C_{6-14}$ aryl group", and a "—$CONR^dR^e$ group" is a group in which the two hydrogen atoms on the nitrogen atom of the carbamoyl group are substituted with $R^d$ and $R^e$.

In this Description, unless otherwise specified, a "$C_{1-6}$ alkoxycarbonyl group" is a group in which the hydrogen atom of a carboxy group is substituted with a "$C_{1-6}$ alkyl group", or in other words an "ester group", and examples include methoxycarbonyl, ethoxycarbonyl, tert-butoxycarbonyl (Boc) and the like.

In this Description, unless otherwise specified, a "$C_{1-4}$ alkoxycarbonyl group" is a group in which the hydrogen atom of a carboxyl group is substituted with a "$C_{1-4}$ alkyl group", or in other words an "ester group", and examples include methoxycarbonyl, ethoxycarbonyl, tert-butoxycarbonyl (Boc) and the like.

$R^2$ may also bind with $R^1$ or $R^3$ to form a fused cyclic group together with part of a pyrazole ring. That is, as shown in the partial structural formula below, $R^2$, $R^3$ and (part of) a pyrazole ring may bind together to form the fused ring F1, or else $R^2$, $R^1$ and (part of) a pyrazole ring may bind together to form the fused ring F2.

[C3]

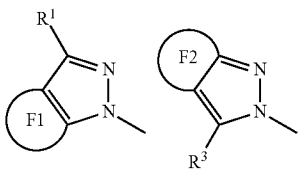

The formed "fused ring F1 or fused ring F2" forms a fused cyclic group together with the adjacent pyrazole ring.

This "fused ring F1 or fused ring F2" is a "$C_{6-10}$ aryl group" or "5- to 10-member heterocyclic group" optionally substituted with 1 to 5 of $R^6$, and forms a "condensed cyclic heteroaryl group" or "partially hydrogenated condensed cyclic heteroaryl group" together with the adjacent pyrazole ring.

In "$R^2$ may also bind with $R^1$ or $R^3$ to form a fused cyclic group together with part of a pyrazole ring", the "fused cyclic" or in other words the "fused ring F1 or fused ring F2" is a cyclic group out of the "aryl groups" described above having 6 to 10 carbon members, or a 5- to 10-member cyclic group out of the "heterocyclic groups".

The fused cyclic group comprising the "fused ring F1 or fused ring F2" and the adjacent pyrazole ring is a fused cyclic group out of the "heterocyclic groups" described above, and specific examples include fused cyclic groups containing pyrazole rings out of the "condensed cyclic heteroaryl groups" and "partially hydrogenated condensed cyclic heteroaryl groups" described above. More specific examples include indazolyl, pyrazolo[3,4-b]pyridyl, pyrazolo[3,4-c]pyridyl, pyrazolo[4,3-c]pyridyl, pyrazolo[4,3-b]pyridyl, pyrazolo[3,4-c]quinolyl, 4,6-dihydropyrrolo[3,4-c]pyrazolyl, 6,7-dihydro-4H-pyrazolo[4,3-c]pyridyl, 4,6,7,8-tetrahydropyrazolo[4,3-c]azepinyl, 4,5,7,8-tetrahydropyrazolo[3,4-d]azepinyl and the like.

In the compound of Formula (I) above, the 3-hydroxy-isothiazolyl group is a group that may become a 3(2H)-isothiazolonyl group through proton tautomerism, and the tautomers that occur are encompassed by Formula (I). The ratios of these structures may vary according to whether the compound represented by Formula (I) is in a solid or a liquid state.

[C4]

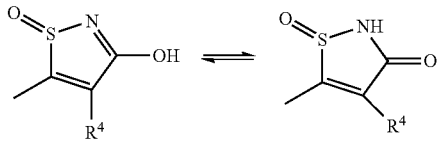

A description of any specific tautomeric form in any structural formulae in this Description is given not with the intent of limiting the Description to that form, but as a representative of the tautomer set as a whole.

[1-1] In the compound of Formula (I) of Embodiment [1] above, $R^1$ is preferably a group arbitrarily selected from a hydrogen atom, a halogen atom, a $C_{1-6}$ alkyl group, a $C_{1-6}$ alkoxy group, a cyano group, a $C_{3-8}$ cycloalkyl group, a $C_{6-14}$ aryl group and a $C_{6-14}$ arylcarbonyl group, and more preferably a group arbitrarily selected from a hydrogen atom, a halogen atom, a $C_{1-4}$ alkyl group, a $C_{1-4}$ alkoxy group, a cyano group, a $C_{3-6}$ cycloalkyl group, a $C_{6-10}$ aryl group and a $C_{6-10}$ arylcarbonyl group, or still more preferably a group arbitrarily selected from a hydrogen atom, a halogen atom, a $C_{1-2}$ alkyl group, a $C_{1-2}$ alkoxy group, a cyano group, a $C_{3-6}$ cycloalkyl group, a phenyl and a phenylcarbonyl group, and each of the alkyl group, alkoxy group, cycloalkyl group, aryl group or arylcarbonyl group in $R^1$ above may also be substituted with 1 to 5 of $R^5$.

[1-1-1] Most preferably in the compound of Formula (I) of Embodiment [1] above, $R^1$ is a group arbitrarily selected from a hydrogen atom, a halogen atom and a phenyl group, the phenyl group in $R^1$ above is optionally substituted with 1 to 5 of $R^5$ (with $R^5$ representing a halogen atom), and more specifically $R^1$ represents a hydrogen atom, a chlorine atom or a phenyl group, while $R^5$ represents a bromine atom.

[1-2] In the compound of Formula (I) of Embodiment [1] above, $R^2$ is preferably a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{3-8}$ cycloalkyl group, a $C_{3-8}$ cycloalkenyl group, a $C_{644}$ aryl group, a non-aromatic heterocyclic group, a heteroaryl group, a $C_{7-20}$ aralkyl group, a heteroaryl $C_{1-6}$ alkyl group, a $C_{644}$ aryloxy $C_{1-6}$ alkyl group and a heteroaryloxy $C_{1-6}$ alkyl group, and more preferably a group arbitrarily selected from a hydrogen atom, a halogen atom, a $C_{1-4}$ alkyl group, $C_{24}$ alkenyl group, a $C_{24}$ alkynyl group, a halogenated $C_{1-4}$ alkyl group, a $C_{3-6}$ cycloalkyl group, a $C_{3-6}$ cycloalkenyl group, a $C_{6-10}$ aryl group, a 5- to 10-member non-aromatic heterocyclic group, a 5- to 10-member heteroaryl group, a $C_{7-14}$ aralkyl group, a 5- to 10-member heteroaryl $C_{1-4}$ alkyl group, a $C_{6-10}$ aryloxy $C_1$-4 alkyl group and a 5- to 10-member heteroaryloxy $C_{1-4}$ alkyl group, or still more preferably a group arbitrarily selected from a hydrogen atom, a halogen atom, a $C_{1-2}$ alkyl group, a $C_{2-3}$ alkenyl group, a $C_{2-3}$ alkynyl group, a halogenated $C_{1-2}$ alkyl group, a $C_{3-6}$ cycloalkyl group, a $C_{3-6}$ cycloalkenyl group, $C_{640}$ aryl group, a 5- to 10-member non-aromatic heterocyclic group, a 5- to 10-member heteroaryl group, a $C_{742}$ aralkyl group, a 5- to 10-member heteroaryl $C_{1-2}$ alkyl group, a $C_{640}$ aryloxy $C_{1-2}$ alkyl group and a 5- to 10-member heteroaryloxy $C_{1-2}$ alkyl group, and each of the alkyl group, alkenyl group, alkynyl group, cycloalkyl group, cycloalkenyl group, aryl group, non-aromatic heterocyclic group, heteroaryl group, aralkyl group, heteroarylalkyl group, aryloxyalkyl group and heteroaryloxyalkyl group in $R^2$ above may be substituted with 1 to 5 of $R^5$.

[1-3] In the compound of Formula (I) of Embodiment [1] above, $R^3$ is preferably a group arbitrarily selected from a hydrogen atom and a $C_{1-6}$ alkyl group, and more preferably is a group arbitrarily selected from a hydrogen atom and a $C_{1-4}$ alkyl group, or still more preferably a hydrogen atom or a $C_{1-2}$ alkyl group, and each alkyl group in $R^3$ above may also be substituted with 1 to 5 of $R^5$.

[1-4] In the compound of Formula (I) of Embodiment [1] above, $R^4$ is preferably a hydrogen atom.

[1-5] In the compound of Formula (I) of Embodiment [1] above, $R^5$ is preferably a group arbitrarily selected from a halogen atom, a $C_{1-6}$ alkyl group, a halogenated $C_{1-6}$ alkyl group, a $C_{1-6}$ alkoxy group, a $C_{1-6}$ alkoxycarbonyl group, a —$NR^bR^c$ group (in which each of $R^b$ and $R^c$ independently represents a hydrogen atom, a $C_{1-6}$ alkyl group or a non-aromatic heterocyclic group), a di-$C_{1-6}$ alkylamino $C_{1-6}$ alkyl group, a $C_{3-8}$ cycloalkyl group, a $C_{6-14}$ aryl group, a non-aromatic heterocyclic group, a heteroaryl group, a $C_{3-8}$ cycloalkyl $C_{1-6}$ alkyl group, a $C_{6-14}$ aryloxy group, a heteroaryloxy group and a $C_{7-20}$ aralkyloxy group, or more preferably a group arbitrarily selected from a halogen atom, a $C_{1-4}$ alkyl group, a halogenated $C_{1-4}$ alkyl group, a $C_{1-4}$ alkoxy group, a $C_{1-4}$ alkoxycarbonyl group, a —NR$^b$R$^c$ group (in which each of R$^b$ and R$^c$ independently represents a hydrogen atom, a $C_{1-4}$ alkyl group or a 5- to 10-member non-aromatic heterocyclic group), a di-$C_{1-4}$ alkylamino $C_{1-4}$ alkyl group, a $C_{3-6}$ cycloalkyl group, a $C_{6-10}$ aryl group, a 5- to 10-member non-aromatic heterocyclic group, a 5- to 10-member heteroaryl group, a $C_{3-6}$ cycloalkyl $C_{1-4}$ alkyl group, a $C_{6-10}$ aryloxy group, 5- to 10-member heteroaryloxy group and a $C_{7-14}$ aralkyloxy group, or still more preferably a group arbitrarily selected from a halogen atom, a $C_{1-2}$ alkyl group, a halogenated $C_{1-2}$ alkyl group, a $C_{1-2}$ alkoxy group, a $C_{1-4}$ alkoxycarbonyl group, a —NR$^b$R$^c$ group (in which each of R$^b$ and R$^c$ independently represents a hydrogen atom, a $C_{1-2}$ alkyl group or a 5- to 6-member non-aromatic heterocyclic group), a di-$C_{1-2}$ alkylamino $C_{1-2}$ alkyl group, a $C_{3-6}$ cycloalkyl group, a phenyl group, a 5- to 10-member non-aromatic heterocyclic group, a 5- to 10-member heteroaryl group, a $C_{3-6}$ cycloalkyl $C_{1-2}$ alkyl group, a phenoxy group, a 5- to 6-member heteroaryloxy group and a $C_{7-8}$ aralkyloxy group.

Each of the cycloalkyl group, aryl group, non-aromatic heterocyclic group, heteroaryl group, cycloalkylalkyl group, aryloxy group, heteroaryloxy group or aralkyloxy group in R$^5$ above may also be substituted with 1 to 5 of a group arbitrarily selected from a halogen atom, a $C_{1-6}$ alkyl group, a halogenated $C_{1-6}$ alkyl group, a $C_{1-6}$ alkoxy group, a cyano group, a $C_{1-6}$ alkoxycarbonyl group, a $C_{3-8}$ cycloalkyl group, a $C_{6-14}$ aryl group, a non-aromatic heterocyclic group and a heteroaryl group, and preferably with 1 to 3 of a group arbitrarily selected from a halogen atom, a $C_{1-4}$ alkyl group, a halogenated $C_{1-4}$ alkyl group, a $C_{1-4}$ alkoxy group, a cyano group, a $C_{1-4}$ alkoxycarbonyl group, a $C_{3-6}$ cycloalkyl group and a 5- to 10-member non-aromatic heterocyclic group.

[1-6] In the compound of Formula (I) of Embodiment [1] above, R$^6$ is preferably a group arbitrarily selected from a halogen atom, a $C_{1-6}$ alkyl group, a halogenated $C_{1-6}$ alkyl group, a $C_{1-6}$ alkoxy group, a cyano group, a $C_{1-6}$ alkoxycarbonyl group, a $C_{3-8}$ cycloalkyl group, a $C_{3-8}$ cycloalkenyl group, a $C_{6-14}$ aryl group, a non-aromatic heterocyclic group, a heteroaryl group, a $C_{3-8}$ cycloalkyl $C_{1-6}$ alkyl group, a $C_{7-20}$ aralkyl group, a heteroaryl $C_{1-6}$ alkyl group, a $C_{6-14}$ aryloxy group, a $C_{7-20}$ aralkyloxy group and a heteroaryl $C_{1-6}$ alkyloxy group, or more preferably a group arbitrarily selected from a halogen atom, a $C_{1-4}$ alkyl group, a halogenated $C_{1-4}$ alkyl group, a $C_{1-4}$ alkoxy group, a cyano group, a $C_{1-4}$ alkoxycarbonyl group, a $C_{3-6}$ cycloalkyl group, a $C_{3-6}$ cycloalkenyl group, a $C_{6-10}$ aryl group, a 5- to 10-member non-aromatic heterocyclic group, a 5- to 13-member heteroaryl group, a $C_{3-6}$ cycloalkyl $C_{1-4}$ alkyl group, a $C_{7-14}$ aralkyl group, a 5- to 10-member heteroaryl $C_{1-4}$ alkyl group, a $C_{6-10}$ aryloxy group, a $C_{7-14}$ aralkyloxy group and a 5- to 10-member heteroaryl $C_{1-4}$ alkyloxy group, or still more preferably a group arbitrarily selected from a halogen atom, a $C_{1-2}$ alkyl group, a halogenated $C_{1-2}$ alkyl group, a $C_{1-2}$ alkoxy group, a cyano group, a $C_{1-4}$ alkoxycarbonyl group, a $C_{3-6}$ cycloalkyl group, a $C_{3-6}$ cycloalkenyl group, a phenyl group, a 5- to 10-member non-aromatic heterocyclic group, a 5- to 13-member heteroaryl group, a $C_{3-6}$ cycloalkyl $C_{1-2}$ alkyl group, a $C_{7-8}$ aralkyl group, 5- to 10-member heteroaryl $C_{1-2}$ alkyl group, a phenyloxy group, a $C_{7-8}$ aralkyloxy group and a 5- to 10-member heteroaryl $C_{1-2}$ alkyloxy group, and each of the alkyl group, alkoxy group, alkoxycarbonyl group, cycloalkyl group, cycloalkenyl group, aryl group, non-aromatic heterocyclic group, heteroaryl group, cycloalkylalkyl group, aralkyl group, heteroarylalkyl group, aryloxy group, aralkyloxy group or heteroarylalkyloxy group in R$^6$ above may be substituted with 1 to 5 of R$^7$.

[1-7] In the compound of Formula (I) of Embodiment [1] above, R$^7$ is preferably a group arbitrarily selected from a halogen atom, a $C_{1-6}$ alkyl group, a halogenated $C_{1-6}$ alkyl group, a $C_{1-6}$ alkoxy group, a $C_{1-6}$ alkoxy $C_{1-6}$ alkyl group, a cyano group, a $C_{1-6}$ alkoxycarbonyl group, a —CONR$^d$R$^e$ group (in which each of R$^d$ and R$^e$ independently represents a hydrogen atom, a $C_{1-6}$ alkyl group, a $C_{3-8}$ cycloalkyl group or a $C_{6-14}$ aryl group), a mono-$C_{2-7}$ alkanoylamino group, an amino group, a di-$C_{1-6}$ alkylamino group, a $C_{3-8}$ cycloalkyl group, a non-aromatic heterocyclic group, a $C_{3-8}$ cycloalkyl $C_{1-6}$ alkyl group, a non-aromatic heterocyclic $C_{1-6}$ alkyl group, a $C_{6-14}$ aryloxy group, a $C_{3-8}$ cycloalkylcarbonyl group, a $C_{6-14}$ arylcarbonyl group and a non-aromatic heterocyclic carbonyl group, or more preferably a group arbitrarily selected from a halogen atom, a $C_{1-4}$ alkyl group, a halogenated $C_{1-4}$ alkyl group, a $C_{1-4}$ alkoxy group, a $C_{1-4}$ alkoxy $C_{1-4}$ alkyl group, a cyano group, a $C_{1-4}$ alkoxycarbonyl group, a —CONR$^d$R$^e$ group (in which each of R$^d$ and R$^e$ independently represents a hydrogen atom, a $C_{1-4}$ alkyl group, a $C_{3-6}$ cycloalkyl group or a $C_{6-10}$ aryl group), a mono-$C_{2-5}$ alkanoylamino group, an amino group, di-$C_{1-4}$ alkylamino group, a $C_{3-6}$ cycloalkyl group, a 5- to 10-member non-aromatic heterocyclic group, a $C_{3-6}$ cycloalkyl $C_{1-4}$ alkyl group, a 5- to 10-member non-aromatic heterocyclic $C_{1-4}$ alkyl group, a $C_{6-10}$ aryloxy group, a $C_{3-6}$ cycloalkylcarbonyl group, a $C_{6-10}$ arylcarbonyl group and a 5- to 10-member non-aromatic heterocyclic carbonyl group, or still more preferably a group arbitrarily selected from a halogen atom, $C_{1-4}$ alkyl group, a halogenated $C_{1-2}$ alkyl group, a $C_{1-2}$ alkoxy group, a $C_{1-2}$ alkoxy $C_{1-2}$ alkyl group, a cyano group, a $C_{1-4}$ alkoxycarbonyl group, a —CONR$^d$R$^e$ group (in which each of R$^d$ and R$^e$ independently represents a hydrogen atom, a $C_{1-2}$ alkyl group, a $C_{3-6}$ cycloalkyl group or a phenyl group), a mono-$C_{2-3}$ alkanoylamino group, an amino group, di-$C_{1-2}$ alkylamino group, a $C_{3-6}$ cycloalkyl group, a 5- to 6-member non-aromatic heterocyclic group, a $C_{3-6}$ cycloalkyl $C_{1-2}$ alkyl group, a 5- to 6-member non-aromatic heterocyclic $C_{1-2}$ alkyl group, a phenyloxy group, a $C_{3-6}$ cycloalkylcarbonyl group, a phenylcarbonyl group and a 5- to 6-member non-aromatic heterocyclic carbonyl group, and each of the non-aromatic heterocyclic group or cycloalkylcarbonyl group in R$^7$ above is optionally substituted with 1 to 5 of a halogen atom, $C_{1-6}$ alkyl group or $C_{1-6}$ alkoxy $C_{1-6}$ alkyl group.

[1-8] Examples of the pyrazole ring structure to which R$^1$, R$^2$ and R$^3$ are bound in the compound of Formula (I) of Embodiment [1] above include those represented by partial structural Formula (a1), (a2), (a3), (a4) or (a5) below:

[C5]

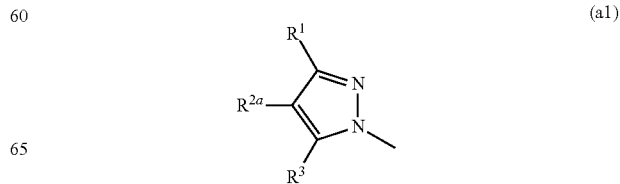

(a1)

-continued

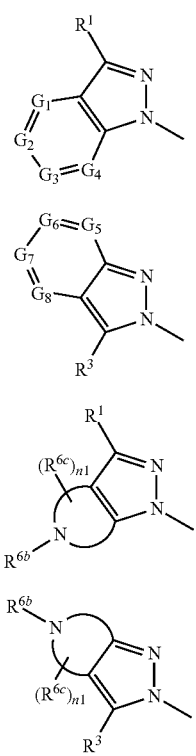

(in Formula (a1), (a2), (a3), (a4) or (a5), $R^1$ and $R^3$ are defined as in Formula (I) above, $R^{2a}$ is defined in the same way as $R^2$ in Formula (I) above except that in Formula (a1), $R^{2a}$ does not form a condensed cyclic group with $R^1$ or $R^3$ and part of the pyrazole ring, each of $G_1$, $G_2$, $G_3$, $G_4$, $G_5$, $G_6$, $G_7$ and $G_8$ independently represents a nitrogen atom, C—H or C—$R^{6a}$, the following partial structural formula

[C6]

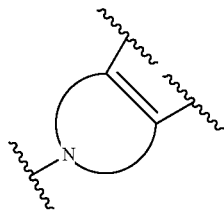

represents a 5- to 7-member non-aromatic heterocyclic group comprising one nitrogen atom and 4 to 6 carbon atoms, each $R^{6a}$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group, a $C_{6-14}$ aryloxy group, a heteroaryloxy group, a $C_{7-20}$ aralkyloxy group and a heteroaryl $C_{1-6}$ alkyloxy group, and each $R^{6a}$ is optionally substituted with 1 to 5 of $R^{7a}$, with $R^{7a}$ being defined in the same way as $R^7$ in Formula (I) above, each $R^{6b}$ independently represents a group arbitrarily selected from a $C_{1-6}$ alkoxycarbonyl group, a $C_{3-8}$ cycloalkyl $C_{1-6}$ alkyl group, a $C_{7-20}$ aralkyl group and a heteroaryl $C_{1-6}$ alkyl group, and each $R^{6b}$ is optionally substituted with 1 to 5 of $R^{7b}$, each $R^{7b}$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{6-14}$ aryloxy group and a heteroaryloxy group, and each $R^{6c}$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group and a cyano group, and each n1 is independently a number from 0 to 5).

More preferably, the pyrazole ring structure to which $R^1$, $R^2$ and $R^3$ are bound in the compound of Formula (I) of Embodiment [1] above is represented by partial structural Formula (a1), (a2) or (a4) above, or more preferably by partial structural Formula (a2) above.

In the partial structural Formula (a2) above, all of $G_1$, $G_2$, $G_3$ and $G_4$ are preferably C—H or C—$R^{6a}$, or else any one of $G_1$, $G_2$, $G_3$ and $G_4$ is a nitrogen atom. More preferably, all of $G_1$, $G_2$, $G_3$ and $G_4$ are preferably C—H or C—$R^{6a}$ in the partial structural Formula (a2) above, or in other words Formula (a2) represents an indazole ring structure. Still more preferably, in the partial structural Formula (a2) above, any one of $G_1$, $G_2$, $G_3$ and $G_4$ is C—$R^{6a}$ and the rest are C—H, and most preferably $G_2$ is C—$R^{6a}$ and $G_1$, $G_3$ and $G_4$ are C—H.

In the partial structural Formula (a3) above, preferably all of $G_5$, $G_6$, $G_7$ and $G_8$ are C—H or C—$R^{6a}$, or else any one of $G_1$, $G_2$, $G_3$ and $G_4$ is a nitrogen atom.

In the partial structural Formula (a2) or (a3), preferably each $R^{6a}$ is independently a group arbitrarily selected from a halogen atom, a $C_{1-6}$ alkyl group, a halogenated $C_{1-6}$ alkyl group, a $C_{1-6}$ alkoxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group, a $C_{6-14}$ aryloxy group, a $C_{7-20}$ aralkyloxy group and a heteroaryl $C_{1-6}$ alkyloxy group, and more preferably each is independently a group arbitrarily selected from a halogen atom, a $C_{1-4}$ alkyl group, a halogenated $C_{1-4}$ alkyl group, a $C_{1-4}$ alkoxy group, a cyano group, a $C_{3-6}$ cycloalkyl group, a $C_{3-6}$ cycloalkenyl group, a $C_{6-10}$ aryl group, a 5- to 10-member non-aromatic heterocyclic group, a 5- to 13-member heteroaryl group, a $C_{6-10}$ aryloxy group, a $C_{7-14}$ aralkyloxy group and a 5- to 10-member heteroaryl $C_{1-4}$ alkyloxy group, and still more preferably each is independently a group arbitrarily selected from a halogen atom, a $C_{1-2}$ alkyl group, a halogenated $C_{1-2}$ alkyl group, a $C_{1-2}$ alkoxy group, a cyano group, a $C_{3-6}$ cycloalkyl group, a $C_{3-6}$ cycloalkenyl group, a phenyl group, a 5- to 10-member non-aromatic heterocyclic group, a 5- to 13-member heteroaryl group, a phenyloxy group, a $C_{7-8}$ aralkyloxy group and a 5- to 10-member heteroaryl $C_{1-2}$ alkyloxy group, and each of the alkyl group, alkoxy group, cycloalkyl group, cycloalkenyl group, aryl group, non-aromatic heterocyclic group, heteroaryl group, aryloxy group, aralkyloxy group or heteroarylalkyloxy group in $R^{6a}$ above is optionally substituted with 1 to 5 of $R^{7a}$.

In the partial structural Formula (a4) or (a5) above, the partial structural formula:

[C7]

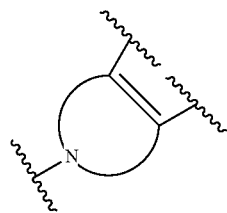

preferably represents a non-aromatic heterocyclic group represented by a partial structural formula selected arbitrarily from:

[C8]

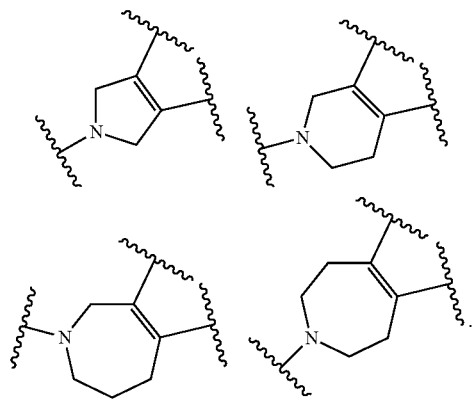

In the partial structural Formula (a4) or (a5) above, preferably each $R^{6b}$ is independently a group arbitrarily selected from a $C_{1-4}$ alkoxycarbonyl group, a $C_{3-6}$ cycloalkyl $C_{1-4}$ alkyl group, a $C_{7-14}$ aralkyl group and a 5- to 10-member heteroaryl $C_{1-4}$ alkyl group, or more preferably each is independently a group arbitrarily selected from a $C_{1-4}$ alkoxycarbonyl group, a $C_{3-6}$ cycloalkyl $C_{1-2}$ alkyl group, a $C_{7-8}$ aralkyl group and a 5- to 6-member heteroaryl $C_{1-2}$ alkyl group.

In the partial structural Formula (a4) or (a5) above, n1 is preferably 0.

The partial structural Formula (a4) above is preferably a structural formula arbitrarily selected from the partial structural formulae (a4-1), (a4-2) and (a4-3) below:

[C9]

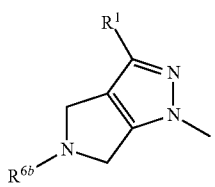 (a4-1)

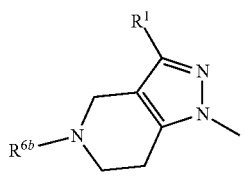 (a4-2)

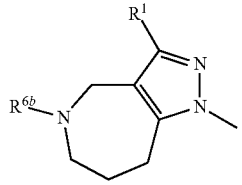 (a4-3)

(in Formula (a4-1), (a4-2) or (a4-3), $R^1$ and $R^{6b}$ are defined as in Formula (a4) above), and more preferably is Formula (a4-1) or (a4-2).

The partial structural Formula (a5) above is preferably a structural formula arbitrarily selected from the following partial structural formulae (a5-1), (a5-2), (a5-3) and (a5-4):

[C10]

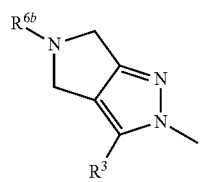 (a5-1)

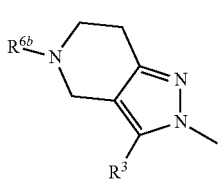 (a5-2)

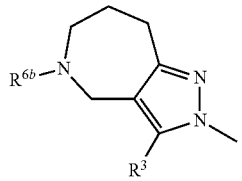 (a5-3)

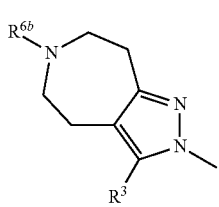 (a5-4)

(in Formula (a5-1), (a5-2), (a5-3) or (a5-4), $R^3$ and $R^{6b}$ are defined as in Formula (a5) above).

[1-8-1] In the partial structural Formula (a2) or (a3) above, it is especially desirable that each $R^{6a}$ be independently a group arbitrarily selected from a halogen atom, a $C_{1-2}$ alkyl group, a halogenated $C_{1-2}$ alkyl group, a $C_{1-2}$ alkoxy group, a $C_{3-6}$ cycloalkenyl group, a phenyl group, a 5- to 10-member non-aromatic heterocyclic group and a 5- to 13-member heteroaryl group.

Each of the alkyl group, alkoxy group, cycloalkenyl group, phenyl group, non-aromatic heterocyclic group or heteroaryl group in $R^{6a}$ above may be substituted with 1 to 5 of $R^{7a}$, and more specifically $R^{6a}$ is a chlorine atom, a bromine atom, methyl, trifluoromethyl, methoxy, cyclohexyl, phenyl, pyridyl, pyrazolyl, piperidinyl, piperazinyl, 3,6-dihydro-2H-pyranyl, 1,2,3,6-tetrahydropyridyl, furo[3, 2-b]pyridyl, 3,4-dihydro-2H-pyrido[3,2-b][1,4]oxazinyl, 2,3-dihydro-1H-pyrido[2,3-b][1,4]oxazinyl, 3,4-dihyro-2H-pyrido[4,3-b][1,4]oxazinyl, 6,7-dihydro-5H-pyrimido[4,5-b][1,4]oxazinyl, 6a,7,8,9-tetrahydro-6H-pyrido[3,2-b]pyrrolo[1,2-d][1,4]oxazinyl, 2,3-dihydro-1H-pyrrolo[2,3-b]pyridyl, 2,3-dihydro-[1,4]dioxino[2,3-b]pyridyl, 2,3,4,5-tetrahydropyrido[3,2-b][1,4]oxazepinyl, 7,8,9,10-tetrahydro-6H-pyrido[3,2-b][1,4]oxazocinyl, indazolyl or pyrazolo[1,5-a]pyrimidinyl group, and $R^{7a}$ represents deuterium or a fluorine atom or a chlorine atom, methyl, ethyl, isopropyl, isobutyl, difluoromethyl, trifluoromethyl, methoxy, cyclopropyl, cyclopropylmethyl, cyclobutylmethyl, phenoxy, pyrrolidinyl, piperazinyl, piperidinyl, morpholinyl, furo[3,2-b]pyridyl, 2-oxa-7-azaspiro[3,4]octanyl, morpholinemethyl, cyclopropylcarbonyl, tert-butoxycarbonyl (Boc), methoxyethyl, methoxymethyl, cyano, oxo or a dimethylamino group.

[2] In the compound of Formula (I) of Embodiment[1] above or its pharmaceutically acceptable salt or a solvate of these, a preferred embodiment is the compound represented by the following Formula (I)-1:

[C11]

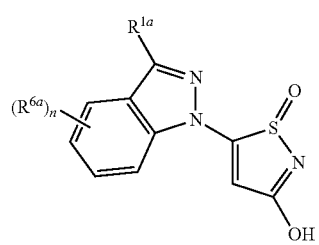

(in Formula (I)-1, $R^{1a}$ represents a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group and a $C_{6-14}$ arylcarbonyl group, and each $R^{1a}$ is optionally substituted with 1 to 5 halogen atoms, $R^{6a}$ is defined in the same way as the $R^{6a}$ in the partial structural Formula (a2) of Embodiment[1] above, and each $R^{6a}$ is optionally substituted with 1 to 5 of $R^{7a}$, $R^{7a}$ is defined in the same way as the $R^7$ of Formula (I) in Embodiment[1] above, and n represents 0, 1 or 2), or its pharmaceutically acceptable salt or a solvate of these.

In the compound of Formula (I)-1 above, n is preferably 0 or 1.

In the compound of Formula (I)-1 above, $R^{1a}$ may preferably be a group arbitrarily selected from a hydrogen atom, a halogen atom, a $C_{1-6}$ alkyl group, a $C_{1-6}$ alkoxy group, a cyano group, a $C_{3-8}$ cycloalkyl group and a $C_{6-14}$ arylcarbonyl group, or more preferably a group arbitrarily selected from a hydrogen atom, a halogen atom, a $C_{1-4}$ alkyl group, a $C_{1-4}$ alkoxy group, a cyano group, a $C_{3-6}$ cycloalkyl group and a $C_{6-10}$ arylcarbonyl group, or still more preferably a group arbitrarily selected from a hydrogen atom, a halogen atom, a $C_{1-2}$ alkyl group, a $C_{1-2}$ alkoxy group, a cyano group, a $C_{3-6}$ cycloalkyl group and phenylcarbonyl group, and each of the alkyl group, alkoxy group, cycloalkyl group or an alkylcarbonyl group in $R^{1a}$ above is optionally substituted with 1 to 5 halogen atoms. In the compound of Formula (I)-1 above, the definitions and preferred ranges of $R^{6a}$ and $R^{7a}$ are as described above with respect to Embodiments [1-1] to [1-8].

[2-1] In the compound of Formula (I)-1 above, it is especially desirable that $R^{1a}$ be a group arbitrarily selected from a hydrogen atom and a halogen atom, and specifically that it represent a hydrogen atom or a chlorine atom.

Thus, preferred embodiments of the compound represented by Formula (I) of Embodiment[1] above may be formed at will by appropriately combining the individual aspects of Embodiments [1] and [2] of the invention and preferred embodiments thereof together with the definitions of the various substituents.

In Embodiments [1] and [2] above and their sub-aspects, more preferred substituents and combinations of substituents in Formula (I) are in accordance with the explanations given in Embodiment1.

[3] As a preferred compound of the compounds represented by Formula (I) in Embodiment[1], Embodiment 3 of the invention is a compound having one of the structures listed below, or a pharmaceutically acceptable salt thereof or a solvate of these, or an optical isomer of these.

[C12]

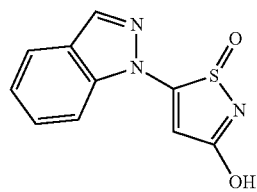

Example 1

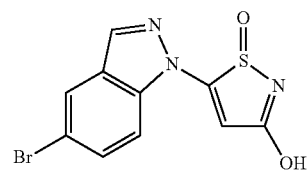

Example 2

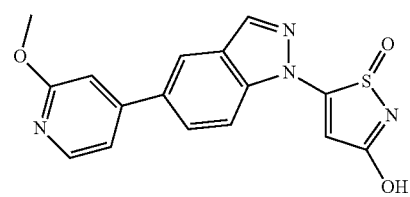

Example 3

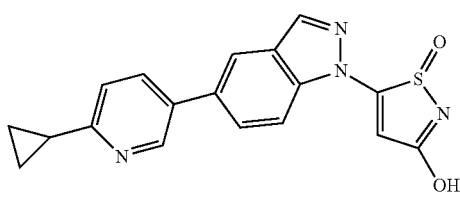

Example 4

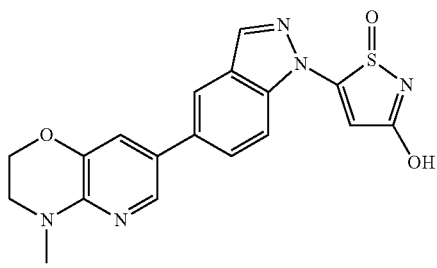

Example 5

Example 6
Example 7
Example 8
Example 9
Example 10
Example 11
Example 12
Example 13
Example 14
Example 15
Example 16
Example 17
Example 18
Example 19

Example 20
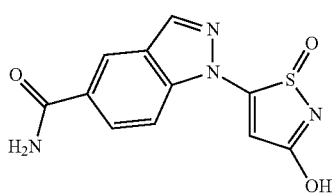
Example 21
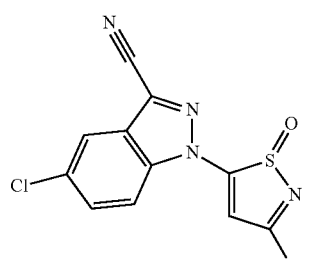
Example 22
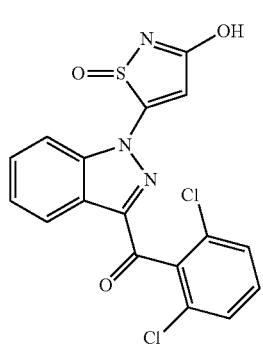
Example 23
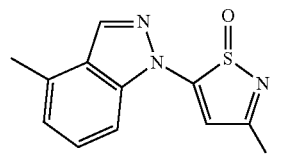
Example 24
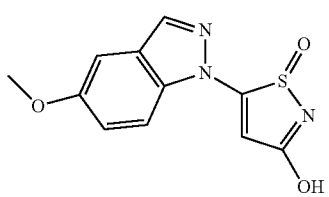
Example 25
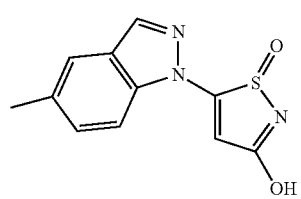
Example 26
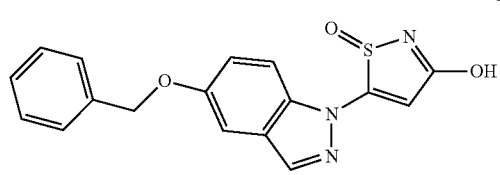
Example 27
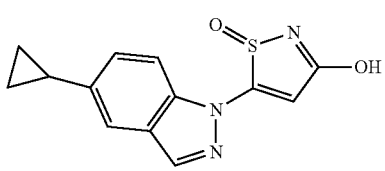
Example 28
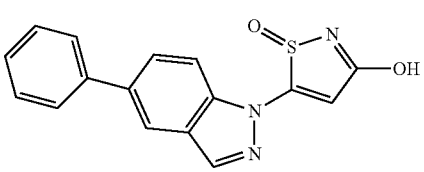
Example 29
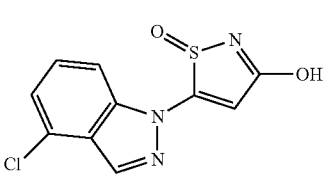
Example 30
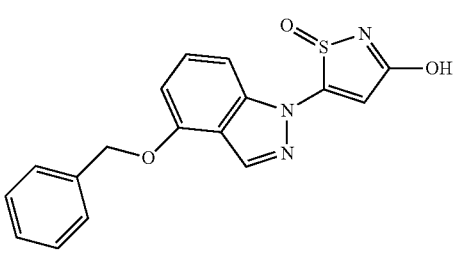
[C14]
Example 31
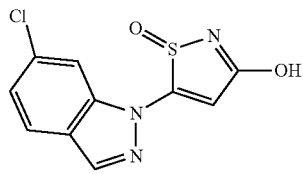
Example 32
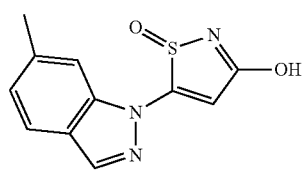
Example 33
Example 34
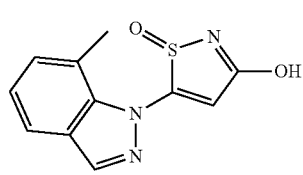

Example 35

Example 36

Example 37

Example 38

Example 39

Example 40

Example 41

Example 42

Example 43

Example 44

Example 45

Example 46

Example 47

Example 48

Example 49
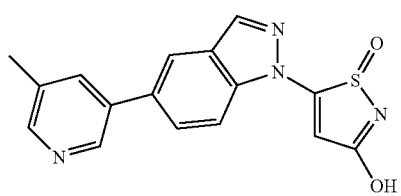
Example 50
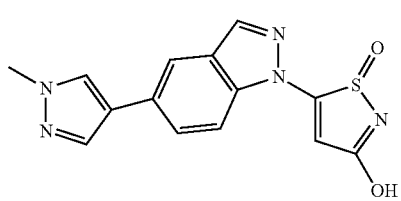
Example 51
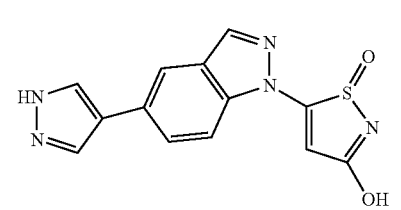
Example 52
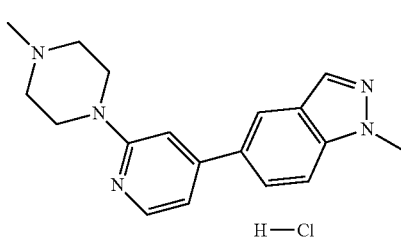
Example 53
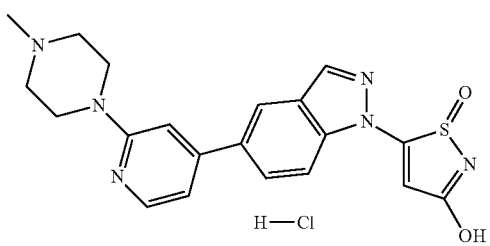
Example 54
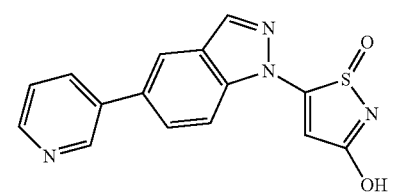
Example 55
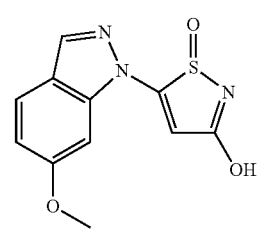
Example 56
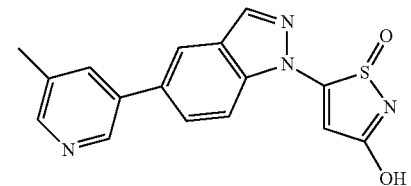
Example 57
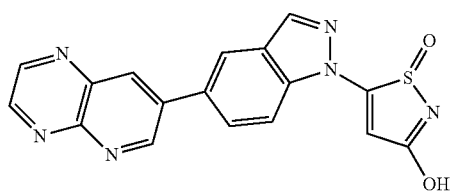
Example 58
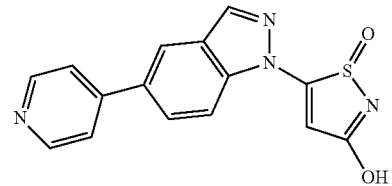
Example 59
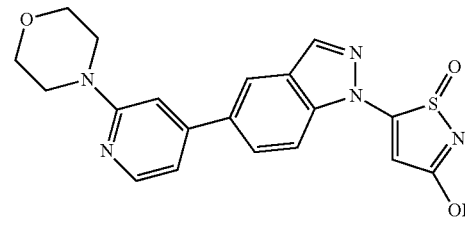
Example 60
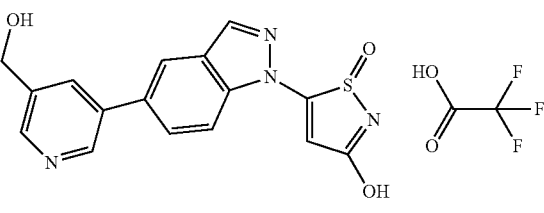
[C16]
Example 61
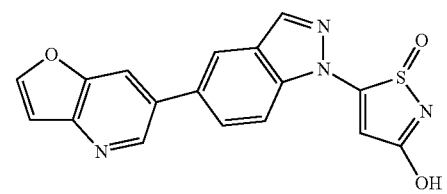
Example 62
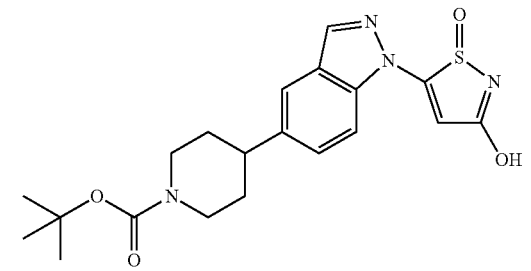

Example 63
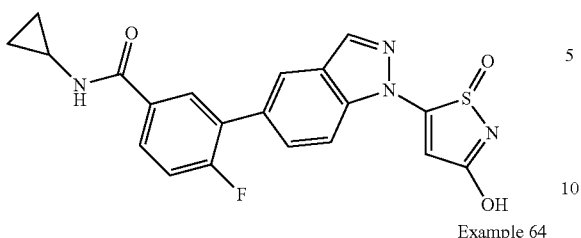
Example 64
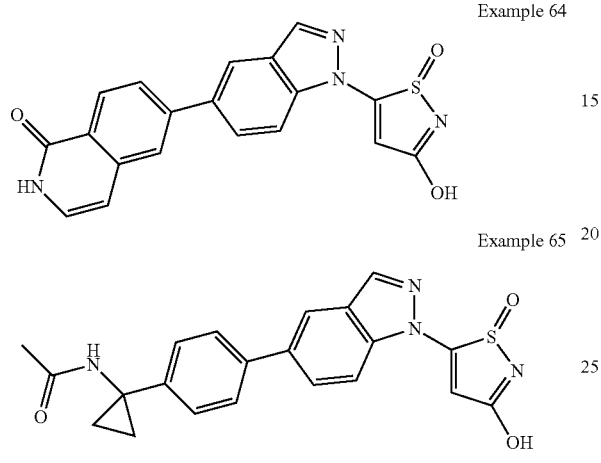
Example 65
Example 66
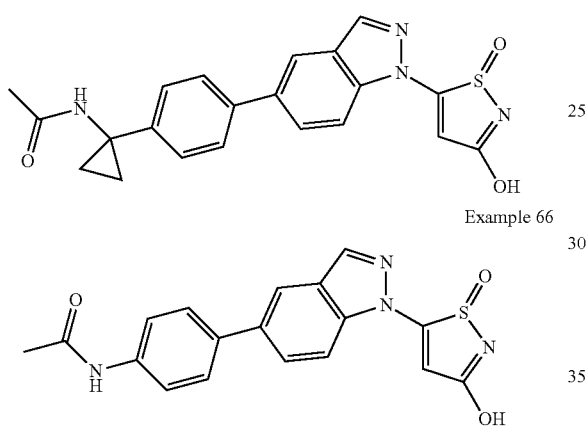
Example 67
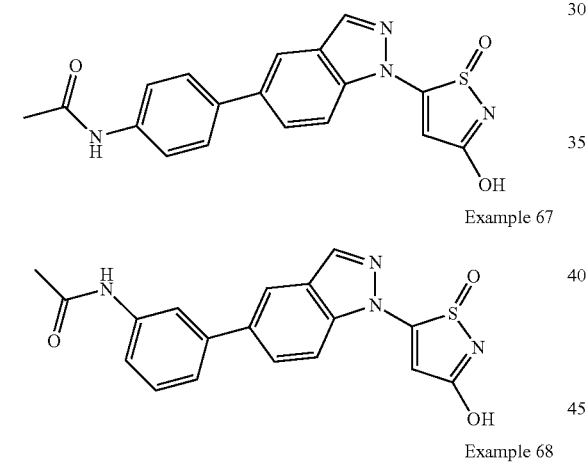
Example 68
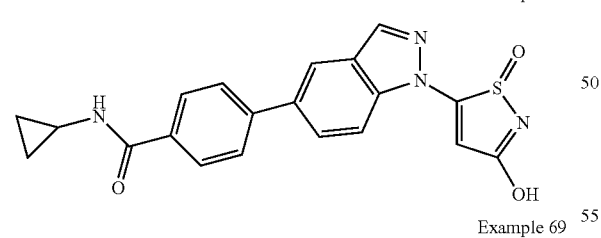
Example 69
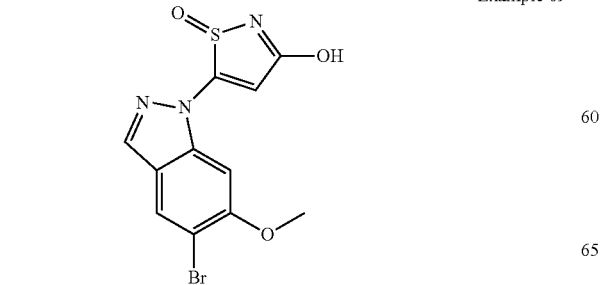
Exampe 70
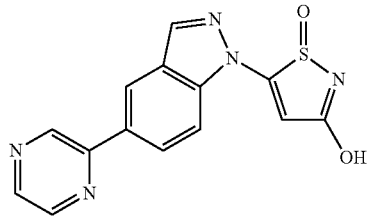
Example 71
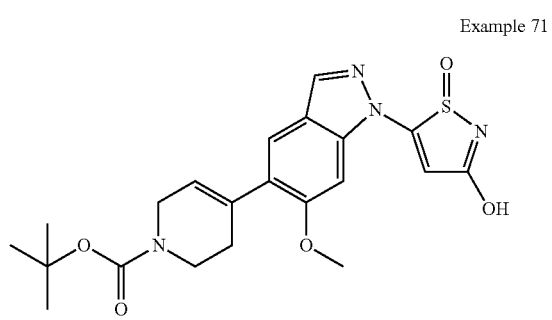
Example 72
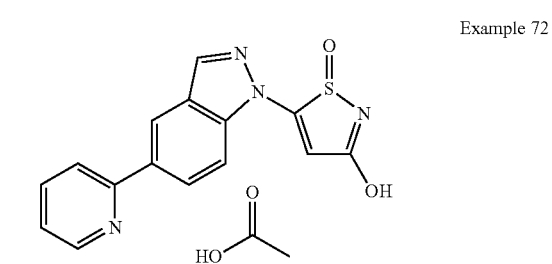
Example 73
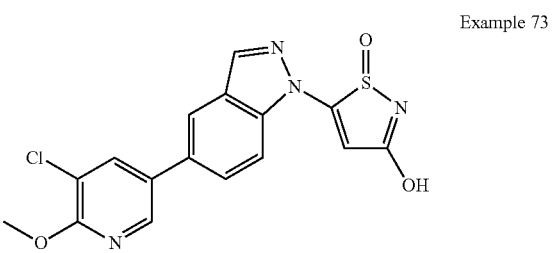
Example 74
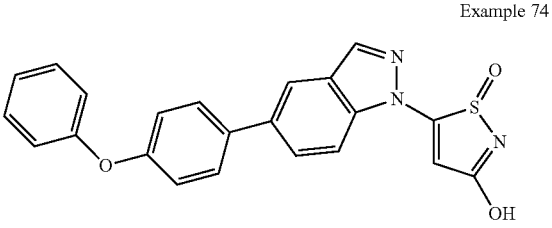
Example 75
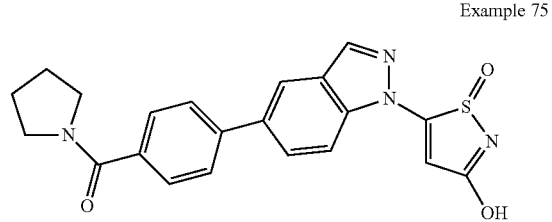

[C17]
Example 76
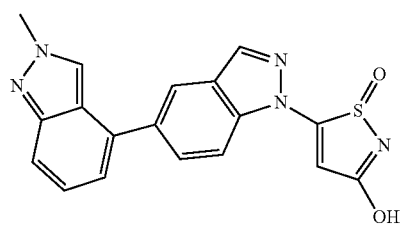
Example 77
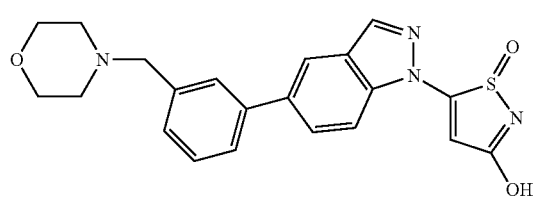
Example 78
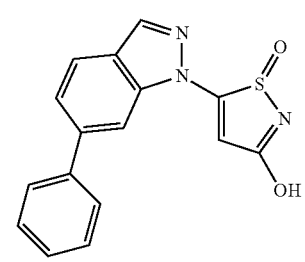
Example 79
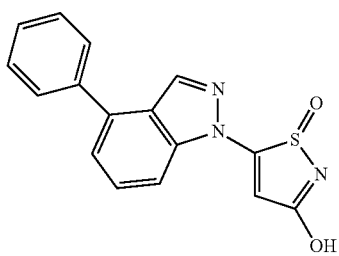
Example 80
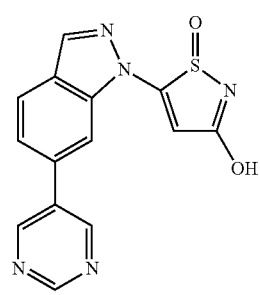
Example 81
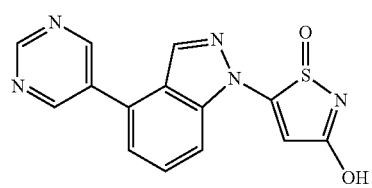
Example 82
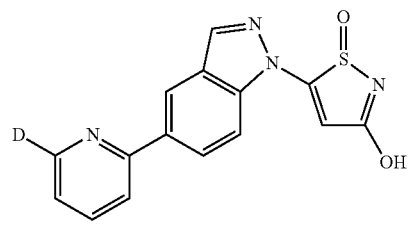
Example 83
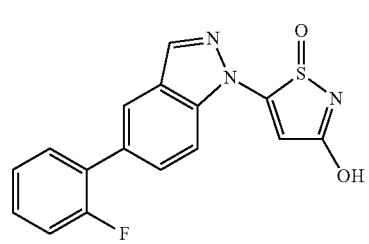
Example 84
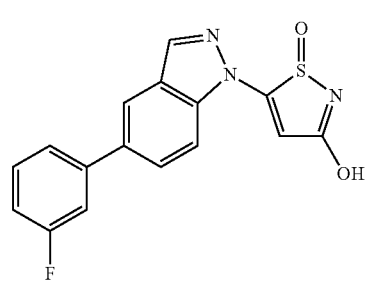
Example 85
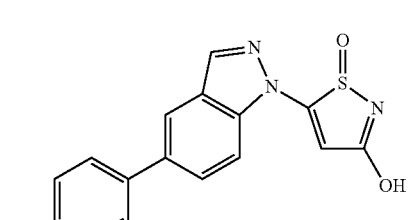
Example 86
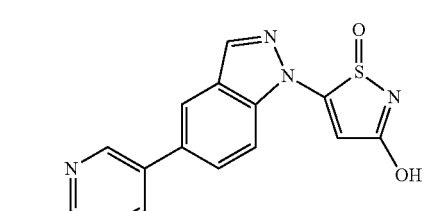
Example 87
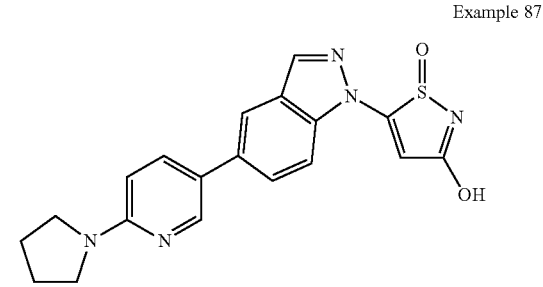

Example 88
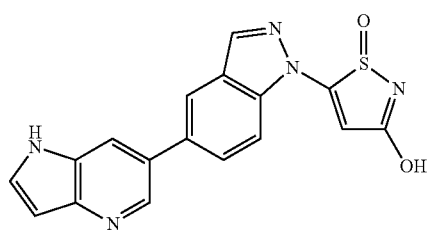
Example 89
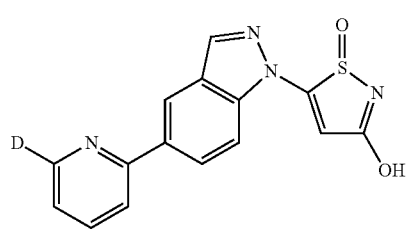
Example 90
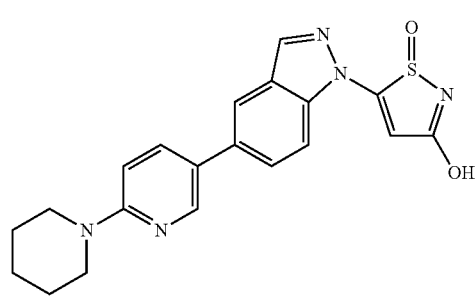
[C18]
Example 91
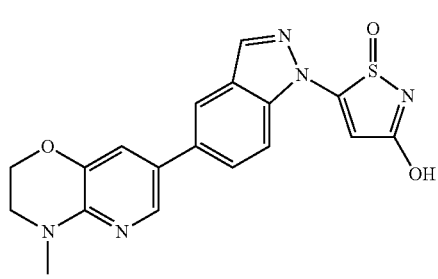
Example 92
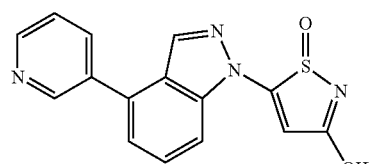
Example 93
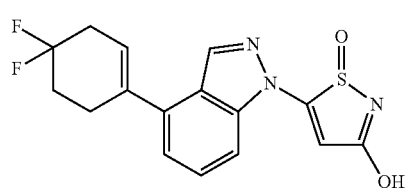
Example 94
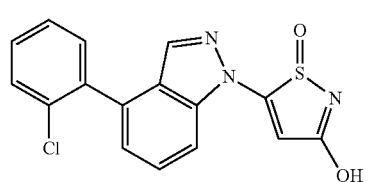
Example 95
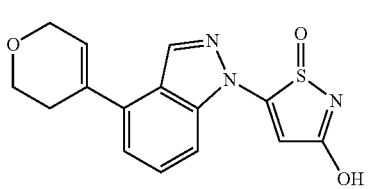
Example 96
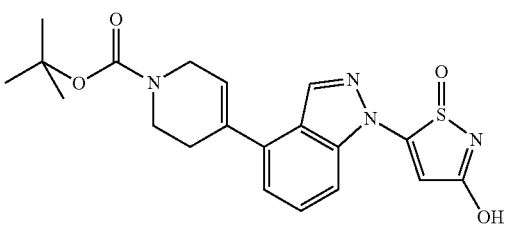
Example 97
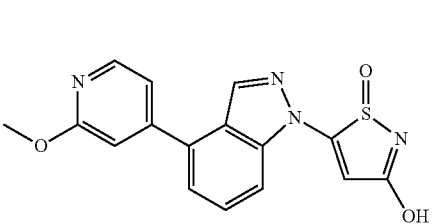
Example 98
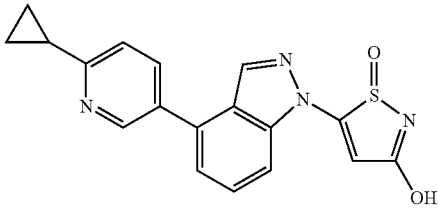
Example 99
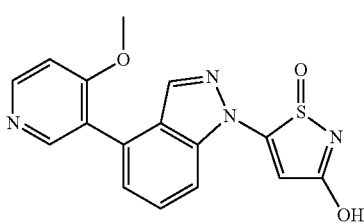
Example 100
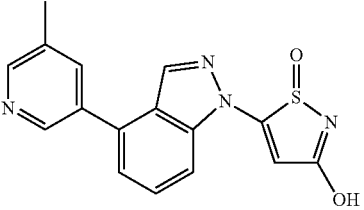
Example 101
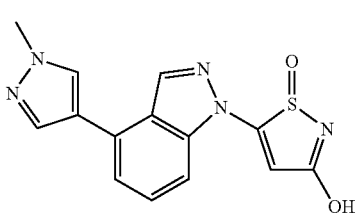

-continued

Example 102
Example 103
Example 104
Example 105
Example 106
Example 107
Example 108
Example 109
Example 110

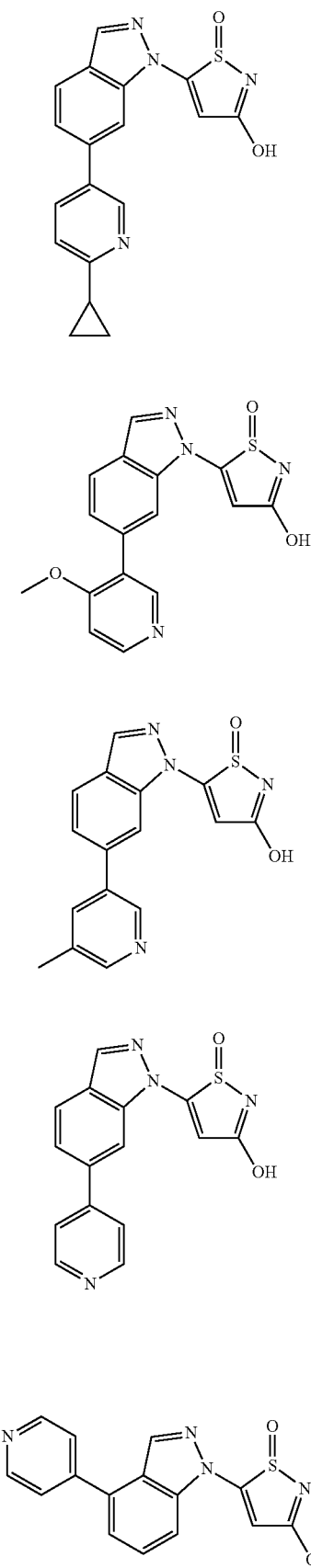
Example 111
Example 112
Example 113
Example 114
Example 115
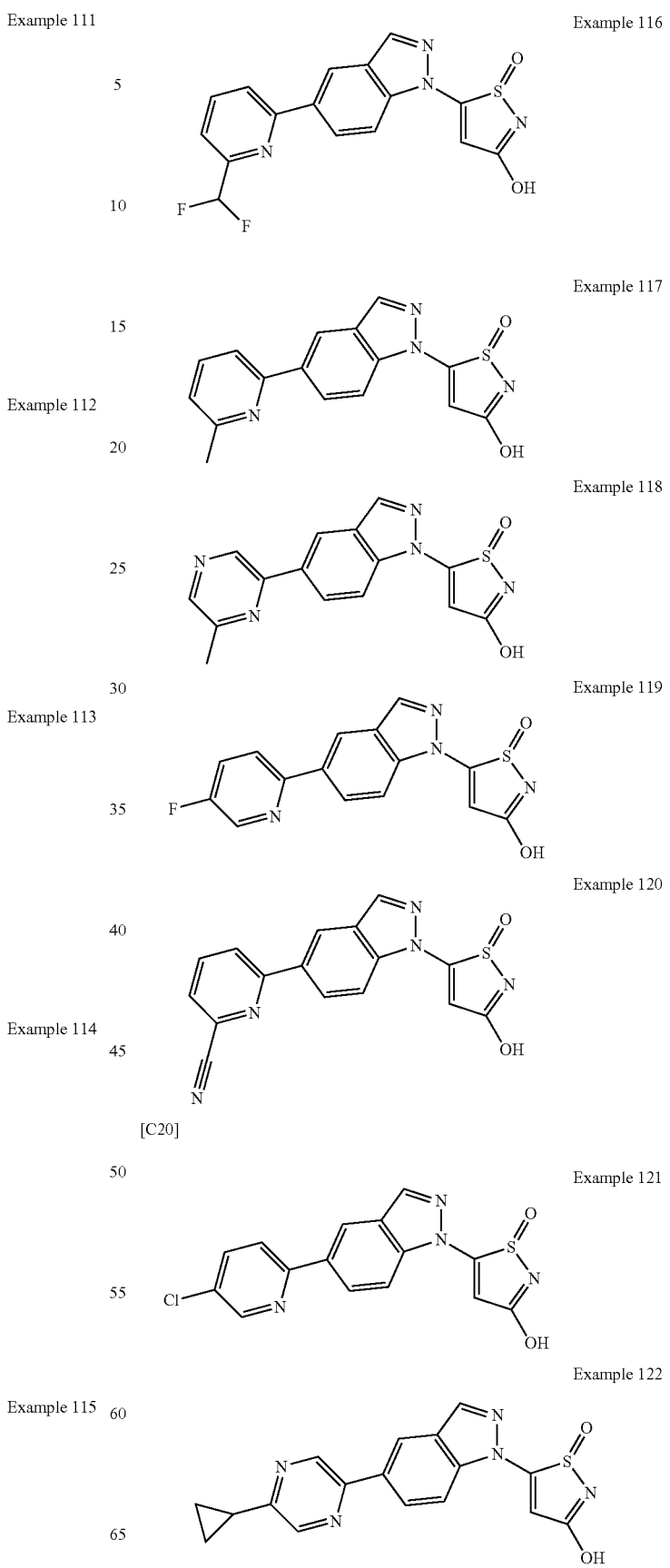
Example 116
Example 117
Example 118
Example 119
Example 120
[C20]
Example 121
Example 122

Example 123
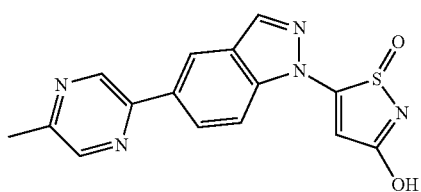
Example 124
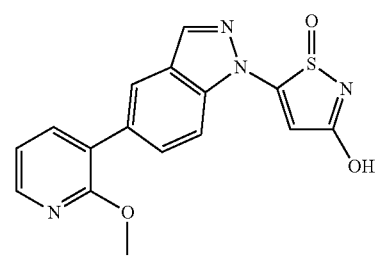
Example 125
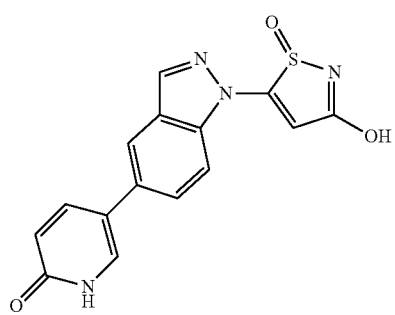
Example 126
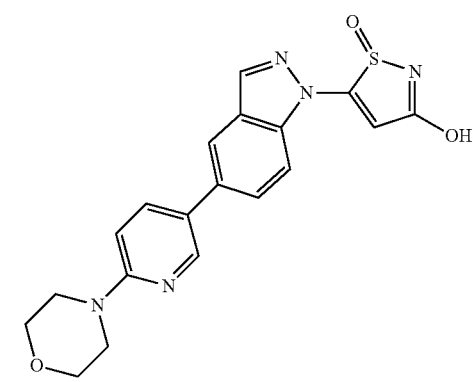
Example 127
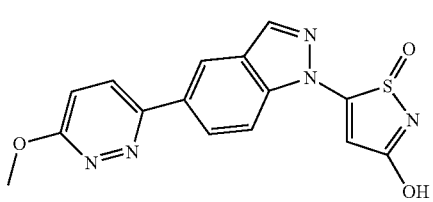
Example 128
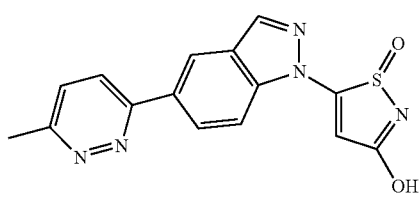
Example 129
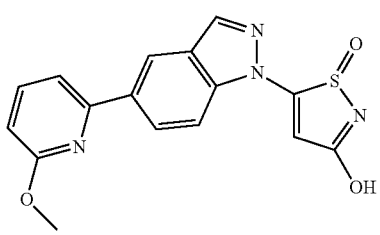
Example 130
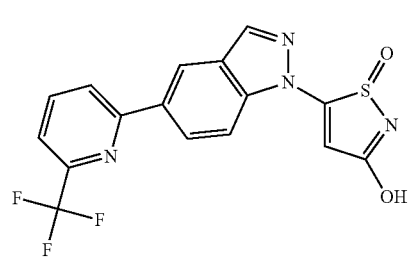
Example 131
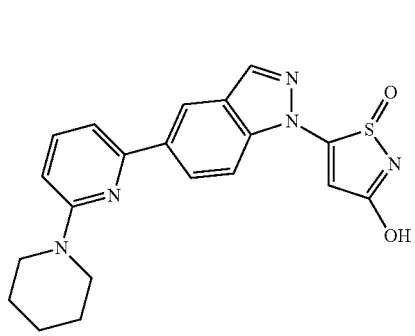
Example 132
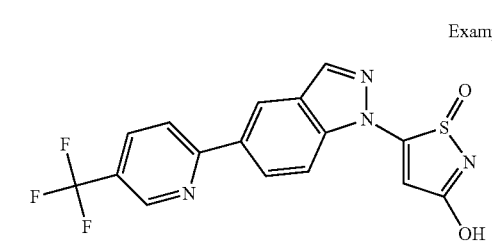
Example 133
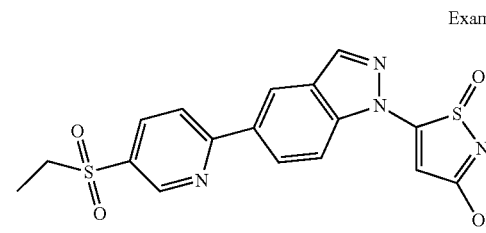
Example 134
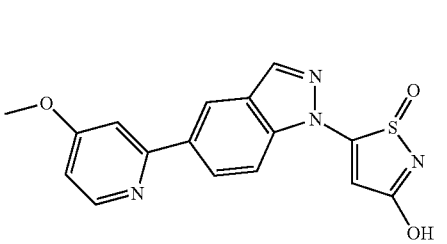

Example 135
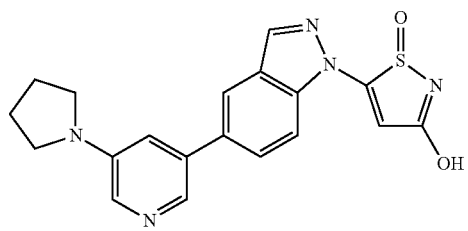
[C21]
Example 136
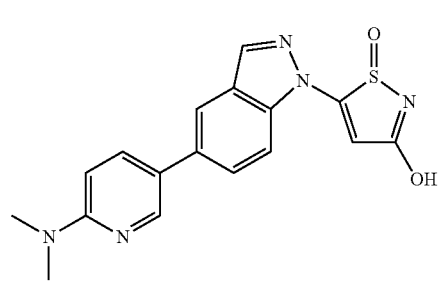
Example 137
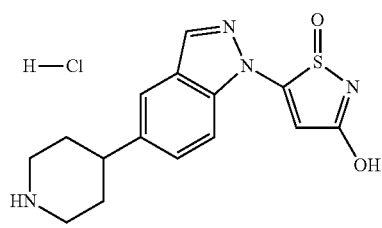
Example 138
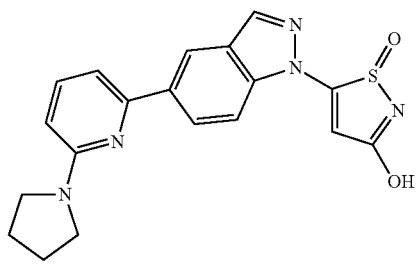
Example 139
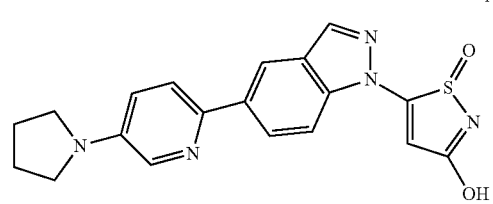
Example 140
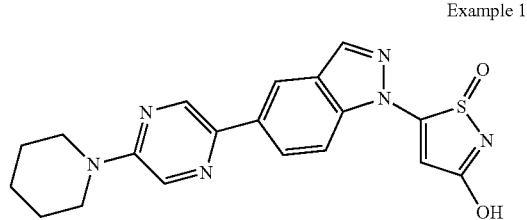
Example 141
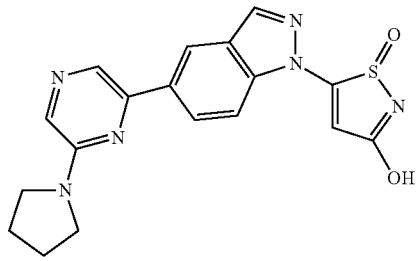
Example 142
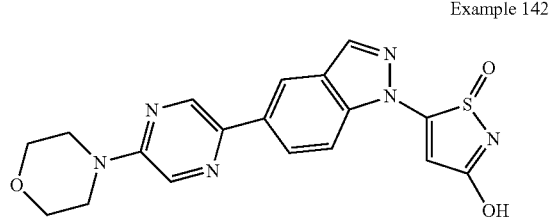
Example 143
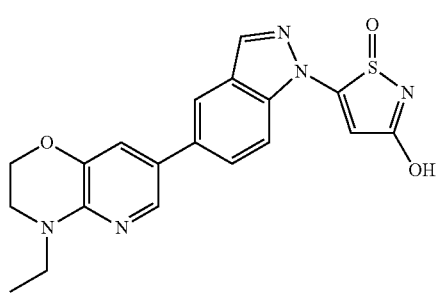
Example 144
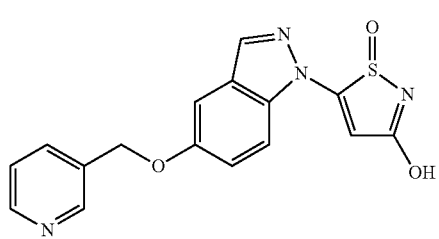
Example 145
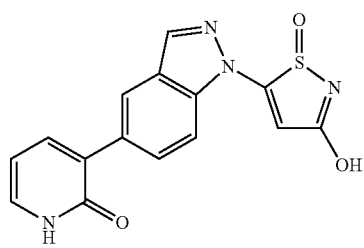
Example 146
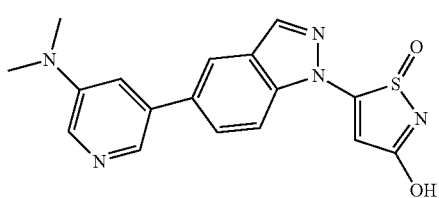

Example 147 — Example 158 (chemical structures)

Example 159
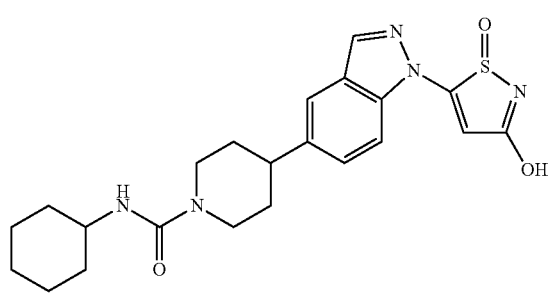
Example 160
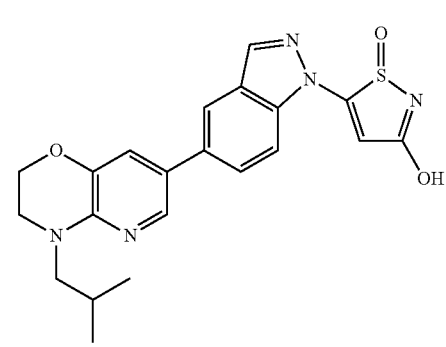
Example 161
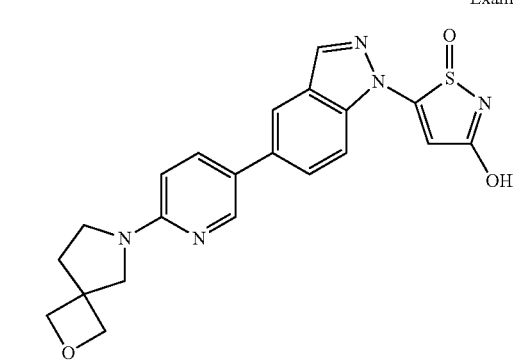
Example 162
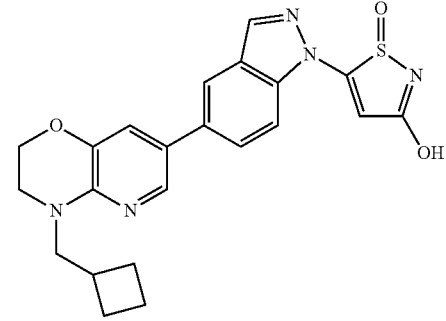
Example 163
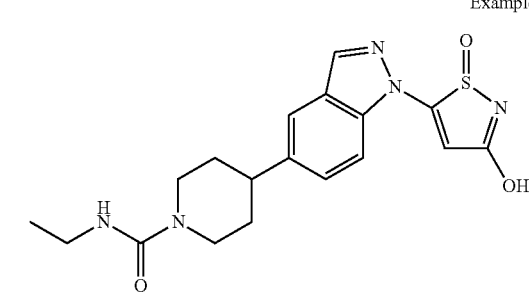
Example 164
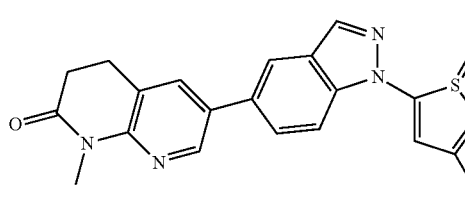
Example 165
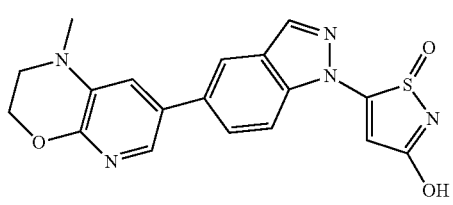
Example 166
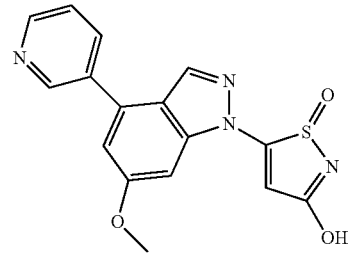
Example 167
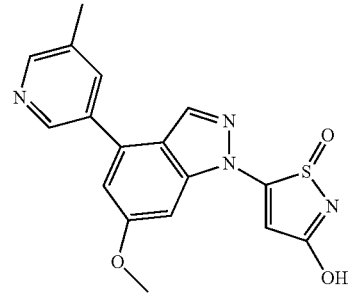
Example 168
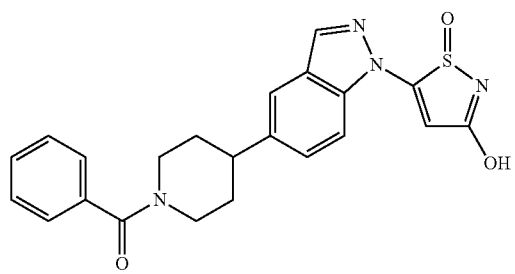
Example 169
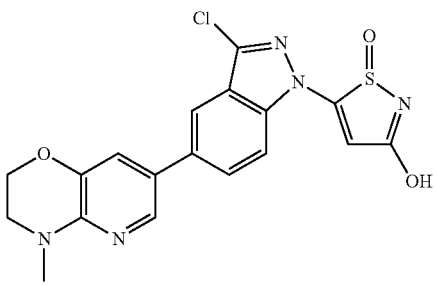

Example 170
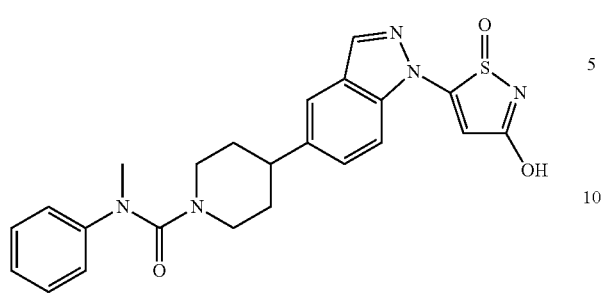
Example 171
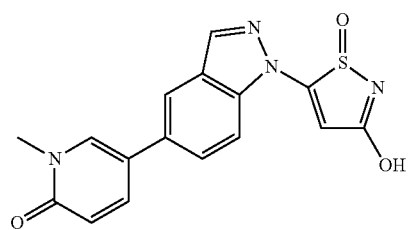
Example 172
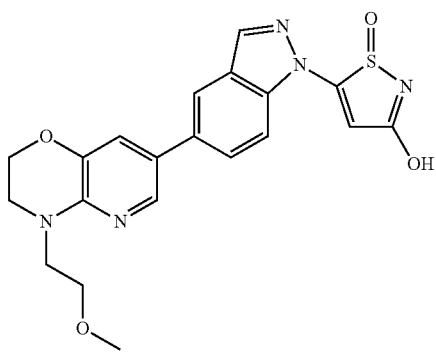
Example 173
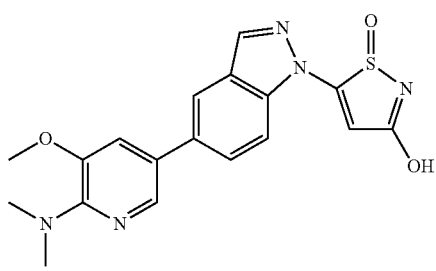
Example 174
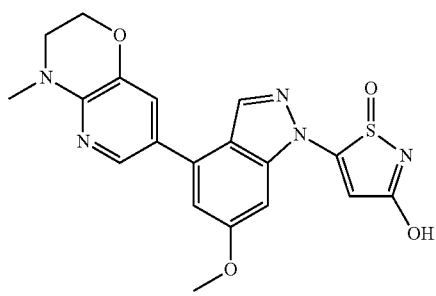
Example 175
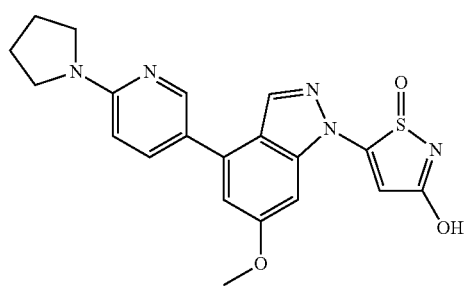
Example 176
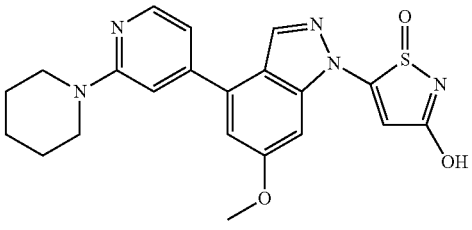
Example 177
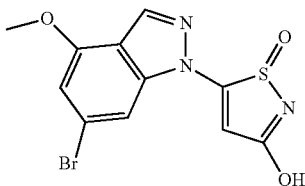
Example 178
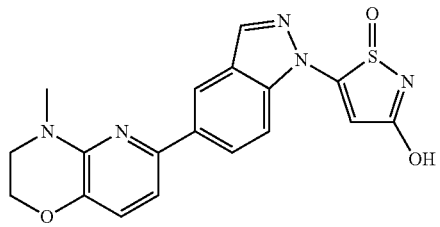
Example 179
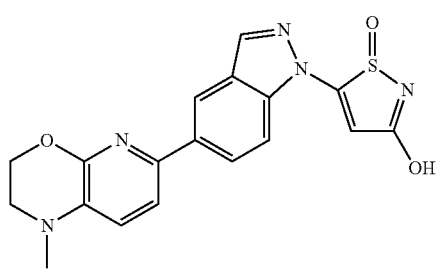
Example 180
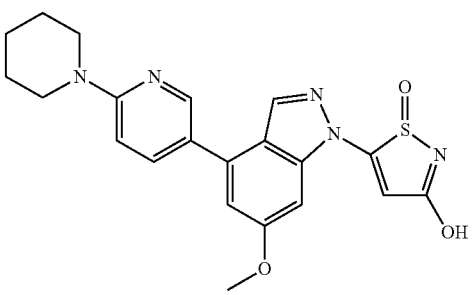

[C24]
Example 181
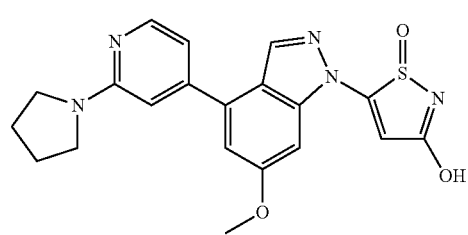
Example 182
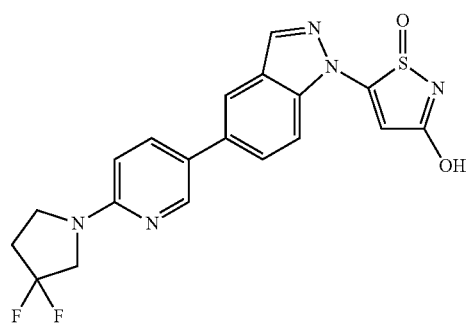
Example 183
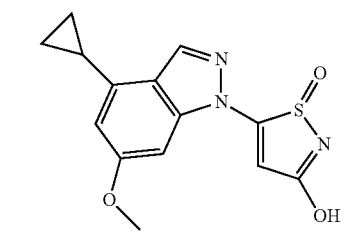
Example 184
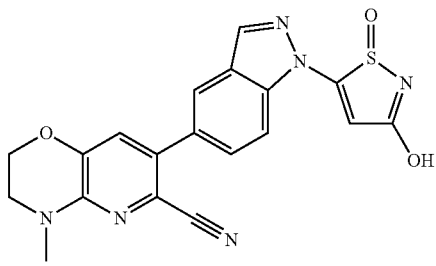
Example 185
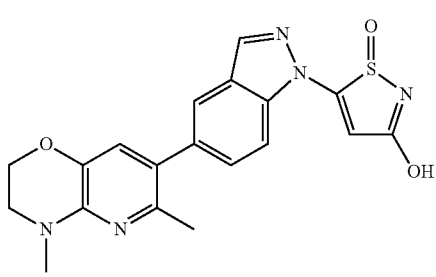
Example 186
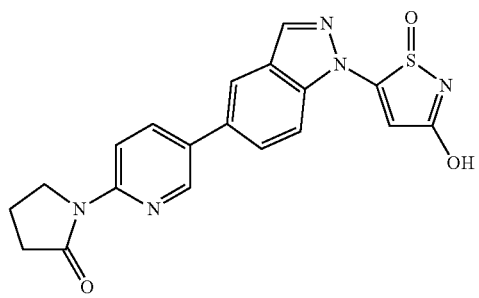
Example 187
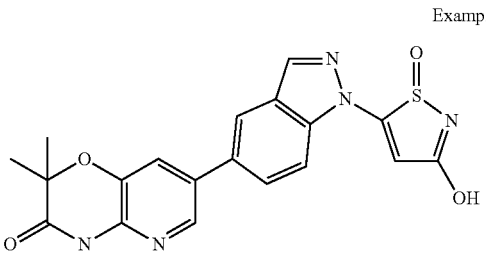
Example 188
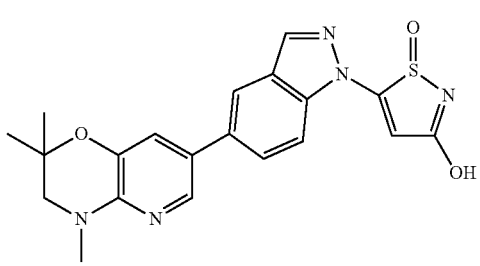
Example 189
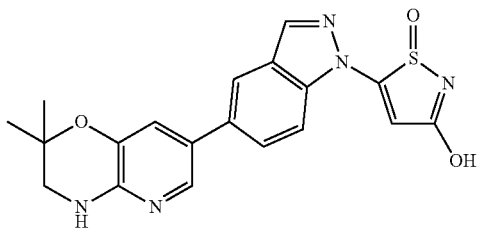
Example 190
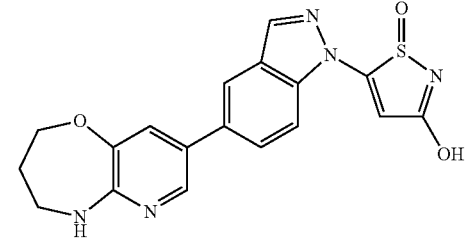
Example 191
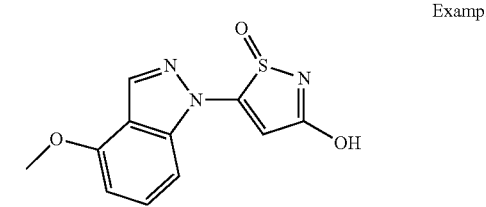

Example 192
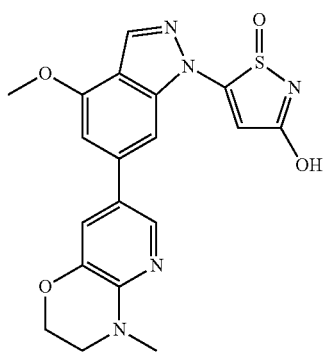
Example 193
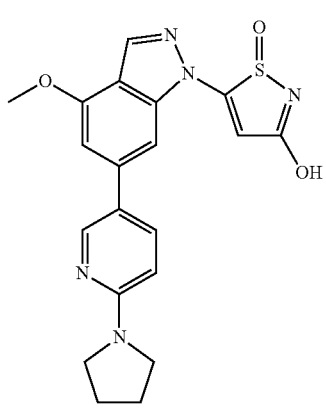
Example 194
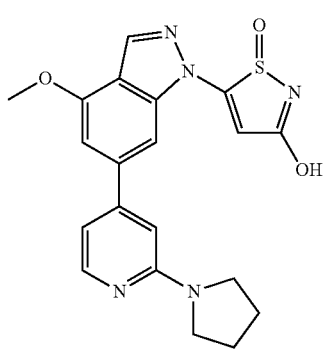
Example 195
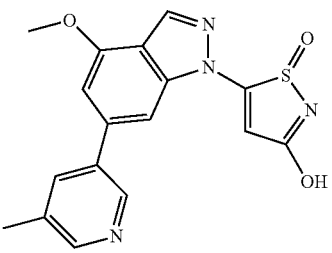
[C25]
Example 196
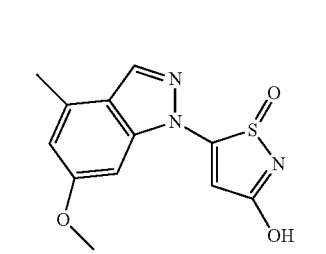
Example 197
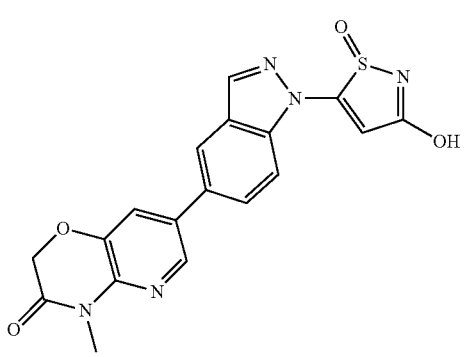
Example 198
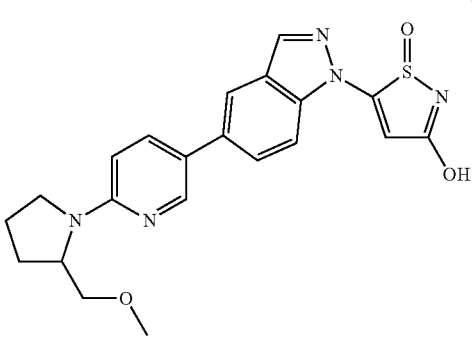
Example 199
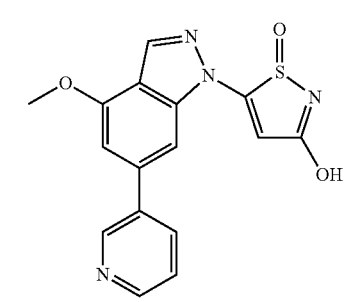
Example 200
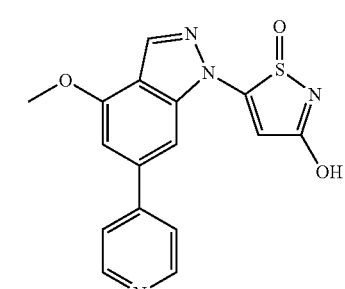
Example 201
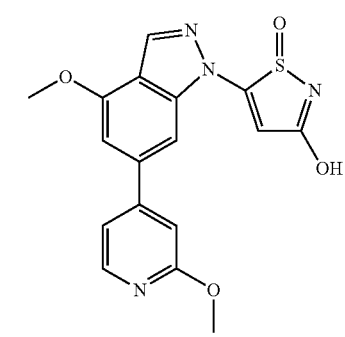

Example 202
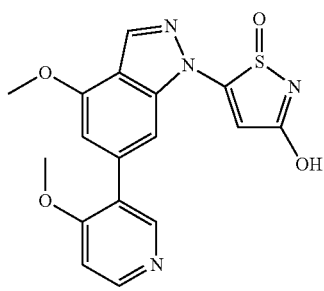
Example 203
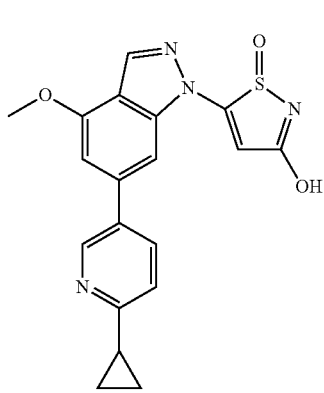
Example 204
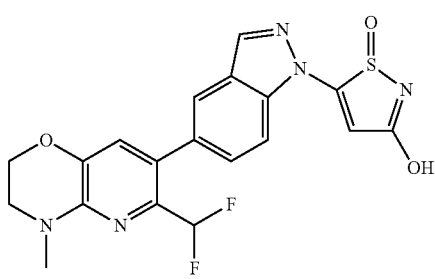
Example 205
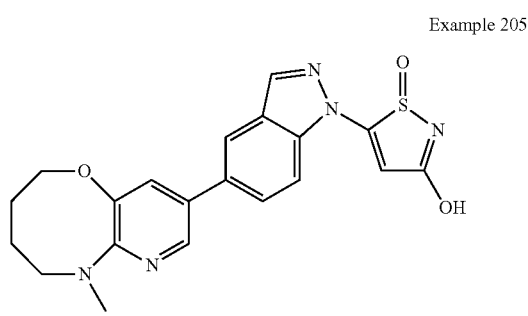
Example 206
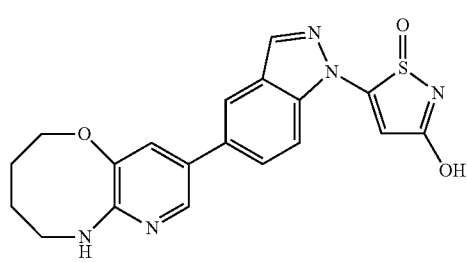
Example 207
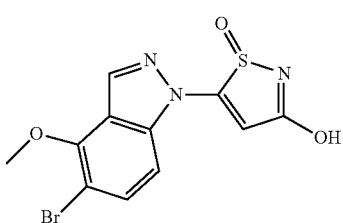
Example 208
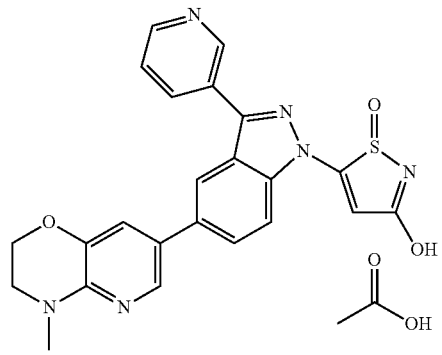
Example 209
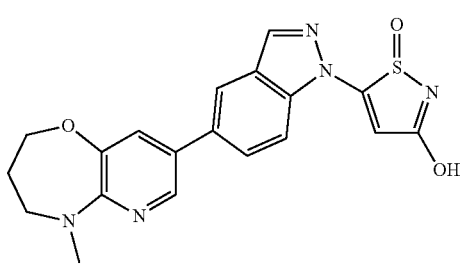
Example 210
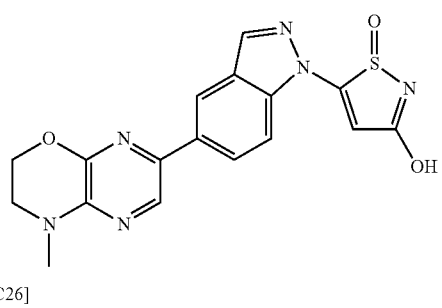
[C26]
Example 211
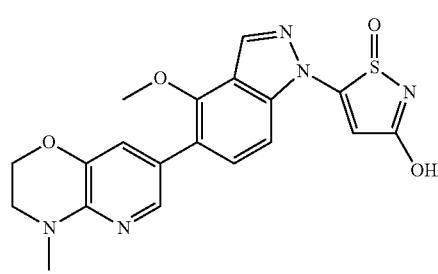

Example 212
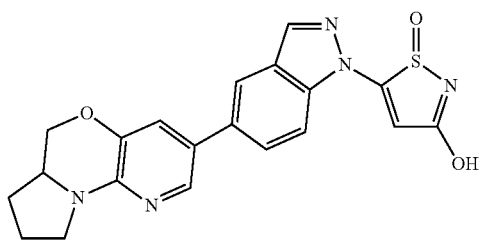
Example 213
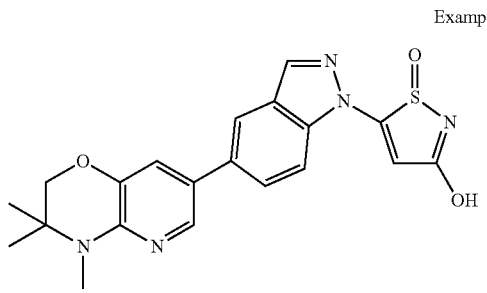
Example 214
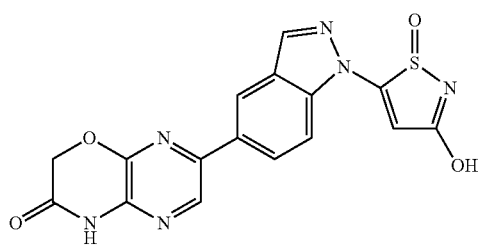
Example 215
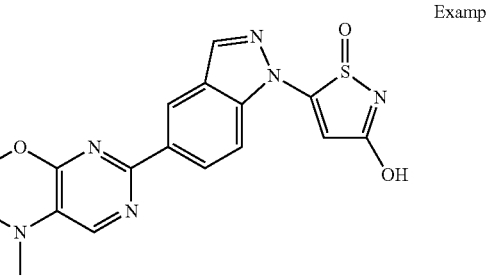
Example 216
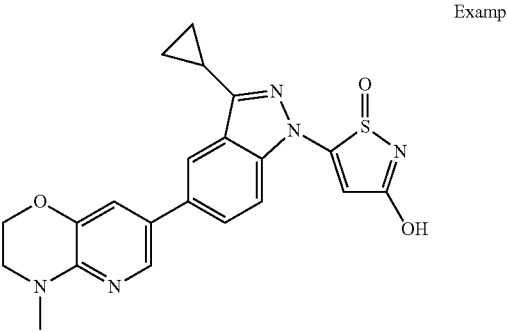
Example 217
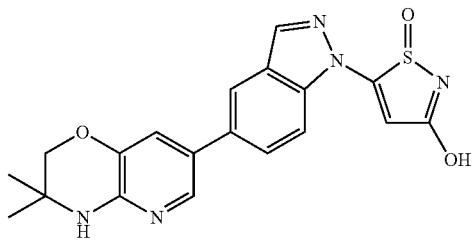
Example 218
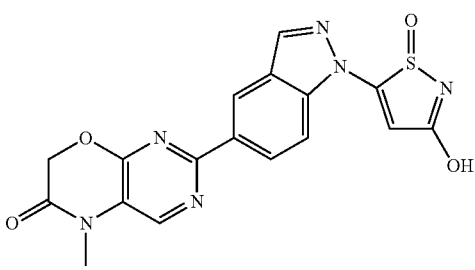
Example 219
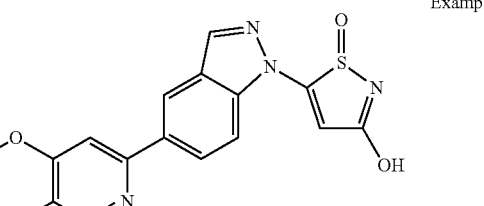
Example 220
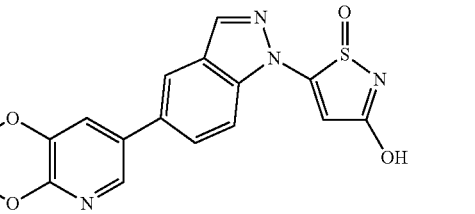
Example 221
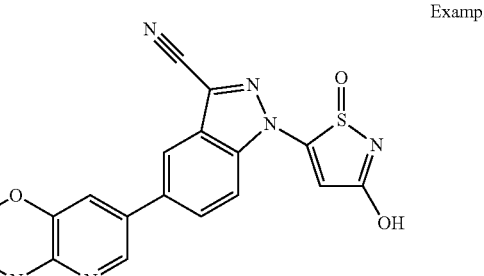
Example 222
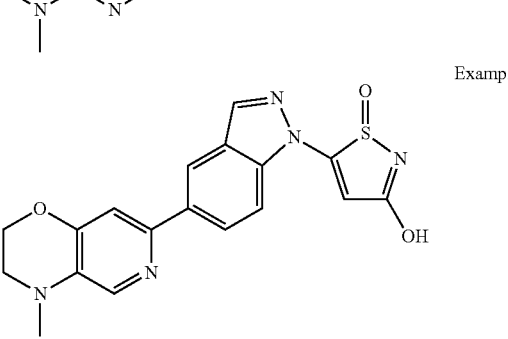

Example 223
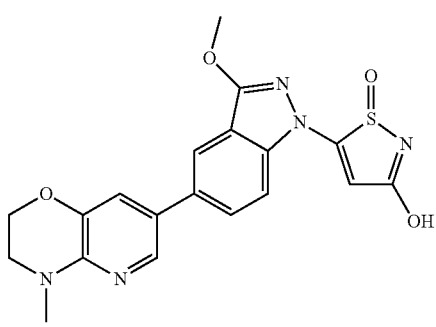
Example 224
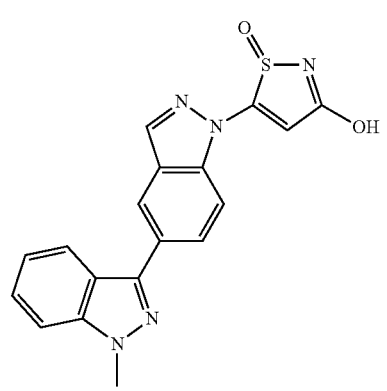
Example 225
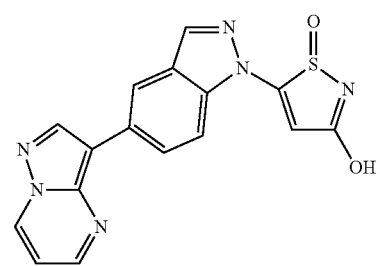
[C27]
Example 226
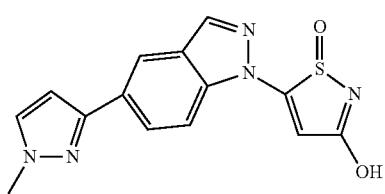
Example 227
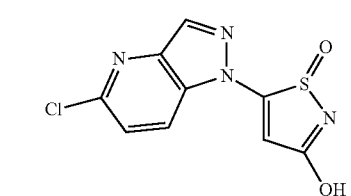
Example 228
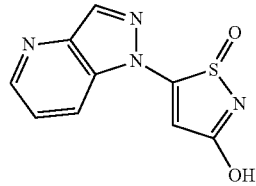
Example 229
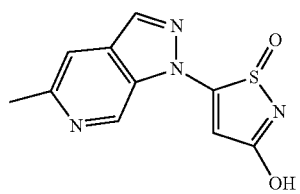
Example 230
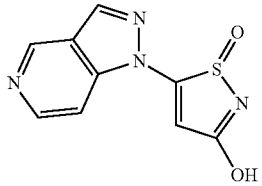
Example 231
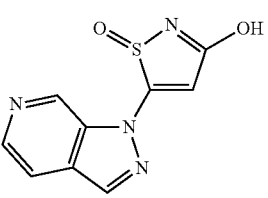
Example 232
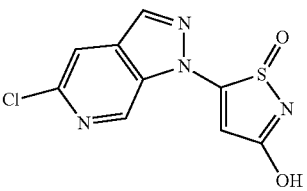
Example 233
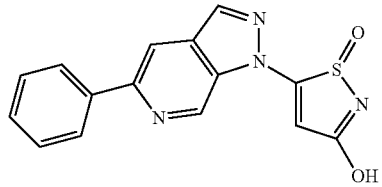
Example 234
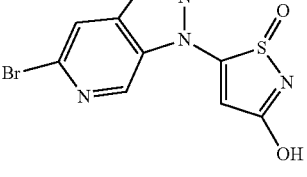
Example 235
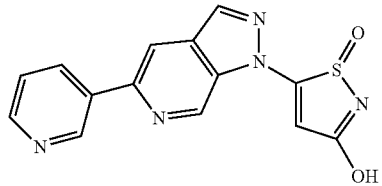

Example 236
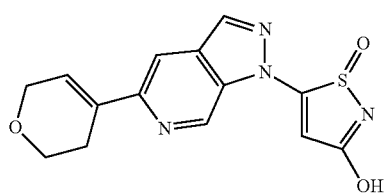
Example 237
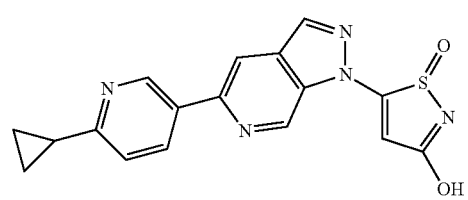
Example 238
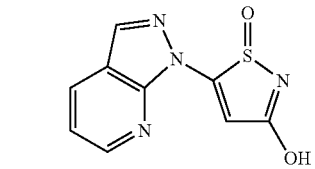
Example 239
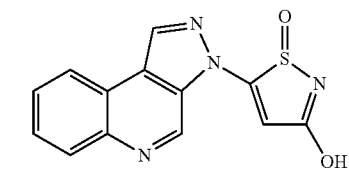
Example 240
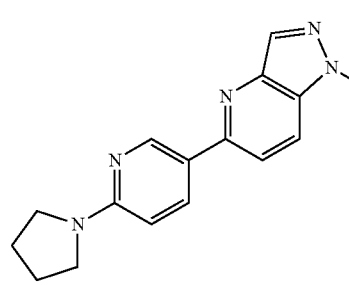
Example 241
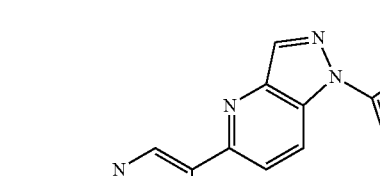
Example 242
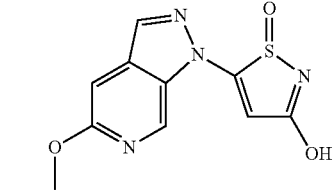
Example 243
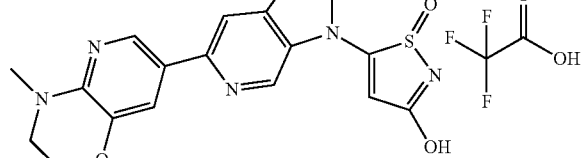
Example 244
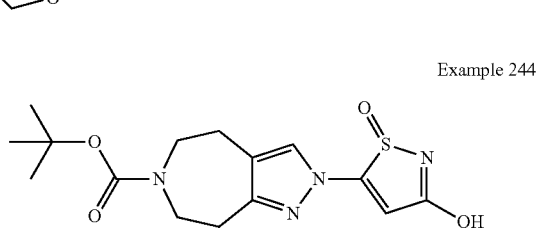
Example 245
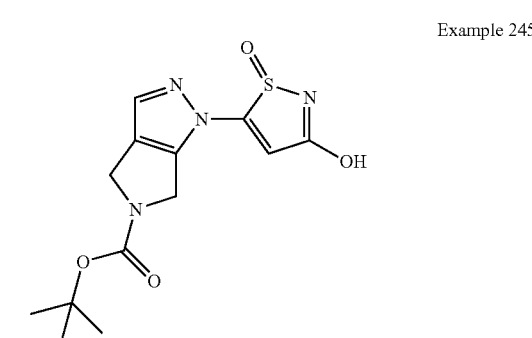
Example 246
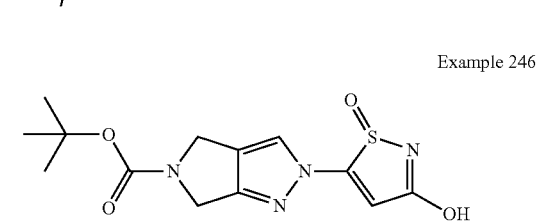
Example 247
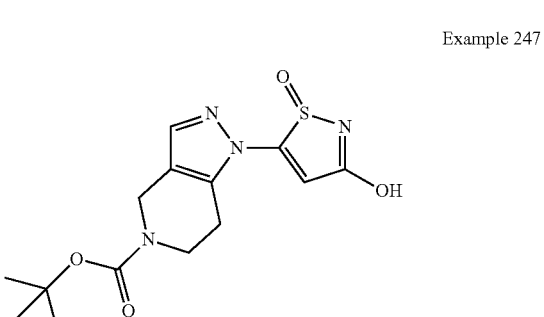
Example 248
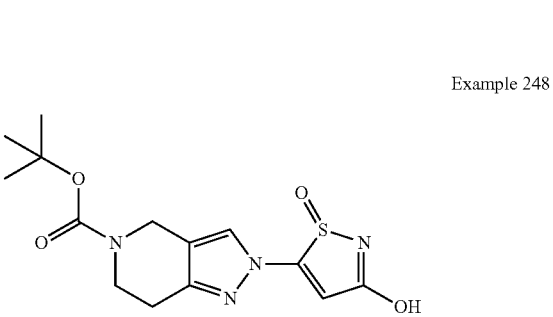

Example 249
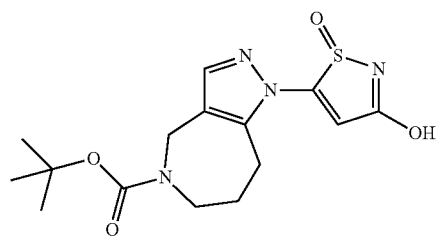
Example 250
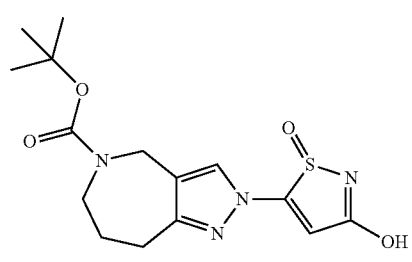
Example 251
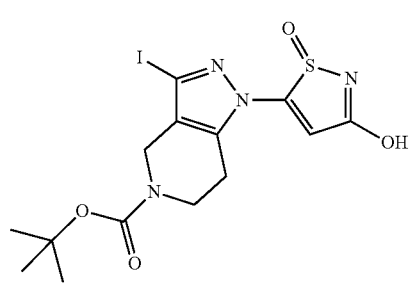
Example 252
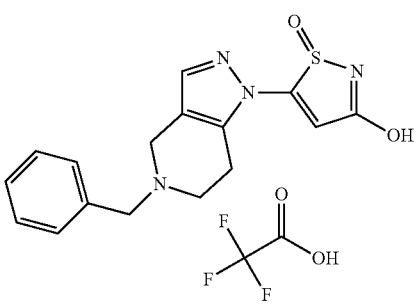
Example 253
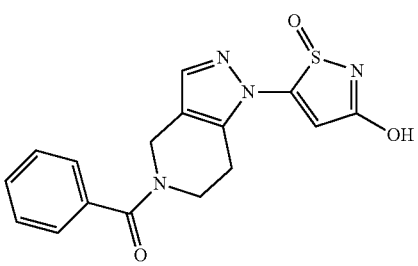
Example 254
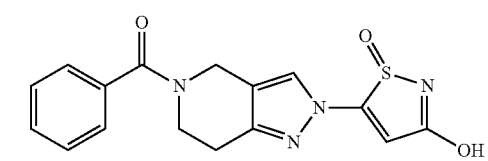
Example 255
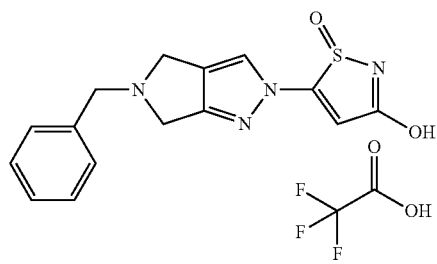
[C29]
Example 256
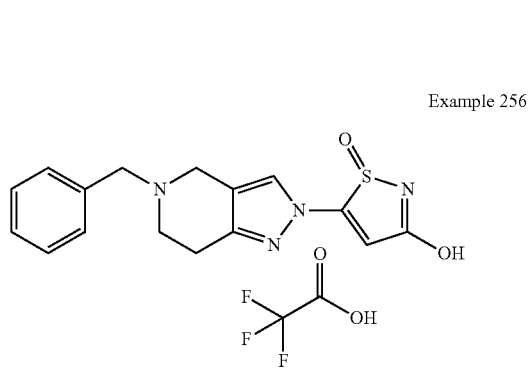
Example 257
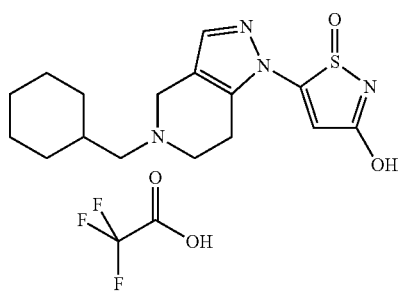
Example 258
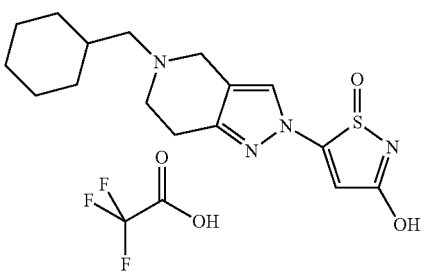
Example 259
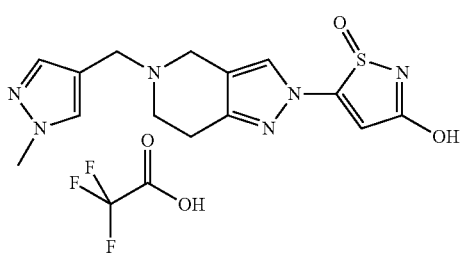

-continued

Example 260

Example 261

Example 262

Example 263

Example 264

Example 265

-continued

Example 266

Example 267

Example 268

Example 269

[C30]

Example 270

Example 271

Example 272

Example 273
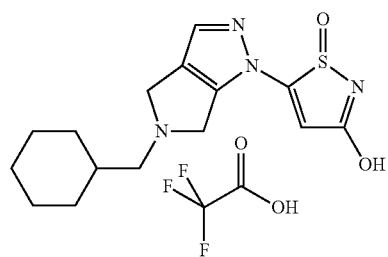
Example 274
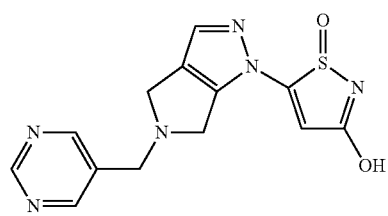
Example 275
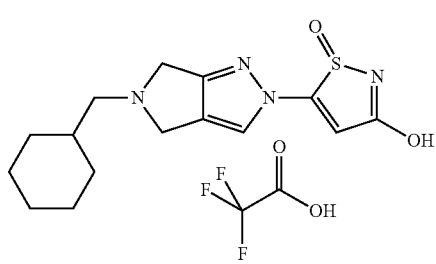
Example 276
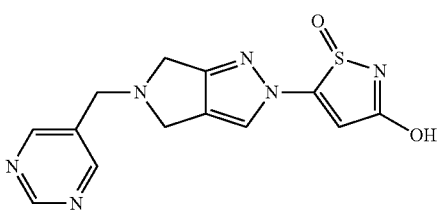
Example 277
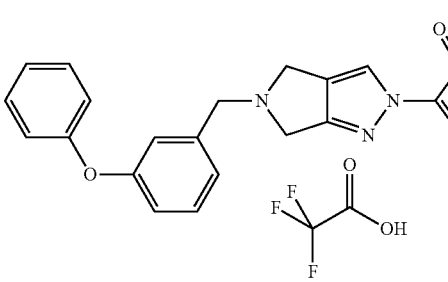
Example 278
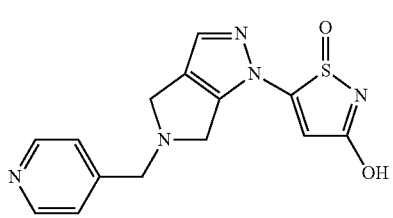
Example 279
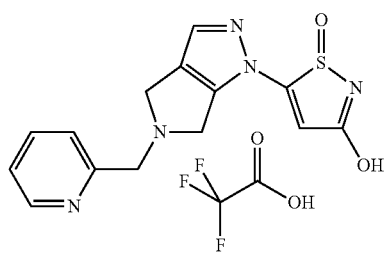
Example 280
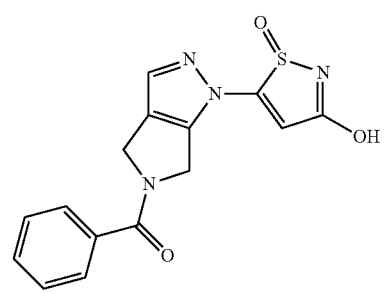
Example 281
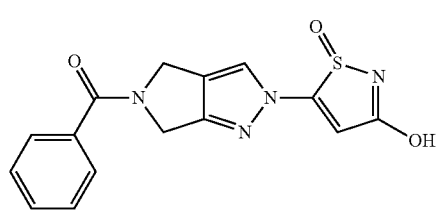
Example 282
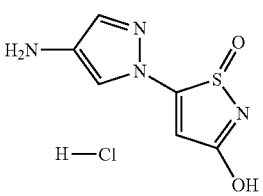
Example 283
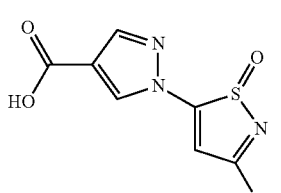
Example 284

Example 285
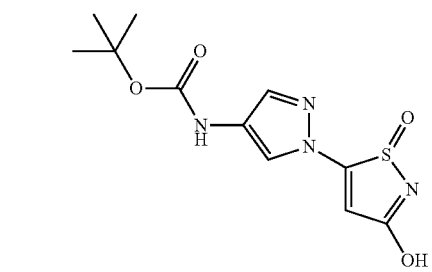
[C31]
Example 286
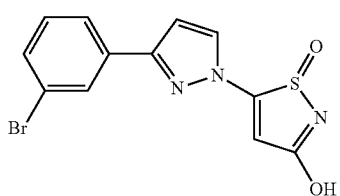
Example 287
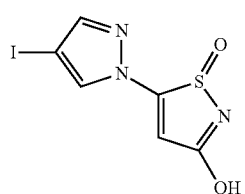
Example 288
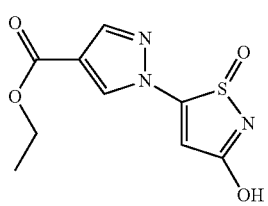
Example 289
Example 290
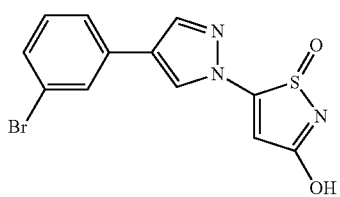
Example 291
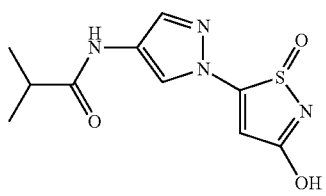
Example 292
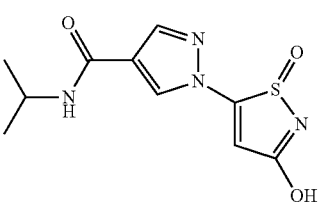
Example 293
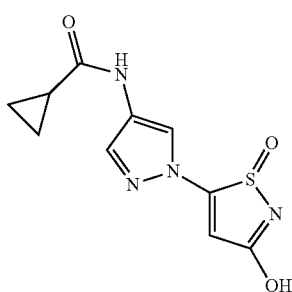
Example 294
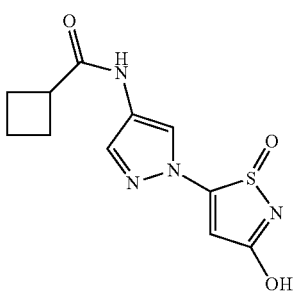
Example 295
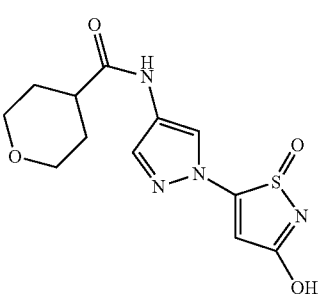
Example 296
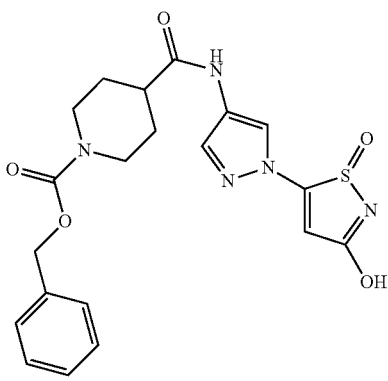

Example 297
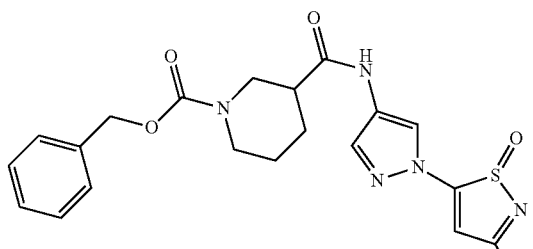
Example 298
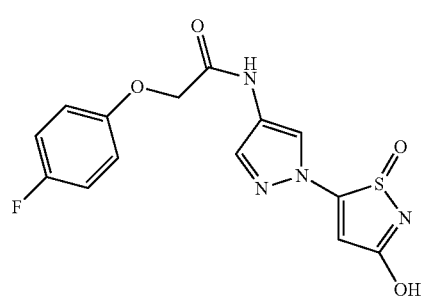
Example 299
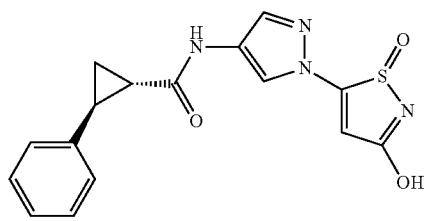
Example 300
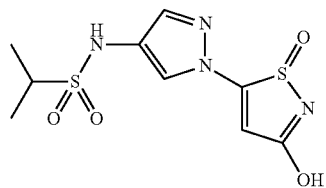
[C32]
Example 301
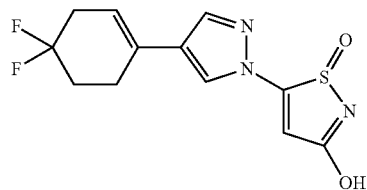
Example 302
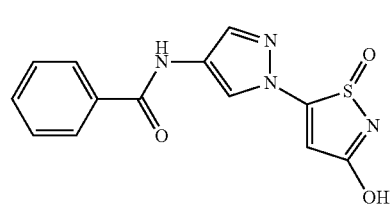
Example 303
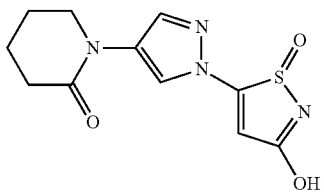
Example 304
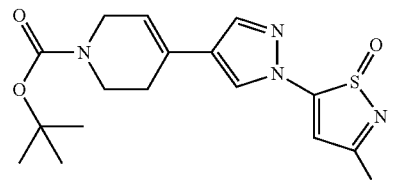
Example 305
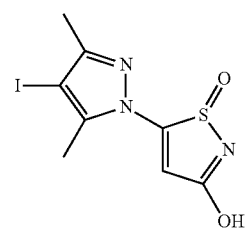
Example 306
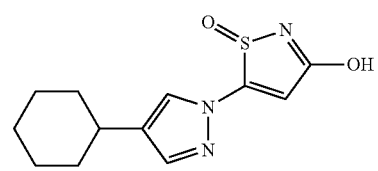
Example 307
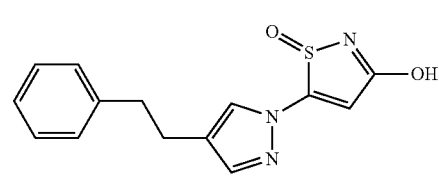
Example 308
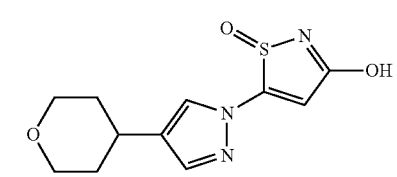
Example 309
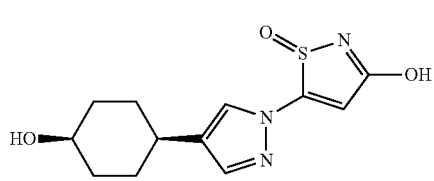
Example 310
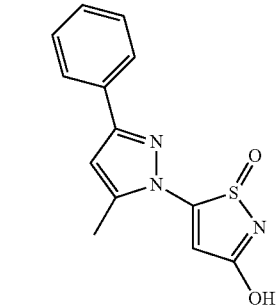

Example 311
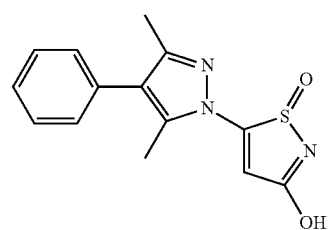
Example 312
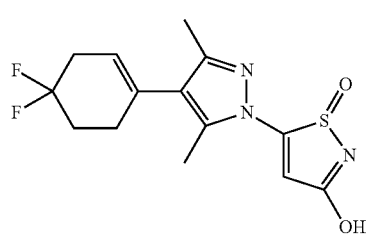
Example 313
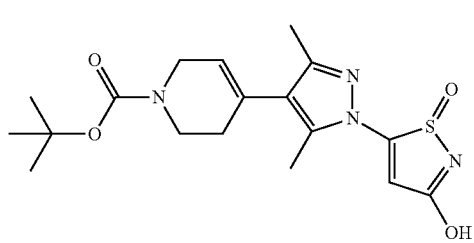
Example 314
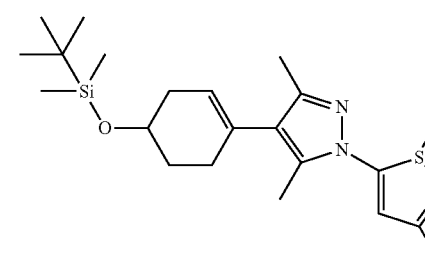
Example 315
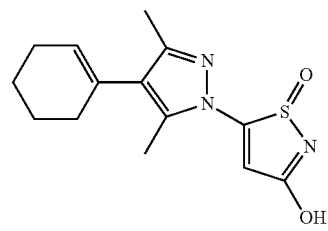
Example 316
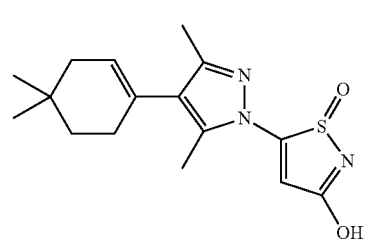
Example 317
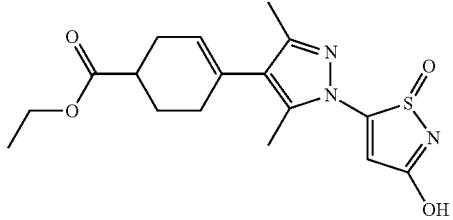
Example 318
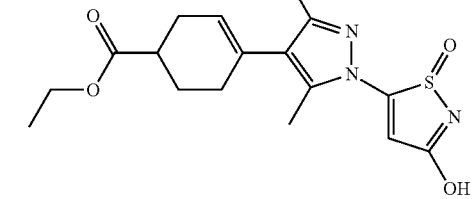
Example 319
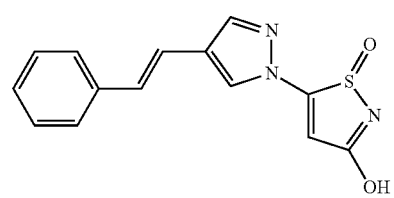
Example 320
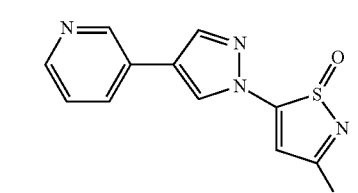
Example 321
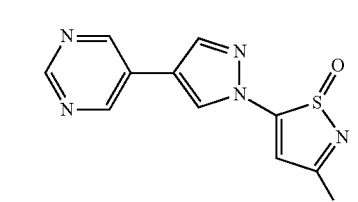
Example 322
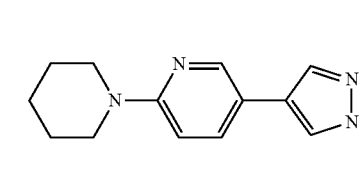
Example 323
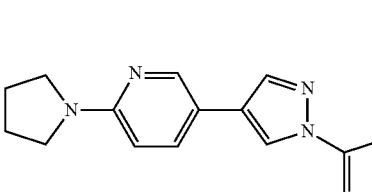

Example 324
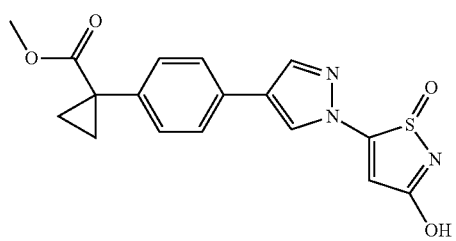
Example 325
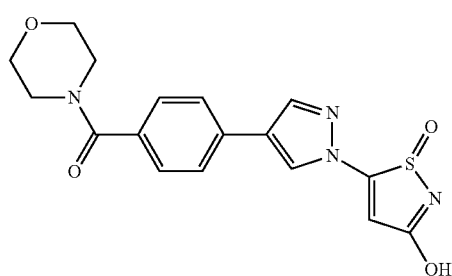
[C34]
Example 326
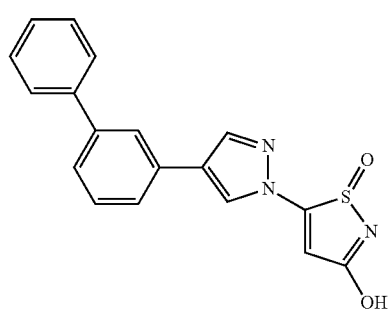
Example 327
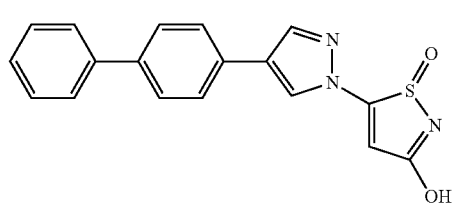
Example 328
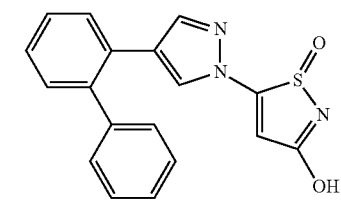
Example 329
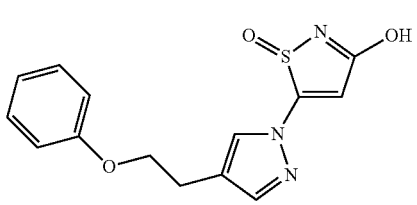
Example 330
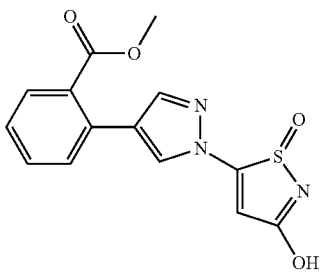
Example 331
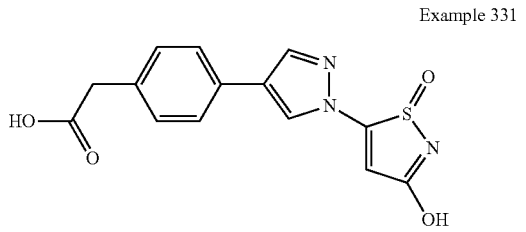
Example 332
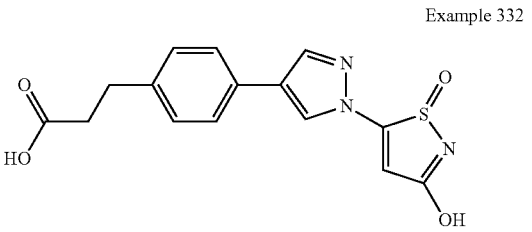
Example 333
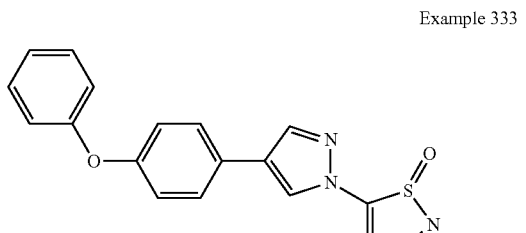
Example 334
Example 335
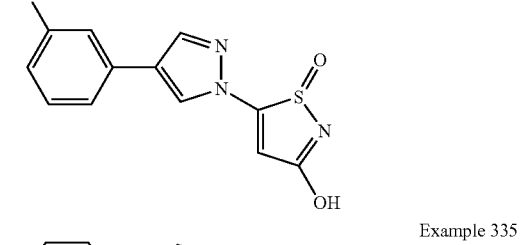

Example 336
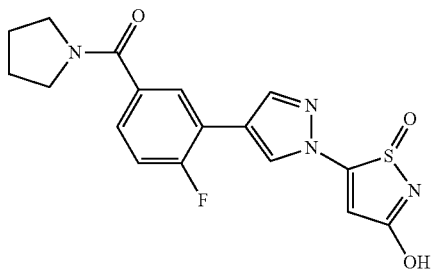
Example 337
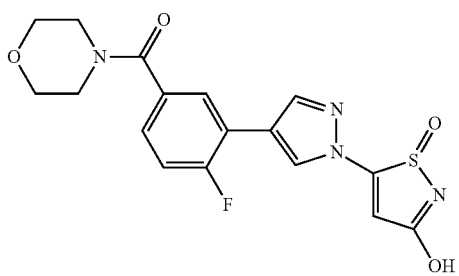
Example 338
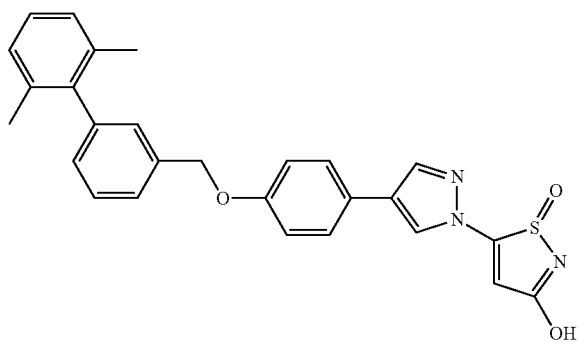
Example 339
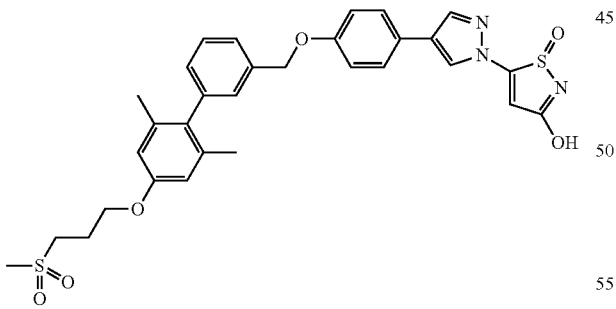
Example 340
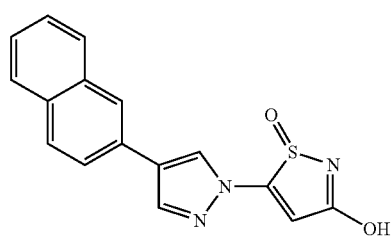
Example 341
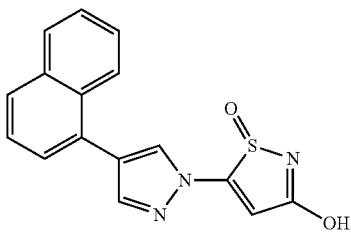
Example 342
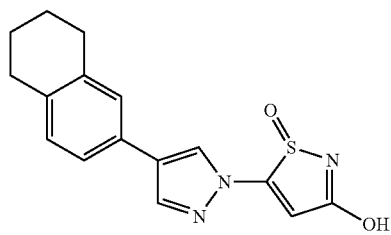
Example 343
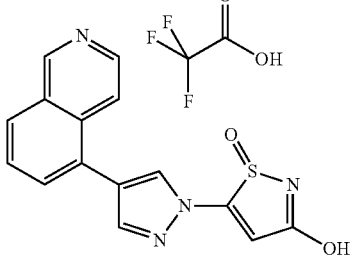
Example 344
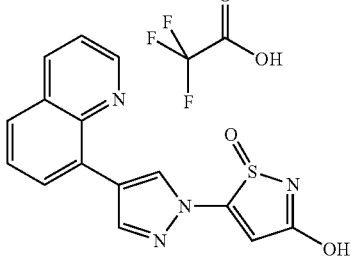
Example 345
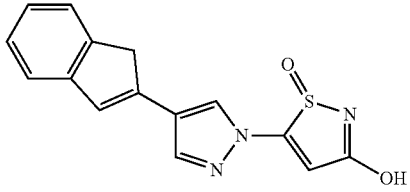
[C35]
Example 346
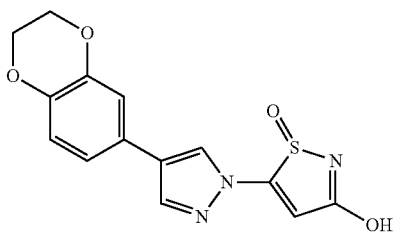

Example 347
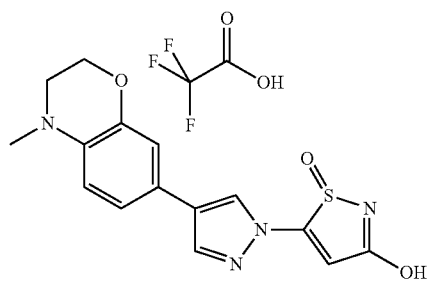
Example 348
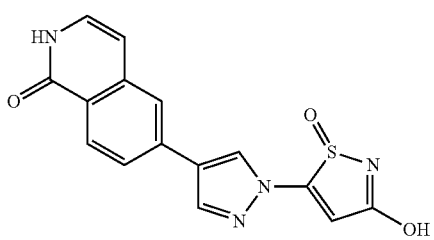
Example 349
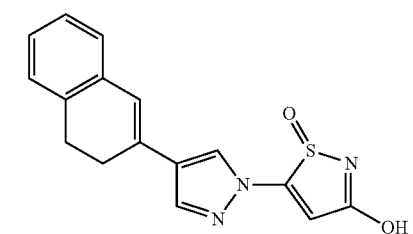
Example 350
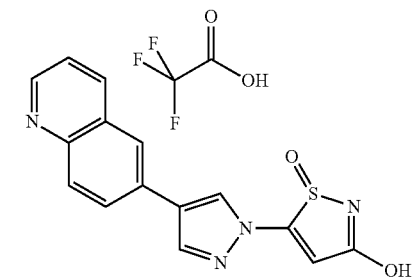
Example 351
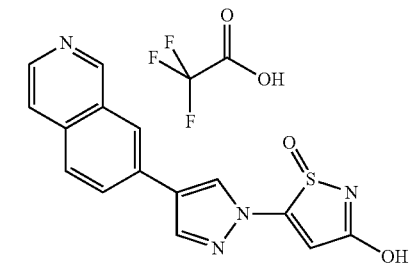
Example 352
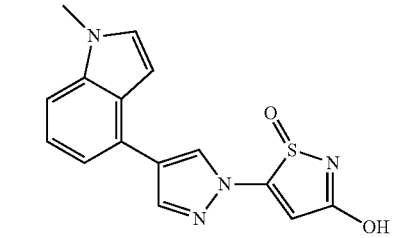
Example 353
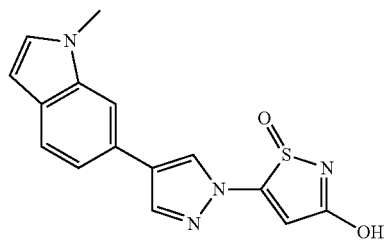
Example 354
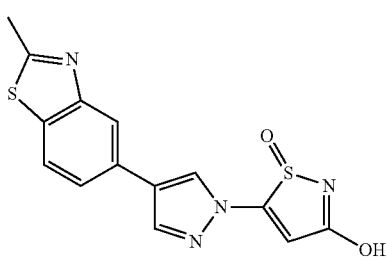
Example 355
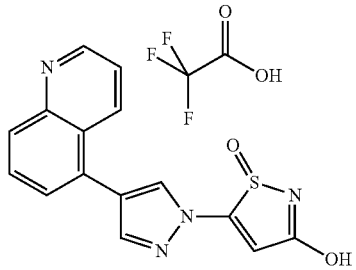
Example 356
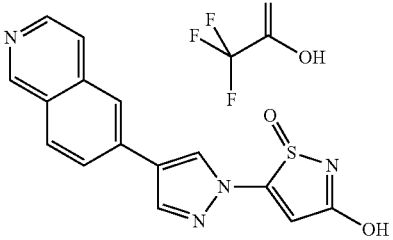
Example 357
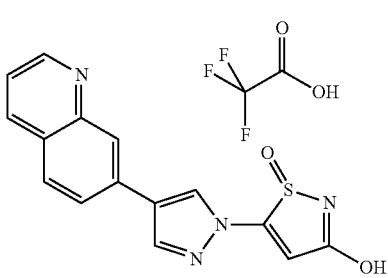
Example 358
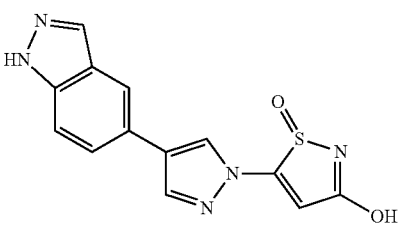

Example 359
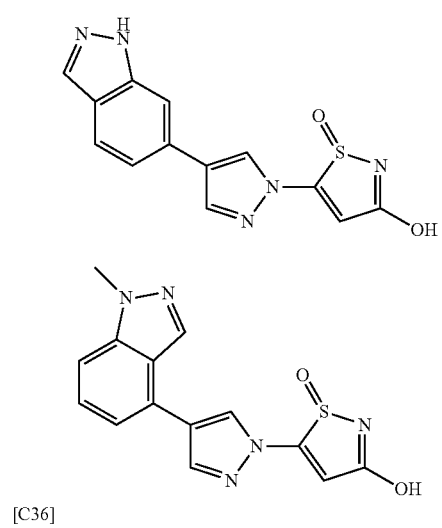
Example 360
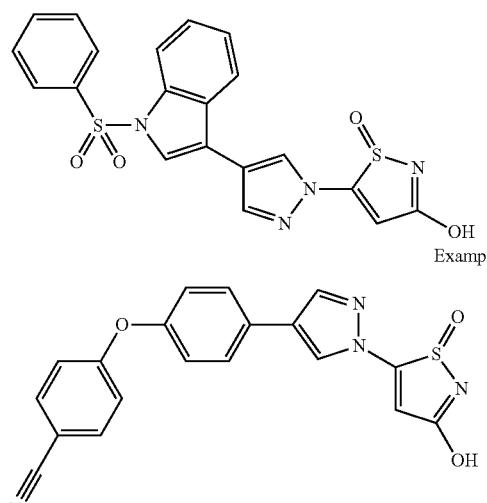
[C36]
Example 361
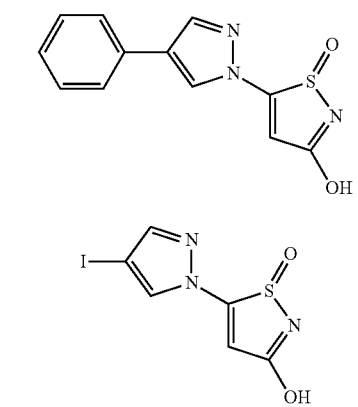
Example 362
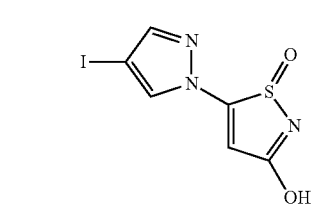
Example 363
Example 364
Example 365
Example 366
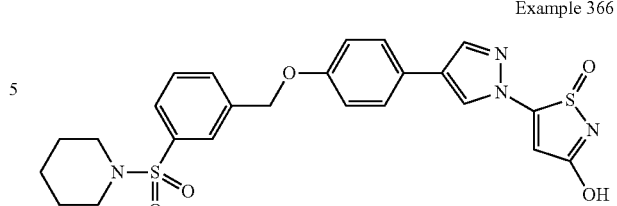
Example 367
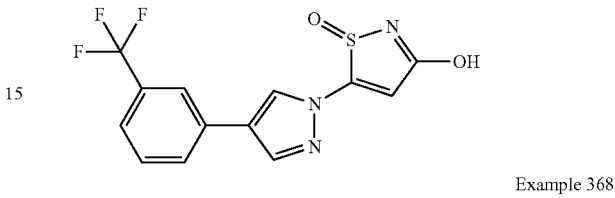
Example 368
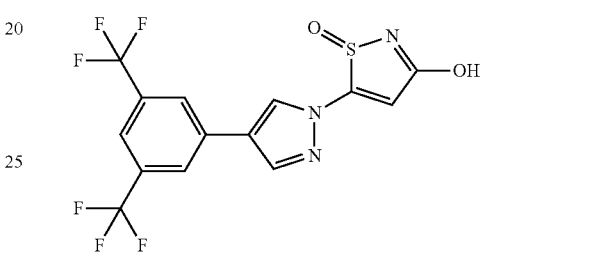
Example 369
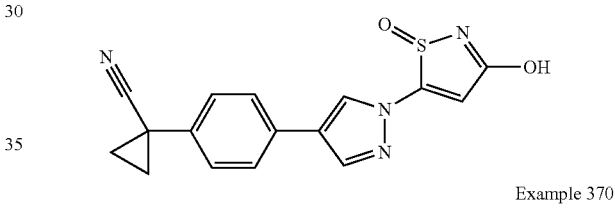
Example 370
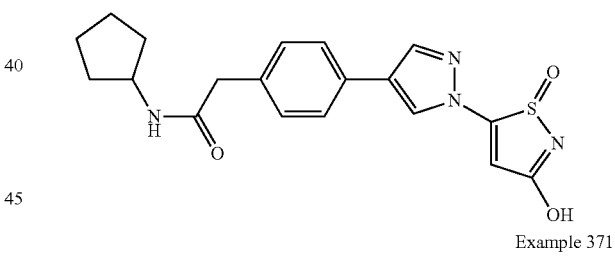
Example 371
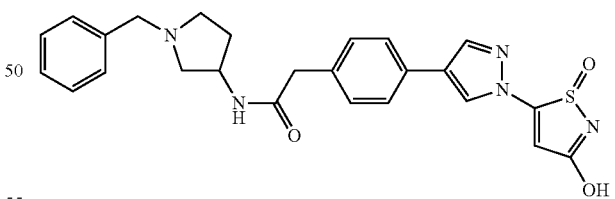
Example 372
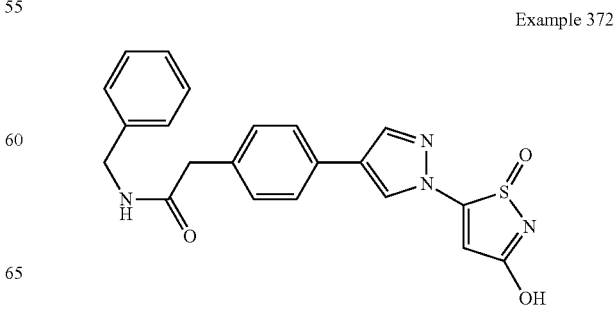

Example 373
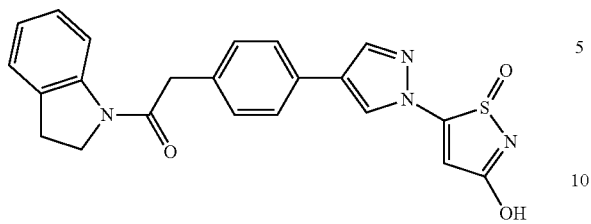
Example 374
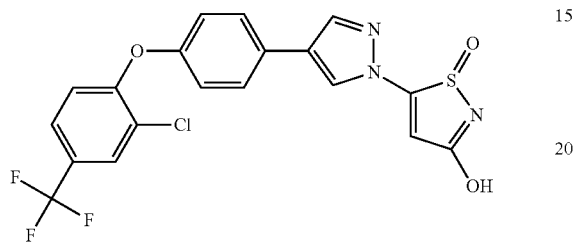
Example 375
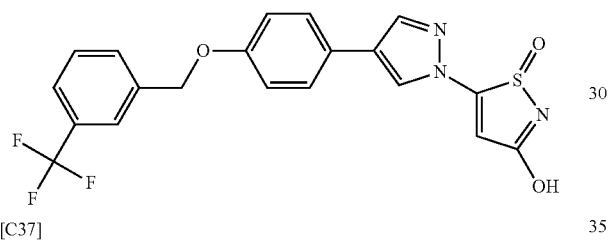
Example 376
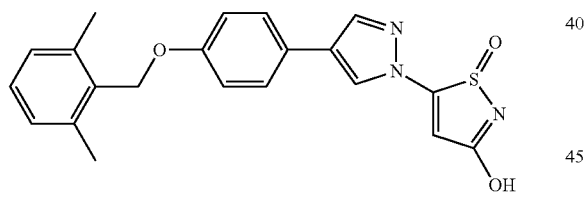
Example 377
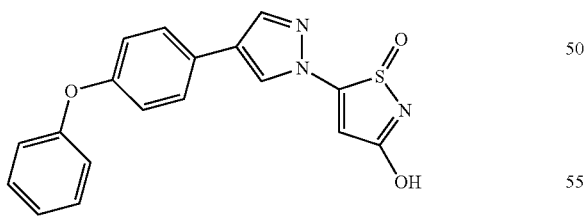
Example 378
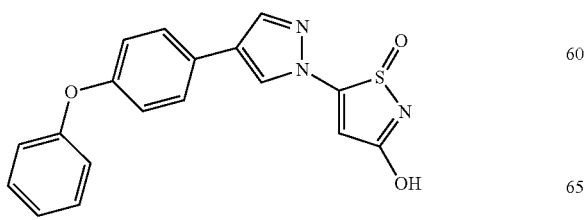
Example 379
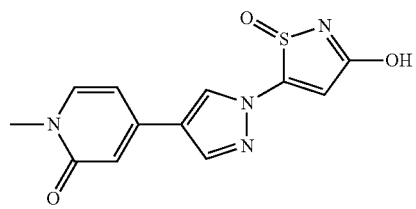
Example 380
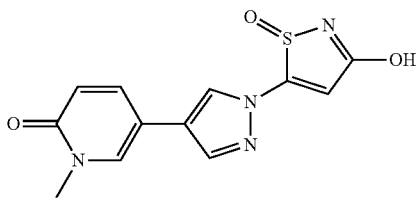
Example 381
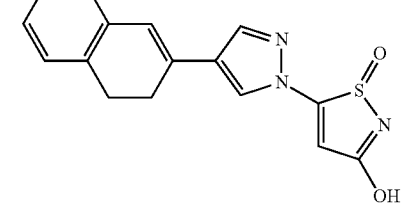
Example 382
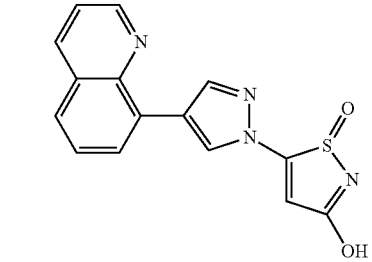
Example 383
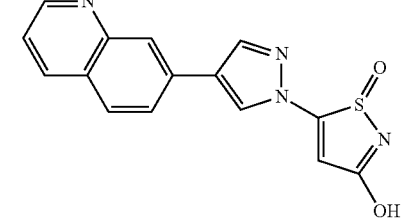
Example 384
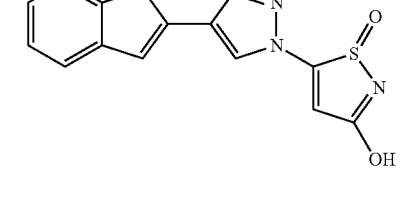
Example 385
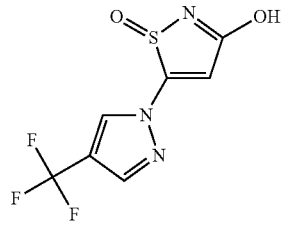

Example 386
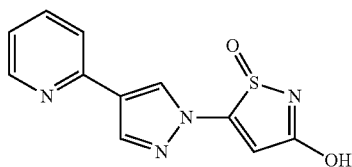
Example 387
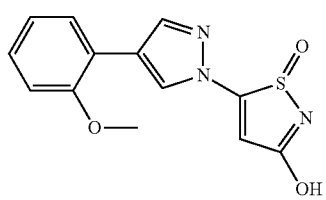
Example 388
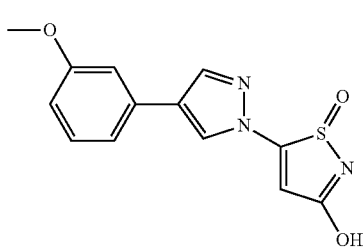
Example 389
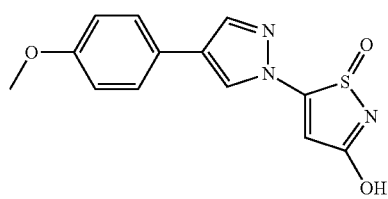
Example 390
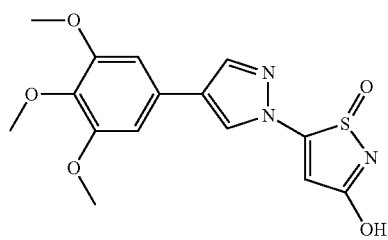
[C38]
Example 391
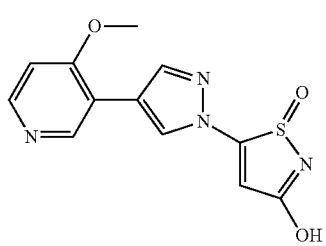
Example 392
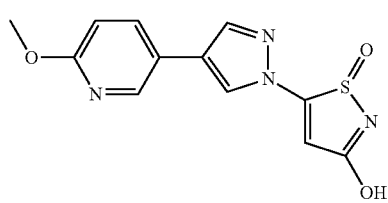
Example 393
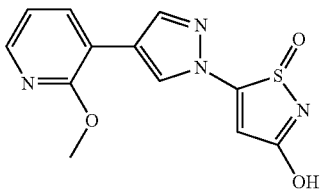
Example 394
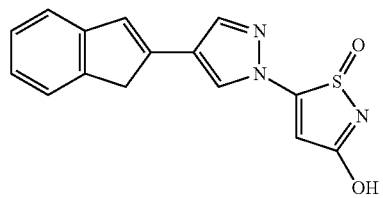
Example 395
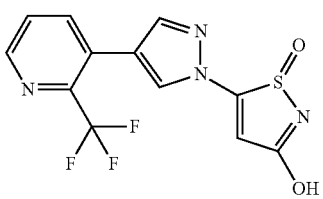
Example 396
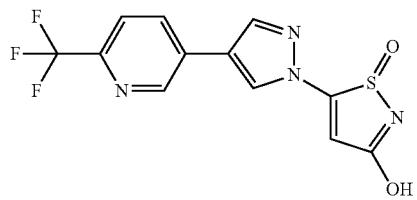
Example 397
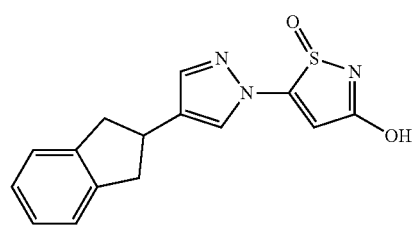
Example 398
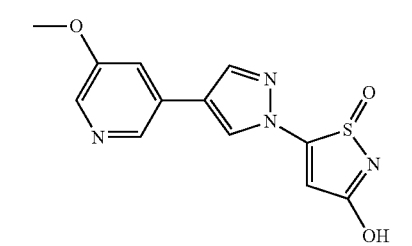
Example 399
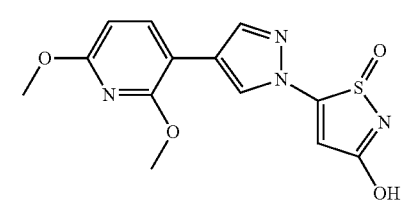

Example 400
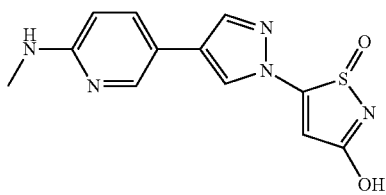
Example 401
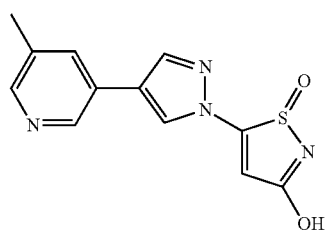
Example 402
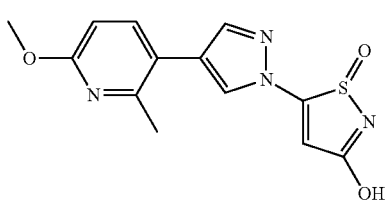
Example 403
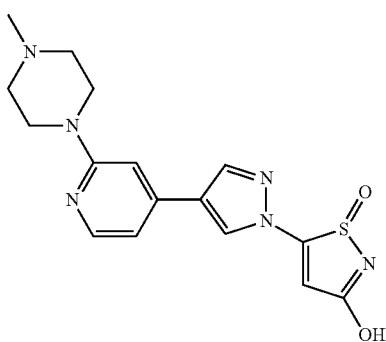
Example 404
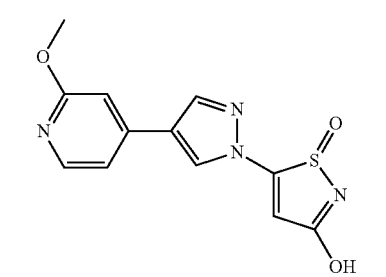
Example 405
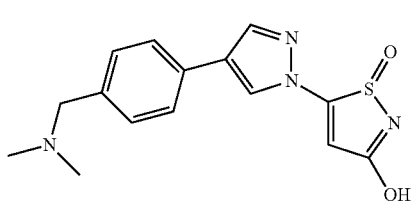
Example 406
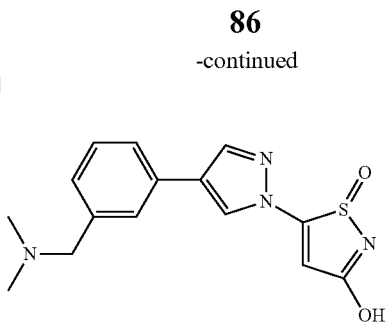
Example 407
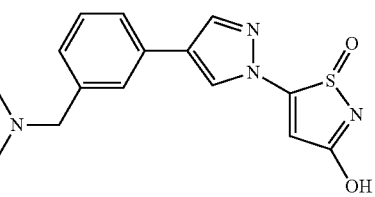
Example 408
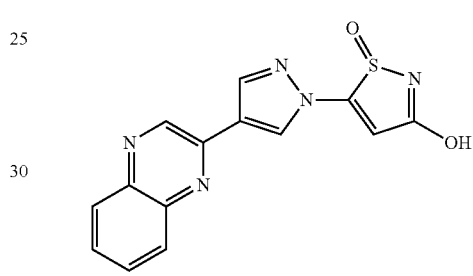
Example 409
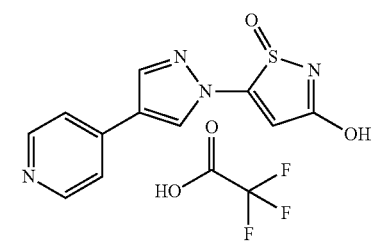
Example 410
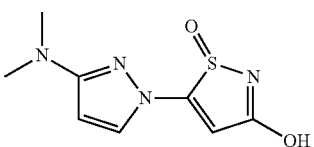
Example 411
Example 412
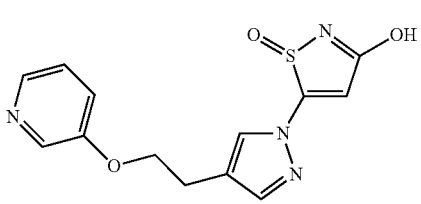

Example 413
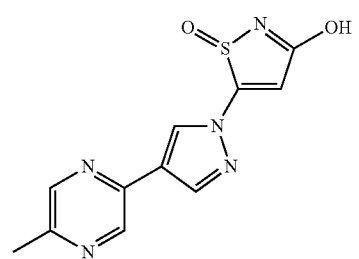
Example 414
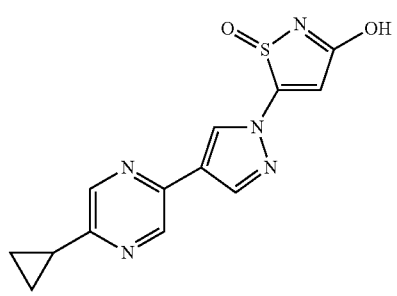
Example 415
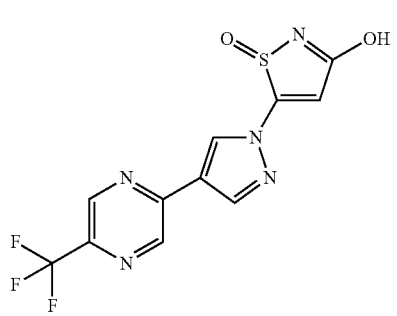
Example 416
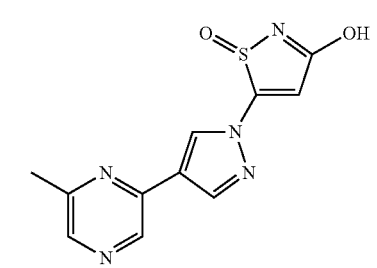
Example 417
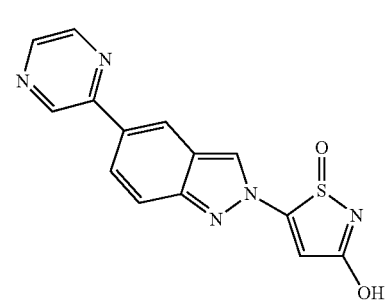
Example 418
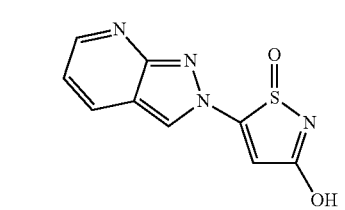
Example 419
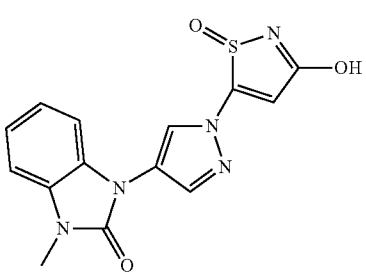
Example 420
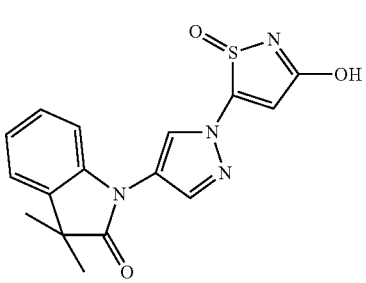
[C40]
Example 421
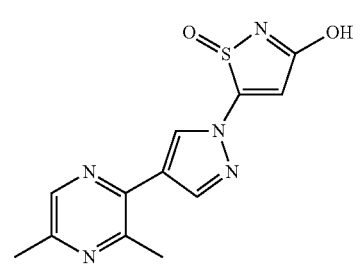
Example 422
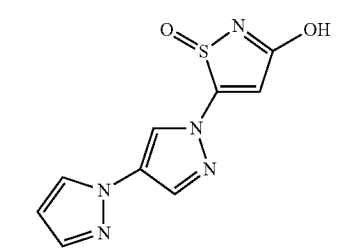
Example 423
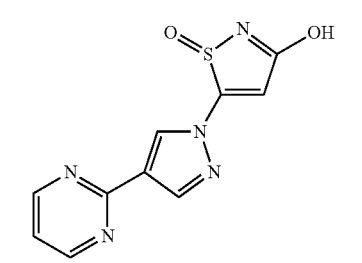
Example 424
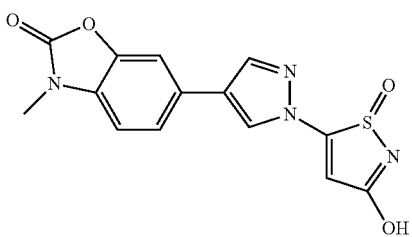

Example 425
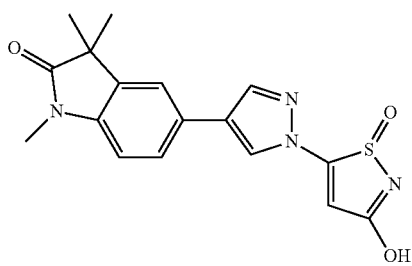
Example 426
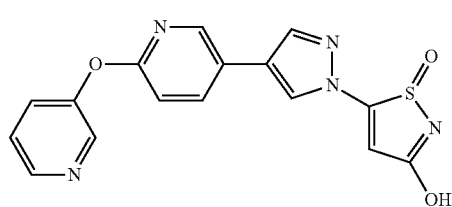
Example 427
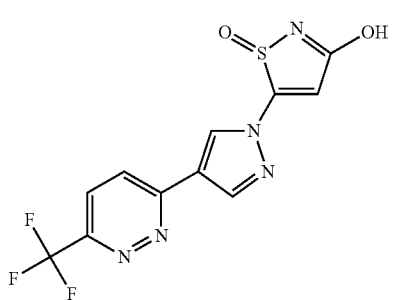
Example 428
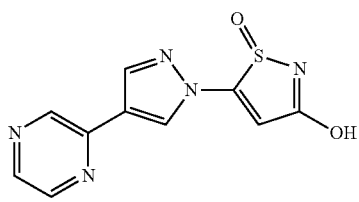
Example 429
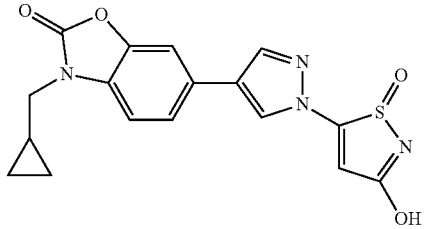
Example 430
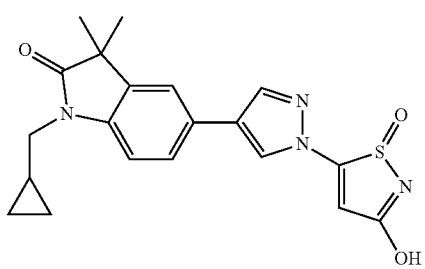
Example 431
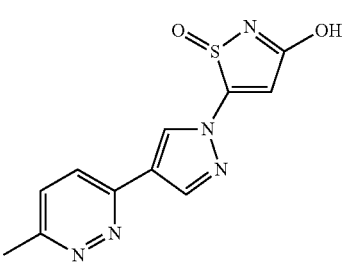
Example 432
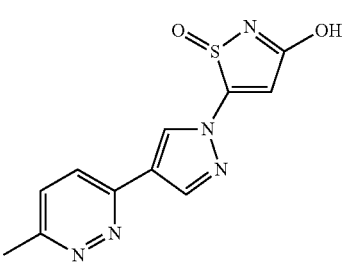
Example 433
Example 434
Example 435
Example 436
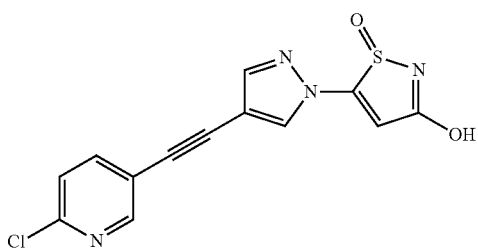

-continued
Example 437
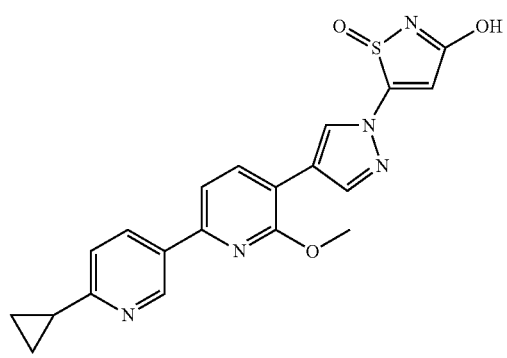
Example 438
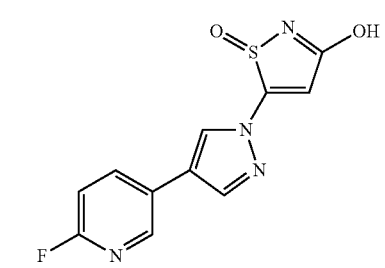
Example 439
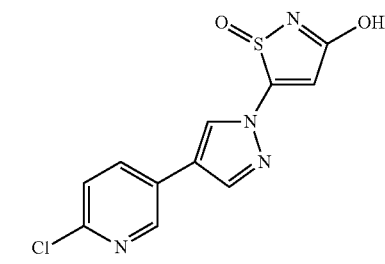
Example 440
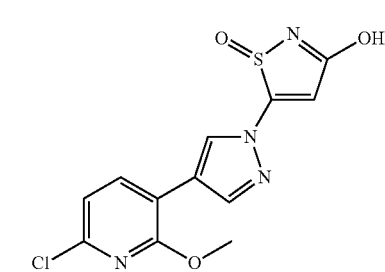
Example 441
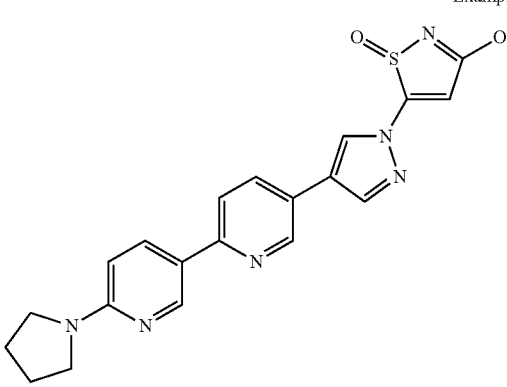
-continued
Example 442
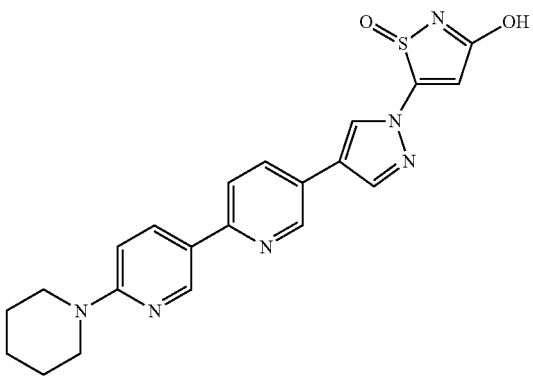
Example 443
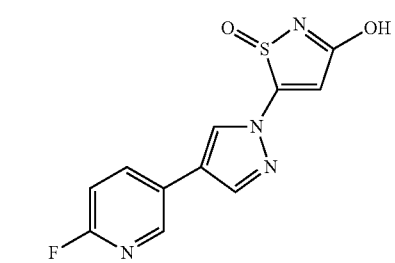
Example 444
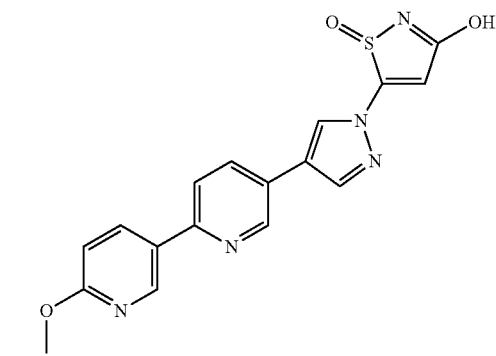
Example 445
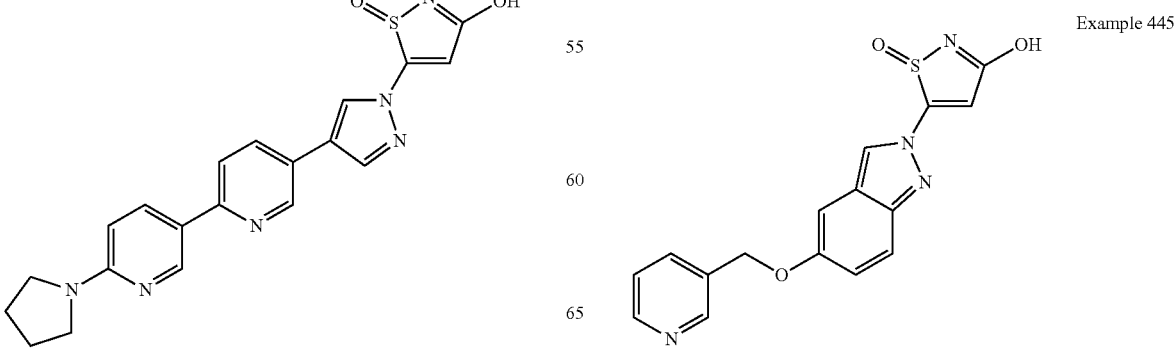

Example 446
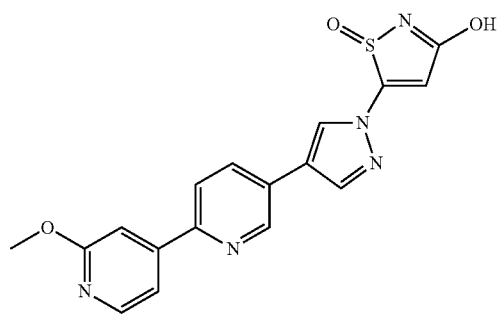
Example 447
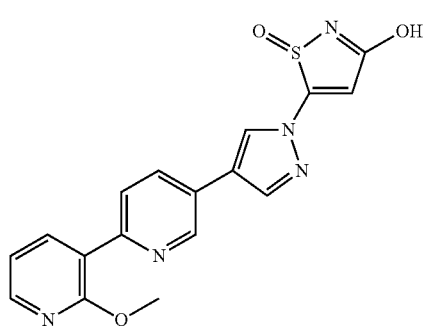
Example 448
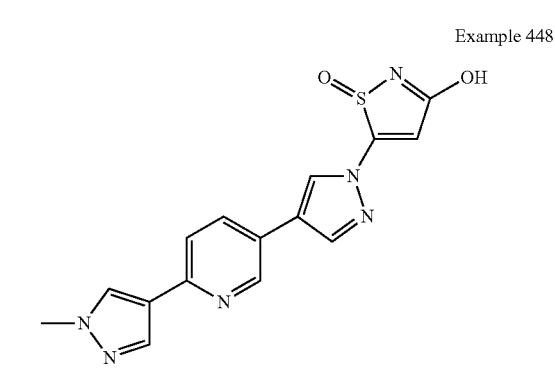
Example 449
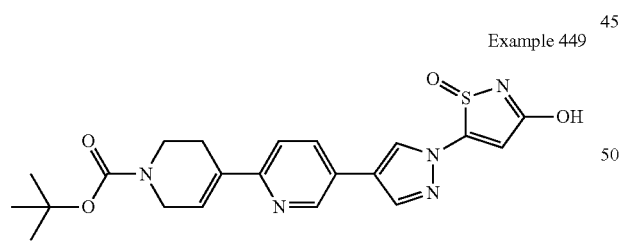
Example 450
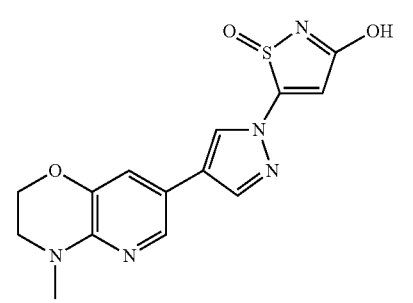
Example 451
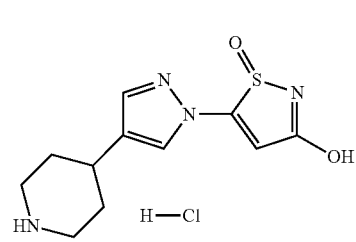
Example 452
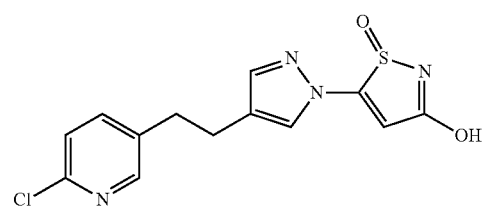
Example 453
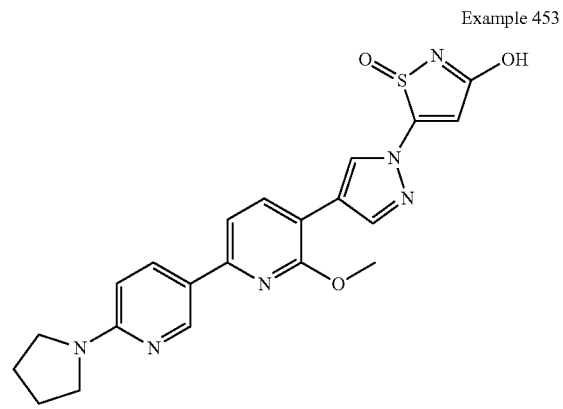
Example 454
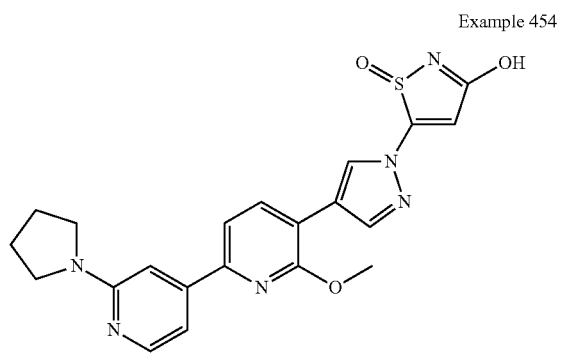
Example 455
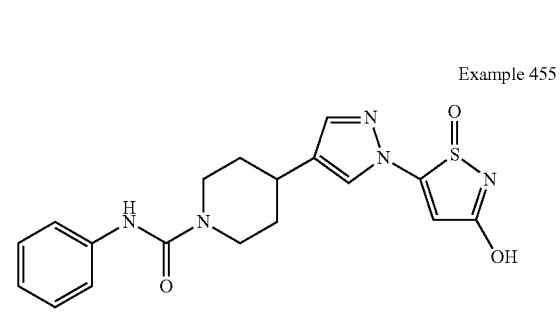

Example 456
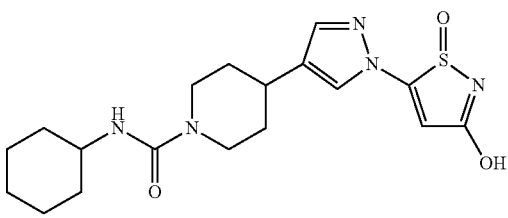

Example 457
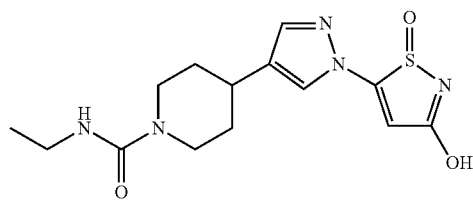

Example 458
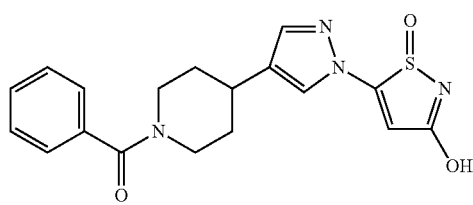

Example 459
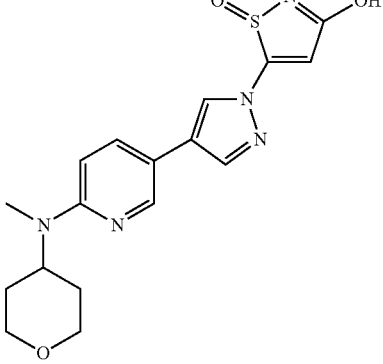

Example 460
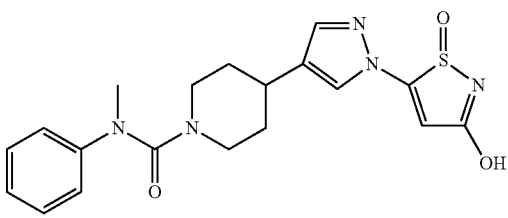

Example 461
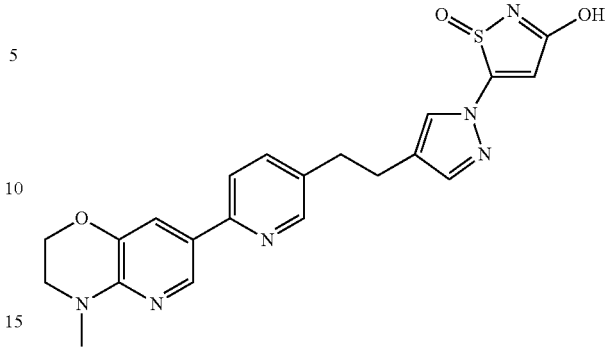

[3-1] In the compound of Formula (I) of Embodiment[1] above, examples of more preferred compounds include those listed below, or pharmaceutically acceptable salts thereof or solvates of these, or optical isomers of these. The names of the compounds shown below are based on English names obtained in accordance with the compound-naming program of BIOVIA Pipeline Pilot 9.5.0.831, Molecule to Chemical Name component (Name Style: IUPAC).

5-(indazol-1-yl)-1-oxo-1,2-thiazol-3-ol (Example 1);
5-(5-bromoindazol-1-yl)-1-oxo-1,2-thiazol-3-ol (Example 2);
5-[5-(2-methoxypyridin-4-yl) indazol-1-yl]-1-oxo-1,2-thiazol-3-ol (Example 3);
5-[5-(6-cyclopropylpyridin-3-yl) indazol-1-yl]-1-oxo-1,2-thiazol-3-ol (A) (Example 4); and
5-[5-(4-methyl-2, 3-dihydropyrido[3,2-b][1, 4]oxazin-7-yl)indazol-1-yl]-1-oxo-1,2-thiazol-3-ol (A) (Example 5).

[4] Embodiment 4 of the present invention is a pharmaceutical composition containing as an active ingredient at least one of the compound represented by Formula (I) above or a pharmaceutically acceptable salt thereof or a solvate of these.

[5] Embodiment 5 of the present invention is a preventative and/or treatment agent for diseases associated with Nrf2, containing as an active ingredient at least one of the compound represented by Formula (I) above or a pharmaceutically acceptable salt thereof or a solvate of these.

[5-1] Embodiment 5-1 of the present invention is the compound represented by Formula (I) above or a pharmaceutically acceptable salt thereof or a solvate of these for use in preventing and/or treating a disease associated with Nrf2.

Examples of diseases associated with Nrf2 include autoimmune diseases (multiple sclerosis, psoriasis, rheumatoid arthritis, systemic lupus erythematosus, scleroderma, ulcerative colitis, etc.), central nervous system diseases (Friedreich ataxia, mitochondrial myopathy, amyotrophic lateral sclerosis, Parkinson's disease, Alzheimer's disease, Huntington's disease, etc.), respiratory diseases (chronic occlusive pulmonary disease, etc.), malignant tumors (melanoma, lung cancer, medulloblastoma, neuroblastoma, etc.), eye diseases (ocular inflammation, ocular pain, age-related macular degeneration, corneal endothelial disorder, etc.), skin diseases (dermatitis, radiation skin disorders, epidermolysis bullosa, etc.), kidney diseases (diabetic nephropathy, etc.), circulatory diseases (pulmonary arterial hypertension, etc.), liver diseases (hepatitis, liver cirrhosis, etc.), traumatic brain injury, aging, diabetes, obesity and the like.

[6] Embodiment 6 of the present invention is a preventative and/or treatment agent for multiple sclerosis, psoriasis, rheumatoid arthritis, systemic lupus erythematosus, scleroderma, ulcerative colitis, Friedreich ataxia, mitochondrial myopathy, amyotrophic lateral sclerosis, Parkinson's disease, Alzheimer's disease, Huntington's disease, melanoma, lung cancer, medulloblastoma, neuroblastoma, chronic occlusive pulmonary disease, ocular inflammation, ocular pain, age-related macular degeneration, corneal endothelial disorder, dermatitis, radiation skin disorders, epidermolysis bullosa, diabetic nephropathy, pulmonary arterial hypertension, hepatitis, liver cirrhosis, traumatic brain injury, aging, diabetes or obesity, containing at least one of the compound represented by Formula (I) above or a pharmaceutically acceptable salt thereof or a solvate of these as an active ingredient.

[6-1] Embodiment 6-1 of the present invention is the compound represented by Formula (I) above or a pharmaceutically acceptable salt thereof or a solvate of these for use in preventing and/or treating multiple sclerosis, psoriasis, rheumatoid arthritis, systemic lupus erythematosus, scleroderma, ulcerative colitis, Friedreich ataxia, mitochondrial myopathy, amyotrophic lateral sclerosis, Parkinson's disease, Alzheimer's disease, Huntington's disease, melanoma, lung cancer, medulloblastoma, neuroblastoma, chronic occlusive pulmonary disease, ocular inflammation, ocular pain, age-related macular degeneration, corneal endothelial disorder, dermatitis, radiation skin disorders, epidermolysis bullosa, diabetic nephropathy, pulmonary arterial hypertension, hepatitis, liver cirrhosis, traumatic brain injury, aging, diabetes or obesity.

Preferred is a preventative and/or treatment agent for multiple sclerosis or psoriasis, containing at least one of the compound represented by Formula (I) above or a pharmaceutically acceptable salt thereof or a solvate of these as an active ingredient.

Also preferred is the compound represented by Formula (I) above or a pharmaceutically acceptable salt thereof or a solvate of these for use in preventing and/or treating multiple sclerosis or psoriasis.

[7] Embodiment 7 of the invention is an Nrf2 activation agent comprising at least one of the compound represented by Formula (I) above or a pharmaceutically acceptable salt thereof or a solvate of these.

[7-1] Embodiment 7-1 of the present invention is the compound represented by Formula (I) above or a pharmaceutically acceptable salt thereof or a solvate of these for use in Nrf2 activation.

[8] Embodiment 8 of the invention is the use of at least one of the compound represented by Formula (I) above or a pharmaceutically acceptable salt thereof or a solvate of these as a pharmaceutical composition.

[8-1] Embodiment 8-1 of the present invention is the use of at least one of the compound represented by Formula (I) above or a pharmaceutically acceptable salt thereof or a solvate of these in the manufacture of a pharmaceutical composition.

[9] Embodiment 9 of the present invention is the use of at least one of the compound represented by Formula (I) above or a pharmaceutically acceptable salt thereof or a solvate of these as an Nrf2 activation agent.

[9-1] Embodiment 9-1 of the present invention is the use of at least one of the compound represented by Formula (I) above or a pharmaceutically acceptable salt thereof or a solvate of these in the manufacture of an Nrf2 activation agent.

[10] Embodiment 10 of the present invention is a method for treating a disease selected from multiple sclerosis, psoriasis, rheumatoid arthritis, systemic lupus erythematosus, scleroderma, ulcerative colitis, Friedreich ataxia, mitochondrial myopathy, amyotrophic lateral sclerosis, Parkinson's disease, Alzheimer's disease, Huntington's disease, melanoma, lung cancer, medulloblastoma, neuroblastoma, chronic occlusive pulmonary disease, ocular inflammation, ocular pain, age-related macular degeneration, corneal endothelial disorder, dermatitis, radiation skin disorders, epidermolysis bullosa, diabetic nephropathy, pulmonary arterial hypertension, hepatitis, liver cirrhosis, traumatic brain injury, aging, diabetes and obesity, which is a method comprising the administration of at least one of the compound represented by Formula (I) above or a pharmaceutically acceptable salt thereof or a solvate of these to a subject in need of treatment for such a disease or condition.

Preferably, this is a method for treating multiple sclerosis or psoriasis, which is a method comprising the administration of at least one of the compound represented by Formula (I) above or a pharmaceutically acceptable salt thereof or a solvate of these to a subject in need of treatment for such a disease or condition.

In this Description, unless otherwise specified, "treatment" as in "treatment for a disease or condition" means to cure, alleviate or suppress the progress of "diseases or conditions" or at least one or a plurality of "diseases or conditions". Moreover, depending on the patient's condition, in this Description "treatment" encompasses preventing the occurrence of the "disease or condition" or of any symptoms associated with the "disease or condition", as well as reducing the severity of the "disease or condition" or any symptoms thereof prior to occurrence. In this Description, "treating" is considered to include preventing or improving the reoccurrence of a "disease or condition".

[11] Embodiment 11 of the invention is the preventative and/or treatment agent according to Embodiment [6] or the method according to Embodiment [10] in which the disease is selected from the group consisting of multiple sclerosis, psoriasis, rheumatoid arthritis, systemic lupus erythematosus, scleroderma, ulcerative colitis, Friedreich ataxia, mitochondrial myopathy, amyotrophic lateral sclerosis, Parkinson's disease, Alzheimer's disease, Huntington's disease, melanoma, lung cancer, medulloblastoma, neuroblastoma, chronic occlusive pulmonary disease, ocular inflammation, ocular pain, age-related macular degeneration, corneal endothelial disorder, dermatitis, radiation skin disorders, epidermolysis bullosa, diabetic nephropathy, pulmonary arterial hypertension, hepatitis, liver cirrhosis, traumatic brain injury, aging, diabetes and obesity.

The compound of the present invention is preferably a compound with an $EC_{50}$ value of not more than 10 μM with respect to Nrf2 as measured on the basis of a method, in which Nrf2 activation ability is suitably selected, for example, Pharmacological Test Example 1 below (Nrf2 activation ability evaluation). More preferably, it is a compound with an $EC_{50}$ value of not more than 5 μM, or more preferably not more than 1 μM for Nrf2.

In all of the embodiments above, the word "compound" is also considered to refer also to a "pharmaceutically acceptable salt thereof".

Moreover, in this Description unless otherwise specified descriptions of the "compound of Formula (I)", "compound represented by Formula (I)" and the like are considered to refer also to subordinate concepts of the "compound of Formula (I)", such as "the compound of Formula (I)-1" for example.

Depending on the kinds of substituents, the compound of the present invention may sometimes form an acid-addition salt or a salt with a base. These salts are not particularly limited as long as they are pharmaceutically acceptable, but examples include metal salts, ammonium salts, salts with organic bases, salts with inorganic acids, salts with organic acids, and salts with basic or acidic amino acids and the like.

These salts can be obtained by ordinary methods by first mixing the compound of the invention with a solution containing a suitable amount of an acid or base to form the target salt, and then either fractionating by filtration or distilling off the mixing solvent. Moreover, the compound of the invention or a salt thereof may also form a solvate with a solvent such as water, ethanol, glycerol or the like.

The compound of the present invention may be present in a non-solvated form or solvated form. In this Description, a "solvate" is a molecular complex containing the compound of the invention and one or more kinds of pharmaceutically acceptable solvent molecules (such as water or ethanol). When the solvent molecule is water, the solvate is called a "hydrate".

The following descriptions of the compound of the present invention encompass descriptions relating to salts, solvates, and solvates of salts thereof.

When the compound of the present invention has isomers such as geometric isomers, configurational isomers, tautomers, optical isomers, stereoisomers, regioisomers and rotamers, any of these isomers and mixtures of these isomers are included in the compound of the invention. Moreover, when the compound of the invention has optical isomers, optical isomers that have been separated from a racemic mixture are included in the compound of the invention.

When the compound of the invention has geometric isomers, configurational isomers, stereoisomers, conformers and the like, these can each be isolated by known methods.

When the compound of the invention is optically active, it can be separated into the (+) form or (−) form [D form or L form] from the corresponding racemic mixture by ordinary optical resolution means.

The compound of the invention may also be a crystal, and both single crystal forms and crystal form mixtures are included in the compound of the invention.

The compound of the invention may also be a pharmaceutically acceptable co-crystal or co-crystal salt. A co-crystal or co-crystal salt here means a crystalline substance composed of two or more independent solids at room temperature, each having different physical properties (such as structure, melting point, heat of fusion, hygroscopicity, solubility, and stability). A co-crystal or co-crystal salt can be produced by known co-crystallization methods.

The compound of the invention also includes compounds that have been isotopically labeled or substituted with isotopes such as hydrogen isotopes ($^2$H, $^3$H, etc.), carbon isotopes ($^{11}$C, $^{13}$C, $^{14}$C, etc.), chlorine isotopes ($^{36}$Cl, etc.), fluorine isotopes ($^{18}$F, etc.), iodine isotopes ($^{123}$I, $^{125}$I, etc.), nitrogen isotopes ($^{13}$N, $^{15}$N, etc.), oxygen isotopes ($^{15}$O, $^{17}$O, $^{18}$O, etc.), phosphorus isotopes ($^{32}$P, etc.) and sulfur isotopes ($^{35}$S, etc.).

[Method for Manufacturing Compound of Invention]

A method for manufacturing the compound represented by Formula (I) of the invention is explained below. A compound represented by Formula (I) that is a compound of the invention, or a salt thereof or a solvate of these, can be easily manufactured by a combination of known ordinary chemical manufacturing methods using commercial compounds or compounds easily obtained from commercial compounds by production methods known in the literature as starting materials or synthesis intermediates, and can be manufactured by the typical manufacturing methods described below. However, the present invention is in no way limited to the manufacturing methods explained below.

Unless otherwise specified, the definitions of $R^1$, $R^2$ and the like in the individual formulae in the manufacturing method below are the same as the corresponding definitions in Formula (I) as described in the embodiments above. Unless otherwise specified, Y in the manufacturing method is defined as a halogen atom. Unless otherwise specified, W in the manufacturing method is defined as boronic acid or a boronic acid ester, trifluoroborate salt or boronic acid N-methyliminodiacetate ester.

The formulae in each step in the manufacturing method may also form salts, and examples of these salts include the salts of Formula (I) described above. The raw material compounds in each step in the manufacturing method may be used in the following reactions either as reaction solutions or as coarse products. They may also be isolated from a reaction mixture by ordinary methods, and easily purified by separation methods that are themselves well known, such as extraction, concentration, neutralization, filtration, distillation, re-crystallization and chromatography for example.

The solvent used in the above-mentioned re-crystallization may be water, methanol, ethanol, 2-propanol, butanol, diethyl ether, tetrahydrofuran, 1,4-dioxane, n-hexane, cyclohexane, heptane, benzene, toluene, xylene, N,N-dimethylformamide, N,N-dimethylacetamide, 1,3-dimethyl-2-imidazolidinone, chloroform, methylene chloride, 1,2-dichloroethane, acetonitrile, acetone, diphenylketone, methyl acetate, ethyl acetate, dimethylsulfoxide, acetic acid, trifluoroacetic acid, methanesulfonic acid or the like for example. These solvents may be used individually, or two or more solvents may be mixed in appropriate proportions, such as a ratio of 1:1 to 1:10 for example. When the compounds in the formulae are commercially available, the commercial products may be used as is, or the compounds may be manufactured by known methods or analogous methods.

When the individual formulae in each step in the manufacturing method include convertible functional groups (such as carboxy, amino, hydroxyl, carbonyl, mercapto, $C_{1-6}$ alkoxycarbonyl, $C_{6-14}$ aryloxycarbonyl, $C_{7-20}$ aralkyloxycarbonyl or sulfo groups or halogen atoms or the like), these functional groups may be converted by well-known methods or analogous methods to manufacture various compounds.

In the above-mentioned conversion reactions, when a compound is obtained in a free form it may be converted into a salt by ordinary methods, while when it is obtained as a salt it may be converted into a free form or into another salt by ordinary methods.

Conversion of these functional groups may be accomplished by methods such as those described in Comprehensive Organic Transformations, 2nd Ed. (Larock, 1999, Wiley-VCH) for example.

When the various formulae in each step in the manufacturing method contain reactive groups such as hydroxyl groups, amino groups, carboxy groups, and thiol groups as substituents, these groups may be protected appropriately in each reaction step, and the protective groups may be removed at the appropriate stage.

Methods for introducing and removing protecting groups may be adapted to the type of protected group and protective group, and the methods described in Greene's Protective Groups in Organic Synthesis, 5th Ed. (Wuts, 2014, John Wiley & Song) may be followed for example.

Unless otherwise specified, the reaction temperature at each step in the manufacturing method is not restricted as long as it is within the range of from −78° C. to the reflux temperature of the solvent. Moreover, unless otherwise specified the reaction time is not limited as long as it is a time that allows the reaction to progress sufficiently.

With reference to the reaction temperature, "within the range of from −78° C. to the reflux temperature of the solvent" means a temperature within the range of from −78° C. to the temperature at which the solvent (or mixed solvent) used in the reaction undergoes reflux. When the solvent is methanol for example, "at a temperature of from −78° C. to the reflux temperature of the solvent" means at a temperature in the range of from −78° C. to the temperature at which methanol undergoes reflux. Similarly, "at a temperature of from −78° C. to the reflux temperature of the reaction solution" means at a temperature in the range of from −78° C. to the temperature at which the reaction solution undergoes reflux.

The reactions in each step of the manufacturing method may be performed without a solvent, or else the raw material compounds may be dissolved or suspended before the reaction in a reaction inert solvent.

Examples of solvents that do not participate in the reaction include water, cyclohexane, hexane, benzene, chlorobenzene, toluene, xylene, methanol, ethanol, 1-propanol, 2-propanol, tert-butyl alcohol, N,N-dimethylformamide, N,N-dimethylacetamide, hexamethyl phosphoric triamide, 1,3-dimethyl-2-imidazolidinone, dimethyl sulfoxide, acetonitrile, propionitrile, diethyl ether, diisopropyl ether, diphenyl ether, tetrahydrofuran, 1,4-dioxane, 1,2-dimethoxyethane, methyl acetate, ethyl acetate, butyl acetate, acetone, methyl ethyl ketone, dichloromethane, chloroform, carbon tetrachloride, 1,2-dichloroethane, triethylamine, N,N-diisopropylethylamine, pyridine, lutidine, acetic anhydride, formic acid, acetic acid, propionic acid, trifluoroacetic acid, methanesulfonic acid, hydrochloric acid, sulfuric acid and the like. These solvents may be used individually, or two or more different solvents may be selected appropriately according to the reaction conditions and mixed and used in suitable proportions.

Unless otherwise specified, when a "reaction inert solvent" is described in the manufacturing method it may be one kind of solvent or a mixed solvent of two or more kinds.

Examples of bases (or deacidifiers) used in each step of the manufacturing process include lithium hydroxide, sodium hydroxide, potassium hydroxide, magnesium hydroxide, lithium carbonate, sodium carbonate, potassium carbonate, cesium carbonate, calcium carbonate, sodium hydrogencarbonate, triethylamine, N,N-diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole, sodium methoxide, sodium ethoxide, potassium tert-butoxide, sodium tert-butoxide, sodium hydride, potassium hydride, sodium amide, lithium diisopropylamide, lithium hexamethyldisilazide, methyl lithium, n-butyl lithium, sec-butyl lithium, tert-butyl lithium and the like. However, examples are not necessarily limited to those listed above.

Examples of acids or acid catalysts used in each step of the manufacturing method include hydrochloric acid, sulfuric acid, nitric acid, hydrobromic acid, phosphoric acid, acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, boron trifluoride ether complex, zinc iodide, anhydrous aluminum chloride, anhydrous zinc chloride, anhydrous iron chloride and the like. However, examples are not necessarily limited to those listed above.

The compound represented by Formula (I) in the present invention can be obtained from a substitution reaction of the heterocyclic ring represented by Formula (HA) and the isothiazole ring represented by Formula (IT).

[C43]

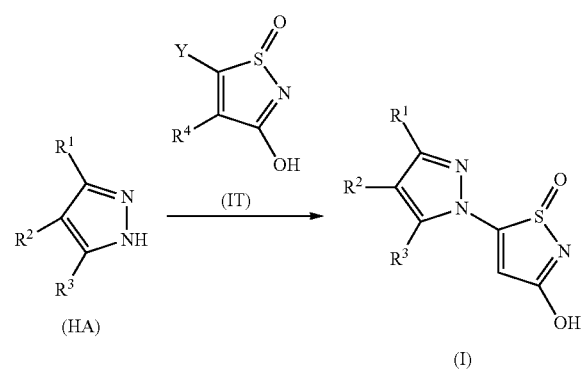

Methods for manufacturing the compound represented by Formula (I) are shown below.

<Manufacturing Method A>

[C43]

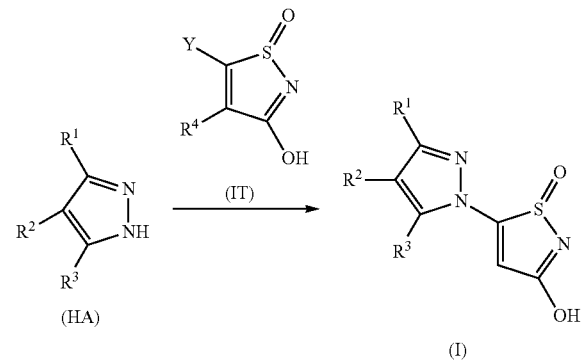

The compound of Formula (I) can be manufactured using the compound of Formula (HA) [the compound of Formula (HA) is a commercial compound or a compound that can be manufactured from commercial compounds by methods known in the literature or by Step 3 of Manufacturing Method B or Step 3 of Manufacturing Method C below] and the compound of Formula (IT) [the compound of Formula (IT) is a compound that can be manufactured by methods known in the literature, such as for example "Manufacturing Method I" or "Reference Example 1" of WO 2012/147518] by performing a reaction with or without a base such as sodium hydride, sodium hydroxide, potassium carbonate, triethylamine or pyridine in a solvent that does not affect the reaction, such as diethyl ether, tetrahydrofuran, benzene, toluene, N,N-dimethylformamide, dichloromethane or chloroform, at a temperature between 0° C. and the reflux temperature of the solvent, in accordance with a known method such as the method described in "Jikken Kagaku Koza, the fourth edition (The Fourth Series of Experimental Chemistry). 20, Organic Synthesis II, alcohols and amines, pp. 187-200 and pp. 284-292, 1992, Maruzen" and "Jikken Kagaku Koza, the fourth edition (The Fourth Series of Experimental Chemistry). 20, Organic Synthesis VI, Hetero elements and typical metal element compounds, pp. 319-350, 1992, Maruzen".

<Manufacturing Method B>

<When any of $R^1$, $R^2$ and $R^6$ in Formula (I) above is a cyclic group, or in other words when Formula (I) is represented by Formula (Ia):

[C45]

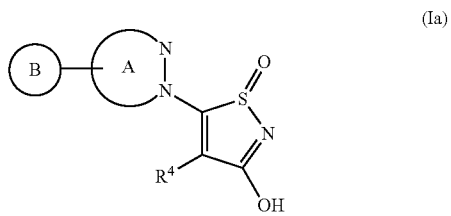

(in which ring A represents a pyrazole ring or fused ring partially having a pyrazole ring, and when ring A is a pyrazole ring, ring A is substituted with $R^1$, $R^2$ and $R^3$, and ring B represents a cyclic group of $R^1$ or $R^2$, while when ring A is a fused ring partially having a pyrazole ring, ring A is substituted with $R^1$ or $R^3$ and 1 to 5 of $R^6$, and B represents a cyclic group of $R^6$), and ring B binds to a carbon atom of ring A>

[C46]

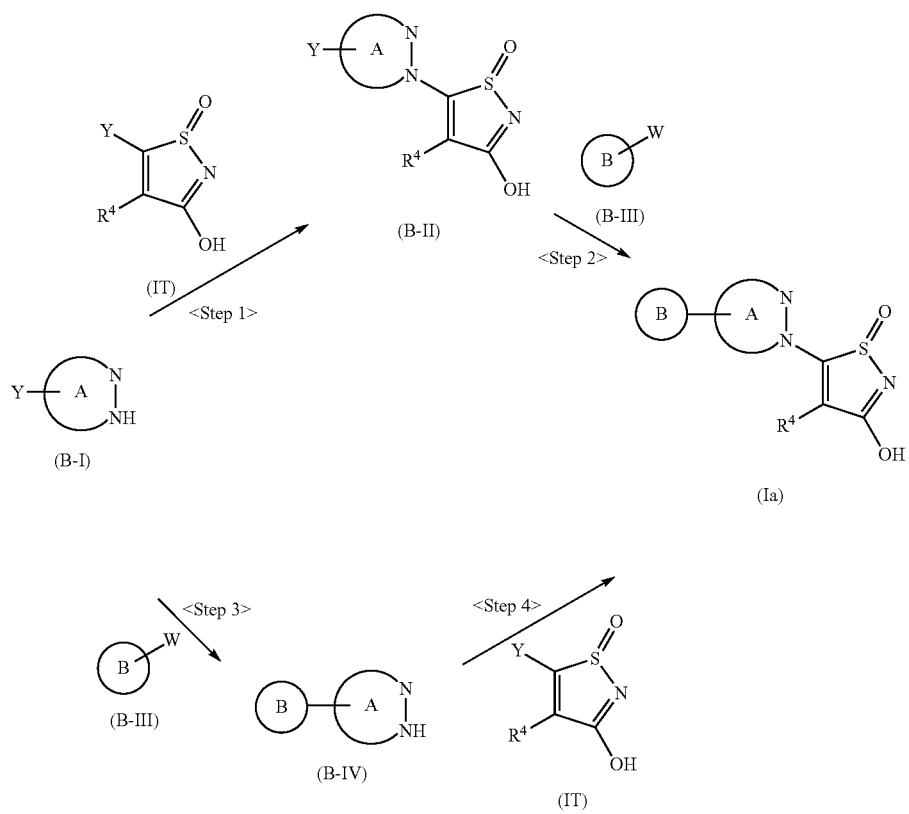

<Step 1>

The compound of Formula (B-II) can be manufactured using the compound of Formula (IT) and the compound of Formula (B-I) [the compound of Formula (B-I) is a commercial compound or a compound that can be manufactured by methods known in the literature from commercial compounds] by performing a reaction in accordance with Manufacturing Method A.

<Step 2>

Using the compound of Formula (B-II) obtained in Step 1 of Manufacturing Method B and the compound of Formula (B-III) [the compound of Formula (B-III) is a commercial compound or a compound that can be manufactured by methods known in the literature from commercial compounds], the compound represented by Formula (1a) can be manufactured in accordance with the methods described in known literature, such as for example the methods described in "Jikken Kagaku Koza, the fifth edition (The Fifth Series of Experimental Chemistry). 18, Synthesis of Organic Compounds VI, Organic synthesis using metals, pp. 327-352, 2004, Maruzen" and "Journal of Medicinal Chemistry, 48(20), 6326-6339, 2005", by performing a reaction in the presence of a palladium catalyst such as palladium (II) acetate (Pd(OAc)$_2$), tetrakis(triphenylphosphine)palladium (Pd(PPh$_3$)$_4$), tris(dibenzilideneacetone)dipalladium (Pd$_2$(dba)$_3$), bis(dibenzylideneacetone)palladium (Pd(dba)$_2$) or [1,1'-bis(diphenylphosphino)ferrocene]dichloropalladium (II) (PdCl$_2$(dppf)), a phosphine reagent such as triphenylphosphine, tris(tert-butyl)phosphine, tris(o-tolyl)phosphine, 2-dicyclohexylphosphino-2',6'-dimethoxybiphenyl, or 2-dicyclohexylphosphino-2',4',6'-triisopropylbiphenyl, and an organic or inorganic base such as triethylamine, N,N-diisopropylethylamine, potassium phosphate, potassium carbonate or cesium carbonate, in a solvent that does not affect the reaction, such as toluene, xylene, N,N-dimethylformamide, N,N-dimethylacetamide, dimethoxyethane, acetonitrile (acetonitrile/water), dioxane (dioxane/water), tetrahydrofuran (tetrahydrofuran/water) or a mixed solvent of these, at a temperature between 0° C. and the reflux temperature of the solvent. It can also be manufactured by a similar reaction using tetramethylammonium chloride, tetrabutylammonium chloride or the like in place of the phosphine reagent.

<Step 3>

The compound of Formula (B-IV) can be manufactured by performing a reaction in accordance with Step 2 of Manufacturing Method B using the compound of Formula (B-I) and the compound of Formula (B-III) [the compound of Formula (B-III) is a commercial compound or a compound that can be manufactured from commercial compounds by methods known in the literature].

<Step 4>

The Compound of Formula (1a) can be manufactured by performing a reaction in accordance with Manufacturing Method A using the compound of Formula (B-IV) obtained in Step 3 of Manufacturing Method B and the compound of Formula (IT).

<Manufacturing Method C>

<When the pyrazole ring structure to which $R^1$, $R^2$ and $R^3$ are bound in Formula (I) above is represented by the partial structural Formula (a4) or (a5) above, and $R^{6b}$ is a $C_{3-8}$ cycloalkylmethyl group, $C_{6-14}$ arylmethyl group or heteroarylmethyl group, or in other words when Formula (I) is represented by Formula (Ib):

[C47]

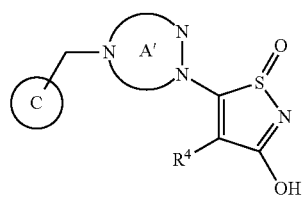
(Ib)

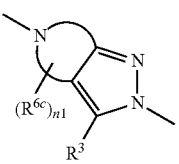
(a5')

a nitrogen atom on ring A' is substituted with a cyclic C-methyl group, ring C represents a $C_{3-8}$ cycloalkyl group, $C_{6-14}$ aryl group or heteroaryl group, and ring C may be substituted with 1 to 5 of $R^{7b}$)>

[C49]

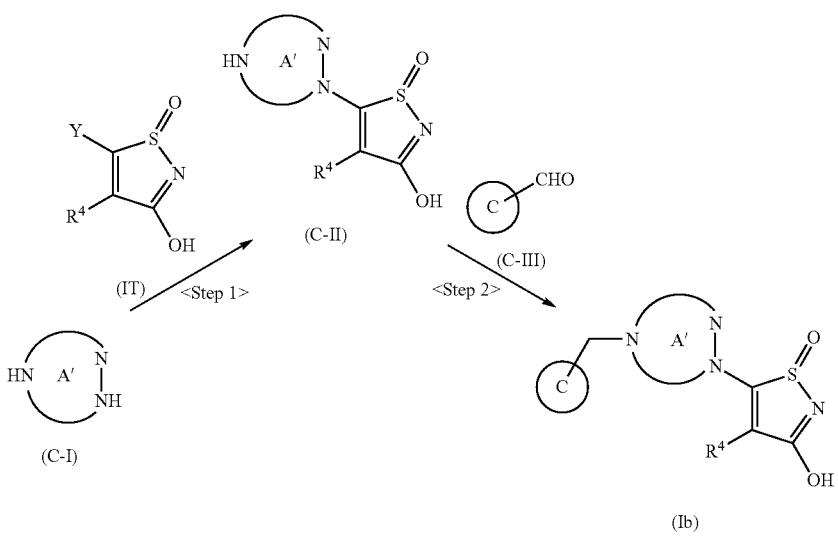

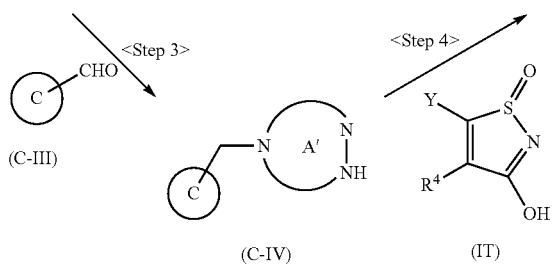

(in which ring A' represents a fused ring part consisting of the non-aromatic heterocyclic ring and pyrazole ring in the partial structural Formula (a4) or (a5), or in other words (a4') or (a5'):

[C48]

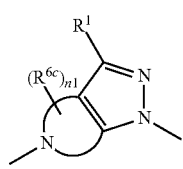
(a4')

<Step 1>

The compound of Formula (C-II) can be manufactured by performing a reaction in accordance with Manufacturing Method A using the compound of Formula (C-1) [the compound of Formula (C-1) is a commercial compound or a compound that can be manufactured from commercial compounds by methods known in the literature] and the compound of Formula (IT).

<Step 2>

Using the compound of Formula (C-II) obtained in Step 1 of Manufacturing Method C and the compound of Formula (C-III) [the compound of Formula (C-III) is a commercial compound or a compound that can be manufactured by methods known in the literature from commercial compounds], the compound represented by Formula (Ib) can be manufactured by methods described in known literature, such as for example "Journal of Medicinal Chemistry, 23(12), 1405-1410, 1980", by performing a reaction using a reaction inert solvent such as a halogen solvent such as dichloromethane or chloroform, an ether solvent such as diethyl ether, tetrahydrofuran, 1,2-dimethoxyethane or 1,4-dioxane, an aromatic hydrocarbon solvent such as benzene or toluene, or a mixed solvent of these, at a temperature between 0° C. and the reflux temperature of the solvent to form an imine, and then performing another reaction in the presence of sodium borohydride in a solvent that does not participate in the reaction, such as an alcohol solvent such as methanol, ethanol or 2-propanol or an ether solvent such as diethyl ether, tetrahydrofuran, 1,2-dimethoxyethane or 1,4-dioxane, or a mixed solvent of these, at a temperature between 0° C. and the reflux temperature of the solvent.

The compound of Formula (1 b) can also be manufactured using the compound (C-II) obtained in Step 1 of Manufacturing Method C and the compound (C-III) by the methods described in "The Journal of Organic Chemistry, 61, 3849-3862, 1996" for example by performing a reaction at a temperature between 0° C. and the reflux temperature of the solvent in the presence of a reducing agent such as sodium triacetoxyborohydride or sodium cyanoborohydride, with or without a catalytic amount of acetic acid, in a reaction inert solvent such as dichloromethane, 1,2-dichloroethane, tetrahydrofuran, acetonitrile, toluene, methanol, ethanol or 2-propanol, or a mixed solvent of these.

<Step 3>

The compound of Formula (C-IV) can be manufactured by performing a reaction using the compound of Formula (C-I) and the compound of Formula (C-III) in accordance with Step 2 of Manufacturing Method C.

<Step 4>

The compound of Formula (Ib) can be manufactured by performing a reaction using the compound of Formula (C-IV) obtained in Step 3 of Manufacturing Method C and the compound of Formula (IT) in accordance with Manufacturing Method A.

[Formulating Preventative and/or Treatment Agent of Invention]

The drug of the present invention is administered in the form of a pharmaceutical composition.

The pharmaceutical composition of the present invention may be any that contains at least one or more of the compound represented by Formula (I) of the invention, optionally combined with any pharmaceutically acceptable additives. More specifically, various dosage forms can be obtained by combining the compound of the invention with suitable kinds of commonly-used additives or solvents, such as excipients (for example, lactose, white sugar, mannitol, crystalline cellulose, silicic acid, corn starch, potato starch), binders (including celluloses such as hydroxypropyl cellulose and hydroxypropyl methyl cellulose, crystal cellulose, sugars such as lactose, mannitol, white sugar, sorbitol, erythritol and xylitol, starches such as corn starch and potato starch, pregelatinized starch, dextrin, polyvinylpyrrolidone, macrogol and polyvinyl alcohol), lubricants (such as magnesium stearate, calcium stearate, talc and carboxymethyl cellulose), disintegrants (including starches such as corn starch and potato starch, and carboxymethyl starch sodium, carmellose, carmellose calcium, croscarmellose sodium and crospovidone), coating agents (for example, celluloses such as hydroxypropyl cellulose and hydroxypropyl methyl cellulose, and aminoalkyl methacrylate copolymer E and methacrylic acid copolymer LD), plasticizers (such as triethyl citrate and macrogol), concealing agents (such as titanium oxide), colorants, flavorings, antiseptics (such as benzalkonium chloride and paraoxybenzoic acid ester), isotonic agents (such as glycerin, sodium chloride, calcium chloride, mannitol and glucose), pH adjusters (such as sodium hydroxide, potassium hydroxide, sodium carbonate, hydrochloric acid, sulfuric acid, and buffers such as phosphate buffers), stabilizers (such as sugars, sugar alcohols and xanthan gum), dispersants, antioxidants (such as ascorbic acid, butyl hydroxy anisole, propyl gallate and dl-α-tocopherol), buffers, preservatives (such as paraben, benzyl alcohol and benzalkonium chloride), aromatics (such as vanillin, 1-menthol and rose oil), solubilizing agents (such as polyoxyethylene hardened castor oil, polysorbate 80, polyethylene glycol, phospholipid cholesterol and triethanolamine), absorption enhancers (such as sodium glycolate, sodium edetate, sodium caproate, acylcarnitine and limonene), gelling agents, suspension agents or emulsifiers.

Examples of various dosage forms include tablets, capsules, granules, powders, pills, aerosols, inhalants, ointments, patches, suppositories, injections, troches, liquids, alcoholic preparations, suspension, extracts, elixirs, eye drops and the like. The drug of the present invention may also be administered to a patient by oral, subcutaneous, intramuscular, intranasal, percutaneous, intravenous, intraarterial, perineural, epidural, intrathecal, intracerebroventricular, intrarectal, inhalation, intravitreal, intracameral, subconjunctival, Tenon's capsule or ophthalmic administration or the like.

PHARMACOLOGICAL TEST EXAMPLES

The present invention is explained in detail below with examples, but the present invention is in no way limited to these.

The following Pharmacological Test Examples 1 to 7 present methods for testing the efficacy of the compounds of the present invention.

Pharmacological Test Example 1

Evaluation of Nrf2 Activation Ability

HEK293 cells constantly expressing Nrf2d-LacZ (human Nrf2 degron region fused to LacZ; Hirotsu et al, Genes to Cell, Vol. 16, pp. 406-415 (2011)) and human Keap1 were seeded 7,000 cells/27 μl/well on 384-well plates (Corning 384 Well Flat Clear Bottom White Polystyrene TC-Treated Microplates, Cat. #3707), and cultured overnight at 5% $CO_2$, 37° C. in DMEM medium containing 10% FBS, 100 U/mL penicillin and 100 μg/mL streptomycin. 3 μL/well of a 0.1% DMSO solution of the compound of the invention was added to the cells, which were then cultured for 3 hours at 5% $CO_2$, 37° C. Beta-Glo® reagent (Promega, Beta-Glo Assay System, Cat. #E4740) was added 15 μL/well and incubated for 1 hour at room temperature, and luminescence intensity was measured with a luminometer. Using CDDO-Im as a standard, Nrf2 activation ability was calculated given 100% as the luminescence under stimulus with 100 nM CDDO-Im.

The Nrf2 activation ability of the test compound is represented as an $EC_{50}$ value, and the results of the test examples below are given in Table 2, with compounds with an $EC_{50}$ value of less than 1 μM rated as A, those with $EC_{50}$ values of at least 1 μM and less than 5 μM rated as B and those with $EC_{50}$ values of at least 5 μM and less than 10 μM rated as C.

Pharmacological Test Example 2

Solubility Test (1) DMSO Precipitation Solubility (Kinetic Solubility)

A 10 mM DMSO solution of the compound of the invention is added to 50 mM phosphate buffer (pH 7.4) to a final concentration of 100 µM. This solution is incubated with stirring at 600 rpm for 1.5 hours at room temperature, then filtered with filter plate, and the absorbance of the filtrate is measured at the maximum absorption wavelength. At the same time, absorbance is measured using DMSO solutions of the test compound at known concentrations (such as 1, 3, 10, 30, and 100 µM) as standard solutions, and the solubility (µM) of the test compound is calculated from the absorbance values of a calibration curve.

(2) Crystal Solubility (Thermodynamic Solubility)

The compound of the invention is added to a solvent (such as water or buffer) to a concentration of 1 mg/mL. This solution is incubated for 24 hours at 25° C. or 37° C. with stirring at 1,000 rpm, and then filtered with filter plate. The filtrate is analyzed by HPLC, a peak is detected at the maximum absorption wavelength, and the peak area is measured. Similarly, the peak areas are measured using solutions (in DMSO, 1,4-dioxane or methanol for example) of the test compound with known concentrations (such as 0.01, 0.03, 0.1, 0.3, 1, 3, and 10 µg/mL) as standard solutions, and the solubility (µg/mL) of the test compound is calculated from the peak areas of the calibration curve.

Pharmacological Test Example 3

Metabolic Stability Test

A 10 mM DMSO solution of the test compound is added to a liver microsome (human, rat, mouse, dog, monkey, etc.)/NADPH-generating system (β-NADP, glucose-6-phosphate, G-6-PDH(Y), aqueous solution containing $MgCl_2$) to a final concentration of 1 µM. This solution is incubated for an appropriate time (such as 5, 10, 20 or 30 minutes) at 37° C., and the reaction is stopped by addition of acetonitrile. The reaction solution is filtered with filter plate, and the test compound in the filtrate is measured by high-performance liquid chromatographwith mass spectrometry (HPLC/MS). Similarly, a sample of 0 minute reaction time is measured as a control, and the residual rate (%) is calculated at each time point. The reaction times are plotted on the vertical axis and the residual rates on the horizontal axis, and the clearance (µl/min/mg protein) is calculated from the slope.

Similarly metabolic stability tests of the compound of the invention can be performed using hepatic cell suspensions (human, rat, dog, monkey, etc.).

Pharmacological Test Example 4 hERG Inhibition Test

The effect on the hERG (human ether-a-go-go related gene) channel can be confirmed by measuring the hERG $I_{Kr}$ current of hERG-expressing cells using a fully-automated patch clamp system.

Pharmacological Test Example 5

Pharmacokinetics (PK) Test

The compound of the invention is administered orally to rats (7- or 8-week-old male CD(SD)IGS Jcl) at a dose of 1 mg/kg (administration solvent of DMSO:Tween80:ultrapure water=1:1:8, 10 mL/kg), and after 0.5, 1, 2 and 4 hours blood is taken from the abdominal vena cava. The test compound in plasma is then measured by HPLC/MS. Standard solutions of the test compound at known concentrations are also measured in the same way, the plasma concentrations (µg/mL) are calculated from the calibration curve, and the maximum plasma concentration is given as Cmax (µg/mL).

Similarly, the compound of the invention is also administered (intravenously or orally) to animals such as male beagles and male cynomolgus monkeys, and the plasma concentrations of the test compound are measured to evaluate PK profiles in other animal species.

Pharmacological Test Example 6

Protein Binding Test

A 10 mM DMSO solution of the compound of the invention is added to normal plasma (human, rat, dog, monkey, etc.) to a final concentration of 10 µM. This is dialyzed for 4 hours at 37° C. in an equilibrium dialyzer, and the concentrations of the test compound in the plasma side and those in PBS side solutions are measured by HPLC/MS. The unbonded fraction (%) is calculated from the ratio of the PBS side and the serum side, and the protein binding rate (%) is calculated as 100−unbonded fraction (%).

Pharmacological Test Example 7

Safety Test

When the compound of the invention is administered orally one time to mice or rats, there is no mortality, and no obvious behavioral abnormalities are observed, indicating that the compound of the invention is safe.

These results have shown that the compound of the invention has excellent Nrf2 activation ability. Moreover, it is confirmed from the above tests that the compound of the invention is favorable in terms of solubility, metabolic stability, avoidance of hERG channel inhibition, pharmacokinetics, protein binding, safety and the like.

Consequently, the compound of the invention is expected, as a Nrf2 activator, preferably to be useful as a preventative and/or treatment agent for diseases associated with Nrf2, or in other words for diseases including autoimmune diseases (multiple sclerosis, psoriasis, rheumatoid arthritis, systemic lupus erythematosus, scleroderma, ulcerative colitis, etc.), central nervous system diseases (Friedreich ataxia, mitochondrial myopathy, amyotrophic lateral sclerosis, Parkinson's disease, Alzheimer's disease, Huntington's disease, etc.), respiratory diseases (chronic occlusive pulmonary disease, etc.), malignant tumors (melanoma, lung cancer, medulloblastoma, neuroblastoma, etc.), eye diseases (ocular inflammation, ocular pain, age-related macular degeneration, corneal endothelial disorder, etc.), skin diseases (dermatitis, radiation skin disorders, epidermolysis bullosa, etc.), kidney diseases (diabetic nephropathy, etc.), circulatory diseases (pulmonary arterial hypertension, etc.), liver diseases (hepatitis, liver cirrhosis, etc.), and traumatic brain injury, aging, diabetes, obesity and the like.

Preferably the compound of the invention is expected to exhibit the desired preventative or therapeutic effect against the various diseases shown below. Specifically, it is expected to have the desired therapeutic effect against multiple sclerosis, psoriasis, rheumatoid arthritis, systemic lupus erythematosus, scleroderma, ulcerative colitis, Friedreich ataxia, mitochondrial myopathy, amyotrophic lateral sclerosis, Parkinson's disease, Alzheimer's disease, Huntington's disease, melanoma, lung cancer, medulloblastoma, neuroblastoma, chronic occlusive pulmonary disease, ocular inflammation, ocular pain, age-related macular degeneration, corneal endothelial disorder, dermatitis, radiation skin disorders, epidermolysis bullosa, diabetic nephropathy, pulmonary arterial hypertension, hepatitis, liver cirrhosis, traumatic brain injury, aging, diabetes, obesity and the like.

EXAMPLES

Examples for explaining the present invention in further detail are given next, but these are only examples that do not limit the present invention, and may be changed to the extent that the changes do not deviate from the scope of the present invention.

A JEOL JNM-ECX400 FT-NMR (Jeol Resonance Inc.) or JEOL JNM-ECX300 FT-NMR (Jeol Resonance Inc.) was used for nuclear magnetic resonance spectroscopy (NMR).

In the $^1$H-NMR data, s in the NMR signal pattern represents a singlet, d is a doublet, t is a triplet, q is a quartet, m is a multiplex, br means broad, J is a coupling constant, Hz means hertz, $CDCl_3$ represents deuterated chloroform, and $DMSO-d_6$ represents deuterated dimethylsulfoxide. In the $^1$H-NMR data, no data is given for signals that cannot be confirmed in broadband, such as protons of hydroxyl groups, amino groups and carboxyl groups.

Liquid-chromatography-mass spectrometry spectrum (LC-Mass) was measured by any of the following methods. [UPLC][Method A] Using a Waters UPLC-ZQ MS system (Waters.) and a column (2.1 mm×5 cm, 3 μm) (Shiseido Company, Limited), the mobile phase was methanol:0.05% trifluoroacetic acid aqueous solution with a gradient condition of 5:95 (0 min) to 100:0 (1 min) to 100:0 (2 min). [LCMS] Using a Waters FractionLynx MS System (Waters.) and a SunFire column (4.6 mm×5 cm, 5 μm) (Waters.), the mobile phase [Method B] was methanol:0.05% trifluoroacetic acid aqueous solution with a gradient condition of 10:90 (0 min) to 100:0 (5 min) to 100:0 (7 min), or [Method C] methanol:0.05% acetic acid aqueous solution with a gradient condition of 10:90 (0 min) to 100:0 (5 min) to 100:0 (7 min), or [Method D] methanol:0.05% trifluoroacetic acid aqueous solution with a gradient condition of 0:90 (0 min) to 100:0 (2.0 min) to 100:0 (3.0 min) to 10:90 (4.5 min) or [Method E] methanol:0.05% acetic acid aqueous solution with a gradient condition of 0:90 (0 min) to 100:0 (2.0 min) to 100:0 (3.0 min) to 10:90 (4.5 min). The gradient conditions in the preparative system were changed appropriately according to the compound.

In the LC-Mass data, the measurement methods of each example are designated as A for "UPLC [Method A]", B for "LCMS [Method B]", C for "LCMS [Method C]", D for "LCMS [Method D]" and E for "LCMS [Method E]". In the LC-Mass data, MS-ESI means electrospray ionization mass spectrometry, M means molecular weight, RT means retention time, and $[M+H]^+$ and $[M+Na]^+$ represent molecular ion peaks.

"Room temperature" in the examples and manufacturing examples means the temperature in the laboratory, which is normally 20±15° C.

A compound synthesized using enantiomer A (Reference Example 1 (A) of the 5-chloro-1-oxo-1,2-thiazol-3-ol(5-chloroisothiazol-3-ol 1-oxide) described in Reference Example 1 of WO 2012/147518 is designated with an (A) after the compound name or in the structure field of Table 2.

A compound synthesized using enantiomer B (Reference Example 1 (B)) is designated with a (B) after the compound name or in the structure field of Table 2. When racemic 5-chloro-1-oxo-1,2-thiazol-3-ol is used, r is given in the structure field of Table 2.

Example 1

Synthesis of 5-(indazol-1-yl)-1-oxo-1,2-thiazol-3-ol

60% sodium hydride (10.6 g) was added to a tetrahydrofuran (600 mL) solution of 1H-indazole (15.6 g), and stirred for 30 minutes at 20° C., after which 5-chloro-1-oxo-1,2-thiazol-3-ol (20 g) was added and stirred for 16 hours. Water (20 mL) and 12 N hydrochloric acid aqueous solution (300 mL) were added to the reaction solution, which was then extracted three times with ethyl acetate (200 mL), washed with saturated saline (20 mL), and dried with sodium sulfate. The solvent was distilled off under reduced pressure, and acetone (300 mL) was added to solidify the residue and obtain the title compound (9.3 g) as a yellow solid.

Example 2

Synthesis of 5-(5-bromoindazol-1-yl)-1-oxo-1,2-thiazol-3-ol

60% sodium hydride (2.64 g) was added to a tetrahydrofuran (150 mL) solution of 5-bromo-1H-indazole (6.5 g) and 5-chloro-1-oxo-1,2-thiazol-3-ol (5 g), and stirred for 2.5 hours at 60° C. Water (300 mL) was added to the reaction solution, which was then washed twice with ethyl acetate (300 mL), after which 1 N hydrochloric acid aqueous solution was added to the water layer to lower the pH to 3 and precipitate a solid. The precipitated solid was collected by filtration, and washed twice with ethyl acetate (300 mL) to obtain the title compound (5.7 g) as a yellow solid.

Example 3

Synthesis of 5-[5-(2-methoxypyridin-4-yl)indazol-1-yl]-1-oxo-1,2-thiazol-3-ol 2-methoxypyridin-4-boronic acid (1.15 g), 2-dicyclohexylphosphino-2',6'-dimethoxy-1,1'-biphenyl (0.47 g), potassium carbonate (4.78 g) and bis(dibenzylideneacetone) palladium (0.33 g) were added to a solution of the 5-(5-bromoindazol-1-yl)-1-oxo-1,2-thiazol-3-ol (1.8 g) synthesized in Example 2 in a mixture of 1,4-dioxane (60 mL) and water (20 mL), and stirred for 2 hours at 100° C. Water (10 mL) was added to the reaction solution, which was then washed with ethyl acetate (5 mL). 1 N hydrochloric acid aqueous solution (5 mL) was added to the water layer to make it acidic, and this was extracted with ethyl acetate, washed sequentially with water and saturated saline, and dried with sodium sulfate. The solvent was distilled off under reduced pressure to obtain the title compound (0.67 g) as a brown solid.

Example 4

Synthesis of 5-[5-(6-cyclopropylpyridin-3-yl)indazol-1-yl]-1-oxo-1,2-thiazol-3-ol (A)

<Step 1> Synthesis of 5-(5-bromoindazol-1-yl)-1-oxo-1,2-thiazol-3-ol (A)

60% sodium hydride (260 mg) was added to a tetrahydrofuran (30 mL) solution of a 5-chloro-1-oxo-1,2-thiazol- 3-ol enantiomer (Reference Example 1 (A) described in WO 2012/147518 (Reference Example 1 (A)) (500 mg) and 5-bromo-1H-indazole (650 mg), and stirred for 16 hours at 60° C. Water was added to the reaction solution, which was then washed with ethyl acetate, after which 1 N hydrochloric acid aqueous solution was added to the water layer to make it acidic and precipitate a solid. The precipitated compound was collected by filtration and washed with ethyl acetate to obtain the title compound (650 mg) as a brown solid.

<Step 2> Synthesis of 5-[5-(6-cyclopropylpyridin-3-yl)indazol-1-yl]-1-oxo-1,2-thiazol-3-ol (A)

2-dicyclohexylphosphino-2',-6'-dimethoxy-1-1'-biphenyl (47 mg), potassium carbonate (480 mg) and bis(dibenzylideneacetone) palladium (33 mg) were added to a solution of the 5-(5-bromoindazol-1-yl)-1-oxo-1,2-thiazol-3-ol (A) (180 mg) obtained in Step 1 of Example 4 and 2-cyclopropyl-5-(4,4,5,5-tetramethyl-1,3,2-dioxaborolan-2-yl)pyridine (280 mg) dissolved in a mixed solvent of 1,4-dioxane (4.0 ml) and water (2.0 ml), and stirred for 18 hours at 100° C. Water was added to the reaction solution, which was then washed with ethyl acetate, and 1 N hydrochloric acid aqueous solution was added to the water layer to make it acidic and precipitate a solid. The precipitated compound was collected by filtration and washed with ethyl acetate to obtain the title compound (31 mg) as a brown solid.

Example 5

Synthesis of 5-[5-(4-methyl-2,3-dihydropyrido[3,2-b][1,4]oxadin-7-yl)indazol-1-yl]-1-oxo-1,2-thiazol-3-ol (A)

Potassium carbonate (770 mg) and [1,1'-bis(diphenylphosphino)ferrocene]dichloropalladium (II) dichloromethane adduct (92 mg) were added to a solution of the 5-(5-bromoindazol-1-yl)-1-oxo-1,2-thiazol-3-ol (A) (350 mg) obtained in Step 1 of Example 4 and 4-methyl-7-(4,4,5,5-tetramethyl-1,3,2-dioxaborolan-2-yl)-3,4-dihydro-2H-pyrido[3,2-b][1,4]oxazine (620 mg) dissolved in a mixed solvent of 1,4-dioxane (3 ml) and water (1.5 ml), and stirred for 2 hours at 100° C. Water was added to the reaction solution, which was then washed with ethyl acetate, and 1 N hydrochloric acid aqueous solution was added to the water layer to make it acidic and precipitate a solid. The precipitated compound was collected by filtration and washed with ethyl acetate to obtain the title compound (245 mg) as a brown solid.

The $^1$H-NMR data (unmarked: 400 MHz NMR, marked *: 300 MHz NMR) for the final compounds and intermediate compounds of Examples 1 to 5 are shown in Table 1 below.

TABLE 1

| Example | NMR data (δ: ppm) <*300 MHz> |
|---|---|
| 1 | $^1$H-NMR (DMSO-d$_6$*) δ: 11.14 (s, 1H), 8.70 (d, 1H, J = 1.0 Hz), 8.18 (dd, 1H, J = 8.4, 1.0 Hz), 7.98-8.01 (m, 1H), 7.66-7.72 (1H, m), 7.45-7.51 (m, 1H), 7.03 (s, 1H) |
| 2 | $^1$H-NMR (DMSO-d$_6$) δ: 11.23 (s, 1H), 8.67 (s, 1H), 8.26 (d, 1H, J = 1.5 Hz), 8.18 (d, 1H, J = 8.9 Hz), 7.80 (dd, 1H, J = 8.9, 1.5 Hz), 7.09 (s, 1H) |
| 3 | $^1$H-NMR (DMSO-d$_6$*) δ: 11.19 (s, 1H), 8.77 (s, 1H), 8.42-8.43 (m, 1H), 8.26-8.32 (m, 2H), 8.08 (dd, 1H, J = 8.9, 1.7 Hz), 7.44 (dd, 1H, J = 5.3, 1.5 Hz), 7.24-7.25 (m, 1H), 7.13 (s, 1H), 3.92 (s, 3H) |

TABLE 1-continued

| Example | NMR data (δ: ppm) <*300 MHz> |
|---|---|
| 4-1 | $^1$H-NMR (DMSO-d$_6$); 11.2 (brs, 1H), 8.66 (d, 1H, J = 3.0 Hz), 8.26 (d, 1H, J = 1.5 Hz), 8.18 (1H, d, J = 9.0 Hz), 7.81 (1H, dd, J = 1.5, 9.0 Hz), 7.08 (s, 1H) |
| 4 | $^1$H-NMR (DMSO-d$_6$); 11.2 (brs, 1H), 8.81 (d, 1H, J = 2.5 Hz), 8.73 (s, 1H), 8.27-8.29 (m, 2H), 8.05 (dd, 1H, J = 3.0, 8.5 Hz), 7.99 (dd, 1H, 1.5, 8.5 Hz), 7.43 (d, 1H, J = 8.5 Hz), 7.07 (s, 1H), 2.16-2.19 (m, 1H), 0.97-1.01 (m, 4H) |
| 5 | $^1$H-NMR (DMSO-d$_6$); 11.1 (brs, 1H), 8.67 (s, 1H), 8.19 (1H, d, J = 8.5 Hz), 8.15 (d, 1H, J = 2.0 Hz), 8.11 (d, 1H, J = 2.0 Hz), 7.90 (dd, 1H, J = 2.0, 8.5 Hz), 7.37 (d, 1H, J = 2.0 Hz), 7.01 (s, 1H), 4.27 (t, 2H, J = 4.0 Hz), 3.49 (t, 2H, J = 4.0 Hz), 3.08 (s, 3H) |

The compounds of Examples 6 to 461 under Embodiment [3] above were synthesized using commercial compounds or known compounds, in accordance with methods similar to those used in Example 4 or Example 5 or analogous methods.

The LC-Mass data, mass measurement method (method), isothiazole ring isomer structure (structure) and pharmacological activity value (EC$_{50}$) for the final compounds of Examples 1 to 461 are given in Table 2 below.

For the activity values in Table 2, EC$_{50}$ values measured by the methods of Pharmacological Test Example 1 are rated as A (EC$_{50}$<1 μM), B (1 μM EC$_{50}$<5 μM) or C (5 μM≤EC$_{50}$<10 μM).

TABLE 2

| Example | MS-ESI (m/z) [M + H]$^+$ | RT (min) | Method | Structure | EC$_{50}$ |
|---|---|---|---|---|---|
| 1 | 234 | 0.78 | A | r | B |
| 2 | 312 | 0.91 | A | r | A |
| 3 | 341 | 0.93 | A | r | A |
| 4 | 351 | 0.71 | A | A | A |
| 5 | 382 | 0.72 | A | A | A |
| 6 | 355 | 0.89 | A | r | B |
| 7 | 312 | 3.20 | D | r | B |
| 8 | 410 | 0.79 | A | r | A |
| 9 | 342 | 1.03 | A | A | B |
| 10 | 382 | 0.75 | A | A | A |
| 11 | 274** | 0.8 | A | r | B |
| 12 | 268 | 0.89 | A | r | A |
| 13 | 312 | 0.89 | A | r | |
| 14 | 302 | 0.93 | A | r | A |
| 15 | 282 | 0.98 | A | r | B |
| 16 | 234 | 0.77 | A | A | B |
| 17 | 234 | 0.77 | A | B | C |
| 18 | 262 | 0.93 | A | r | A |
| 19 | 281** | 0.7 | A | r | B |
| 20 | 277 | 0.61 | A | r | B |
| 21 | 293 | 0.93 | A | r | B |
| 22 | 406 | 1.09 | A | r | B |
| 23 | 248 | 0.88 | A | r | B |
| 24 | 264 | 0.84 | A | r | B |
| 25 | 248 | 0.88 | A | r | C |
| 26 | 340 | 1.05 | A | r | B |
| 27 | 274 | 0.97 | A | r | B |
| 28 | 310 | 1.05 | A | r | B |
| 29 | 268 | 0.93 | A | r | B |
| 30 | 340 | 1.07 | A | r | C |
| 31 | 268 | 0.88 | A | r | B |
| 32 | 248 | 0.88 | A | r | B |
| 33 | 302 | 0.92 | A | r | B |
| 34 | 248 | 0.92 | A | r | B |
| 35 | 302 | 1.00 | A | r | |
| 36 | 264 | 0.80 | A | r | |
| 37 | 268 | 0.90 | A | r | B |
| 38 | 311 | 0.59 | A | r | A |
| 39 | 350 | 0.98 | A | r | A |

TABLE 2-continued

| Example | MS-ESI (m/z) [M + H]+ | RT (min) | Method | Structure | EC50 |
|---|---|---|---|---|---|
| 40 | 344 | 1.03 | A | r | A |
| 41 | 312 | 0.76 | A | r | B |
| 42 | 316 | 0.89 | A | r | A |
| 43 | 311* | 0.69 | A | r | A |
| 44 | 415 | 1.08 | A | r | A |
| 45 | 326 | 0.65 | A | r | B |
| 46 | 351 | 0.71 | A | r | A |
| 47 | 341 | 0.61 | A | r | B |
| 48 | 316* | 0.59 | A | r | |
| 49 | 325 | 0.65 | A | r | A |
| 50 | 314 | 0.84 | A | r | A |
| 51 | 300 | 0.8 | A | r | C |
| 52 | 409* | 0.67 | A | r | A |
| 53 | 409* | 0.67 | A | A | A |
| 54 | 311 | 0.61 | A | A | A |
| 55 | 264 | 0.73 | A | r | A |
| 56 | 325 | 0.65 | A | A | A |
| 57 | 363 | 0.84 | A | r | |
| 58 | 311 | 0.6 | A | r | A |
| 59 | 396 | 0.68 | A | r | A |
| 60 | 341* | 0.6 | A | r | |
| 61 | 351 | 0.9 | A | r | A |
| 62 | 417 | 1.07 | A | r | A |
| 63 | 411 | 0.96 | A | r | C |
| 64 | 377 | 0.91 | A | r | B |
| 65 | 407 | 0.91 | A | r | C |
| 66 | 367 | 0.91 | A | r | B |
| 67 | 367 | 0.92 | A | r | |
| 68 | 393 | 0.92 | A | r | B |
| 69 | 342 | 0.96 | A | r | B |
| 70 | 312 | 0.83 | A | r | A |
| 71 | 445 | 3.6 | D | r | B |
| 72 | 311* | 3.17 | E | A | A |
| 73 | 375 | 1.1 | A | r | A |
| 74 | 402 | 1.17 | A | r | A |
| 75 | 407 | 0.95 | A | r | B |
| 76 | 364 | 0.97 | A | r | B |
| 77 | 409 | 0.72 | A | r | A |
| 78 | 310 | 1.04 | A | r | B |
| 79 | 310 | 1.05 | A | r | B |
| 80 | 312 | 0.79 | A | r | |
| 81 | 312 | 0.77 | A | r | C |
| 82 | 312 | 4.38 | B | r | A |
| 83 | 328 | 1.03 | A | r | A |
| 84 | 328 | 1.04 | A | r | A |
| 85 | 328 | 1.04 | A | r | A |
| 86 | 341 | 0.96 | A | r | A |
| 87 | 380 | 0.73 | A | r | B |
| 88 | 350 | 0.68 | A | r | |
| 89 | 312 | 4.38 | B | A | A |
| 90 | 394 | 0.76 | A | r | A |
| 91 | 382 | 0.72 | A | r | A |
| 92 | 311 | 0.64 | A | r | B |
| 93 | 350 | 1.01 | A | r | B |
| 94 | 344 | 1.06 | A | r | |
| 95 | 316 | 0.89 | A | r | C |
| 96 | 437** | 1.08 | A | r | |
| 97 | 341 | 0.96 | A | r | B |
| 98 | 351 | 0.75 | A | r | B |
| 99 | 341 | 0.60 | A | r | |
| 100 | 325 | 0.66 | A | r | B |
| 101 | 314 | 0.85 | A | r | B |
| 102 | 350 | 1.02 | A | r | B |
| 103 | 316 | 0.90 | A | r | B |
| 104 | 437** | 1.08 | A | r | B |
| 105 | 314 | 0.87 | A | r | |
| 106 | 380 | 0.72 | A | r | B |
| 107 | 380 | 0.7 | A | r | B |
| 108 | 336 | 0.89 | A | r | B |
| 109 | 311 | 0.63 | A | r | |
| 110 | 341 | 0.95 | A | r | B |
| 111 | 351 | 0.72 | A | r | B |
| 112 | 341 | 0.63 | A | r | |
| 113 | 325 | 0.66 | A | r | C |
| 114 | 311 | 0.61 | A | r | |
| 115 | 311 | 0.59 | A | r | |
| 116 | 361 | 0.98 | A | r | A |
| 117 | 325 | 0.64 | A | r | A |
| 118 | 326 | 0.89 | A | r | B |
| 119 | 329 | 0.93 | A | r | B |
| 120 | 336 | 0.93 | A | r | B |
| 121 | 345 | 1.01 | A | r | B |
| 122 | 352 | 1 | A | r | B |
| 123 | 326 | 0.88 | A | r | A |
| 124 | 341 | 0.95 | A | r | A |
| 125 | 327 | 0.75 | A | r | B |
| 126 | 396 | 0.71 | A | r | B |
| 127 | 342 | 0.86 | A | r | |
| 128 | 326 | 0.77 | A | r | |
| 129 | 341 | 1.05 | A | r | A |
| 130 | 379 | 1.04 | A | r | A |
| 131 | 394 | 0.98 | A | r | |
| 132 | 379 | 1.05 | A | r | A |
| 133 | 403 | 0.87 | A | r | |
| 134 | 341 | 0.65 | A | r | |
| 135 | 380 | 0.75 | A | r | A |
| 136 | 354 | 0.68 | A | r | A |
| 137 | 317* | 0.61 | A | r | |
| 138 | 380 | 0.74 | A | r | A |
| 139 | 380 | 0.79 | A | r | A |
| 140 | 395 | 1.11 | A | r | A |
| 141 | 381 | 1.06 | A | r | A |
| 142 | 397 | 0.96 | A | r | B |
| 143 | 396 | 0.75 | A | r | A |
| 144 | 341 | 4.17 | B | r | B |
| 145 | 327 | 0.78 | A | r | |
| 146 | 354 | 0.69 | A | r | |
| 147 | 396 | 0.69 | A | r | |
| 148 | 326 | 5.43 | B | r | B |
| 149 | 408 | 0.74 | A | r | A |
| 150 | 422 | 0.83 | A | r | A |
| 151 | 472 | 5.27 | B | r | A |
| 152 | 368 | 3.57 | B | r | B |
| 153 | 394 | 0.8 | A | r | A |
| 154 | 382 | 0.83 | A | r | |
| 155 | 352 | 0.69 | A | r | |
| 156 | 380 | 0.84 | A | r | |
| 157 | 408 | 0.9 | A | r | B |
| 158 | 366 | 0.7 | A | A | A |
| 159 | 442 | 1.01 | A | A | C |
| 160 | 424 | 0.85 | A | A | A |
| 161 | 422 | 3.47 | B | r | A |
| 162 | 436 | 5.88 | B | r | A |
| 163 | 388 | 0.86 | A | A | A |
| 164 | 394 | 0.94 | A | A | C |
| 165 | 382 | 0.81 | A | A | B |
| 166 | 341 | 0.74 | A | A | B |
| 167 | 355 | 0.75 | A | A | B |
| 168 | 421 | 0.96 | A | A | C |
| 169 | 416 | 5.63 | B | A | A |
| 170 | 450 | 1.03 | A | A | B |
| 171 | 341 | 0.79 | A | A | C |
| 172 | 426 | 0.78 | A | A | A |
| 173 | 384 | 0.74 | A | A | A |
| 174 | 412 | 0.8 | A | A | B |
| 175 | 410 | 0.75 | A | A | A |
| 176 | 424 | 0.79 | A | A | B |
| 177 | 342 | 0.97 | A | A | A |
| 178 | 382 | 0.97 | A | A | A |
| 179 | 382 | 0.94 | A | A | A |
| 180 | 424 | 0.82 | A | A | A |
| 181 | 410 | 0.75 | A | A | B |
| 182 | 416 | 0.77 | A | A | A |
| 183 | 304 | 1.01 | A | A | B |
| 184 | 407 | 5.08 | B | A | A |
| 185 | 396 | 3.85 | B | A | A |
| 186 | 394 | 0.95 | A | A | A |
| 187 | 424 | 1.05 | A | A | A |
| 188 | 410 | 0.8 | A | A | A |
| 189 | 396 | 0.8 | A | A | A |
| 190 | 382 | 0.75 | A | A | A |
| 191 | 264 | 4.28 | C | A | B |

TABLE 2-continued

| Example | MS-ESI (m/z) [M + H]+ | RT (min) | Method | Structure | EC50 |
|---|---|---|---|---|---|
| 192 | 412 | 0.81 | A | A | A |
| 193 | 410 | 0.79 | A | A | A |
| 194 | 410 | 0.79 | A | A | A |
| 195 | 355 | 0.76 | A | A | B |
| 196 | 278 | 4.73 | B | A | B |
| 197 | 396 | 4.95 | B | A | A |
| 198 | 424 | 3.9 | B | A | A |
| 199 | 341 | 4.55 | B | A | B |
| 200 | 341 | 4.22 | B | A | B |
| 201 | 371 | 5.45 | B | A | A |
| 202 | 371 | 3.18 | B | A | |
| 203 | 381 | 5.3 | B | A | A |
| 204 | 432 | 1.03 | A | A | A |
| 205 | 410 | 4.63 | B | A | A |
| 206 | 396 | 3.85 | B | A | A |
| 207 | 342 | 0.95 | A | A | A |
| 208 | 459* | 5.10 | B | A | |
| 209 | 396 | 0.76 | A | A | A |
| 210 | 383 | 4.68 | C | A | A |
| 211 | 412 | 0.75 | A | A | A |
| 212 | 408 | 0.75 | A | A | A |
| 213 | 410 | 0.78 | A | A | A |
| 214 | 383 | 4.18 | B | A | |
| 215 | 383 | 4.62 | B | A | A |
| 216 | 422 | 5.32 | B | A | B |
| 217 | 396 | 0.79 | A | A | A |
| 218 | 397 | 4.38 | B | A | B |
| 219 | 368 | 3.08 | B | A | A |
| 220 | 369 | 4.53 | B | A | A |
| 221 | 407 | 5.90 | C | A | B |
| 222 | 382 | 3.23 | B | A | A |
| 223 | 412 | 0.82 | A | A | B |
| 224 | 364 | 5.4 | B | A | A |
| 225 | 351 | 0.92 | A | A | A |
| 226 | 314 | 0.85 | A | A | A |
| 227 | 269 | 0.77 | A | r | B |
| 228 | 235 | 0.6 | A | r | |
| 229 | 249 | 0.56 | A | r | B |
| 230 | 235 | 2.22 | B | r | |
| 231 | 235 | 0.53 | A | r | C |
| 232 | 269 | 0.7 | A | r | |
| 233 | 311 | 0.92 | A | r | A |
| 234 | 313 | 0.76 | A | r | B |
| 235 | 312 | 0.57 | A | r | B |
| 236 | 317 | 0.8 | A | r | B |
| 237 | 352 | 0.67 | A | r | A |
| 238 | 235 | 0.72 | A | r | B |
| 239 | 285 | 4.75 | B | r | A |
| 240 | 381 | 0.7 | A | r | B |
| 241 | 395 | 0.75 | A | r | B |
| 242 | 265 | 0.76 | A | A | A |
| 243 | 383* | 0.69 | A | A | A |
| 244 | 375** | 0.96 | A | A | B |
| 245 | 347** | 0.9 | A | A | B |
| 246 | 347** | 0.92 | A | A | B |
| 247 | 361** | 0.9 | A | A | B |
| 248 | 361** | 0.91 | A | A | B |
| 249 | 375** | 0.89 | A | A | |
| 250 | 376** | 0.92 | A | A | B |
| 251 | 487** | 1.01 | A | A | C |
| 252 | 329* | 0.54 | A | A | B |
| 253 | 343 | 0.76 | A | A | |
| 254 | 343 | 0.79 | A | A | |
| 255 | 315* | 0.53 | A | A | B |
| 256 | 329* | 0.53 | A | A | B |
| 257 | 335* | 0.62 | A | A | B |
| 258 | 335* | 0.63 | A | A | |
| 259 | 333* | 0.42 | A | A | |
| 260 | 333* | 0.40 | A | A | |
| 261 | 360* | 0.51 | A | A | B |
| 262 | 330* | 0.46 | A | A | |
| 263 | 366 | 3.75 | B | A | B |
| 264 | 407 | 5.22 | B | A | B |
| 265 | 384 | 4.25 | B | A | C |
| 266 | 346* | 2.68 | B | A | C |
| 267 | 366 | 3.38 | B | A | |
| 268 | 316 | 0.82 | B | A | |
| 269 | 384 | 3.83 | B | A | |
| 270 | 316* | 0.40 | A | A | |
| 271 | 346 | 2.27 | B | A | |
| 272 | 307 | 0.69 | A | A | |
| 273 | 321* | 0.59 | A | A | A |
| 274 | 317 | 2.18 | B | A | |
| 275 | 321* | 0.60 | A | A | B |
| 276 | 317 | 1.47 | B | A | |
| 277 | 407* | 0.81 | A | A | B |
| 278 | 316 | 1.08 | B | A | |
| 279 | 316* | 0.45 | A | A | |
| 280 | 329 | 0.78 | A | A | A |
| 281 | 329 | 0.78 | A | A | A |
| 282 | 199* | 0.3 | A | r | |
| 283 | 228 | 0.53 | A | r | |
| 284 | 184 | 0.48 | A | r | B |
| 285 | 321** | 0.87 | A | r | |
| 286 | 338 | 1.03 | A | r | A |
| 287 | 310 | 0.73 | A | r | B |
| 288 | 256 | 0.74 | A | r | |
| 289 | 212 | 0.66 | A | r | |
| 290 | 338 | 1.01 | A | r | A |
| 291 | 269 | 0.71 | A | r | |
| 292 | 269 | 0.66 | A | r | |
| 293 | 267 | 0.68 | A | r | |
| 294 | 281 | 0.76 | A | r | |
| 295 | 311 | 0.65 | A | r | |
| 296 | 444 | 0.95 | A | r | |
| 297 | 466** | 0.96 | A | r | |
| 298 | 351 | 0.87 | A | r | |
| 299 | 343 | 0.94 | A | r | |
| 300 | 305 | 0.62 | A | r | |
| 301 | 300 | 0.88 | A | r | A |
| 302 | 303 | 0.83 | A | r | |
| 303 | 281 | 0.68 | A | r | |
| 304 | 387** | 1 | A | r | B |
| 305 | 338 | 0.87 | A | r | B |
| 306 | 266 | 1.00 | A | r | B |
| 307 | 288 | 0.95 | A | r | A |
| 308 | 268 | 0.69 | A | r | C |
| 309 | 304** | 0.74 | A | r | |
| 310 | 274 | 0.93 | A | r | B |
| 311 | 288 | 0.96 | A | r | C |
| 312 | 328 | 0.94 | A | r | C |
| 313 | 393 | 1.01 | A | r | C |
| 314 | 422 | 1.27 | A | r | |
| 315 | 292 | 1.05 | A | r | B |
| 316 | 320 | 1.14 | A | r | B |
| 317 | 364 | 1 | A | r | B |
| 318 | 286 | 0.97 | A | r | B |
| 319 | 261 | 0.47 | A | r | |
| 320 | 262 | 0.61 | A | r | |
| 321 | 344 | 0.66 | A | r | B |
| 322 | 330 | 0.61 | A | r | B |
| 323 | 301 | 0.58 | A | r | A |
| 324 | 358 | 0.94 | A | r | A |
| 325 | 373 | 0.74 | A | r | |
| 326 | 336 | 1.11 | A | r | A |
| 327 | 336 | 1.09 | A | r | B |
| 328 | 336 | 1.06 | A | r | B |
| 329 | 304 | 0.92 | A | r | B |
| 330 | 340** | 0.85 | A | r | B |
| 331 | 318 | 0.79 | A | r | |
| 332 | 332 | 0.84 | A | r | |
| 333 | 352 | 1.08 | A | r | A |
| 334 | 352 | 1.07 | A | r | |
| 335 | 352 | 1.07 | A | r | B |
| 336 | 375 | 0.86 | A | r | |
| 337 | 391 | 0.78 | A | r | |
| 338 | 470 | 1.23 | A | r | B |
| 339 | 606 | 1.13 | A | r | B |
| 340 | 310 | 1.03 | A | r | A |
| 341 | 310 | 1.01 | A | r | B |
| 342 | 314 | 1.10 | A | r | A |
| 343 | 311* | 0.58 | A | r | B |

TABLE 2-continued

| Example | MS-ESI (m/z) [M + H]+ | RT (min) | Method | Structure | EC50 |
|---|---|---|---|---|---|
| 344 | 311* | 0.85 | A | r | A |
| 345 | 298 | 1.00 | A | r | A |
| 346 | 318 | 0.89 | A | r | B |
| 347 | 331* | 0.92 | A | r | A |
| 348 | 327 | 0.78 | A | r | |
| 349 | 312 | 1.05 | A | r | A |
| 350 | 311* | 0.64 | A | r | A |
| 351 | 311* | 0.61 | A | r | B |
| 352 | 313 | 0.95 | A | r | A |
| 353 | 313 | 0.96 | A | r | A |
| 354 | 331 | 0.91 | A | r | A |
| 355 | 311* | 0.60 | A | r | B |
| 356 | 311* | 0.61 | A | r | B |
| 357 | 311* | 0.65 | A | r | A |
| 358 | 300 | 0.79 | A | r | |
| 359 | 300 | 0.82 | A | r | |
| 360 | 314 | 0.87 | A | r | A |
| 361 | 439 | 1.05 | A | r | |
| 362 | 377 | 0.99 | A | r | A |
| 363 | 260 | 0.88 | A | r | A |
| 364 | 310 | 0.72 | A | r | B |
| 365 | 310 | 0.72 | A | B | |
| 366 | 513 | 1.03 | A | r | B |
| 367 | 328 | 0.99 | A | r | A |
| 368 | 396 | 1.09 | A | r | A |
| 369 | 325 | 0.88 | A | r | B |
| 370 | 385 | 0.88 | A | r | |
| 371 | 476 | 0.73 | A | r | |
| 372 | 407 | 0.89 | A | r | |
| 373 | 419 | 0.98 | A | r | C |
| 374 | 454 | 1.16 | A | r | B |
| 375 | 434 | 1.12 | A | r | B |
| 376 | 394 | 1.13 | A | r | B |
| 377 | 352 | 1.06 | A | A | A |
| 378 | 352 | 1.07 | A | B | A |
| 379 | 291 | 0.64 | A | r | |
| 380 | 291 | 0.63 | A | r | |
| 381 | 312 | 1.04 | A | A | A |
| 382 | 311 | 0.85 | A | A | A |
| 383 | 311 | 0.64 | A | A | A |
| 384 | 298 | 1 | A | A | A |
| 385 | 252 | 0.76 | A | r | |
| 386 | 261 | 0.56 | A | r | B |
| 387 | 290 | 0.91 | A | r | A |
| 388 | 290 | 0.89 | A | r | A |
| 389 | 290 | 0.87 | A | r | A |
| 390 | 350 | 0.84 | A | r | B |
| 391 | 291 | 0.5 | A | r | |
| 392 | 291 | 0.8 | A | r | A |
| 393 | 291 | 0.83 | A | r | A |
| 394 | 298 | 0.99 | A | B | B |
| 395 | 329 | 0.81 | A | r | B |
| 396 | 329 | 0.89 | A | r | B |
| 397 | 322** | 1.02 | A | r | A |
| 398 | 291 | 0.57 | A | r | B |
| 399 | 321 | 0.96 | A | r | A |
| 400 | 290 | 0.54 | A | r | B |
| 401 | 275 | 0.51 | A | r | C |
| 402 | 305 | 0.75 | A | r | B |
| 403 | 359 | 0.55 | A | r | |
| 404 | 291 | 0.73 | A | r | A |
| 405 | 317 | 0.59 | A | r | B |
| 406 | 317 | 0.6 | A | r | C |
| 407 | 262* | 0.68 | A | r | B |
| 408 | 312 | 0.93 | A | r | A |
| 409 | 261* | 0.45 | A | r | |
| 410 | 227 | 0.72 | A | r | |
| 411 | 227 | 0.79 | A | r | |
| 412 | 305 | 0.53 | A | r | B |
| 413 | 276 | 0.75 | A | r | B |
| 414 | 302 | 0.89 | A | r | A |
| 415 | 330 | 0.92 | A | r | B |
| 416 | 276 | 0.76 | A | r | B |
| 417 | 312 | 0.83 | A | r | B |
| 418 | 235 | 0.65 | A | r | |
| 419 | 330 | 0.87 | A | r | B |
| 420 | 343 | 0.94 | A | r | B |
| 421 | 290 | 0.79 | A | r | B |
| 422 | 250 | 0.68 | A | r | C |
| 423 | 262 | 0.7 | A | r | B |
| 424 | 331 | 0.85 | A | r | C |
| 425 | 357 | 0.91 | A | r | B |
| 426 | 354 | 0.73 | A | r | |
| 427 | 330 | 0.83 | A | r | |
| 428 | 262 | 0.68 | A | r | C |
| 429 | 371 | 0.95 | A | r | B |
| 430 | 397 | 1 | A | r | B |
| 431 | 276 | 0.61 | A | r | |
| 432 | 262 | 0.57 | A | r | |
| 433 | 276 | 0.77 | A | r | B |
| 434 | 276 | 0.68 | A | r | |
| 435 | 325 | 1 | A | r | A |
| 436 | 319 | 0.93 | A | r | A |
| 437 | 408 | 0.88 | A | r | B |
| 438 | 279 | 0.76 | A | r | B |
| 439 | 295 | 0.83 | A | A | A |
| 440 | 325 | 1.01 | A | A | A |
| 441 | 407 | 0.75 | A | A | A |
| 442 | 421 | 0.79 | A | A | A |
| 443 | 279 | 0.76 | A | A | B |
| 444 | 368 | 0.94 | A | A | A |
| 445 | 341 | 4.52 | B | r | B |
| 446 | 368 | 0.94 | A | A | A |
| 447 | 368 | 0.88 | A | A | A |
| 448 | 341 | 0.69 | A | A | |
| 449 | 442 | 5.7 | C | A | B |
| 450 | 332 | 0.61 | A | A | A |
| 451 | 267* | 0.44 | A | r | |
| 452 | 323 | 0.84 | A | r | B |
| 453 | 437 | 0.84 | A | A | A |
| 454 | 437 | 0.85 | A | A | A |
| 455 | 386 | 0.85 | A | r | |
| 456 | 392 | 0.92 | A | r | |
| 457 | 338 | 0.72 | A | r | |
| 458 | 371 | 0.85 | A | r | |
| 459 | 374 | 0.62 | A | A | B |
| 460 | 400 | 5.02 | B | r | |
| 461 | 437 | 0.72 | A | r | B |

*[M + H]+ of free form,
**[M + Na]−

The invention claimed is:
1. A compound represented by Formula (I) below, or a pharmaceutically acceptable salt thereof or a solvate of these:

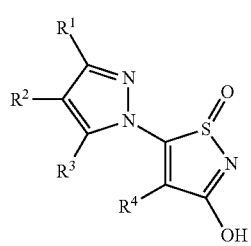

(I)

wherein the formula, $R^1$ represents a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group and a $C_{6-14}$ arylcarbonyl group, R² represents a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group, a $C_{7-20}$ aralkyl group, a heteroaryl $C_{1-6}$ alkyl group, a $C_{6-14}$ aryloxy $C_{1-6}$ alkyl group and a heteroaryloxy $C_{1-6}$ alkyl group, R³ represents a group arbitrarily selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{2-6}$ alkynyloxy group and a cyano group, R⁴ represents a group arbitrarily selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{2-6}$ alkynyloxy group and a cyano group, each of R¹ R² and R³ is optionally substituted with 1 to 5 of R⁵, each R⁵ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{1-6}$ alkoxycarbonyl group, a —NR$^b$R$^c$ group (in which each of R$^b$ and R$^c$ independently represents a hydrogen atom, a $C_{1-6}$ alkyl group or a non-aromatic heterocyclic group), a mono/di-$C_{1-6}$ alkylamino $C_{1-6}$ alkyl group, a $C_{3-8}$ cycloalkyl group, a $C_{3-8}$ cycloalkenyl group, a $C_{6-14}$ aryl group, non-aromatic heterocyclic group, heteroaryl group, a $C_{3-8}$ cycloalkyl $C_{1-6}$ alkyl group, a $C_{7-20}$ aralkyl group, non-aromatic heterocyclic $C_{1-6}$ alkyl group, a heteroaryl $C_{1-6}$ alkyl group, a $C_{6-14}$ aryloxy group, heteroaryloxy group, a $C_{7-20}$ aralkyloxy group and a heteroaryl $C_{1-6}$ alkyloxy group, each of the $C_{3-8}$ cycloalkyl group, $C_{3-8}$ cycloalkenyl group, $C_{6-14}$ aryl group, non-aromatic heterocyclic group, heteroaryl group, $C_{3-8}$ cycloalkyl $C_{1-6}$ alkyl group, $C_{7-20}$ aralkyl group, non-aromatic heterocyclic $C_{1-6}$ alkyl group, heteroaryl $C_{1-6}$ alkyl group, $C_{6-14}$ aryloxy group, heteroaryloxy group, $C_{7-20}$ aralkyloxy group or heteroaryl $C_{1-6}$ alkyloxy group in R⁵ is optionally substituted with 1 to 5 of a group arbitrarily selected from a halogen atom, a $C_{1-6}$ alkyl group, a halogenated $C_{1-6}$ alkyl group, a $C_{1-6}$ alkoxy group, a cyano group, a $C_{1-6}$ alkoxycarbonyl group, a $C_{3-8}$ cycloalkyl group, a $C_{3-8}$ cycloalkenyl group, a $C_{6-14}$ aryl group (which is itself optionally substituted with 1 to 5 $C_{1-6}$ alkyl groups), a non-aromatic heterocyclic group and a heteroaryl group, R² may bind with R¹ or R³ to form a fused ring group together with part of a pyrazole ring, and this fused ring group is a 5- to 10-member heterocyclic group or $C_{6-10}$ aryl group optionally substituted with 1 to 5 of R⁶, each R⁶ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{1-6}$ alkoxycarbonyl group, a $C_{3-8}$ cycloalkyl group, a $C_{3-8}$ cycloalkenyl group, a $C_{6-14}$ aryl group, a non-aromatic heterocyclic group, a heteroaryl group, a $C_{3-8}$ cycloalkyl $C_{1-6}$ alkyl group, a $C_{7-20}$ aralkyl group, a heteroaryl $C_{1-6}$ alkyl group, a $C_{6-14}$ aryloxy group, a heteroaryloxy group, a $C_{7-20}$ aralkyloxy group and a heteroaryl $C_{1-6}$ alkyloxy group, each R₆ is optionally substituted with 1 to 5 of R⁷, each R⁷ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a $C_{1-6}$ alkoxy $C_{1-6}$ alkyl group, a cyano group, a $C_{1-6}$ alkoxycarbonyl group, a —CONR$^d$R$^e$ group (in which each of R$^d$ and R$^e$ independently represents a hydrogen atom, a $C_{1-6}$ alkyl group, a $C_{3-8}$ cycloalkyl group or a $C_{6-14}$ aryl group), a mono/di-$C_{2-7}$ alkanoylamino group, an amino group, a mono/di-$C_{1-6}$ alkylamino group, a mono/di-$C_{1-6}$ alkylamino $C_{1-6}$ alkyl group, a $C_{3-8}$ cycloalkyl group, a $C_{3-8}$ cycloalkenyl group, a $C_{6-14}$ aryl group, a non-aromatic heterocyclic group, a heteroaryl group, a $C_{3-8}$ cycloalkyl $C_{1-6}$ alkyl group, a $C_{7-20}$ aralkyl group, a non-aromatic heterocyclic $C_{1-6}$ alkyl group, a heteroaryl $C_{1-6}$ alkyl group, a $C_{6-14}$ aryloxy group, heteroaryloxy group, a $C_{3-8}$ cycloalkylcarbonyl group, a group, a $C_{6-14}$ arylcarbonyl group and a non-aromatic heterocyclic carbonyl group, and each of the $C_{3-8}$ cycloalkyl group, $C_{3-8}$ cycloalkenyl group, $C_{6-14}$ aryl group, non-aromatic heterocyclic group, heteroaryl group, $C_{3-8}$ cycloalkyl $C_{1-6}$ alkyl group, $C_{7-20}$ aralkyl group, non-aromatic heterocyclic $C_{1-6}$ alkyl group, heteroaryl $C_{1-6}$ alkyl group, $C_{6-14}$ aryloxy group, heteroaryloxy group, $C_{3-8}$ cycloalkylcarbonyl group, $C_{6-14}$ arylcarbonyl group or non-aromatic heterocyclic carbonyl group of R₇ is optionally substituted with 1 to 5 of a halogen atom, a $C_{1-6}$ alkyl group, a halogenated $C_{1-6}$ alkyl group, a $C_{1-6}$ alkoxy group or a $C_{1-6}$ alkoxy $C_{1-6}$ alkyl group.

2. The compound represented by Formula (I)-1 below or a pharmaceutically acceptable salt thereof or a solvate of these according to claim 1:

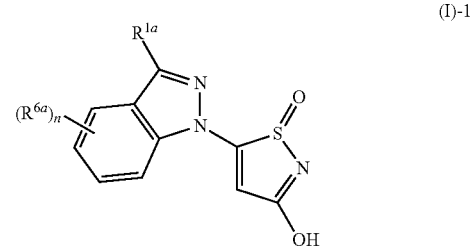

(I)-1 wherein the formula, R$^{1a}$ represents a group arbitrarily selected from a hydrogen atom, a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group and a $C_{6-14}$ arylcarbonyl group, each R$^{1a}$ is optionally substituted with 1 to 5 halogen atoms, each R$^{6a}$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a cyano group, a $C_{3-8}$ cycloalkyl group, a $C_{3-8}$ cycloalkenyl group, a $C_{6-14}$ aryl group, a non-aromatic heterocyclic group, a heteroaryl group, a $C_{6-14}$ aryloxy group, a heteroaryloxy group, a $C_{7-20}$ aralkyloxy group and a heteroaryl $C_{1-6}$ alkyloxy group, each $R^{6a}$ is optionally substituted with 1 to 5 of $R^{7a}$, each $R^{7a}$ independently represents a group arbitrarily selected from a halogen atom, a $C_{1-6}$ alkyl group, a $C_{2-6}$ alkenyl group, a $C_{2-6}$ alkynyl group, a halogenated $C_{1-6}$ alkyl group, a $C_{1-6}$ alkoxy group, a $C_{2-6}$ alkenyloxy group, a $C_{2-6}$ alkynyloxy group, a $C_{1-6}$ alkoxy $C_{1-6}$ alkyl group, a cyano group, a $C_{1-6}$ alkoxycarbonyl group, a —$CONR^dR^e$ group (in which each of $R^d$ and $R^e$ independently represents a hydrogen atom, a $C_{1-6}$ alkyl group, a $C_{3-8}$ cycloalkyl group or a $C_{6-14}$ aryl group), a mono/di-$C_{2-7}$ alkanoylamino group, an amino group, a mono/di-$C_{1-6}$ alkylamino group, a $C_{3-8}$ cycloalkyl group, a $C_{6-14}$ aryl group, a non-aromatic heterocyclic group, a heteroaryl group, a $C_{3-8}$ cycloalkyl $C_{1-6}$ alkyl group, a $C_{7-20}$ aralkyl group, a non-aromatic heterocyclic $C_{1-6}$ alkyl group, a heteroaryl $C_{1-6}$ alkyl group, a $C_{6-14}$ aryloxy group, a heteroaryloxy group, a $C_{3-8}$ cycloalkylcarbonyl group, a $C_{6-14}$ arylcarbonyl group and a non-aromatic heterocyclic carbonyl group, and the $C_{3-8}$ cycloalkyl group, non-aromatic heterocyclic group, $C_{3-8}$ cycloalkyl $C_{1-6}$ alkyl group, non-aromatic heterocyclic $C_{1-6}$ alkyl group, $C_{6-14}$ aryloxy group, $C_{3-8}$ cycloalkylcarbonyl group, $C_{6-14}$ arylcarbonyl group or non-aromatic heterocyclic carbonyl group in each $R^{7a}$ is optionally substituted with 1 to 5 halogen atoms, $C_{1-6}$ alkyl groups, halogenated $C_{1-6}$ alkyl groups, $C_{1-6}$ alkoxy groups or $C_{1-6}$ alkoxy $C_{1-6}$ alkyl groups, and n represents 0, 1 or 2.

3. A compound, a pharmaceutically acceptable salt, a solvate or an optical isomer thereof selected from the following structures:

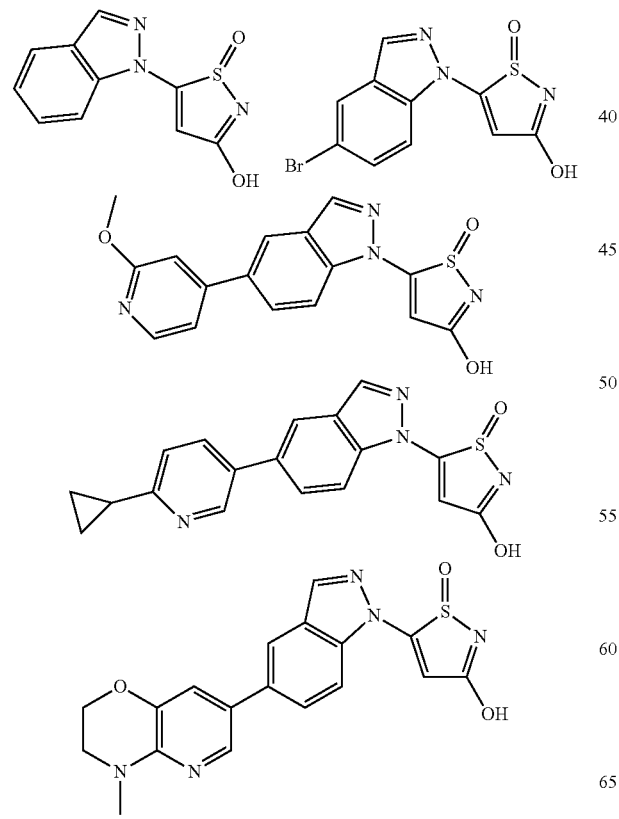

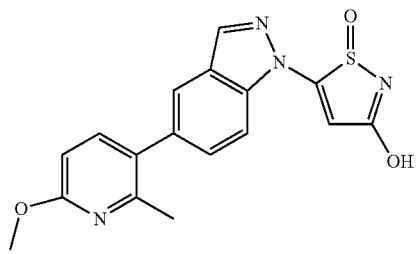

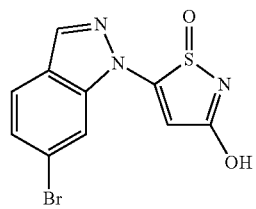

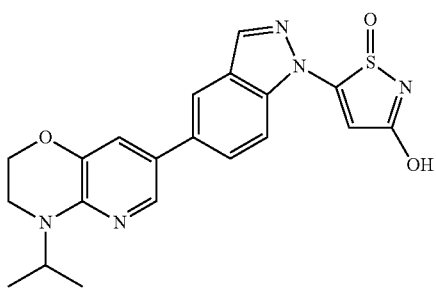

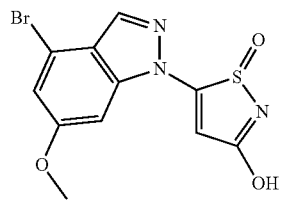

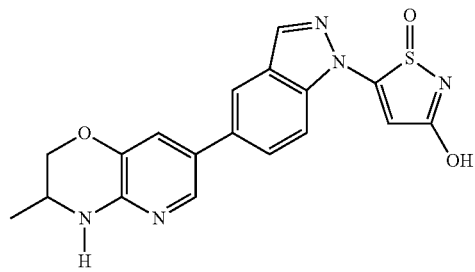

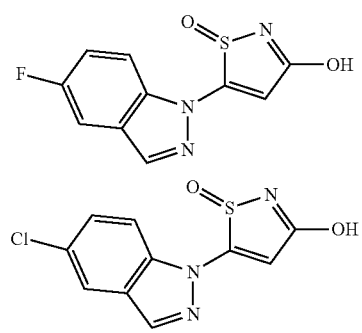

125
-continued
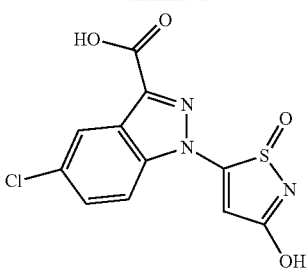
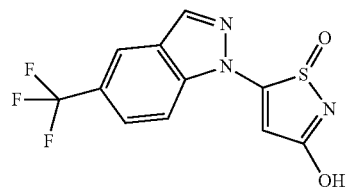
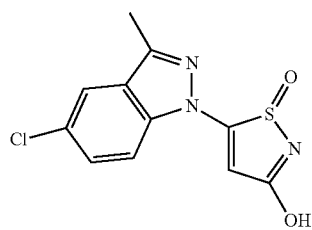
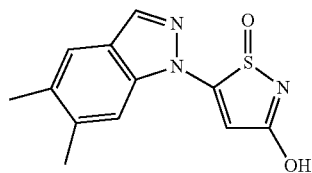
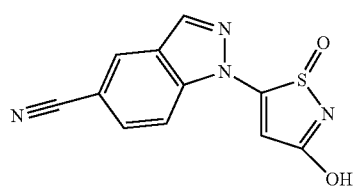
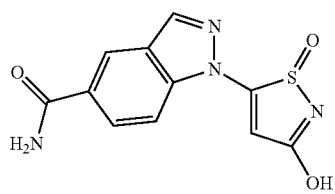
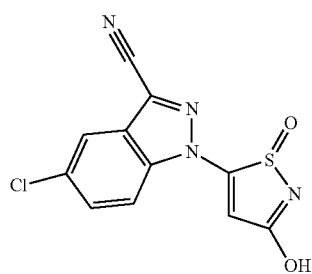
126
-continued
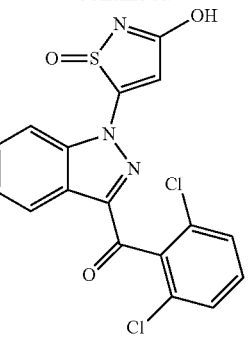
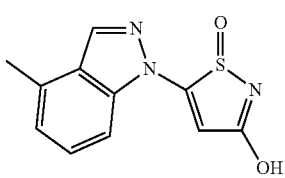
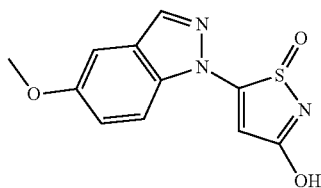
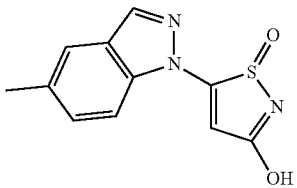
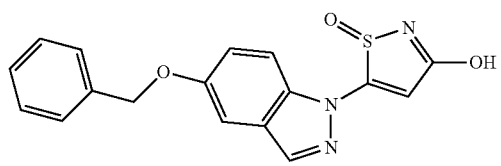
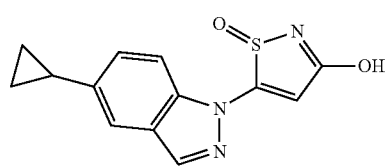
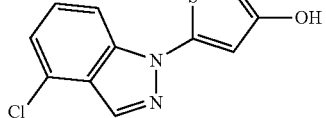

127
-continued
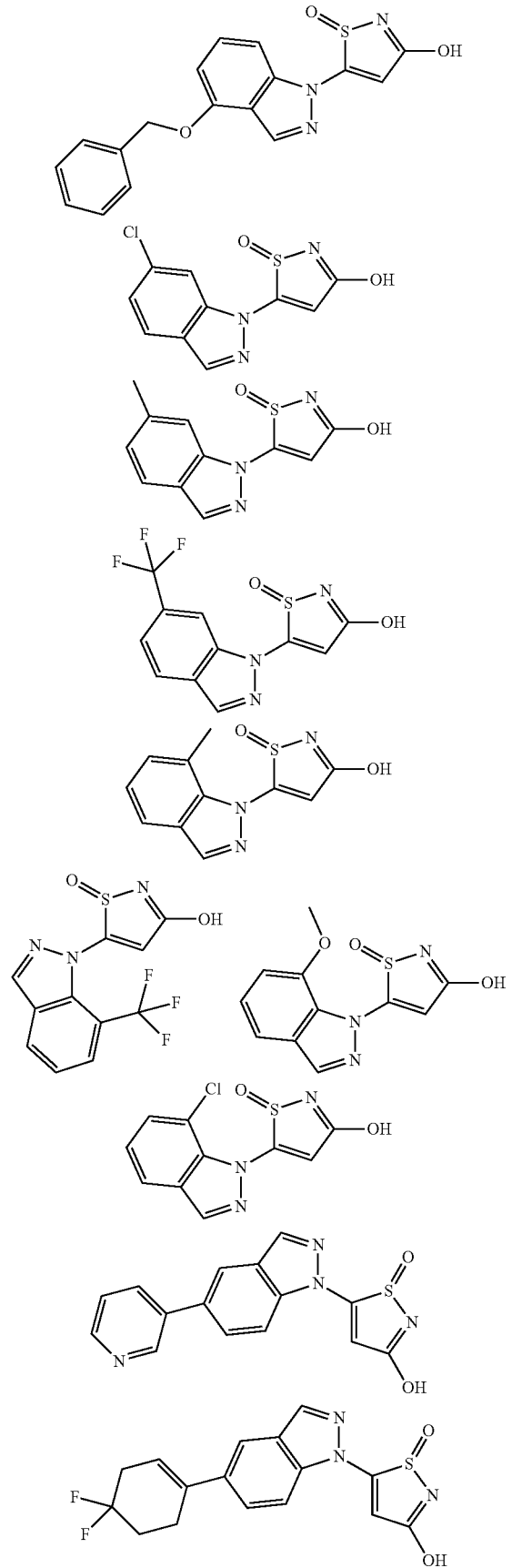
128
-continued
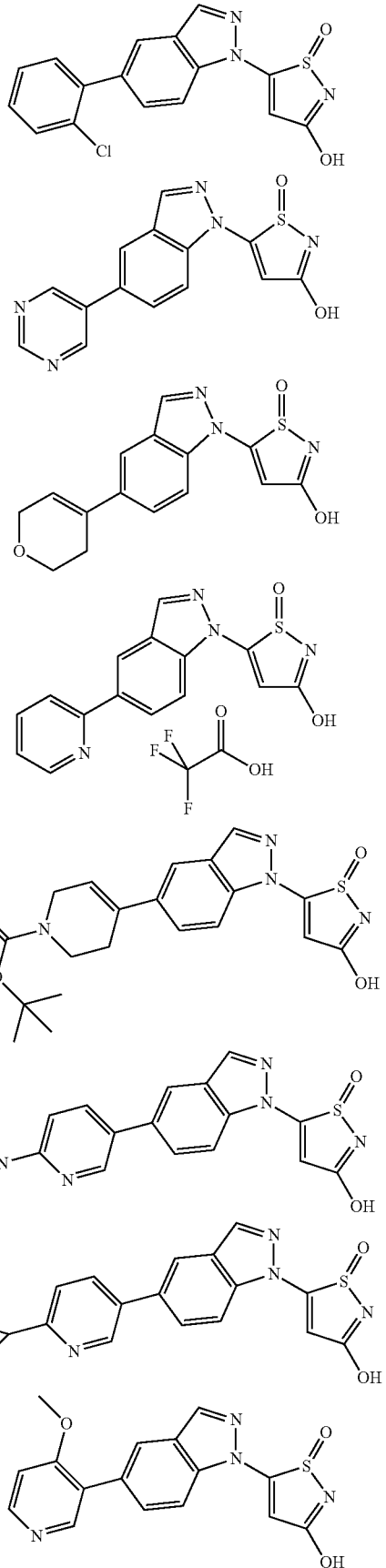

129
-continued
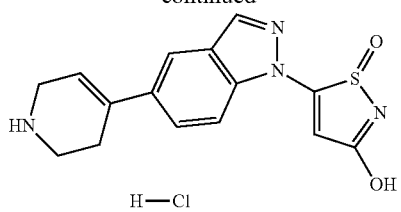
H—Cl
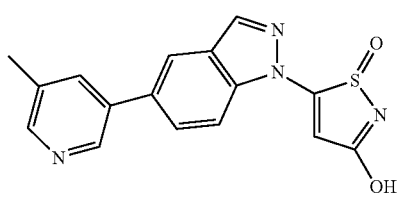
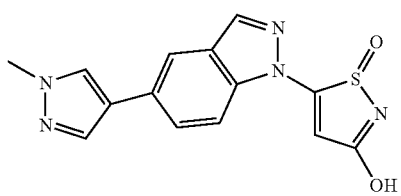
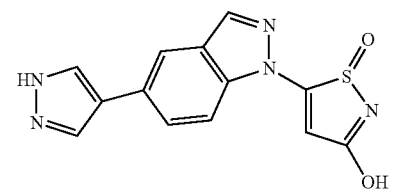
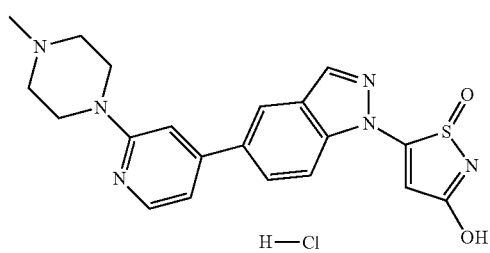
H—Cl
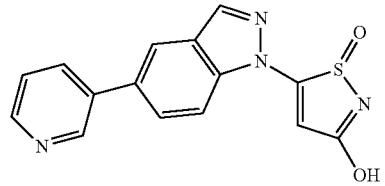
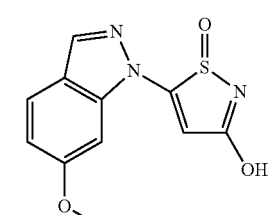
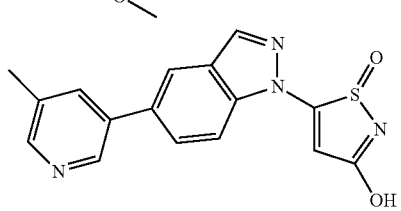
130
-continued
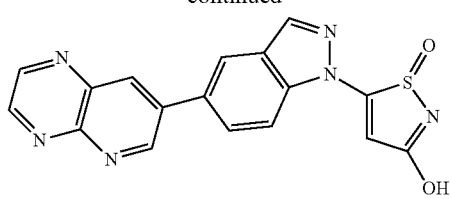
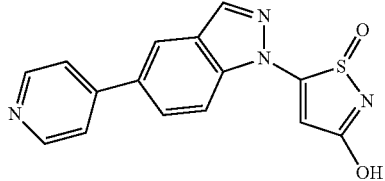
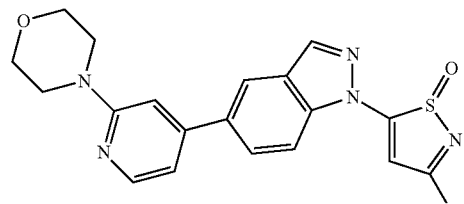
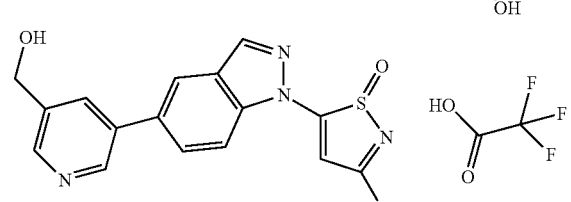
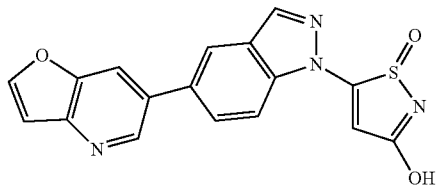
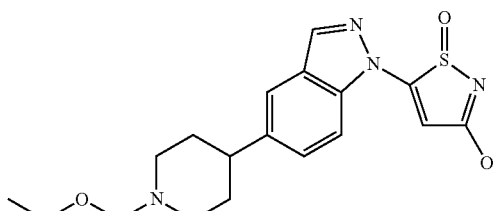
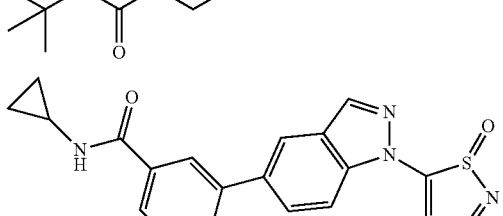
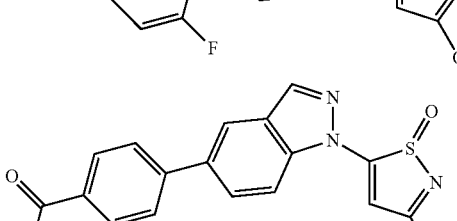

-continued
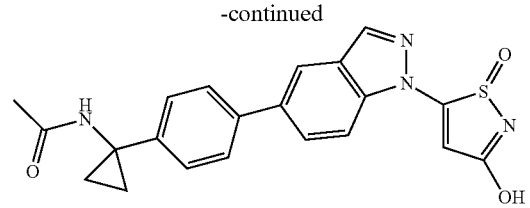
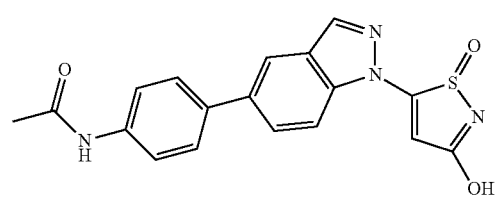
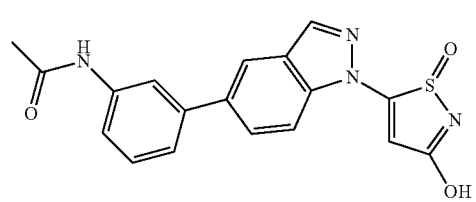
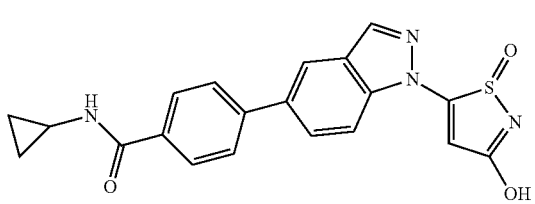
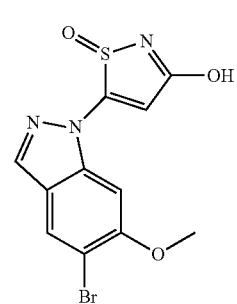
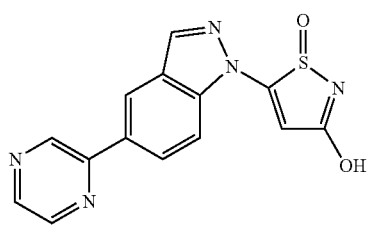
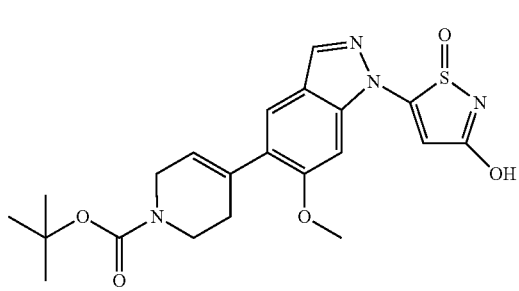
-continued
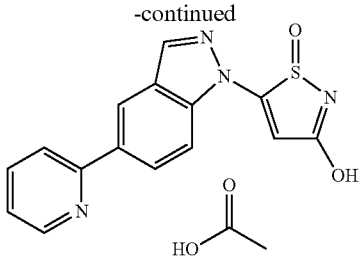
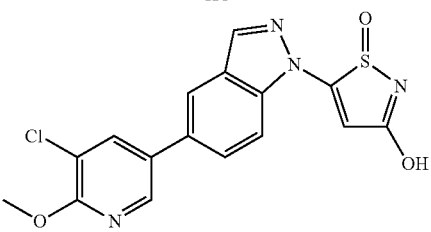
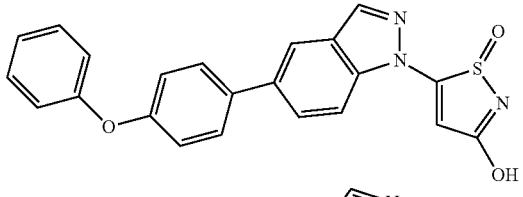
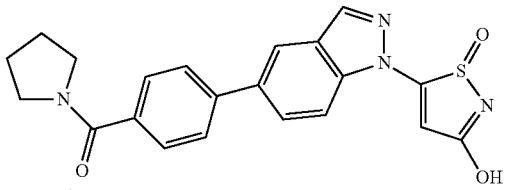
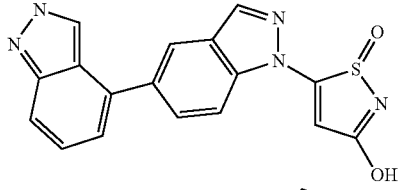
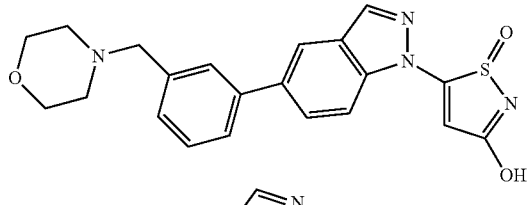
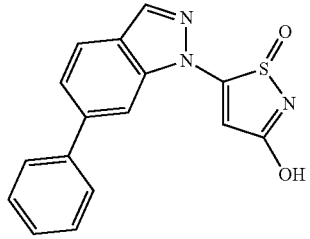
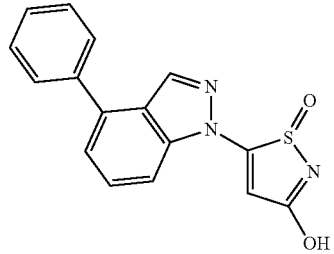

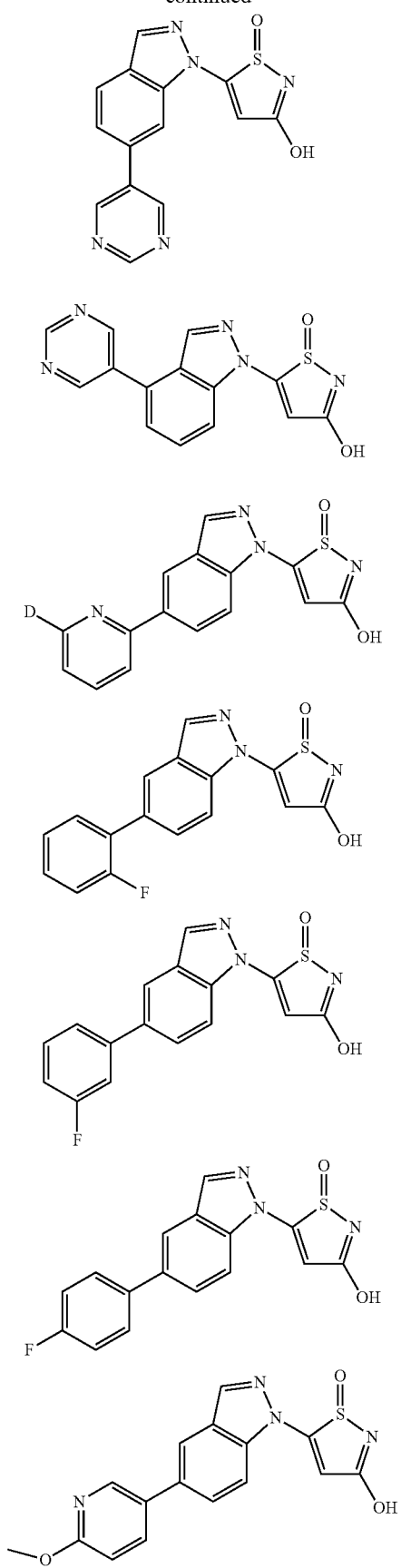
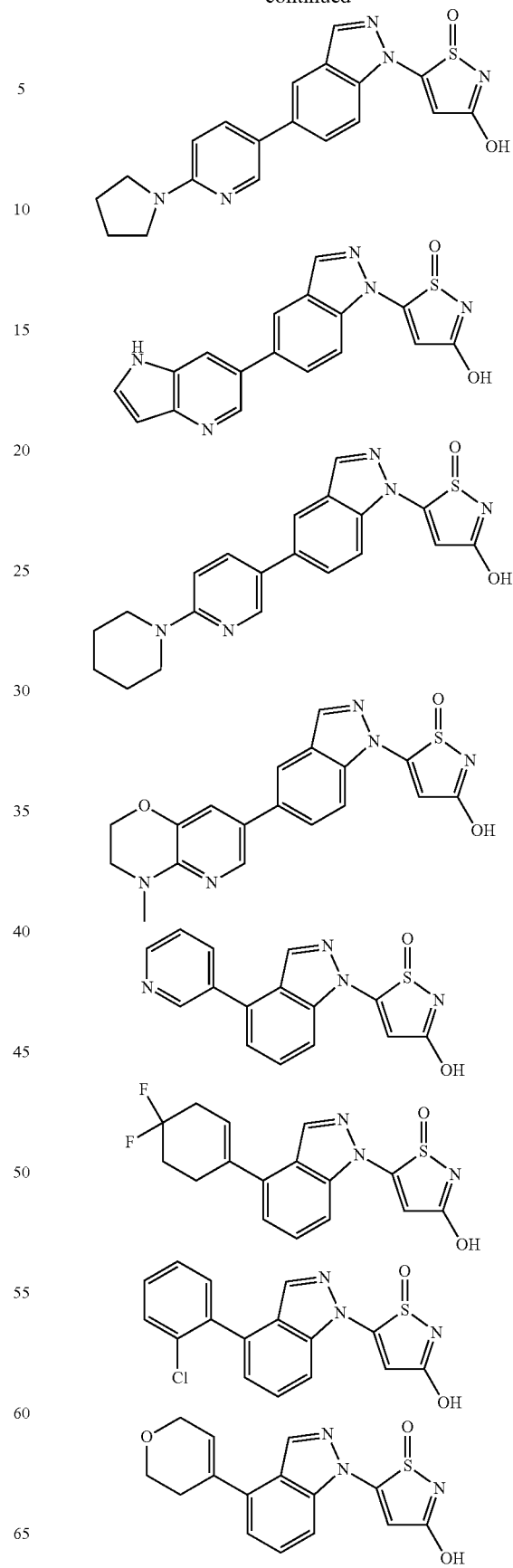

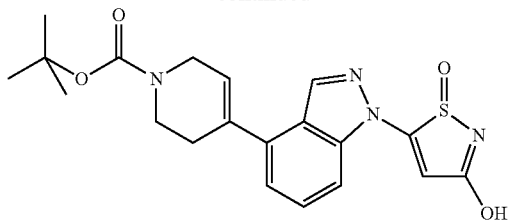
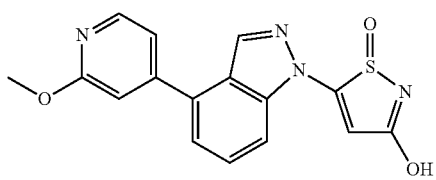
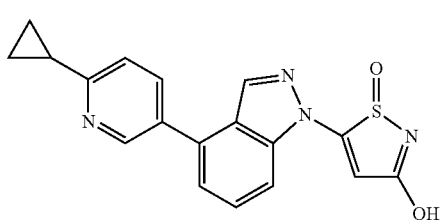
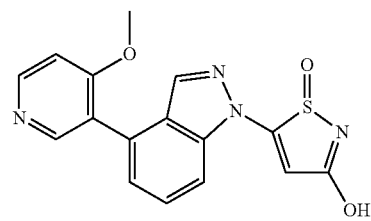
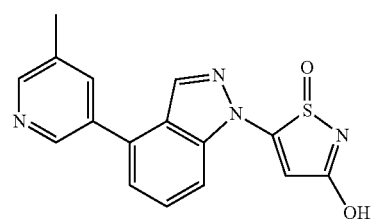
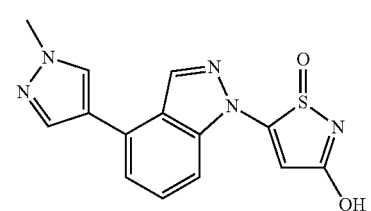
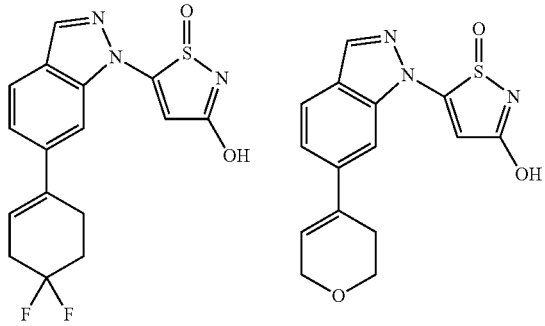
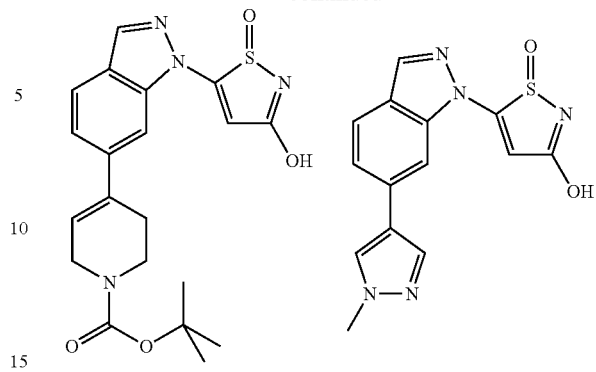
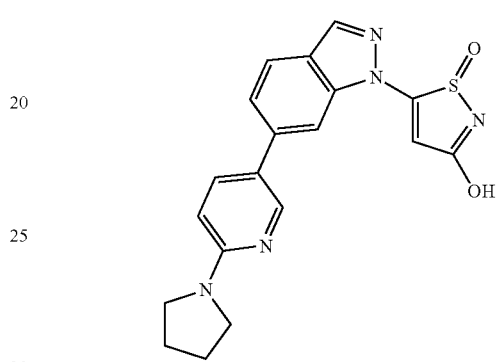
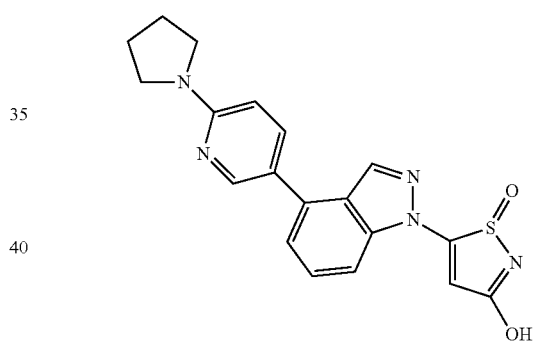
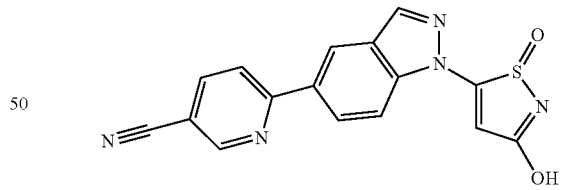
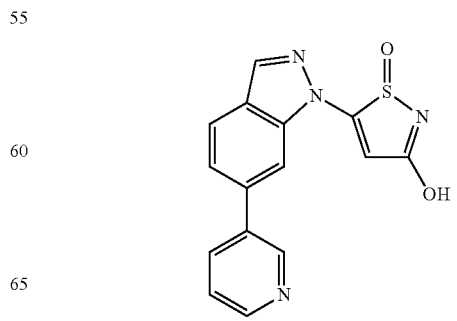

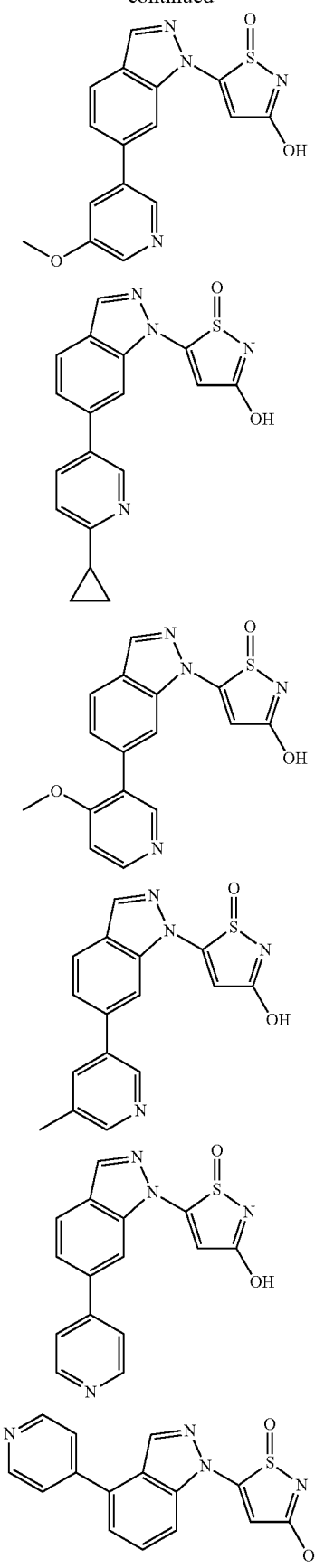
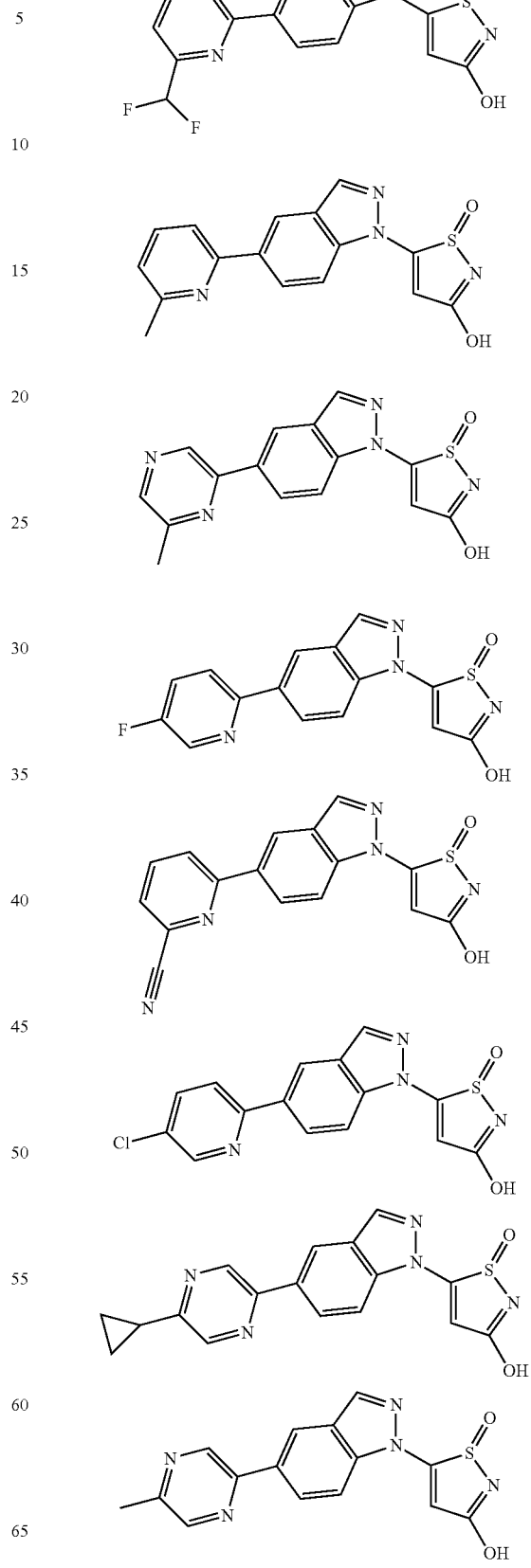

139
-continued
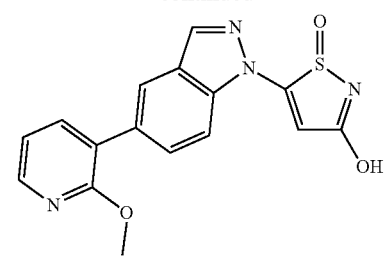
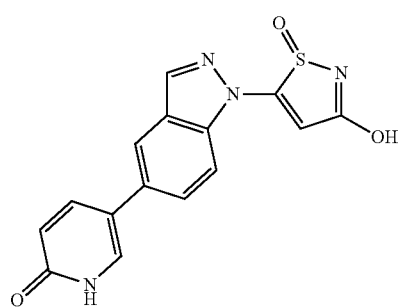
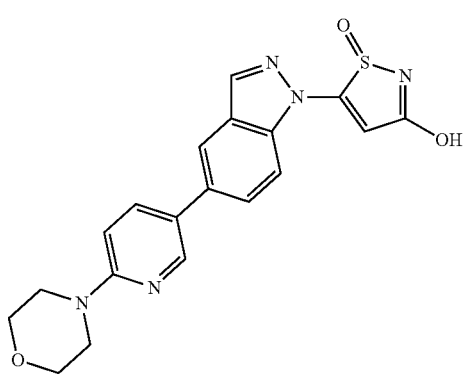
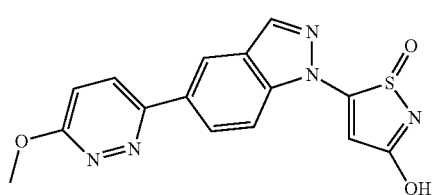
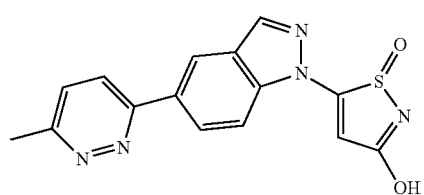
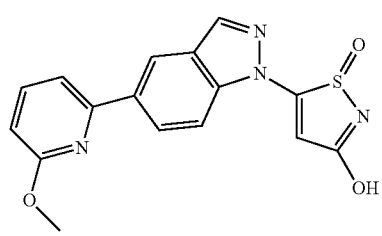
140
-continued
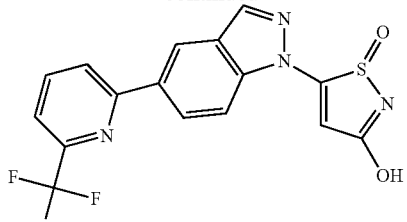
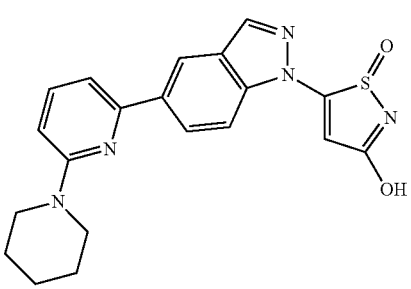
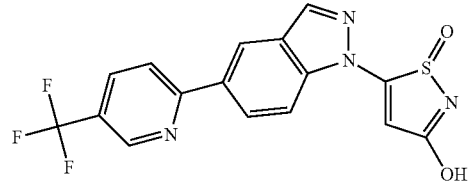
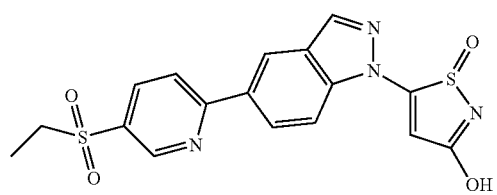
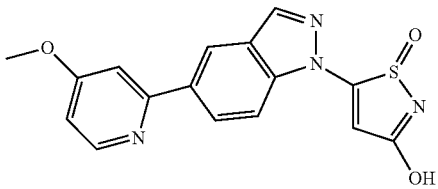
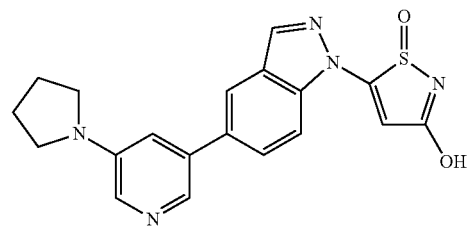
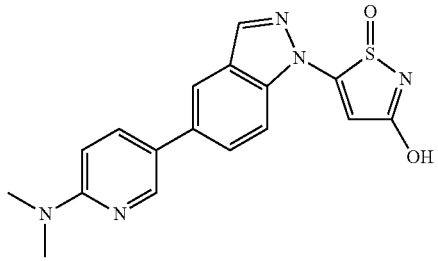

141
-continued
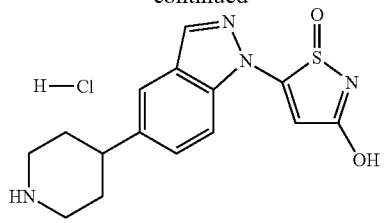
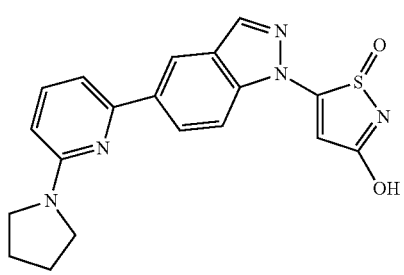
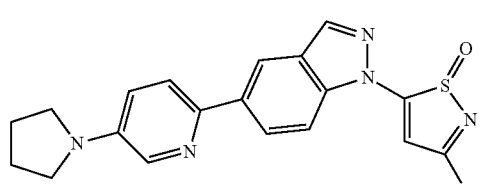
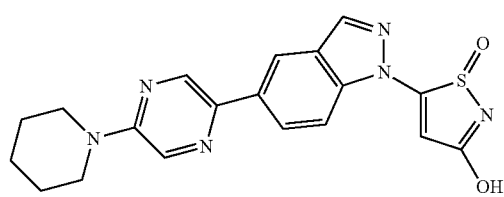
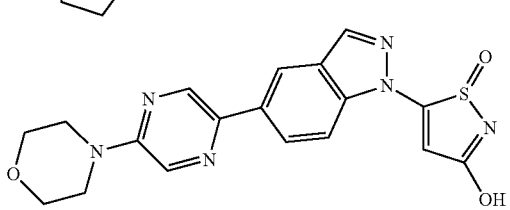
142
-continued
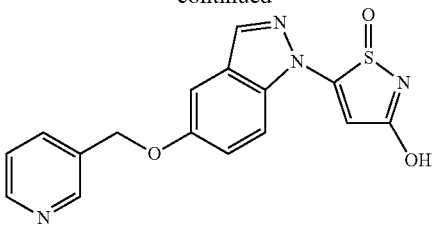
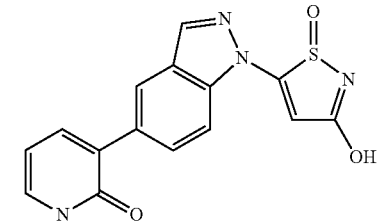
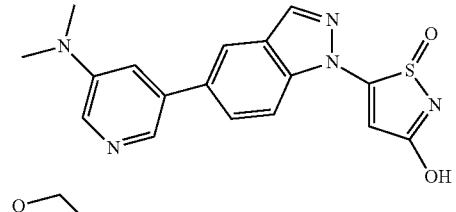
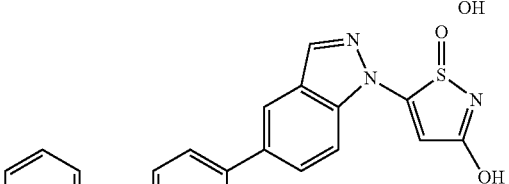
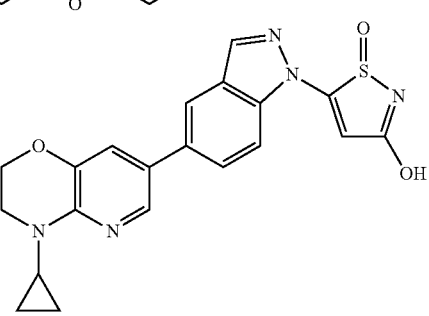
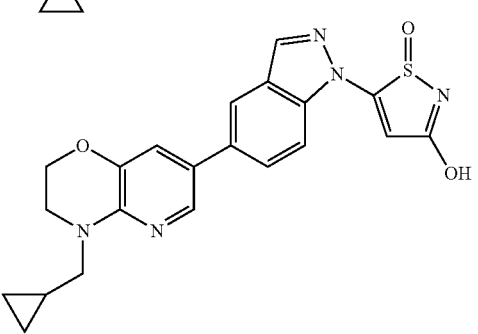

143
-continued
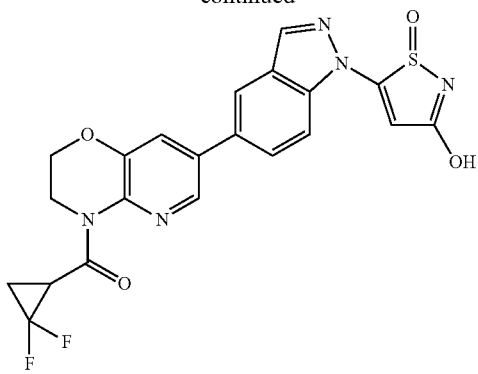
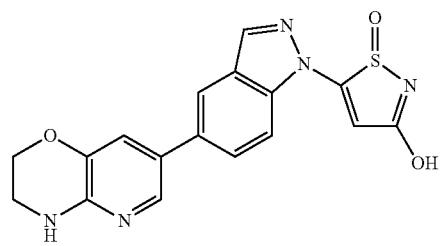
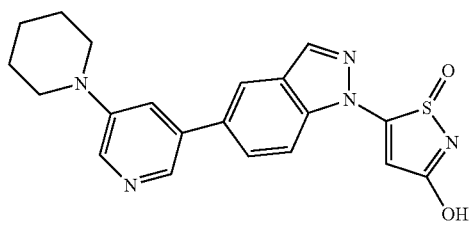
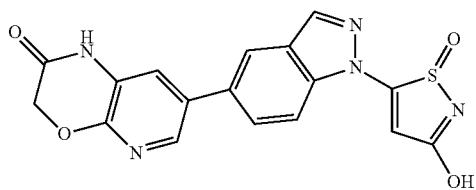
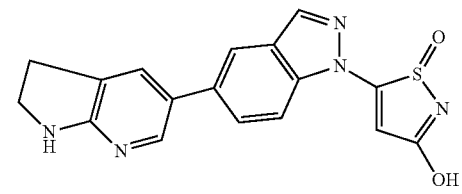
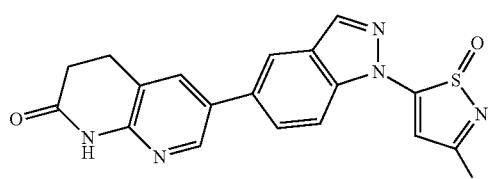
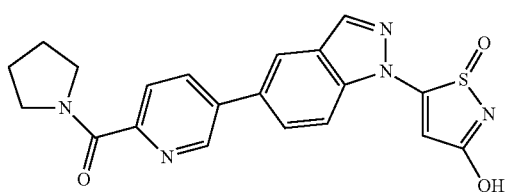
144
-continued
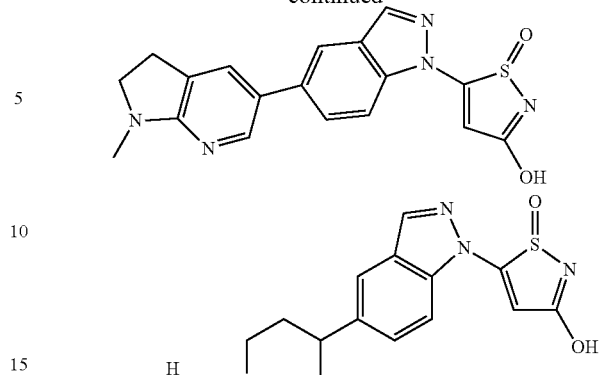
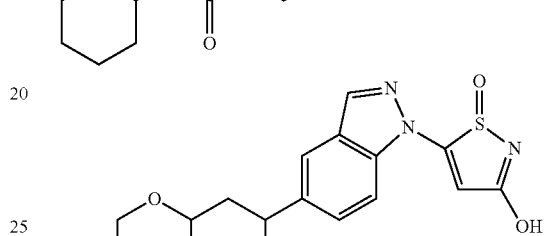
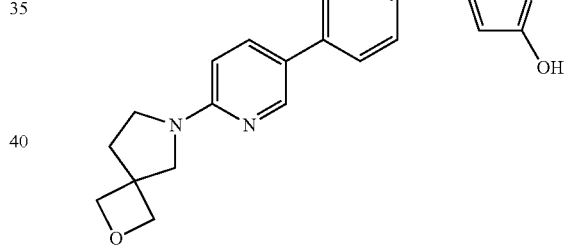
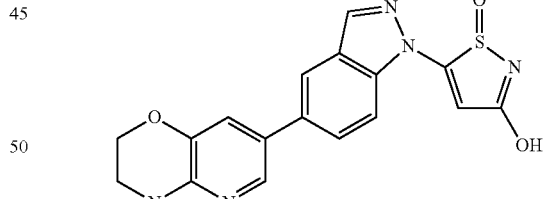
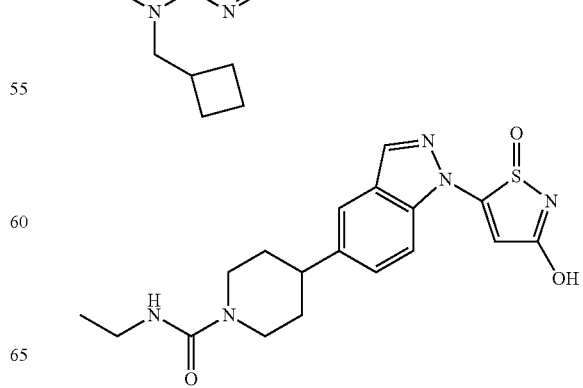

145
-continued
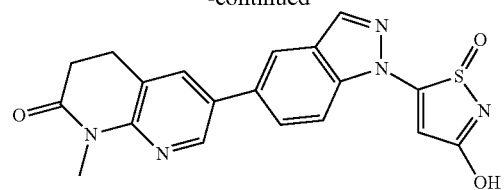
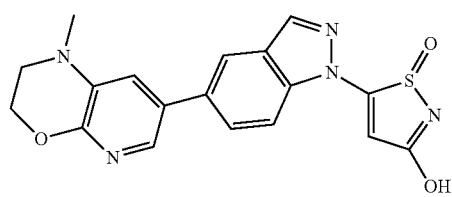
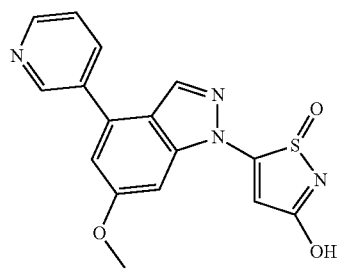
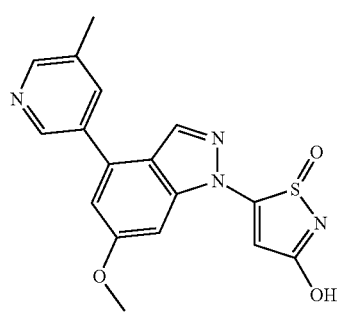
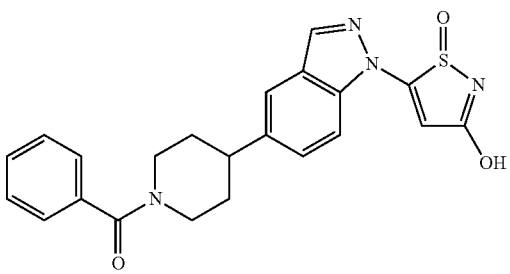
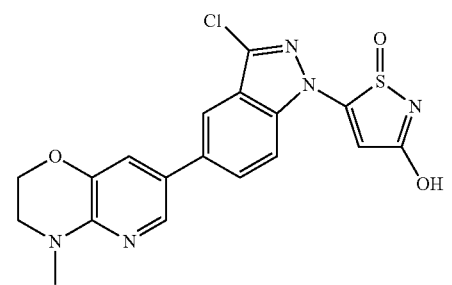
146
-continued
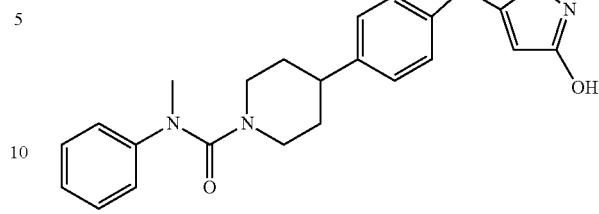
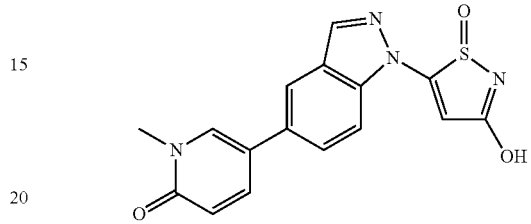
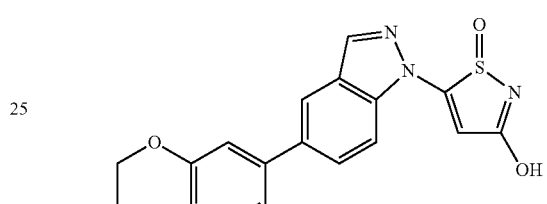
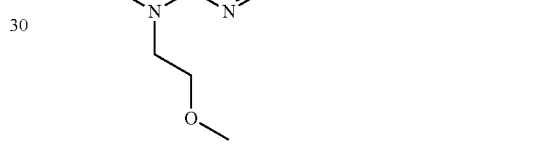
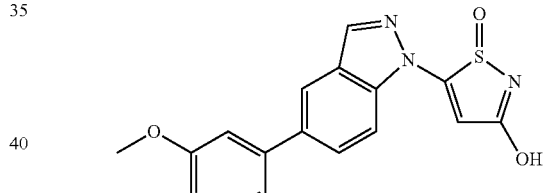
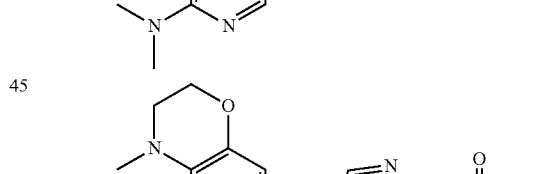
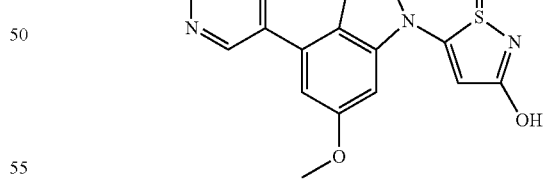
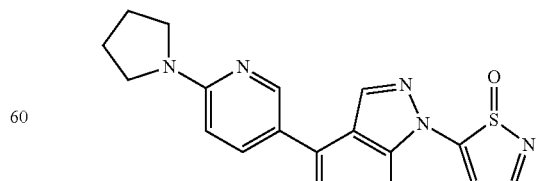
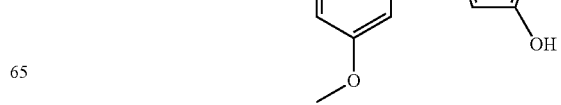

147
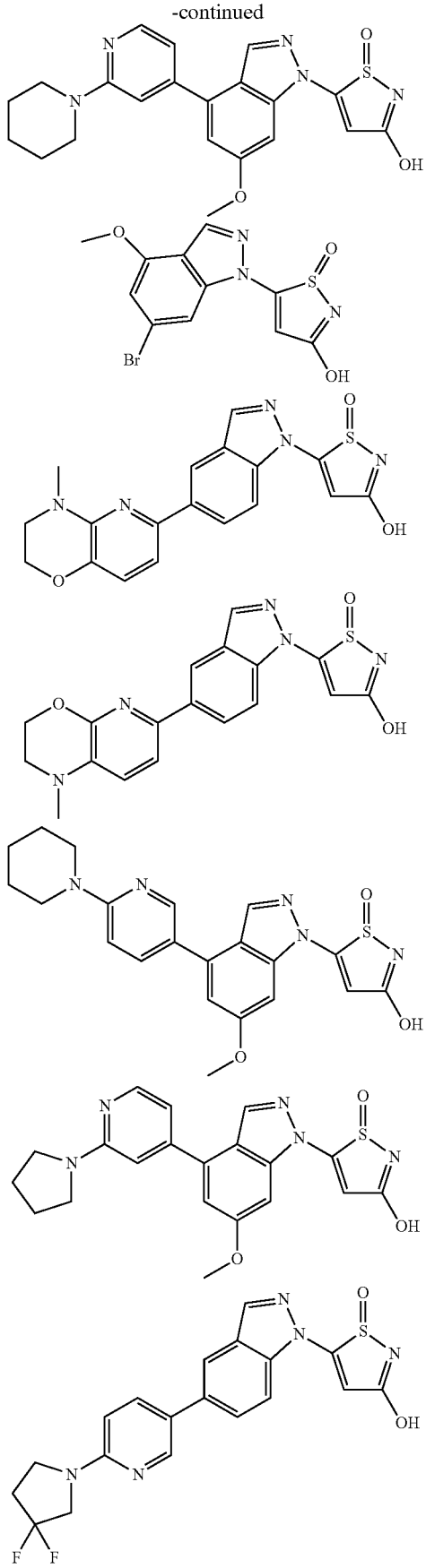
148
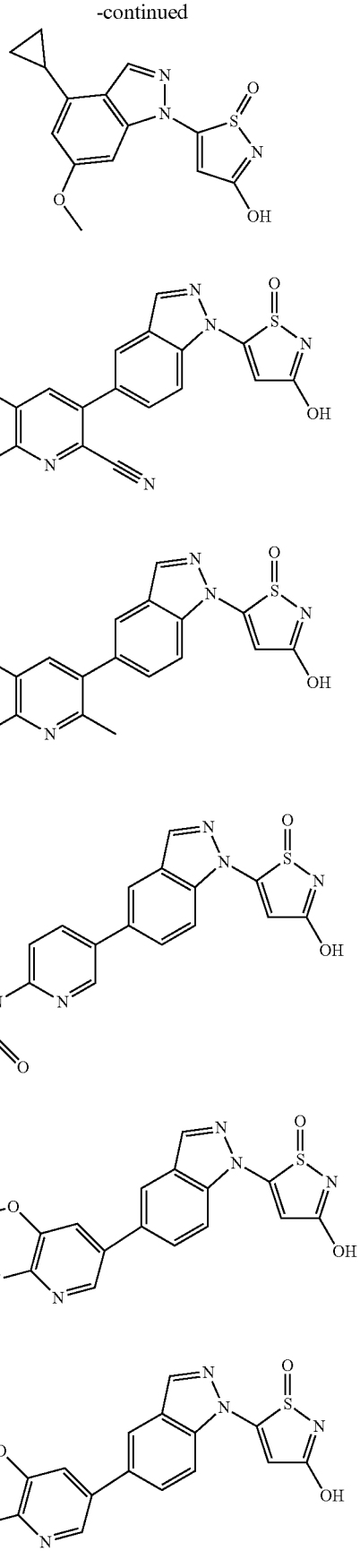

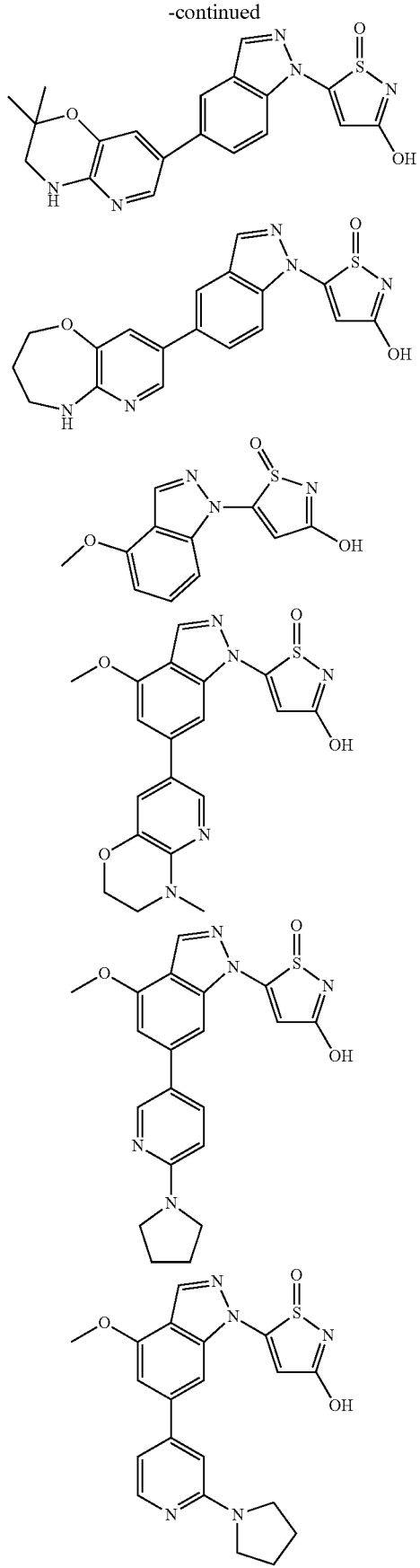
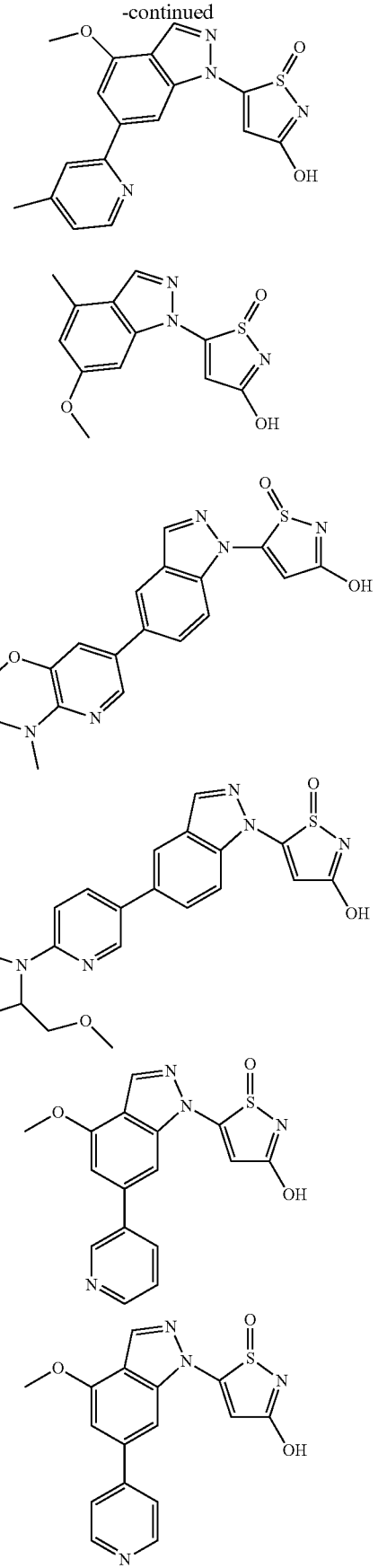

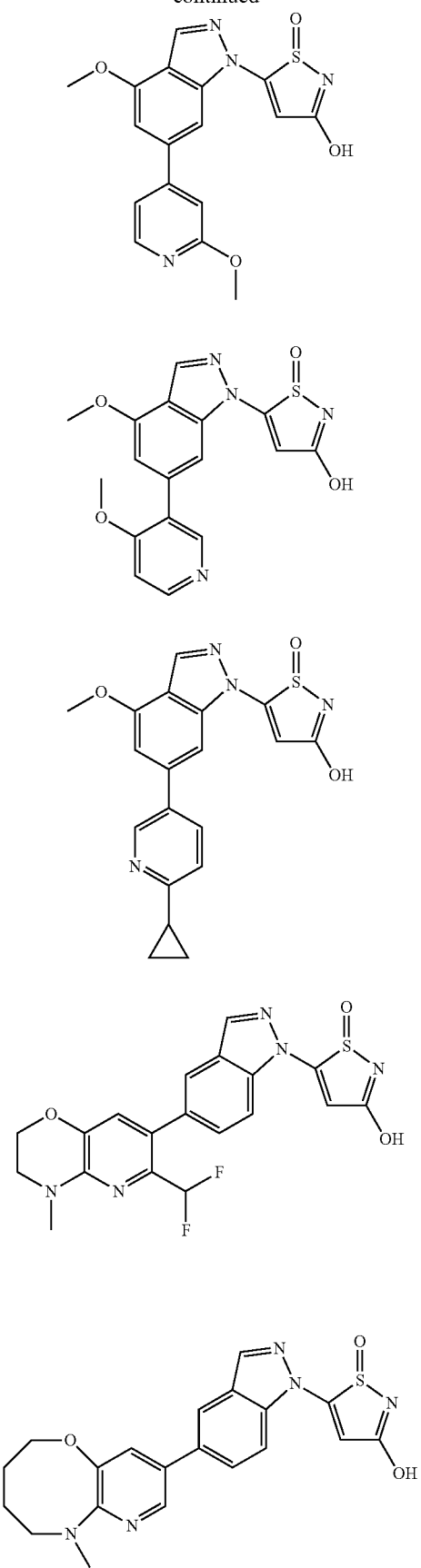
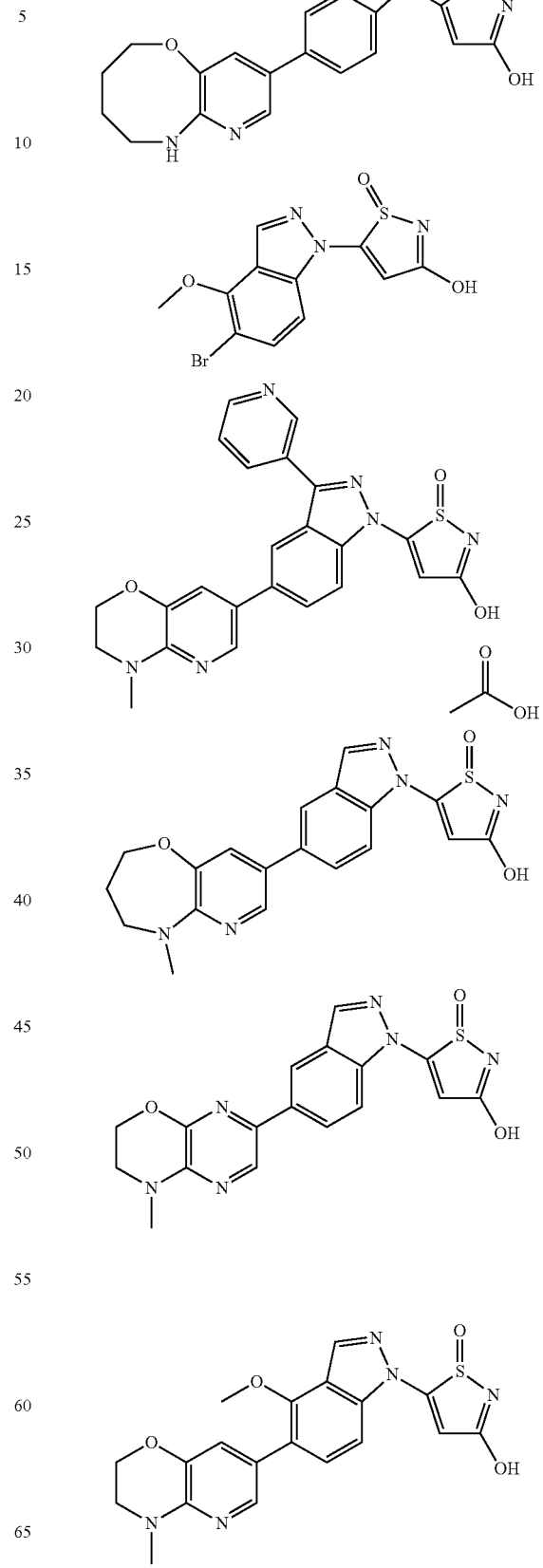

153
-continued
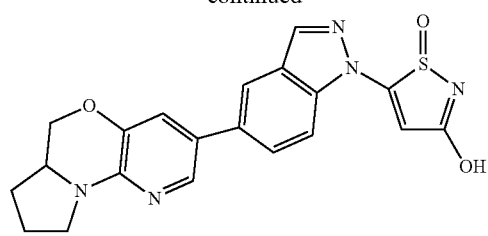
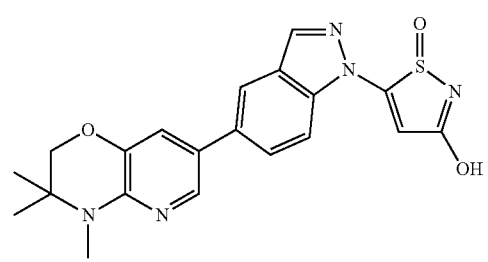
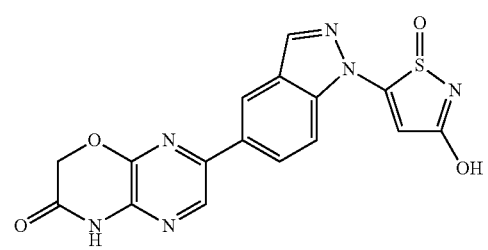
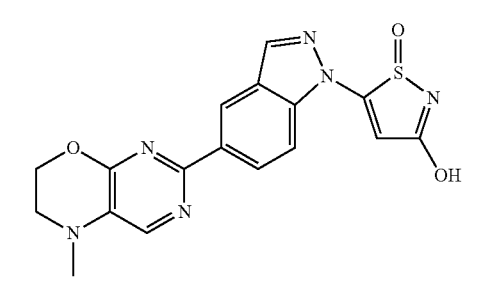
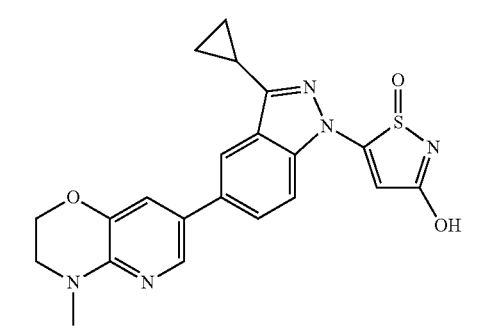
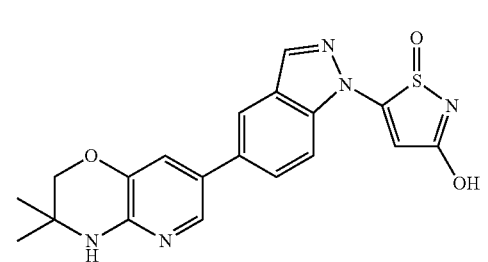
154
-continued
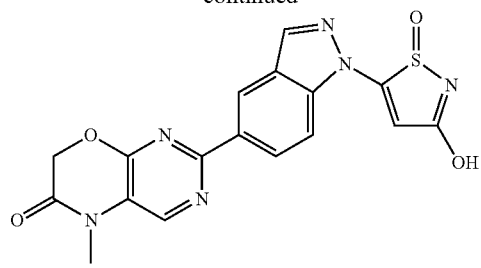
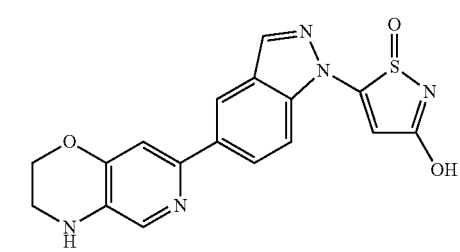
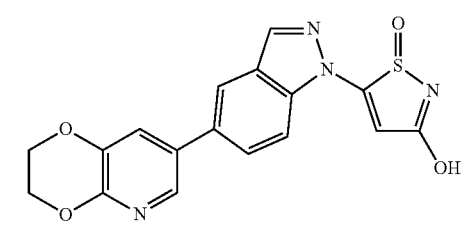
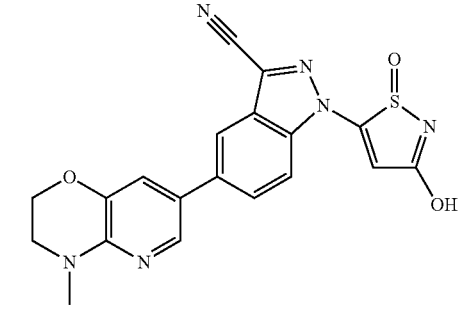
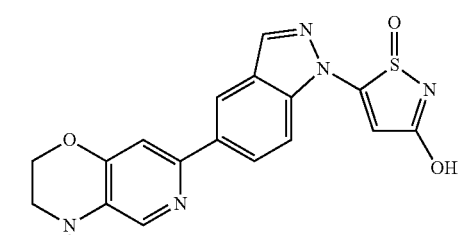
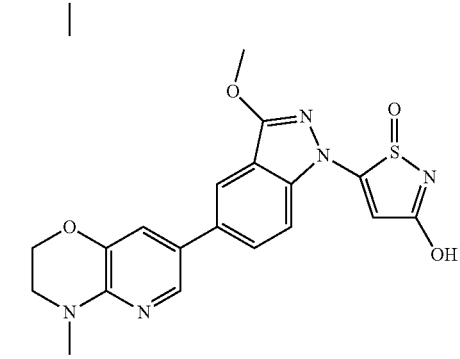

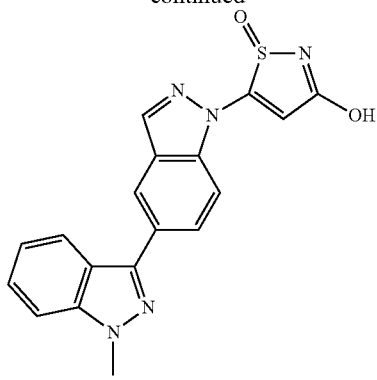
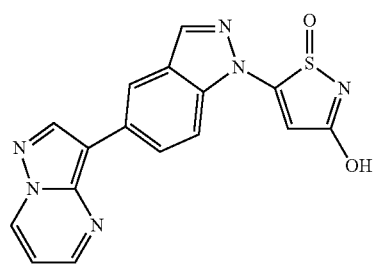
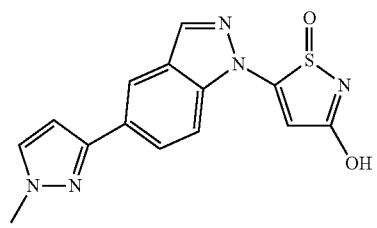
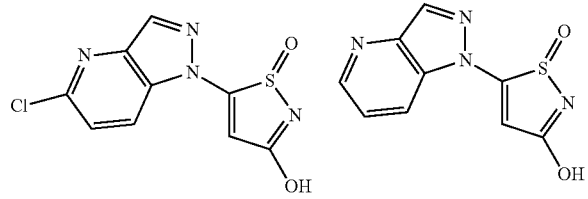
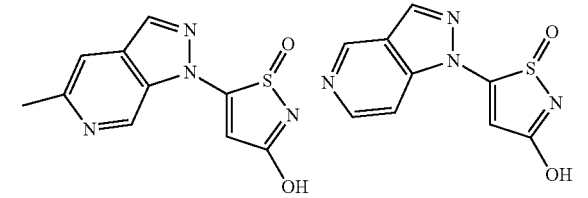
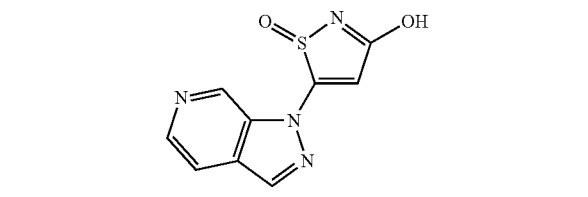
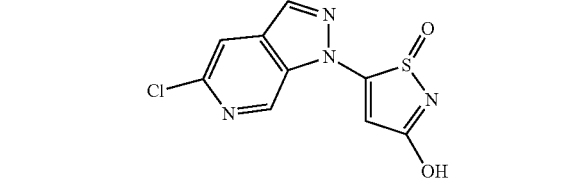
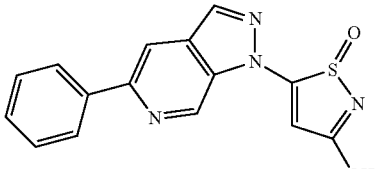
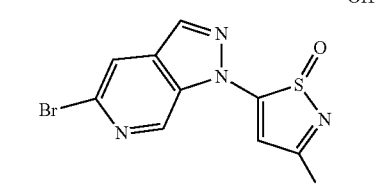
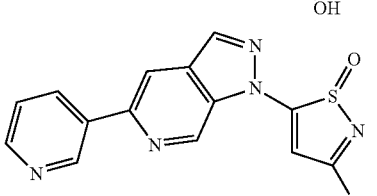
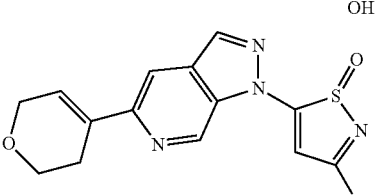
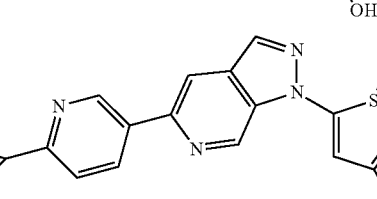
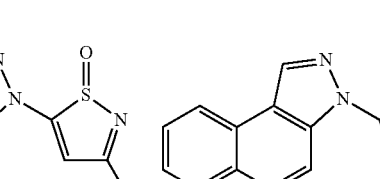
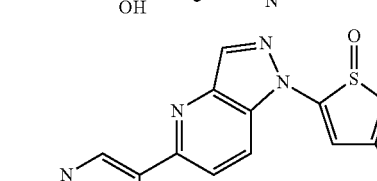
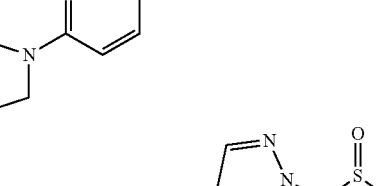

157
-continued
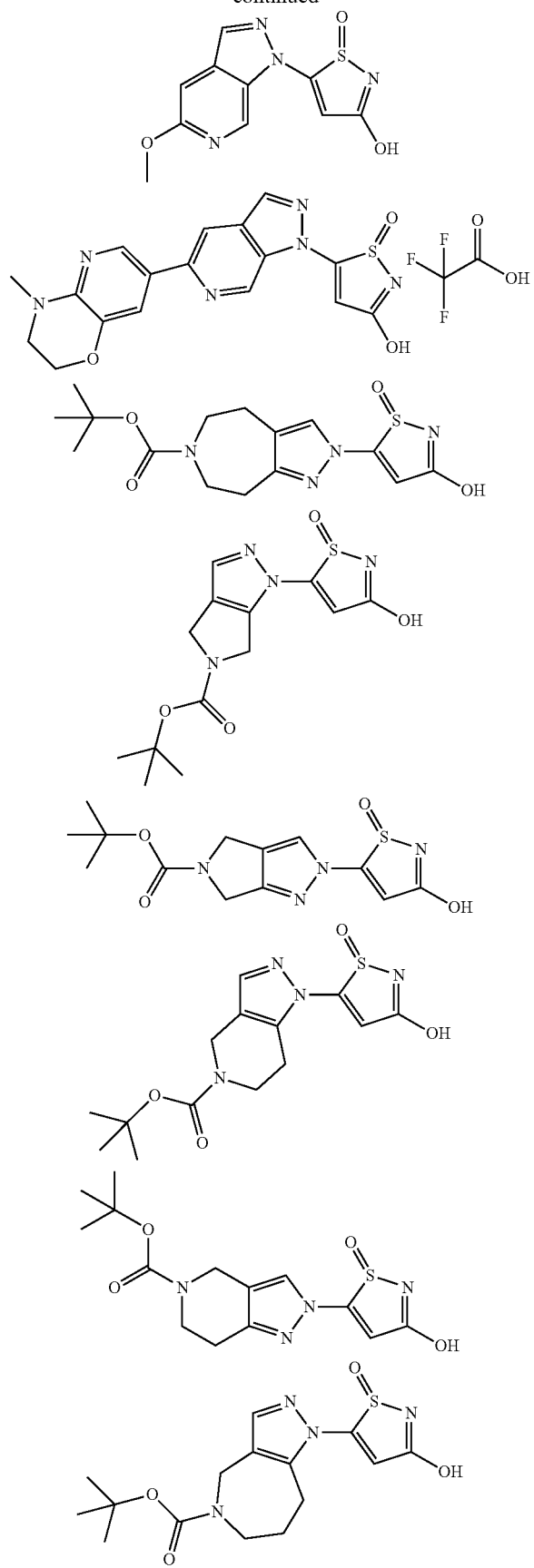
158
-continued
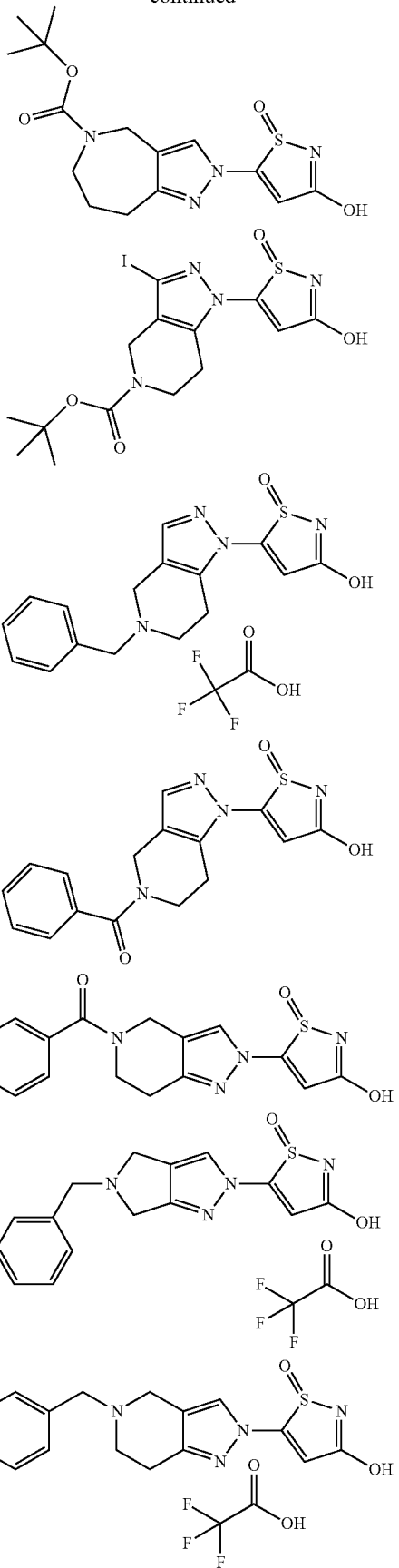

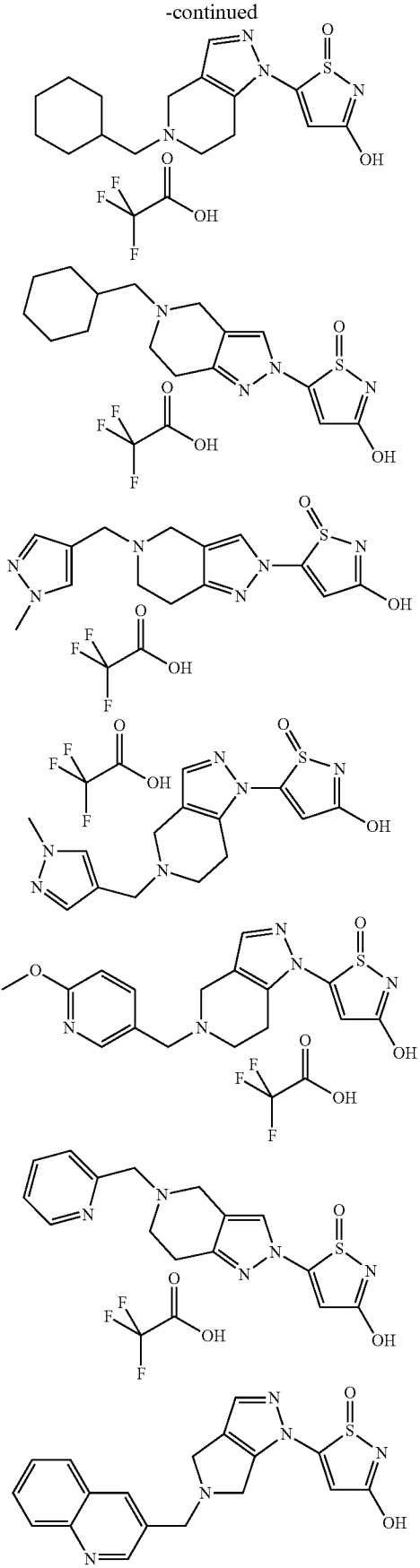
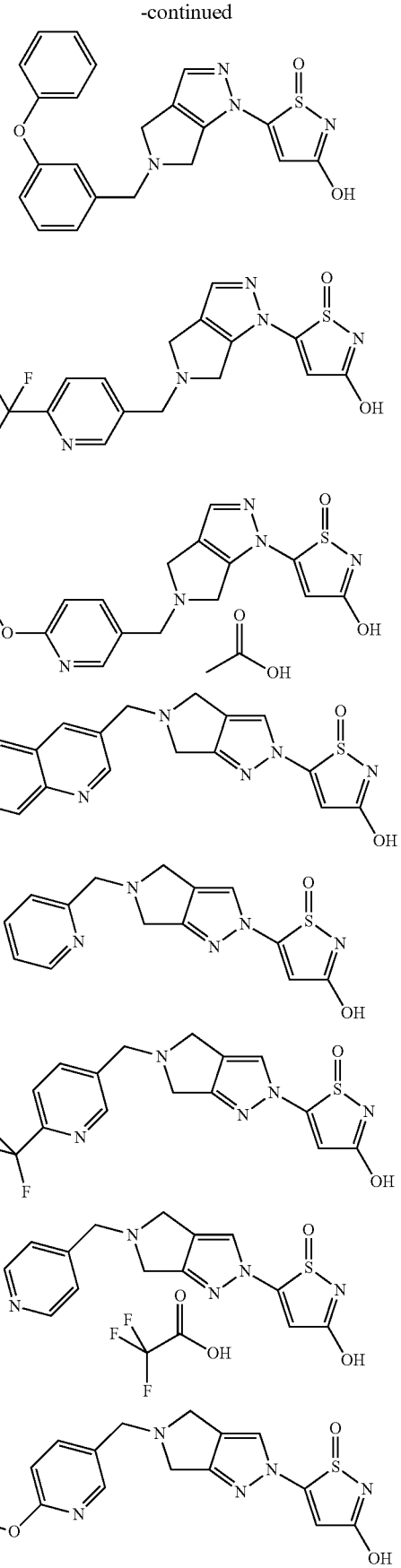

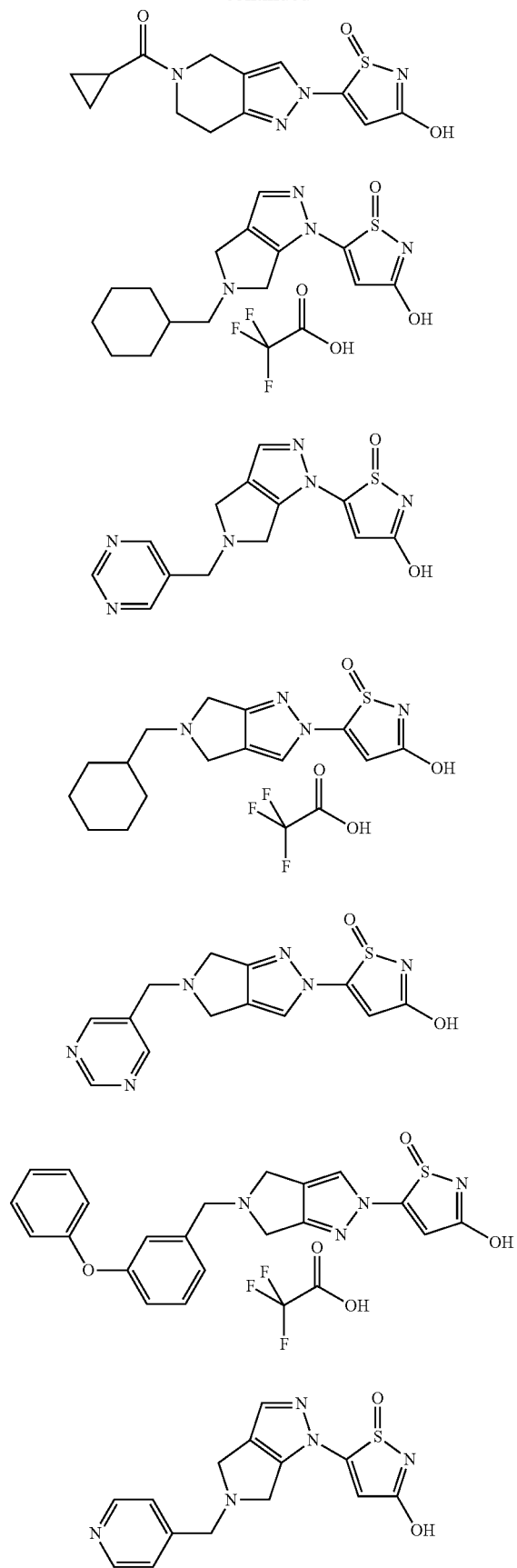
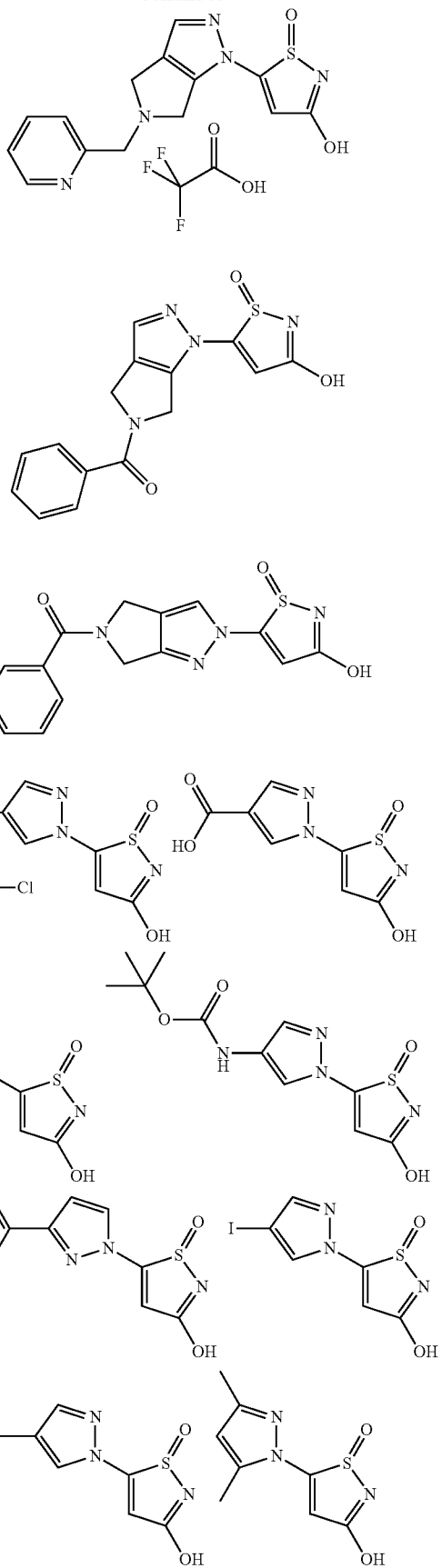

163
-continued
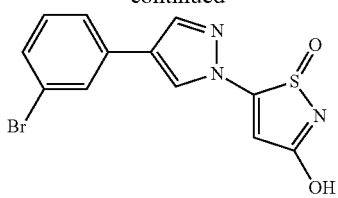
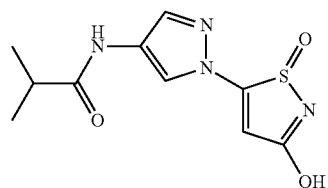
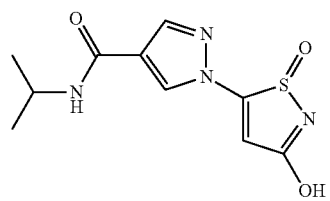
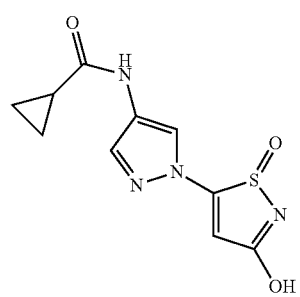
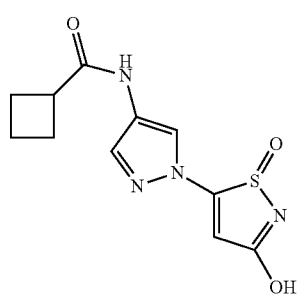
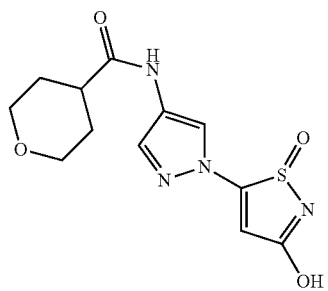
164
-continued
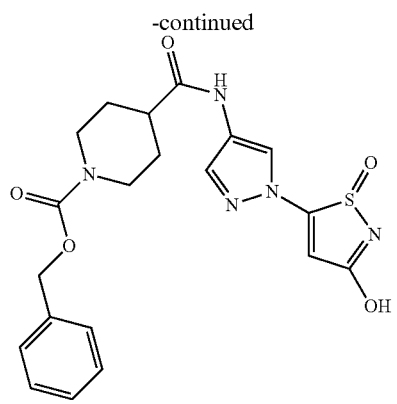
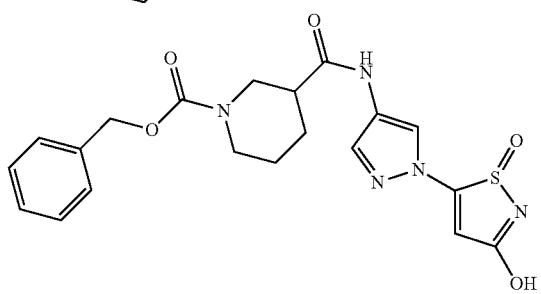
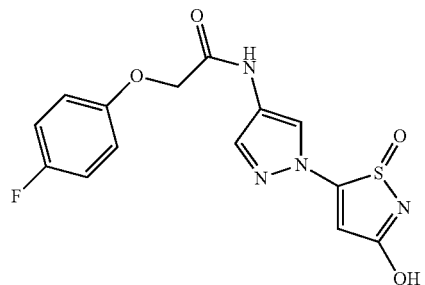
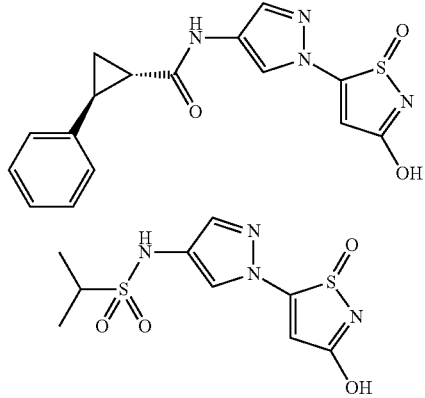
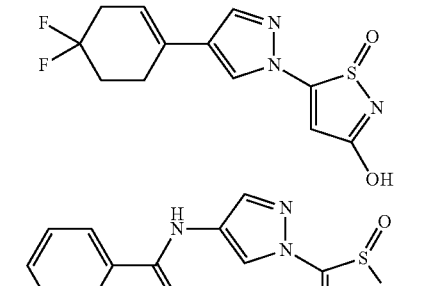
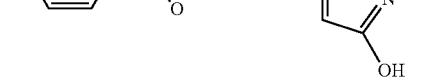

165
-continued
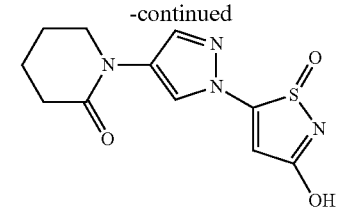
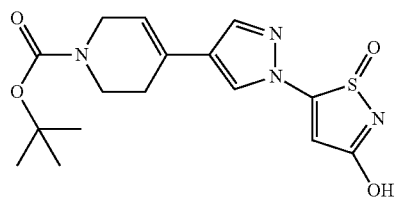
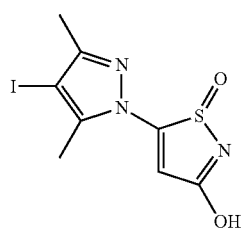
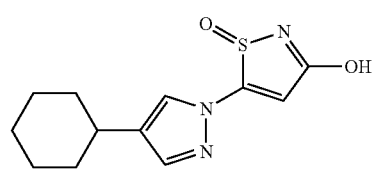
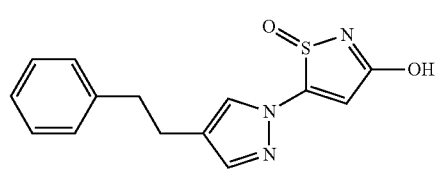
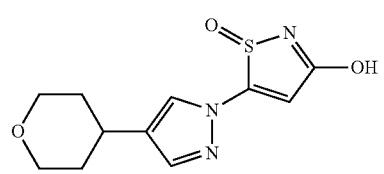
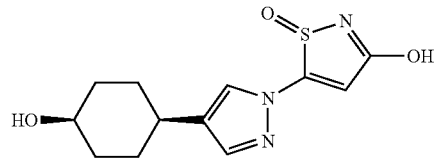
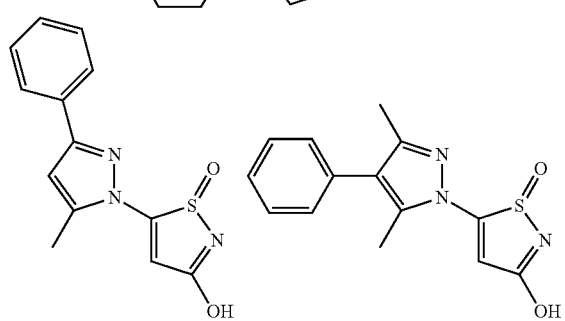
166
-continued
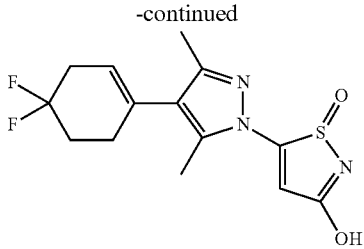
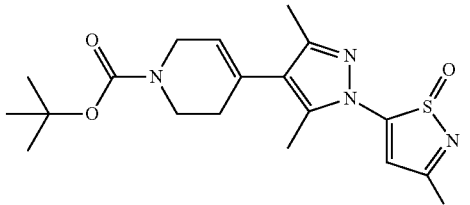
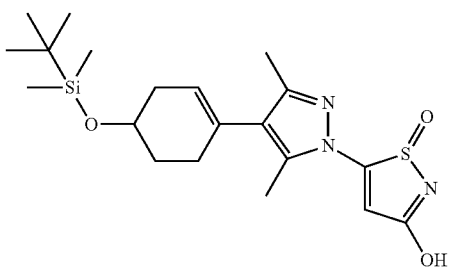
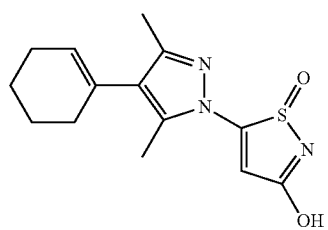
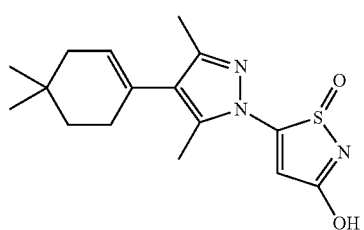
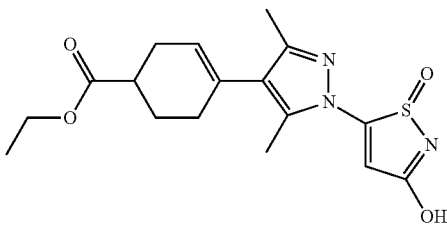
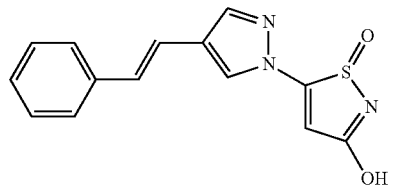

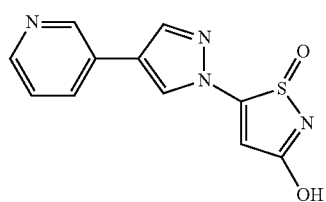
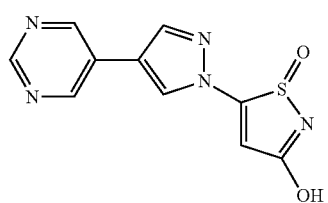
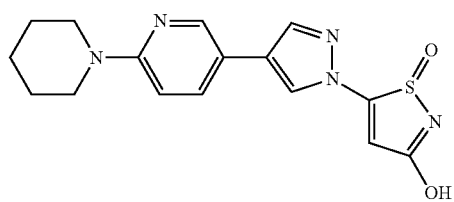
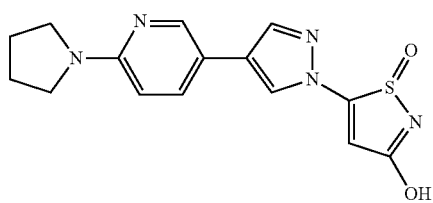
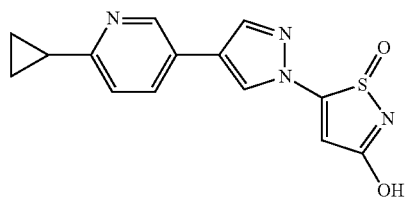
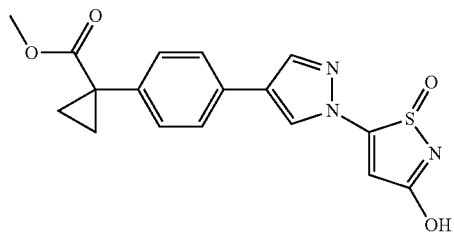
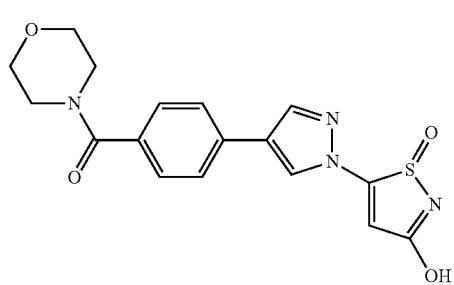
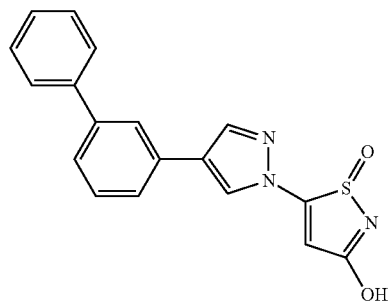
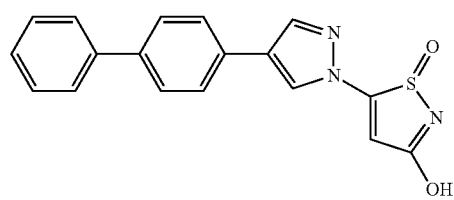
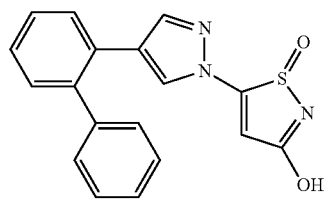
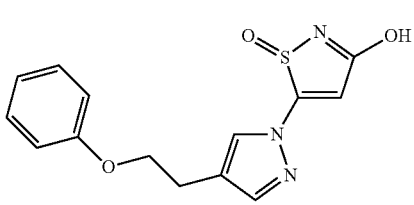
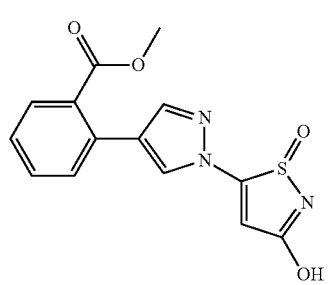
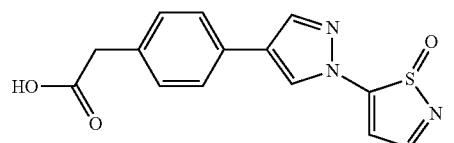
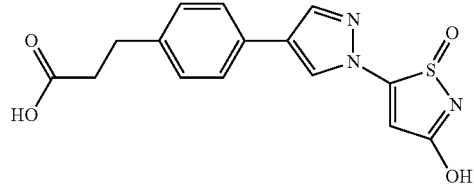

-continued
169
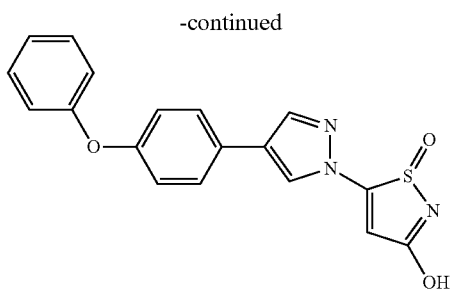
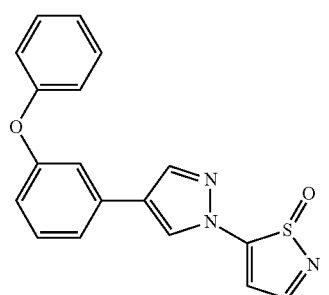
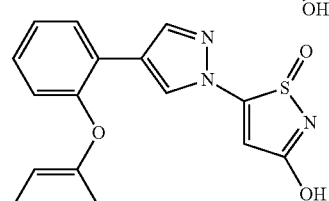
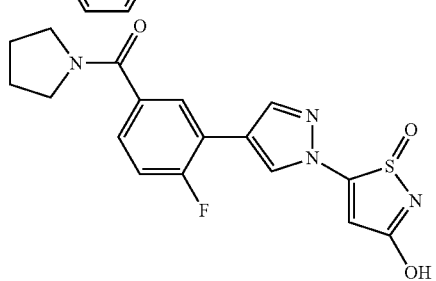
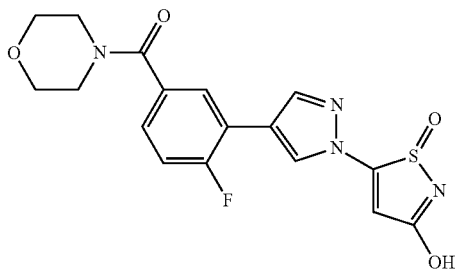
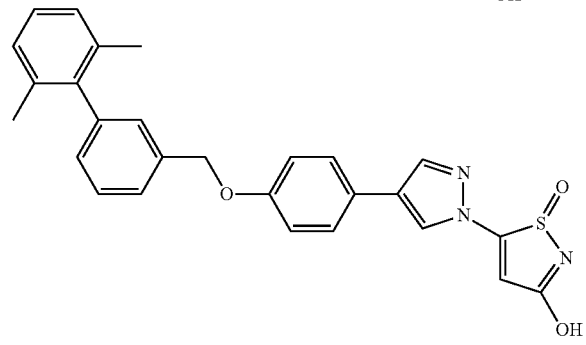
170
-continued
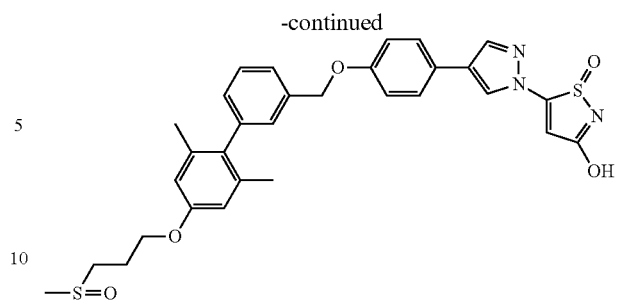
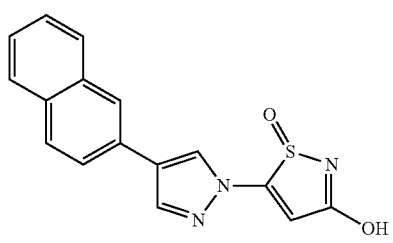
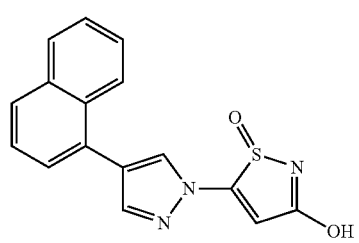
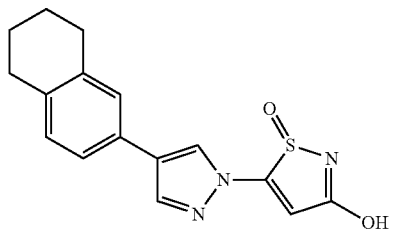
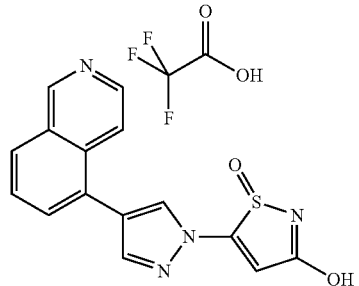
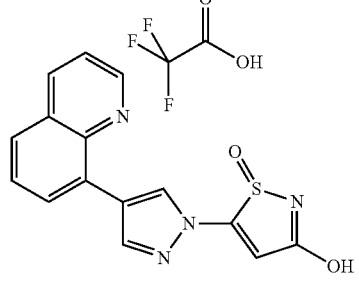

-continued
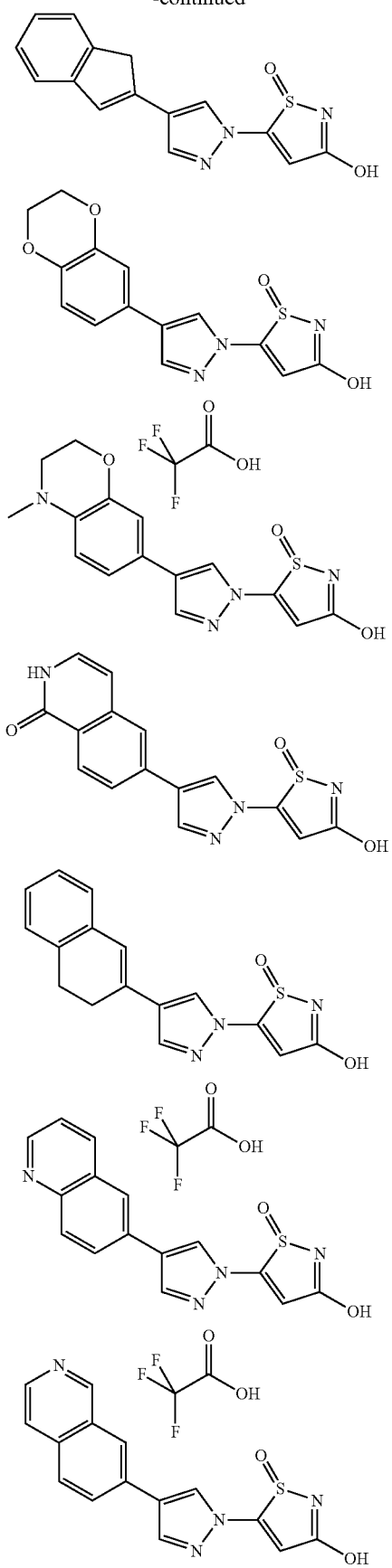
-continued
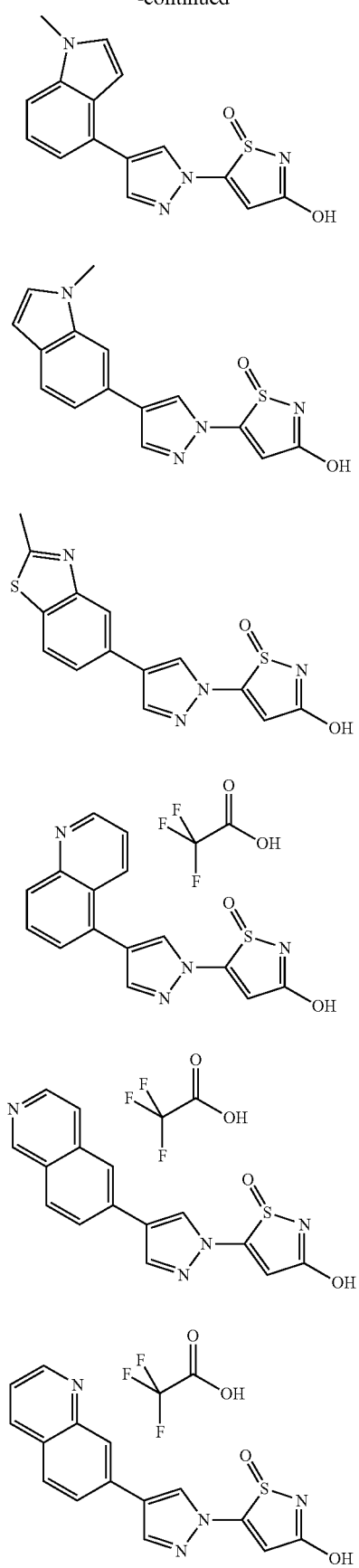

173
-continued
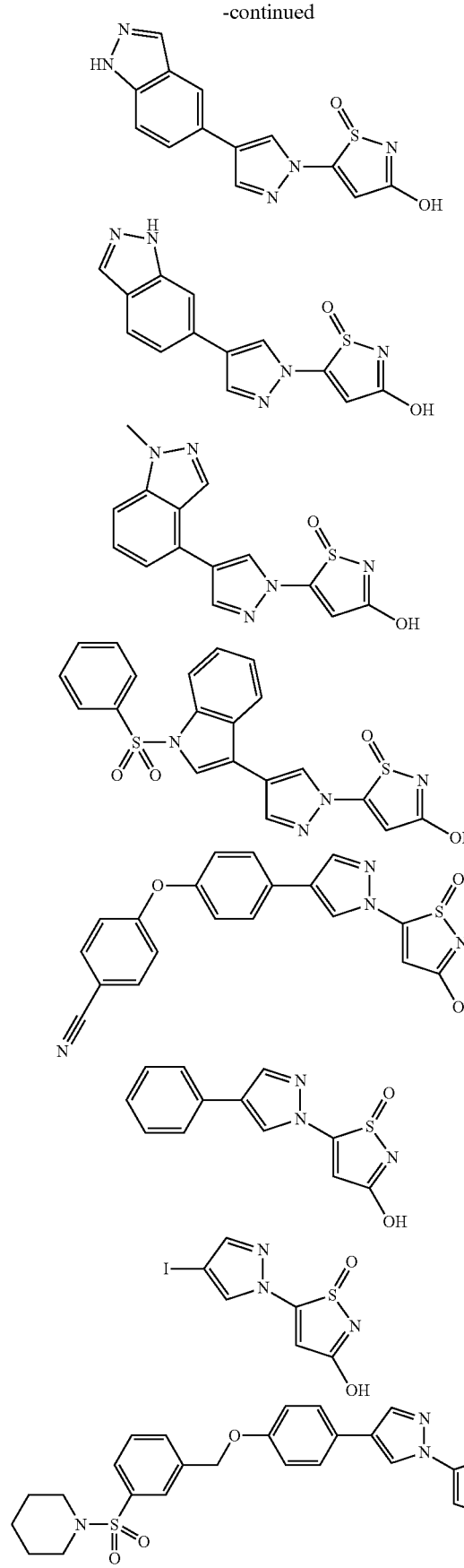
174
-continued
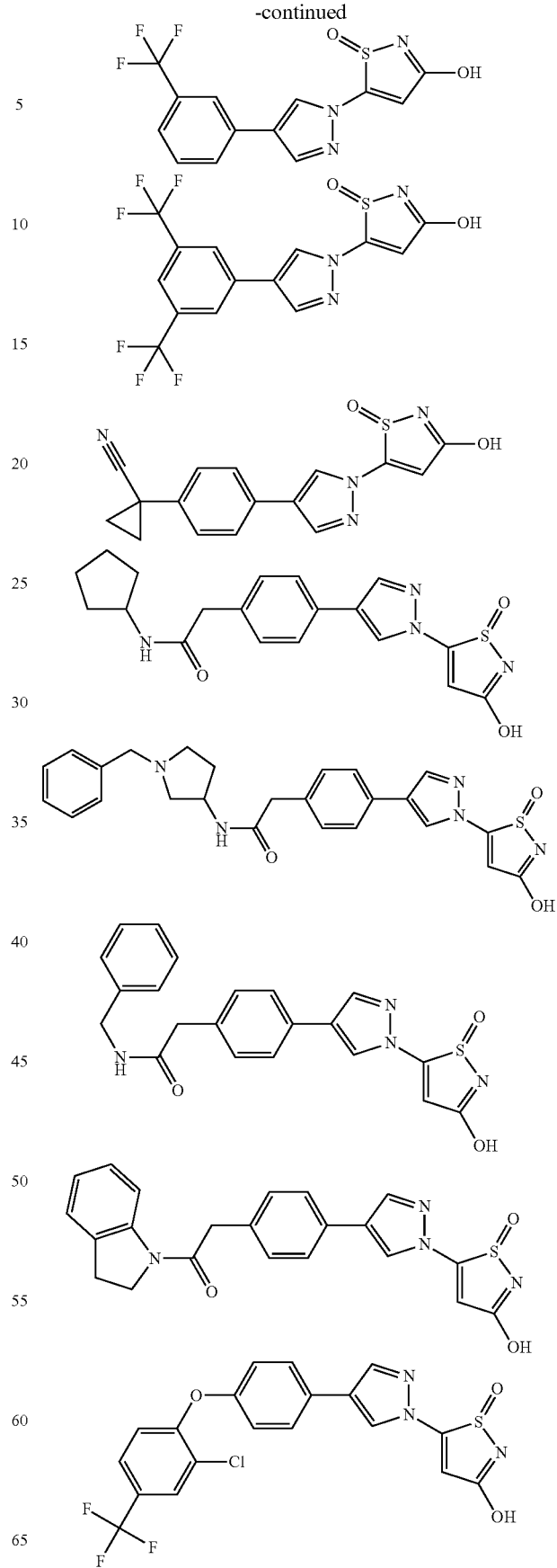

-continued
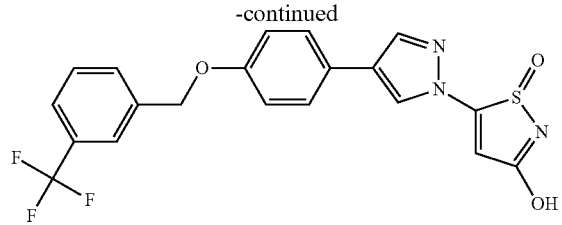
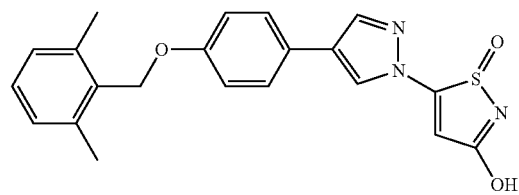
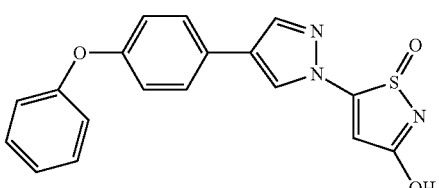
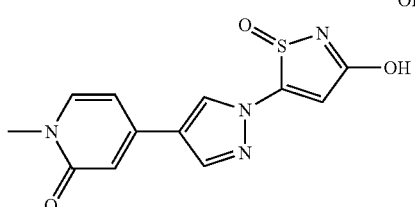
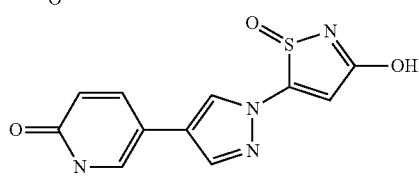
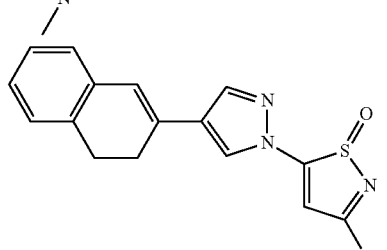
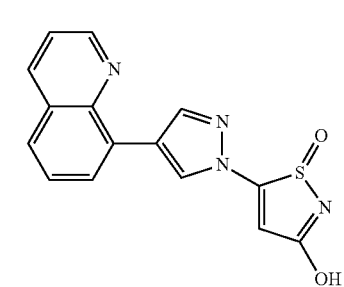
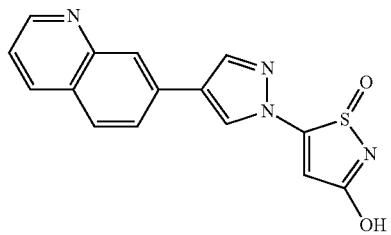
-continued
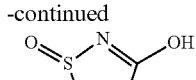
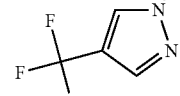
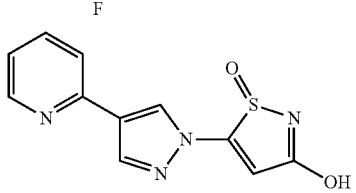
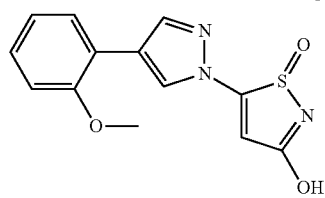
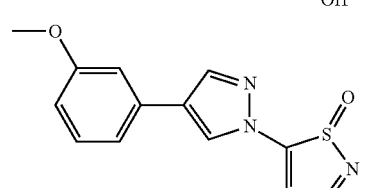
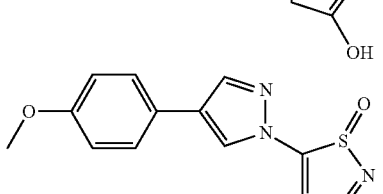
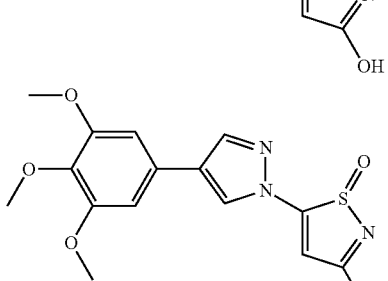
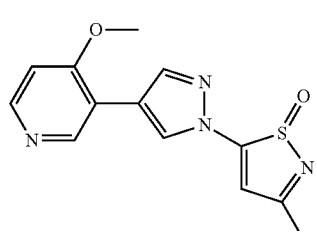
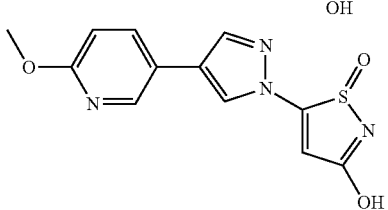

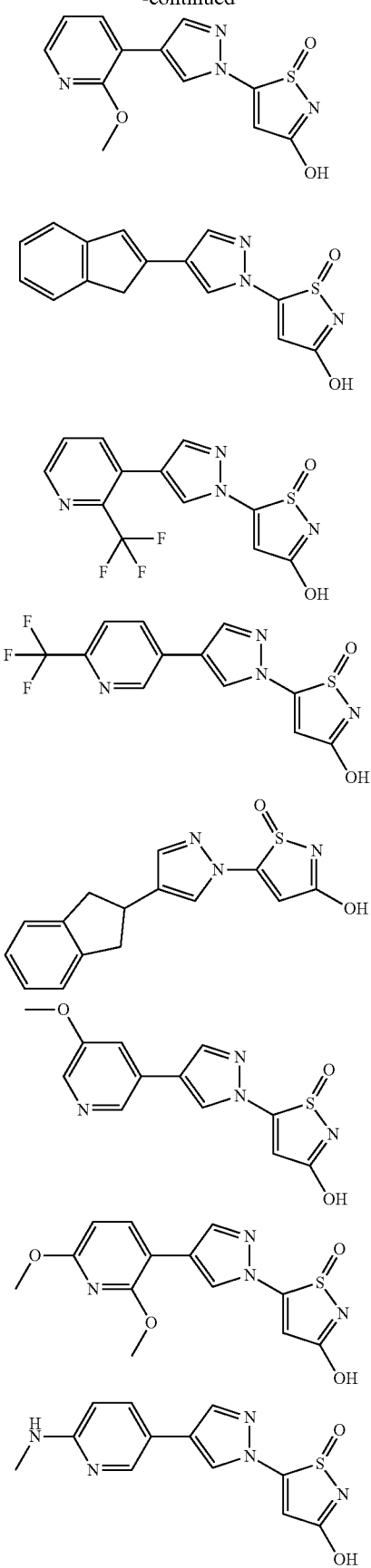
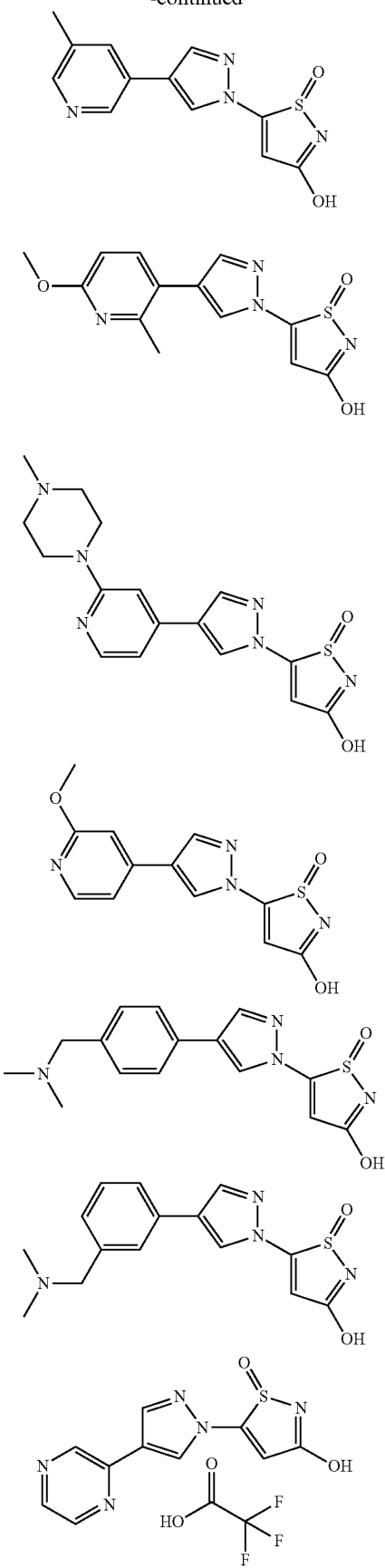

179
-continued
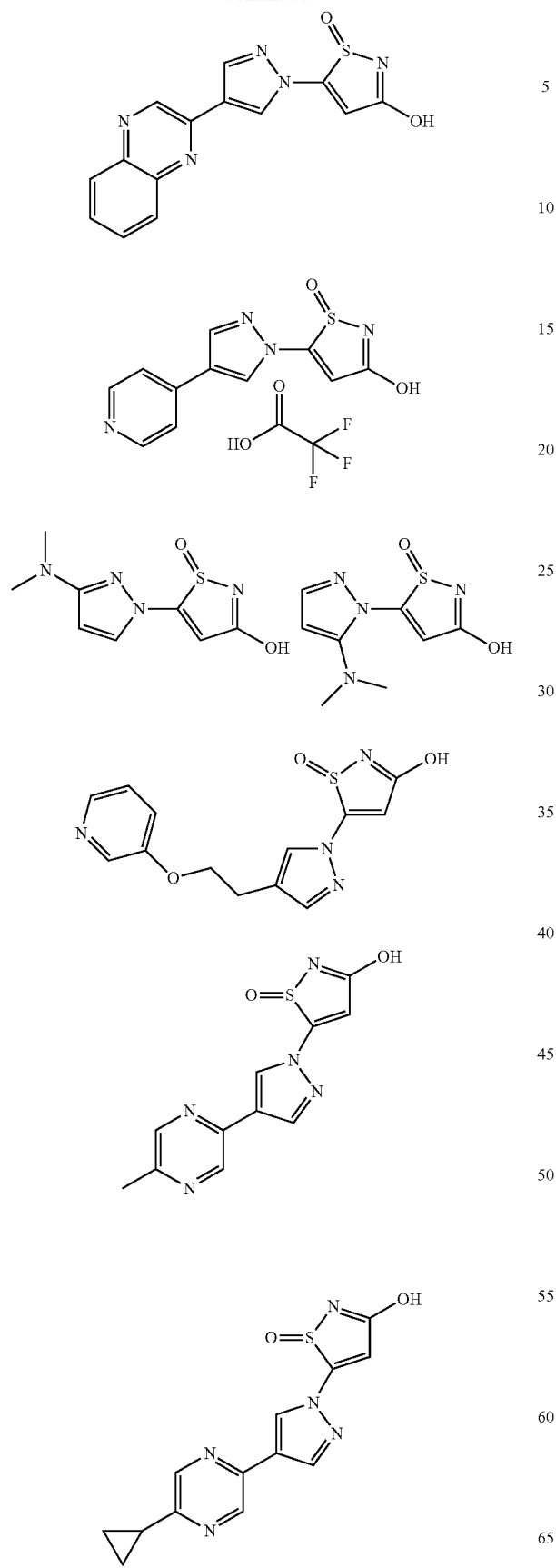
180
-continued
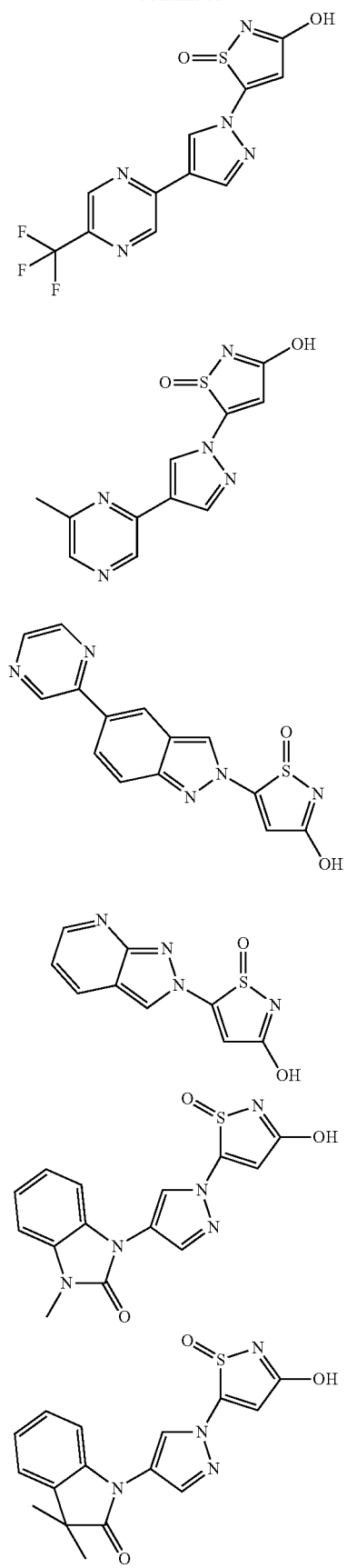

181
-continued
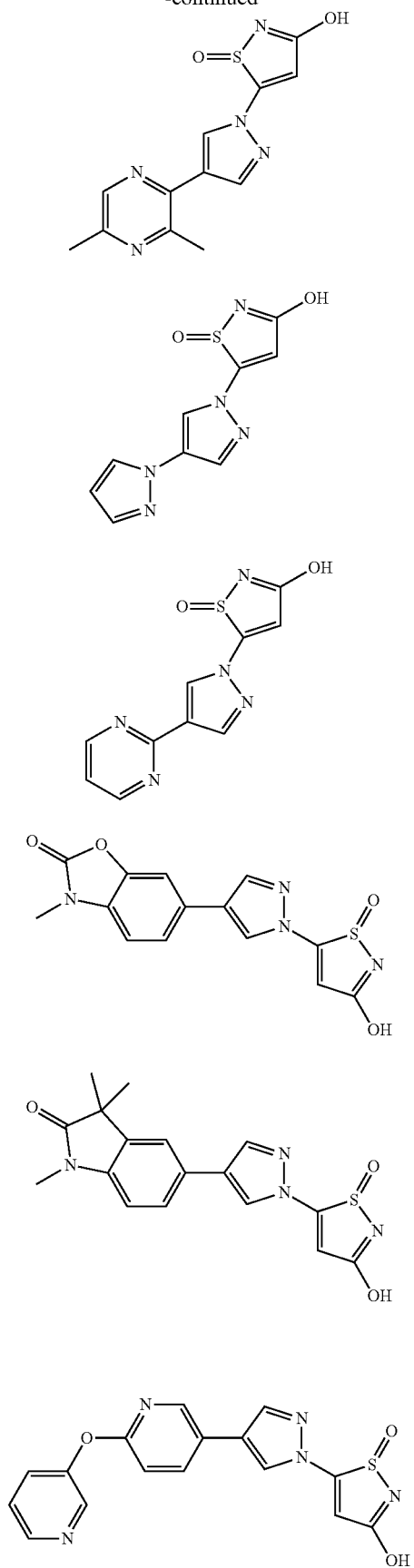
182
-continued
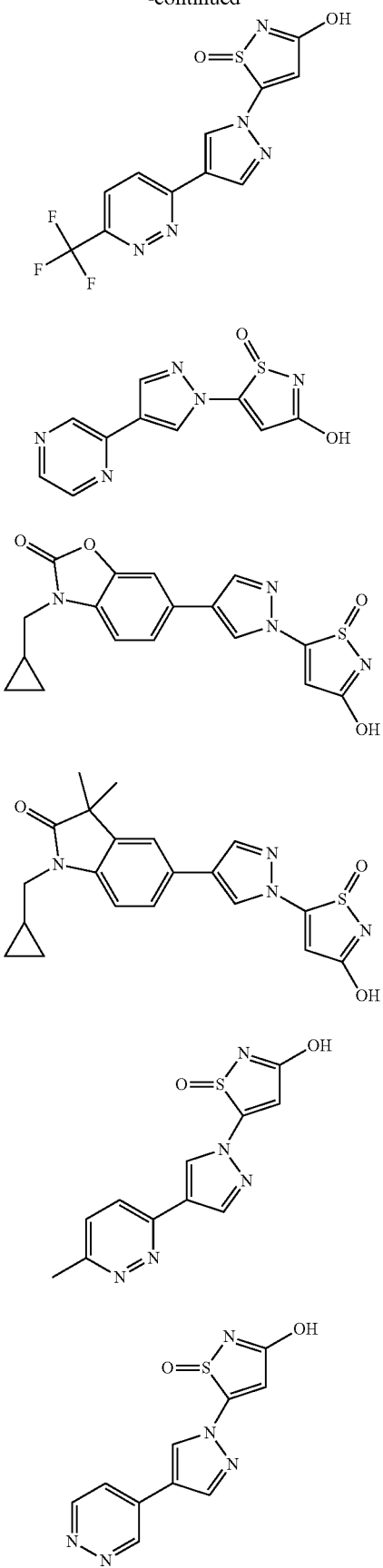

183
-continued
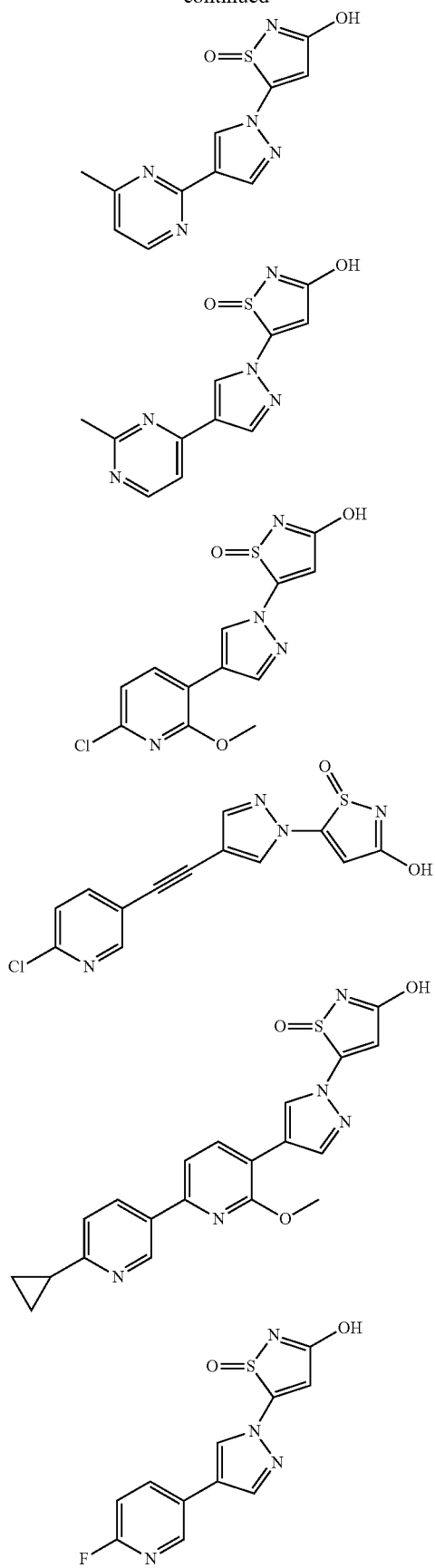
184
-continued
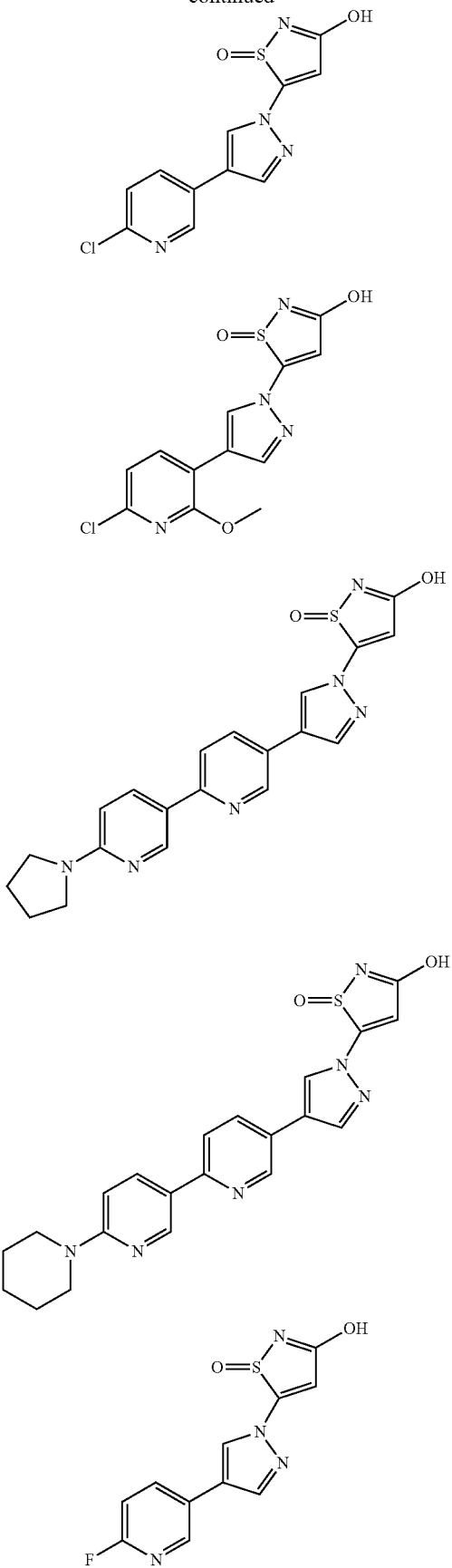

185
-continued
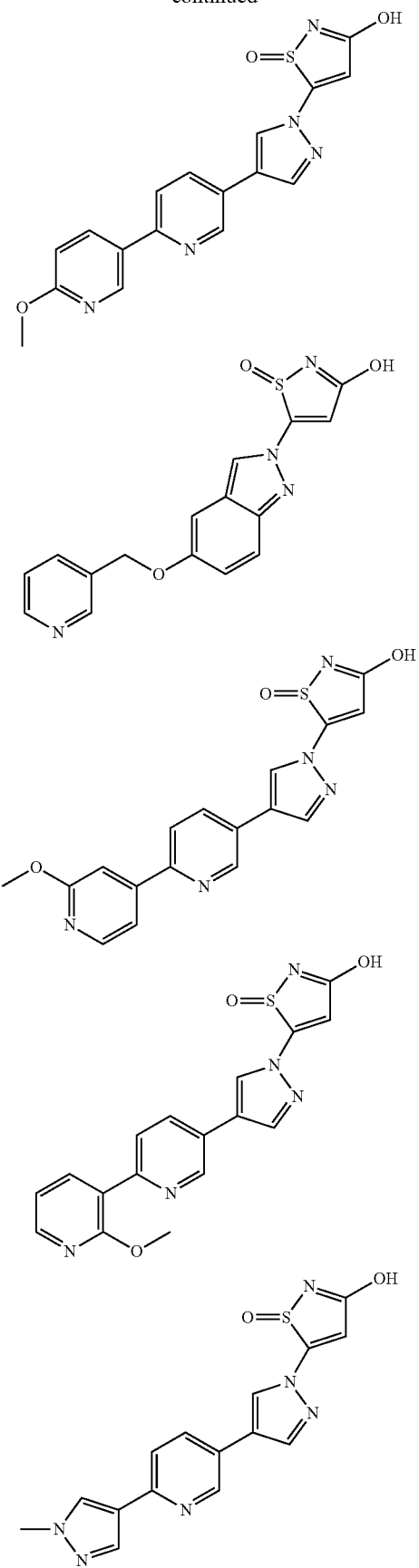
186
-continued
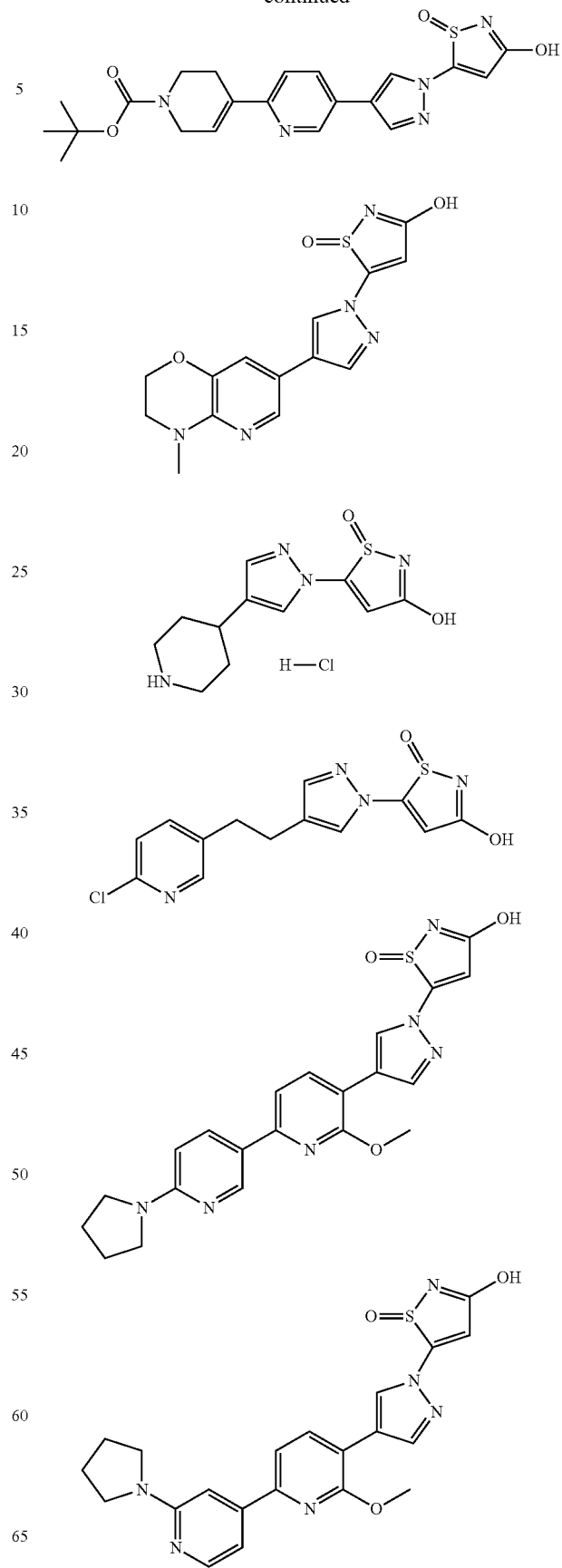

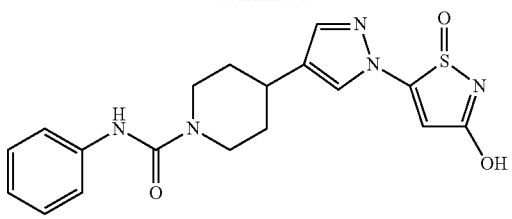

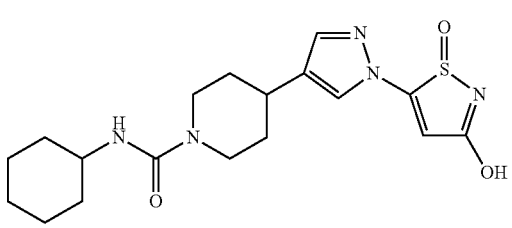

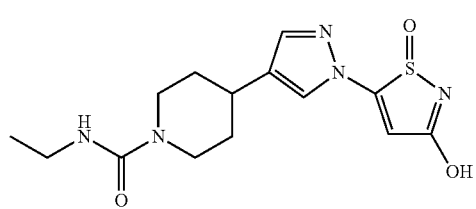

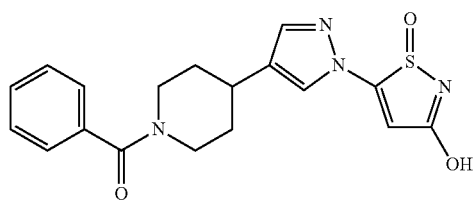

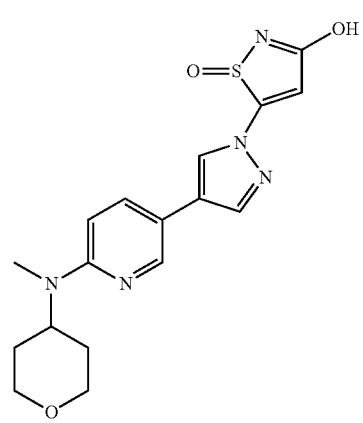

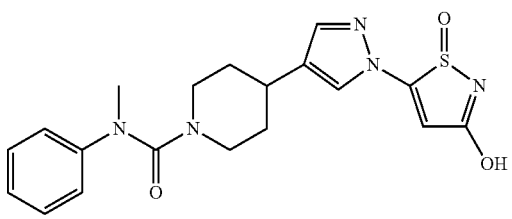

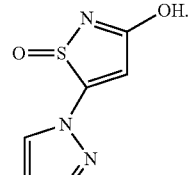

4. A compound which is selected from:
5-(indazol-1-yl)-1-oxo-1,2-thiazol-3-ol,
5-(5-bromoindazol-1-yl)-1-oxo-1,2-thiazol-3-ol,
5-[5-(2-methoxypyridin-4-yl) indazol-1-yl]-1-oxo-1,2-thiazol-3-ol,
5-[5-(6-cyclopropylpyridin-3-yl) indazol-1-yl]-1-oxo-1,2-thiazol-3-ol,
5-[5-(4-methyl-2, 3-dihydropyrido[3,2-b][1, 4]oxazin-7-yl)indazol-1-yl]-1-oxo-1,2-thiazol-3-ol,
or a pharmaceutically acceptable salt thereof or a solvate of these, or an optical isomer of these.

5. 5-(indazol-1-yl)-1-oxo-1,2-thiazol-3-ol, or a pharmaceutically acceptable salt, a solvate or an optical isomer thereof.

6. 5-(5-bromoindazol-1-yl)-1-oxo-1,2-thiazol-3-ol, or a pharmaceutically acceptable salt, a solvate or an optical isomer thereof.

7. 5- [5-(2-methoxypyridin-4-yl) indazol-1-yl]-1-oxo-1,2-thiazol-3-ol, or a pharmaceutically acceptable salt, a solvate or an optical isomer thereof.

8. 5-[5-(6-cyclopropylpyridin-3-yl) indazol-1-yl]-1-oxo-1,2-thiazol-3-ol, or a pharmaceutically acceptable salt, a solvate or an optical isomer thereof.

9. 5-[5-(4-methyl 2, 3-dihydropyrido[3,2-b][1, 4]oxazin-7-yl)indazol-1-yl]-1-oxo-1,2-thiazol-3-ol, or a pharmaceutically acceptable salt, a solvate or an optical isomer thereof.

10. A pharmaceutical composition containing as an active ingredient at least one of the compound or a pharmaceutically acceptable salt, or a solvate thereof according to claim 1, and a pharmaceutically acceptable carrier or excipient.

11. A pharmaceutical composition containing as an active ingredient at least one of the compound or a pharmaceutically acceptable salt or a solvate thereof according to claim 2, and a pharmaceutically acceptable carrier or excipient.

12. A pharmaceutical composition containing as an active ingredient at least one of the compound or a pharmaceutically acceptable salt or a solvate thereof according to claim 3, and a pharmaceutically acceptable carrier or excipient.

13. A pharmaceutical composition containing as an active ingredient at least one of the compound or a pharmaceutically acceptable salt or a solvate thereof according to claim 4, and a pharmaceutically acceptable carrier or excipient.

14. A pharmaceutical composition containing as an active ingredient at least the compound, a pharmaceutically acceptable salt or solvate thereof according to claim 5, and a pharmaceutically acceptable carrier or excipient.

15. A pharmaceutical composition containing as an active ingredient at least the compound, a pharmaceutically acceptable salt or solvate thereof according to claim 6, and a pharmaceutically acceptable carrier or excipient.

16. A pharmaceutical composition containing as an active ingredient at least the compound, a pharmaceutically acceptable salt or solvate thereof according to claim 7, and a pharmaceutically acceptable carrier or excipient.

17. A pharmaceutical composition containing as an active ingredient at least the compound, a pharmaceutically acceptable salt or solvate thereof according to claim 8, and a pharmaceutically acceptable carrier or excipient.

18. A pharmaceutical composition containing as an active ingredient at least the compound, a pharmaceutically acceptable salt or solvate thereof according to claim 9, and a pharmaceutically acceptable carrier or excipient.

* * * * *